US011466282B2

(12) United States Patent
Flasinski

(10) Patent No.: US 11,466,282 B2
(45) **Date of Patent: *Oct. 11, 2022**

(54) PLANT REGULATORY ELEMENTS AND USES THEREOF

(71) Applicant: Monsanto Technology LLC, St. Louis, MO (US)

(72) Inventor: Stanislaw Flasinski, Ballwin, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,717

(22) Filed: Jun. 12, 2020

(65) Prior Publication Data

US 2020/0370061 A1 Nov. 26, 2020

Related U.S. Application Data

(62) Division of application No. 15/798,319, filed on Oct. 30, 2017, now Pat. No. 10,752,910, which is a division of application No. 14/686,602, filed on Apr. 14, 2015, now Pat. No. 9,834,777, which is a division of application No. 13/428,994, filed on Mar. 23, 2012, now Pat. No. 9,062,316.

(60) Provisional application No. 61/467,875, filed on Mar. 25, 2011.

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 15/8222* (2013.01)

(58) Field of Classification Search
None
See application file for complete search history.

(56) References Cited

U.S. PATENT DOCUMENTS

| | | | | |
|---|---|---|---|---|
| 5,633,441 | A | 5/1997 | De Greef et al. | |
| 6,054,574 | A | 4/2000 | Quail et al. | |
| 6,596,925 | B1 | 7/2003 | Perera et al. | |
| 6,878,818 | B1 | 4/2005 | Goldsbrough et al. | |
| 7,211,711 | B2 | 5/2007 | Perera et al. | |
| 7,518,034 | B2 | 4/2009 | Perera et al. | |
| 7,816,581 | B2 | 10/2010 | Gilbertson et al. | |
| 7,932,374 | B2 | 4/2011 | Perera et al. | |
| 9,062,316 | B2 | 6/2015 | Flasinski | |
| 10,752,910 | B2 * | 8/2020 | Flasinski | C07K 14/415 |
| 2002/0042932 | A1 | 4/2002 | Back et al. | |
| 2002/0046415 | A1 | 4/2002 | Albert et al. | |
| 2003/0154509 | A1 | 8/2003 | Pascal et al. | |
| 2005/0198712 | A1 | 9/2005 | Betts et al. | |
| 2010/0058495 | A1 | 3/2010 | Abbitt | |
| 2010/0199371 | A1 | 8/2010 | Castle et al. | |
| 2011/0023183 | A1 | 1/2011 | Neal et al. | |
| 2015/0167012 | A1 | 6/2015 | Flasinski | |
| 2016/0289693 | A1 | 10/2016 | Flasinski | |
| 2018/0057833 | A1 | 3/2018 | Flasinski | |
| 2018/0105823 | A1 | 4/2018 | Flasinski | |
| 2020/0032289 | A1 * | 1/2020 | Anderson | C12N 15/8274 |
| 2020/0080096 | A1 * | 3/2020 | Flasinski | C12N 15/8213 |

FOREIGN PATENT DOCUMENTS

| | | | |
|---|---|---|---|
| CA | 2822289 | | 6/2012 |
| CL | 1646-04 | | 6/2004 |
| EP | 1953232 | | 8/2008 |
| RU | 2181380 | | 4/2002 |
| RU | 2326167 | | 6/2008 |
| WO | WO 99/46976 | | 9/1999 |
| WO | WO 99/58659 | A2 | 11/1999 |
| WO | WO 01/94394 | A2 | 12/2001 |
| WO | WO 2006/101938 | | 9/2006 |
| WO | WO 2006/101938 | A1 | 9/2006 |
| WO | WO 2008/064289 | A2 | 5/2008 |
| WO | WO 2009/126470 | | 10/2009 |
| WO | WO 2009/149304 | A2 | 12/2009 |
| WO | WO 2010/144385 | A1 | 12/2010 |

OTHER PUBLICATIONS

USPTO: Corrected Notice of Allowability regarding U.S. Appl. No. 15/798,319, dated Jul. 2, 2020.
U.S. Appl. No. 15/668,668, filed Aug. 3, 2017, Flasinski.
Christensen et al., "Maize polyubiquitin genes: structure, thermal perturbation of expression and transcript splicing, and promoter activity following transfer to protoplasts by electroporation," *Plant Molec Biol*, 18(4):675-689, 1992.
EMBL Accession No. CW082733, dated May 19, 2010.
EMBL Accession No. CW0938, XP002685119, dated May 19, 2010.
Frank et al., "Drought and rust effects on gene expression in the dominant plant species of tallgrass prairie, *Andropogon gerardii*," abstract 16, <http://www.k-state.edu/ecogen/PosterAbstracts-2006.pdf>, 2006.
Frank, "Rust and drought effects on the gene expression and phytohormone concentration in Big Bluestem," thesis, Kansas State University, p. 24, <http://hdl.handle.net/2097/393>, 2007.
GenBank Accession No. X04753, "Potato light-inducible tissue-specific ST-LS1 gene," <http://www.ncbi.nlm.nih.gov/nuccore/X04753>, accessed on Nov. 1, 2012.
International Search Report and Written Opinion issued in PCT/US2012/029990 dated Oct. 29, 2012.

(Continued)

*Primary Examiner* — Medina A Ibrahim
(74) *Attorney, Agent, or Firm* — Dentons US LLP; Amanda Carmany-Rampey, Esq.

(57) ABSTRACT

The present invention provides novel DNA molecules and constructs, including their nucleotide sequences, useful for modulating gene expression in plants and plant cells. The invention also provides transgenic plants, plant cells, plant parts, seeds, and commodity products comprising the DNA molecules operably linked to heterologous transcribable polynucleotides, along with methods of their use.

20 Claims, 31 Drawing Sheets

Specification includes a Sequence Listing.

(56) References Cited

OTHER PUBLICATIONS

Kim et al., "A 20 nucleotide upstream element is essential for the nopaline synthase (nos) promoter activity," *Plant Molecular Biology* 24:105-117, 1994.
Vettore et al., "The molecular and functional characterization of an Opaque2 homologue gene from Coix and a new classification of plant bZIP proteins," *Plant Molecular Biology* 36(2):249-263, 1998.
Wang et al., "Rice ubiquitin promoters: deletion analysis and potential usefulness in plant transformation systems," *Plant Cell Reproduction* 22:129-134, 2003.
Chilean Office Action regarding 27-7-13, dated Feb. 16, 2015.
Kosugi et al., "Two of three promoter elements identified in a rice gene for proliferating cell nuclear antigen are essential for meristematic tissue-specific expression," The Plant Journal 7(6):877-886, 1995.
Dolferus et al., "Differential interactions of promoter elements in stress response of the *Arabidopsis* Adh gene", *Plant Physiol.*, 105:1075-1087, 1994.
Donald et al., "Mutation of either G box or I box sequences profoundly affects expression from the *Arabidopsis* rbcS-1A promoter", *The EMBO Journal*, 9(6):1717-1726, 1990.
USPTO: Non-final Office Action regarding U.S. Appl. No. 14/625,566 dated Jan. 20, 2017.
Christensen, et al., "Maize polyubiquitin genes: structure, thermal perturbation of expression and transcript splicing, and promoter activity following transfer to protoplasts by electroporation", *Plant Molecular Biology* 18: 675-689, 1992.
GenBank Accession No. EU161568, dated Dec. 7, 2007.
GenBank Accession No. EU161573, dated Dec. 7, 2007.
Himmelbach et al., "A Set of Modular Binary Vecgtors for Transformation of Cereals," *Plant Physiology* 145:1192-1200, 2007.
Response to Non-Final Office Action regarding U.S. Appl. No. 14/625,566, dated Apr. 19, 2017.
USPTO: Notice of Allowance and Fee(s) Due regarding U.S. Appl. No. 14/625,566, dated May 26, 2017.
USPTO: Notice of Allowability regarding U.S. Appl. No. 14/686,602, dated Oct. 12, 2017.
Decision on Grant of Patent for Invention regarding Russian Application No. 2013147604, dated Nov. 14, 2017.
USPTO: Non-Final Office Action regarding U.S. Appl. No. 15/179,635, dated Nov. 22, 2017.
GenBank Accession No. AY37338, dated Nov. 25, 2003.
GenBank Accession No. DQ141598, dated Sep. 6, 2005.
Lee et al., "Enhanced octopamine synthesis through the ectopic expression of tyrosine decarboxylase in rice plants," *Plant Science* 176:46-50, 2009.
USPTO: Final Office Action regarding U.S. Appl. No. 15/179,635, dated Apr. 6, 2018.
Doebley, "Molecular Evidence for Gene Flow among *Zea* Species," *BioScience* 40(6):443-448, 1990.
Streatfield et al., "Analysis of the maize polyubiquitin-1 promoter heat shock elements and generation of promoter variants with modified expression characteristics," *Transgenic Research* 13:299-312, 2004.
Response to Final Office Action regarding U.S. Appl. No. 15/179,635, dated Jul. 6, 2018.
USPTO: Advisory Action regarding U.S. Appl. No. 15/179,635, dated Jul. 23, 2018.
USPTO: Non-Final Office Action regarding U.S. Appl. No. 15/179,635, dated Sep. 11, 2018.
USPTO: Notice of Allowance and Fee(s) Due regarding U.S. Appl. No. 15/668,668, dated Oct. 1, 2018.
Christensen et al., "Ubiquitin promoter-based vectors for high-level expression of selectable and/or screenable marker genes in monocotyledonous plants," *Transgenic Research* 5:213-218, 1996.
USPTO: Non-Final Office Action regarding U.S. Appl. No. 15/798,326, dated Nov. 28, 2018.
Response to Non-Final Office Action regarding U.S. Appl. No. 15/179,635, dated Dec. 11, 2018.
Response to Non-Final Office Action regarding U.S. Appl. No. 15/798,326, dated Feb. 25, 2019.
USPTO: Final Office Action regarding U.S. Appl. No. 15/179,635, dated Jan. 23, 2019.
Response to Final Office Action regarding U.S. Appl. No. 15/179,635, dated Jul. 1, 2019.
USPTO: Final Office Action regarding U.S. Appl. No. 15/798,326, dated May 24, 2019.
Response to Final Office Action regarding U.S. Appl. No. 15/798,326, dated Aug. 22, 2019.
Notice of Allowance regarding U.S. Appl. No. 15/798,326, dated Sep. 6, 2019.
USPTO: Non-Final Office Action regarding U.S. Appl. No. 15/179,635, dated Nov. 4, 2019.
Response to Non-Final Office Action regarding U.S. Appl. No. 15/179,635, dated Mar. 2, 2020.
USPTO: Notice of Allowance regarding U.S. Appl. No. 15/179,635, dated Mar. 27, 2020.
GenBank Accession No. AY342393. *Zea diploperennis* polyubiquitin-1 (Ubi-1) gene, promoter region and 5' UTR. Published Aug. 1, 2004. pp. 1-2.
Response to Non-Final Office Action regarding U.S. Appl. No. 15/179,635, dated Feb. 2, 2018.

* cited by examiner

```
P-ANDge.Ubq1-1:1:9      ------------------------------------------------------------
P-ANDge.Ubq1-1:1:8      ------------------------------------------------------------
P-ANDge.Ubq1-1:1:11     AGCAGACTCGCATTATCGATGGAGGGGTGGGTTTAGAACCCTGAAAACTGGTACTGTTTC
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     GAACTGAAAAACACTGTAGCACTTTTCGTTTGTTTGTGGTAAATATTATCTTACTATGGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     CTAACTAGGCTCAAAAGAATCGTCTCGCAATGTACATCTAAATTATGCAATTAGTTATTT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     TGTTTACCTGCATTTCATACTCCGAGCATGCGTCTTTTGGTACATTTAATGCTTCGATGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     GATGGGAATTTTAAAAATTTTGGAGAAAAGTTGGTTTCTAAACACCCCCGAGGACGAAAT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     TGGATTCGGTCTTTGACGCGGATGCAGCAACTGCAGTGCGCAGGATACCATCTTAGCCGT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------
```

FIG. 1a

```
P-ANDge.Ubq1-1:1:9      ------------------------------------------------------------
P-ANDge.Ubq1-1:1:8      ------------------------------------------------------------
P-ANDge.Ubq1-1:1:11     TGCGTCGAAGTTCGCTTTGCTAACGTTTTGAGAAAATTAAACCAGCTTTGACCAACGTGA
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ------------------------------------------------------------
P-ANDge.Ubq1-1:1:8      ------------------------------------------------------------
P-ANDge.Ubq1-1:1:11     GACGAGCGCCTTACGTGGCAGTGTAATGGAACCGGGCACGGCAAGTTTGACGCTGTAGTG
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      ---------CTCGTTACGTTTGGCACAACTTAGTTGAATCCGGCTTCCGGCAAACTATAT
P-ANDge.Ubq1-1:1:8      ------------------------------------------------------------
P-ANDge.Ubq1-1:1:11     TTAGCCGGTCTCGTTACGTTTGGCACAACTTAGTTGAATCCGGCTTCCGGCAAACTATAT
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      GGCAAGTTAGACCCAAGTGTGAGCCGGCCACCGCAAGTTATTGGGACATTATACGTAGGA
P-ANDge.Ubq1-1:1:8      ------------------------------------------------------------
P-ANDge.Ubq1-1:1:11     GGCAAGTTAGACCCAAGTGTGAGCCGGCCACCGCAAGTTATTGGGACATTATACGTAGGA
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      AGCAAGTGTATAATAAGAATATGAGATAATGTAAGCAGCTATATGAATCATCACGTCATA
P-ANDge.Ubq1-1:1:8      ------------------------------------------------------------
P-ANDge.Ubq1-1:1:11     AGCAAGTGTATAATAAGAATATGAGATAATGTAAGCAGCTATATGAATCATCACGTCATA
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------

P-ANDge.Ubq1-1:1:9      TTTATGTTAAGATGAAGAGGATAGAATAAACGGTATGTAAATTTATAGCGAGTGATAGAC
P-ANDge.Ubq1-1:1:8      ------------------------------------------------------------
P-ANDge.Ubq1-1:1:11     TTTATGTTAAGATGAAGAGGATAGAATAAACGGTATGTAAATTTATAGCGAGTGATAGAC
P-ANDge.Ubq1-1:1:12     ------------------------------------------------------------
P-ANDge.Ubq1-1:1:13     ------------------------------------------------------------
P-ANDge.Ubq1-1:1:14     ------------------------------------------------------------
P-ANDge.Ubq1-1:1:10     ------------------------------------------------------------
```

FIG. 1b

```
P-ANDge.Ubq1-1:1:9     GGGCACAAGGCCTCCTAGCTATTTCCATAAATCGGATTTTGTAAGAACAAAAAAGAGGAC
P-ANDge.Ubq1-1:1:8     ------------------------------------------------------------
P-ANDge.Ubq1-1:1:11    GGGCACAAGGCCTCCTAGCTATTTCCATAAATCGGATTTTGTAAGAACAAAAAAGAGGAC
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TTATTATAAGAGAATGTGGTAAGTAAGTATACTCTCTCCGTTTCAAATTATAAGTTGTTT
P-ANDge.Ubq1-1:1:8     ------------------------------------------------------------
P-ANDge.Ubq1-1:1:11    TTATTATAAGAGAATGTGGTAAGTAAGTATACTCTCTCCGTTTCAAATTATAAGTTGTTT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TGATTTTTTTGGTACATCTATTTTACTATGCATTAGATATAATAATGTGTCTAGATACAT
P-ANDge.Ubq1-1:1:8     ------------------------------------------------------------
P-ANDge.Ubq1-1:1:11    TGATTTTTTTGGTACATCTATTTTACTATGCATTAGATATAATAATGTGTCTAGATACAT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     AACAAAATGGATGAATCAAAAAAGTCAAAGTGATTTACAATTTGGAACGGAGAGAGTAAG
P-ANDge.Ubq1-1:1:8     ------------------------------------------------------------
P-ANDge.Ubq1-1:1:11    AACAAAATGGATGAATCAAAAAAGTCAAAGTGATTTACAATTTGGAACGGAGAGAGTAAG
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    -----------------------------------------------------------G

P-ANDge.Ubq1-1:1:9     TTCAAGCCGTCAAGGCACTTCTATGCAACCACAGTCAACTTGAATGCCGCTTGAGTGCCT
P-ANDge.Ubq1-1:1:8     ------------------------------------------------------------
P-ANDge.Ubq1-1:1:11    TTCAAGCCGTCAAGGCACTTCTATGCAACCACAGTCAACTTGAATGCCGCTTGAGTGCCT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    TTCAAGCCGTCAAGGCACTTCTATGCAACCACAGTCAACTTGAATGCCGCTTGAGTGCCT

P-ANDge.Ubq1-1:1:9     TCTCAAGTTTTTTTTTCTTGCAAAAATCATTTCTTTTTTTTAAAAAAAGTATAATTTGGA
P-ANDge.Ubq1-1:1:8     ------------------------------------------------------------
P-ANDge.Ubq1-1:1:11    TCTCAAGTTTTTTTTTCTTGCAAAAATCATTTCTTTTTTTTAAAAAAAGTATAATTTGGA
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    TCTCAAGTTTTTTTTTCTTGCAAAAATCATTTCTTTTTTTTAAAAAAAGTATAATTTGGA
```

FIG. 1c

```
P-ANDge.Ubq1-1:1:9      TCGTGCAAATTTCTCTCTAGGTGTGTGTGTGACTGTGTGAGTAACAATTTCTCTAGTTGT
P-ANDge.Ubq1-1:1:8      ------------------------------------------------------------
P-ANDge.Ubq1-1:1:11     TCGTGCAAATTTCTCTCTAGGTGTGTGTGTGACTGTGTGAGTAACAATTTCTCTAGTTGT
P-ANDge.Ubq1-1:1:12     ----------------------------------------------------TCTAGTTGT
P-ANDge.Ubq1-1:1:13     ------------------------------------------------------------
P-ANDge.Ubq1-1:1:14     ------------------------------------------------------------
P-ANDge.Ubq1-1:1:10     TCGTGCAAATTTCTCTCTAGGTGTGTGTGTGACTGTGTGAGTAACAATTTCTCTAGTTGT

P-ANDge.Ubq1-1:1:9      GCGCGACTGCTGCTTACTTTGGAGATTACAATATCTTTCTAAAATGCTTCGATTACTTAT
P-ANDge.Ubq1-1:1:8      ------------------------------------------------------------
P-ANDge.Ubq1-1:1:11     GCGCGACTGCTGCTTACTTTGGAGATTACAATATCTTTCTAAAATGCTTCGATTACTTAT
P-ANDge.Ubq1-1:1:12     GCGCGACTGCTGCTTACTTTGGAGATTACAATATCTTTCTAAAATGCTTCGATTACTTAT
P-ANDge.Ubq1-1:1:13     ------------------------------------------------------------
P-ANDge.Ubq1-1:1:14     ------------------------------------------------------------
P-ANDge.Ubq1-1:1:10     GCGCGACTGCTGCTTACTTTGGAGATTACAATATCTTTCTAAAATGCTTCGATTACTTAT

P-ANDge.Ubq1-1:1:9      TTATAAACCGTCTCTAAGGCCAATTGCTCAAGATTCATTCAACAATTGAAACGTCTCACA
P-ANDge.Ubq1-1:1:8      ------------------------------------------------------------
P-ANDge.Ubq1-1:1:11     TTATAAACCGTCTCTAAGGCCAATTGCTCAAGATTCATTCAACAATTGAAACGTCTCACA
P-ANDge.Ubq1-1:1:12     TTATAAACCGTCTCTAAGGCCAATTGCTCAAGATTCATTCAACAATTGAAACGTCTCACA
P-ANDge.Ubq1-1:1:13     ------------------------------------------------------------
P-ANDge.Ubq1-1:1:14     ------------------------------------------------------------
P-ANDge.Ubq1-1:1:10     TTATAAACCGTCTCTAAGGCCAATTGCTCAAGATTCATTCAACAATTGAAACGTCTCACA

P-ANDge.Ubq1-1:1:9      TGATTAAATCATATAAAGTTTCTAAGTCTTGTTTGACAAGATTTTTTTAGATTTTCATCT
P-ANDge.Ubq1-1:1:8      ------------------------------------------------------------
P-ANDge.Ubq1-1:1:11     TGATTAAATCATATAAAGTTTCTAAGTCTTGTTTGACAAGATTTTTTTAGATTTTCATCT
P-ANDge.Ubq1-1:1:12     TGATTAAATCATATAAAGTTTCTAAGTCTTGTTTGACAAGATTTTTTTAGATTTTCATCT
P-ANDge.Ubq1-1:1:13     ------------------------------------------------------------
P-ANDge.Ubq1-1:1:14     ------------------------------------------------------------
P-ANDge.Ubq1-1:1:10     TGATTAAATCATATAAAGTTTCTAAGTCTTGTTTGACAAGATTTTTTTAGATTTTCATCT

P-ANDge.Ubq1-1:1:9      AAATTGGATGAAACTATCAAACACTAATTTTAAAAAATATAAGAGAAGCTCCGGAGATAA
P-ANDge.Ubq1-1:1:8      ------------------------------------------------------------
P-ANDge.Ubq1-1:1:11     AAATTGGATGAAACTATCAAACACTAATTTTAAAAAATATAAGAGAAGCTCCGGAGATAA
P-ANDge.Ubq1-1:1:12     AAATTGGATGAAACTATCAAACACTAATTTTAAAAAATATAAGAGAAGCTCCGGAGATAA
P-ANDge.Ubq1-1:1:13     ------------------------------------------------------------
P-ANDge.Ubq1-1:1:14     ------------------------------------------------------------
P-ANDge.Ubq1-1:1:10     AAATTGGATGAAACTATCAAACACTAATTTTAAAAAATATAAGAGAAGCTCCGGAGATAA

P-ANDge.Ubq1-1:1:9      AAGGTCGTCTATGTTATTATAAGAGTAAAGTCGTCTATTCTCTTCGTCCCAACATATATA
P-ANDge.Ubq1-1:1:8      ------------------------------------------------------------
P-ANDge.Ubq1-1:1:11     AAGGTCGTCTATGTTATTATAAGAGTAAAGTCGTCTATTCTCTTCGTCCCAACATATATA
P-ANDge.Ubq1-1:1:12     AAGGTCGTCTATGTTATTATAAGAGTAAAGTCGTCTATTCTCTTCGTCCCAACATATATA
P-ANDge.Ubq1-1:1:13     ------------------------------------------------------------
P-ANDge.Ubq1-1:1:14     ------------------------------------------------------------
P-ANDge.Ubq1-1:1:10     AAGGTCGTCTATGTTATTATAAGAGTAAAGTCGTCTATTCTCTTCGTCCCAACATATATA
```

FIG. 1d

```
P-ANDge.Ubq1-1:1:9       ATTCTAAGCATGAATTGCTTTCTTTTTGGACAAAAGGAGCATGCCACAACACAAGAATGA
P-ANDge.Ubq1-1:1:8       --------------------------------------------------CACAAGAATGA
P-ANDge.Ubq1-1:1:11      ATTCTAAGCATGAATTGCTTTCTTTTTGGACAAAAGGAGCATGCCACAACACAAGAATGA
P-ANDge.Ubq1-1:1:12      ATTCTAAGCATGAATTGCTTTCTTTTTGGACAAAAGGAGCATGCCACAACACAAGAATGA
P-ANDge.Ubq1-1:1:13      ------------------------------------------------------------
P-ANDge.Ubq1-1:1:14      ------------------------------------------------------------
P-ANDge.Ubq1-1:1:10      ATTCTAAGCATGAATTGCTTTCTTTTTGGACAAAAGGAGCATGCCACAACACAAGAATGA

P-ANDge.Ubq1-1:1:9       TGTCACCGTCATGCTTGGATCCTTTTATGGTAAAGCTTCACCTTCTATAATCTAACAATA
P-ANDge.Ubq1-1:1:8       TGTCACCGTCATGCTTGGATCCTTTTATGGTAAAGCTTCACCTTCTATAATCTAACAATA
P-ANDge.Ubq1-1:1:11      TGTCACCGTCATGCTTGGATCCTTTTATGGTAAAGCTTCACCTTCTATAATCTAACAATA
P-ANDge.Ubq1-1:1:12      TGTCACCGTCATGCTTGGATCCTTTTATGGTAAAGCTTCACCTTCTATAATCTAACAATA
P-ANDge.Ubq1-1:1:13      ------------------------------------------------------------
P-ANDge.Ubq1-1:1:14      ------------------------------------------------------------
P-ANDge.Ubq1-1:1:10      TGTCACCGTCATGCTTGGATCCTTTTATGGTAAAGCTTCACCTTCTATAATCTAACAATA

P-ANDge.Ubq1-1:1:9       GAGAAATCAGGGAAAAATCATGTTTTGGTTGTTTTTATTTCTAACCTCCACAATAACTTT
P-ANDge.Ubq1-1:1:8       GAGAAATCAGGGAAAAATCATGTTTTGGTTGTTTTTATTTCTAACCTCCACAATAACTTT
P-ANDge.Ubq1-1:1:11      GAGAAATCAGGGAAAAATCATGTTTTGGTTGTTTTTATTTCTAACCTCCACAATAACTTT
P-ANDge.Ubq1-1:1:12      GAGAAATCAGGGAAAAATCATGTTTTGGTTGTTTTTATTTCTAACCTCCACAATAACTTT
P-ANDge.Ubq1-1:1:13      ------------------------------------------------------------
P-ANDge.Ubq1-1:1:14      ------------------------------------------------------------
P-ANDge.Ubq1-1:1:10      GAGAAATCAGGGAAAAATCATGTTTTGGTTGTTTTTATTTCTAACCTCCACAATAACTTT

P-ANDge.Ubq1-1:1:9       GGTTTACCATTTTTTGTTTGATTTTAGTTTTAGAGAAGCGTTTATAACAGGACCTAAAAT
P-ANDge.Ubq1-1:1:8       GGTTTACCATTTTTTGTTTGATTTTAGTTTTAGAGAAGCGTTTATAACAGGACCTAAAAT
P-ANDge.Ubq1-1:1:11      GGTTTACCATTTTTTGTTTGATTTTAGTTTTAGAGAAGCGTTTATAACAGGACCTAAAAT
P-ANDge.Ubq1-1:1:12      GGTTTACCATTTTTTGTTTGATTTTAGTTTTAGAGAAGCGTTTATAACAGGACCTAAAAT
P-ANDge.Ubq1-1:1:13      ------------------------------------------------------------
P-ANDge.Ubq1-1:1:14      ------------------------------------------------------------
P-ANDge.Ubq1-1:1:10      GGTTTACCATTTTTTGTTTGATTTTAGTTTTAGAGAAGCGTTTATAACAGGACCTAAAAT

P-ANDge.Ubq1-1:1:9       CTTTTTTCAGTACACAGTACAACGCAGACGCTCATACACGCACGCACACTCACCTCTATG
P-ANDge.Ubq1-1:1:8       CTTTTTTCAGTACACAGTACAACGCAGACGCTCATACACGCACGCACACTCACCTCTATG
P-ANDge.Ubq1-1:1:11      CTTTTTTCAGTACACAGTACAACGCAGACGCTCATACACGCACGCACACTCACCTCTATG
P-ANDge.Ubq1-1:1:12      CTTTTTTCAGTACACAGTACAACGCAGACGCTCATACACGCACGCACACTCACCTCTATG
P-ANDge.Ubq1-1:1:13      ------------------------------------------------------------
P-ANDge.Ubq1-1:1:14      ------------------------------------------------------------
P-ANDge.Ubq1-1:1:10      CTTTTTTCAGTACACAGTACAACGCAGACGCTCATACACGCACGCACACTCACCTCTATG

P-ANDge.Ubq1-1:1:9       AACACACGTAAGAAAACCCTACACCTTGAGCACCTTCGAAGGACTGAGCCGGTAAATATA
P-ANDge.Ubq1-1:1:8       AACACACGTAAGAAAACCCTACACCTTGAGCACCTTCGAAGGACTGAGCCGGTAAATATA
P-ANDge.Ubq1-1:1:11      AACACACGTAAGAAAACCCTACACCTTGAGCACCTTCGAAGGACTGAGCCGGTAAATATA
P-ANDge.Ubq1-1:1:12      AACACACGTAAGAAAACCCTACACCTTGAGCACCTTCGAAGGACTGAGCCGGTAAATATA
P-ANDge.Ubq1-1:1:13      ------------------------------------------------------------
P-ANDge.Ubq1-1:1:14      ------------------------------------------------------------
P-ANDge.Ubq1-1:1:10      AACACACGTAAGAAAACCCTACACCTTGAGCACCTTCGAAGGACTGAGCCGGTAAATATA
```

FIG. 1e

```
P-ANDge.Ubq1-1:1:9      GAGATTCTCGAAGTCACTATTAGCGCCTCGTTGTCAACGGGAATGTCGCTTACCACTTAA
P-ANDge.Ubq1-1:1:8      GAGATTCTCGAAGTCACTATTAGCGCCTCGTTGTCAACGGGAATGTCGCTTACCACTTAA
P-ANDge.Ubq1-1:1:11     GAGATTCTCGAAGTCACTATTAGCGCCTCGTTGTCAACGGGAATGTCGCTTACCACTTAA
P-ANDge.Ubq1-1:1:12     GAGATTCTCGAAGTCACTATTAGCGCCTCGTTGTCAACGGGAATGTCGCTTACCACTTAA
P-ANDge.Ubq1-1:1:13     --------------------------------GTCAACGGGAATGTCGCTTACCACTTAA
P-ANDge.Ubq1-1:1:14     ------------------------------------------------------------
P-ANDge.Ubq1-1:1:10     GAGATTCTCGAAGTCACTATTAGCGCCTCGTTGTCAACGGGAATGTCGCTTACCACTTAA

P-ANDge.Ubq1-1:1:9      AGCATAACGCCGAGAAATCCCGTAATAAATCCAGTAAAATACGAGCACCCGTGCCAAGTT
P-ANDge.Ubq1-1:1:8      AGCATAACGCCGAGAAATCCCGTAATAAATCCAGTAAAATACGAGCACCCGTGCCAAGTT
P-ANDge.Ubq1-1:1:11     AGCATAACGCCGAGAAATCCCGTAATAAATCCAGTAAAATACGAGCACCCGTGCCAAGTT
P-ANDge.Ubq1-1:1:12     AGCATAACGCCGAGAAATCCCGTAATAAATCCAGTAAAATACGAGCACCCGTGCCAAGTT
P-ANDge.Ubq1-1:1:13     AGCATAACGCCGAGAAATCCCGTAATAAATCCAGTAAAATACGAGCACCCGTGCCAAGTT
P-ANDge.Ubq1-1:1:14     ------------------------------------------------------------
P-ANDge.Ubq1-1:1:10     AGCATAACGCCGAGAAATCCCGTAATAAATCCAGTAAAATACGAGCACCCGTGCCAAGTT

P-ANDge.Ubq1-1:1:9      GAATATTTGAACCCGAGTGGGTAGATTCCACCGCAAAGGACCTAACCAGATCATTTCGCA
P-ANDge.Ubq1-1:1:8      GAATATTTGAACCCGAGTGGGTAGATTCCACCGCAAAGGACCTAACCAGATCATTTCGCA
P-ANDge.Ubq1-1:1:11     GAATATTTGAACCCGAGTGGGTAGATTCCACCGCAAAGGACCTAACCAGATCATTTCGCA
P-ANDge.Ubq1-1:1:12     GAATATTTGAACCCGAGTGGGTAGATTCCACCGCAAAGGACCTAACCAGATCATTTCGCA
P-ANDge.Ubq1-1:1:13     GAATATTTGAACCCGAGTGGGTAGATTCCACCGCAAAGGACCTAACCAGATCATTTCGCA
P-ANDge.Ubq1-1:1:14     ------------------------------------------------------------
P-ANDge.Ubq1-1:1:10     GAATATTTGAACCCGAGTGGGTAGATTCCACCGCAAAGGACCTAACCAGATCATTTCGCA

P-ANDge.Ubq1-1:1:9      AACAGGAACTAAAATCGGTAGAGAGCCCAGACAAAAGCCTTTCCTAAGAGCCACTCCAGT
P-ANDge.Ubq1-1:1:8      AACAGGAACTAAAATCGGTAGAGAGCCCAGACAAAAGCCTTTCCTAAGAGCCACTCCAGT
P-ANDge.Ubq1-1:1:11     AACAGGAACTAAAATCGGTAGAGAGCCCAGACAAAAGCCTTTCCTAAGAGCCACTCCAGT
P-ANDge.Ubq1-1:1:12     AACAGGAACTAAAATCGGTAGAGAGCCCAGACAAAAGCCTTTCCTAAGAGCCACTCCAGT
P-ANDge.Ubq1-1:1:13     AACAGGAACTAAAATCGGTAGAGAGCCCAGACAAAAGCCTTTCCTAAGAGCCACTCCAGT
P-ANDge.Ubq1-1:1:14     ------------------------------------------------------------
P-ANDge.Ubq1-1:1:10     AACAGGAACTAAAATCGGTAGAGAGCCCAGACAAAAGCCTTTCCTAAGAGCCACTCCAGT

P-ANDge.Ubq1-1:1:9      GGAAGCCCCTACTTTAGGTATAAAATGCAATACTAGTGGGGCTCCTAAATAAACTTCTAT
P-ANDge.Ubq1-1:1:8      GGAAGCCCCTACTTTAGGTATAAAATGCAATACTAGTGGGGCTCCTAAATAAACTTCTAT
P-ANDge.Ubq1-1:1:11     GGAAGCCCCTACTTTAGGTATAAAATGCAATACTAGTGGGGCTCCTAAATAAACTTCTAT
P-ANDge.Ubq1-1:1:12     GGAAGCCCCTACTTTAGGTATAAAATGCAATACTAGTGGGGCTCCTAAATAAACTTCTAT
P-ANDge.Ubq1-1:1:13     GGAAGCCCCTACTTTAGGTATAAAATGCAATACTAGTGGGGCTCCTAAATAAACTTCTAT
P-ANDge.Ubq1-1:1:14     ------------------------------------------------------------
P-ANDge.Ubq1-1:1:10     GGAAGCCCCTACTTTAGGTATAAAATGCAATACTAGTGGGGCTCCTAAATAAACTTCTAT

P-ANDge.Ubq1-1:1:9      TTTTCATGGCCTTCTAAAATTCACTCCCAAACCCCTAGCTATAGAAGTCTCTTATCCATC
P-ANDge.Ubq1-1:1:8      TTTTCATGGCCTTCTAAAATTCACTCCCAAACCCCTAGCTATAGAAGTCTCTTATCCATC
P-ANDge.Ubq1-1:1:11     TTTTCATGGCCTTCTAAAATTCACTCCCAAACCCCTAGCTATAGAAGTCTCTTATCCATC
P-ANDge.Ubq1-1:1:12     TTTTCATGGCCTTCTAAAATTCACTCCCAAACCCCTAGCTATAGAAGTCTCTTATCCATC
P-ANDge.Ubq1-1:1:13     TTTTCATGGCCTTCTAAAATTCACTCCCAAACCCCTAGCTATAGAAGTCTCTTATCCATC
P-ANDge.Ubq1-1:1:14     ---------------------CACTCCCAAACCCCTAGCTATAGAAGTCTCTTATCCATC
P-ANDge.Ubq1-1:1:10     TTTTCATGGCCTTCTAAAATTCACTCCCAAACCCCTAGCTATAGAAGTCTCTTATCCATC
                                             ***************************************
```

FIG. 1f

```
P-ANDge.Ubq1-1:1:9      CTCTAAATAAAAATGGGAGTCTATTTTATTTCACCAGAGTTGATCGTAAATTTAGTCTCT
P-ANDge.Ubq1-1:1:8      CTCTAAATAAAAATGGGAGTCTATTTTATTTCACCAGAGTTGATCGTAAATTTAGTCTCT
P-ANDge.Ubq1-1:1:11     CTCTAAATAAAAATGGGAGTCTATTTTATTTCACCAGAGTTGATCGTAAATTTAGTCTCT
P-ANDge.Ubq1-1:1:12     CTCTAAATAAAAATGGGAGTCTATTTTATTTCACCAGAGTTGATCGTAAATTTAGTCTCT
P-ANDge.Ubq1-1:1:13     CTCTAAATAAAAATGGGAGTCTATTTTATTTCACCAGAGTTGATCGTAAATTTAGTCTCT
P-ANDge.Ubq1-1:1:14     CTCTAAATAAAAATGGGAGTCTATTTTATTTCACCAGAGTTGATCGTAAATTTAGTCTCT
P-ANDge.Ubq1-1:1:10     CTCTAAATAAAAATGGGAGTCTATTTTATTTCACCAGAGTTGATCGTAAATTTAGTCTCT
                        ************************************************************

P-ANDge.Ubq1-1:1:9      CAAATTTTATAAGTTGAGGGTAGAGGATGACTGGAGTTGCTCTAAACGGACCTATCTTCA
P-ANDge.Ubq1-1:1:8      CAAATTTTATAAGTTGAGGGTAGAGGATGACTGGAGTTGCTCTAAACGGACCTATCTTCA
P-ANDge.Ubq1-1:1:11     CAAATTTTATAAGTTGAGGGTAGAGGATGACTGGAGTTGCTCTAAACGGACCTATCTTCA
P-ANDge.Ubq1-1:1:12     CAAATTTTATAAGTTGAGGGTAGAGGATGACTGGAGTTGCTCTAAACGGACCTATCTTCA
P-ANDge.Ubq1-1:1:13     CAAATTTTATAAGTTGAGGGTAGAGGATGACTGGAGTTGCTCTAAACGGACCTATCTTCA
P-ANDge.Ubq1-1:1:14     CAAATTTTATAAGTTGAGGGTAGAGGATGACTGGAGTTGCTCTAAACGGACCTATCTTCA
P-ANDge.Ubq1-1:1:10     CAAATTTTATAAGTTGAGGGTAGAGGATGACTGGAGTTGCTCTAAACGGACCTATCTTCA
                        ************************************************************

P-ANDge.Ubq1-1:1:9      AGTGACCTCAGTGAGCCCGTTTAACGGCGTCGACAAGTTTAATCTAACGGACACCAACCA
P-ANDge.Ubq1-1:1:8      AGTGACCTCAGTGAGCCCGTTTAACGGCGTCGACAAGTTTAATCTAACGGACACCAACCA
P-ANDge.Ubq1-1:1:11     AGTGACCTCAGTGAGCCCGTTTAACGGCGTCGACAAGTTTAATCTAACGGACACCAACCA
P-ANDge.Ubq1-1:1:12     AGTGACCTCAGTGAGCCCGTTTAACGGCGTCGACAAGTTTAATCTAACGGACACCAACCA
P-ANDge.Ubq1-1:1:13     AGTGACCTCAGTGAGCCCGTTTAACGGCGTCGACAAGTTTAATCTAACGGACACCAACCA
P-ANDge.Ubq1-1:1:14     AGTGACCTCAGTGAGCCCGTTTAACGGCGTCGACAAGTTTAATCTAACGGACACCAACCA
P-ANDge.Ubq1-1:1:10     AGTGACCTCAGTGAGCCCGTTTAACGGCGTCGACAAGTTTAATCTAACGGACACCAACCA
                        ************************************************************

P-ANDge.Ubq1-1:1:9      GAGAAGAGAACCACCGCCAGCGCCGAGCCAAGCGACGTTGACATCTTGGCGCGGCACGGC
P-ANDge.Ubq1-1:1:8      GAGAAGAGAACCACCGCCAGCGCCGAGCCAAGCGACGTTGACATCTTGGCGCGGCACGGC
P-ANDge.Ubq1-1:1:11     GAGAAGAGAACCACCGCCAGCGCCGAGCCAAGCGACGTTGACATCTTGGCGCGGCACGGC
P-ANDge.Ubq1-1:1:12     GAGAAGAGAACCACCGCCAGCGCCGAGCCAAGCGACGTTGACATCTTGGCGCGGCACGGC
P-ANDge.Ubq1-1:1:13     GAGAAGAGAACCACCGCCAGCGCCGAGCCAAGCGACGTTGACATCTTGGCGCGGCACGGC
P-ANDge.Ubq1-1:1:14     GAGAAGAGAACCACCGCCAGCGCCGAGCCAAGCGACGTTGACATCTTGGCGCGGCACGGC
P-ANDge.Ubq1-1:1:10     GAGAAGAGAACCACCGCCAGCGCCGAGCCAAGCGACGTTGACATCTTGGCGCGGCACGGC
                        ************************************************************

P-ANDge.Ubq1-1:1:9      ATCTCCCTGGCGTCTGGCCCCCTCTCGAGACTTCCGCTCCACCTCCCACCGGTGGCGGTT
P-ANDge.Ubq1-1:1:8      ATCTCCCTGGCGTCTGGCCCCCTCTCGAGACTTCCGCTCCACCTCCCACCGGTGGCGGTT
P-ANDge.Ubq1-1:1:11     ATCTCCCTGGCGTCTGGCCCCCTCTCGAGACTTCCGCTCCACCTCCCACCGGTGGCGGTT
P-ANDge.Ubq1-1:1:12     ATCTCCCTGGCGTCTGGCCCCCTCTCGAGACTTCCGCTCCACCTCCCACCGGTGGCGGTT
P-ANDge.Ubq1-1:1:13     ATCTCCCTGGCGTCTGGCCCCCTCTCGAGACTTCCGCTCCACCTCCCACCGGTGGCGGTT
P-ANDge.Ubq1-1:1:14     ATCTCCCTGGCGTCTGGCCCCCTCTCGAGACTTCCGCTCCACCTCCCACCGGTGGCGGTT
P-ANDge.Ubq1-1:1:10     ATCTCCCTGGCGTCTGGCCCCCTCTCGAGACTTCCGCTCCACCTCCCACCGGTGGCGGTT
                        ************************************************************
```

FIG. 1g

```
P-ANDge.Ubq1-1:1:9      TCCAAGTCCGTTCCGCCTCCTCTCACACGGCACGAAACCGTGACGGGCACCGGCAGCACG
P-ANDge.Ubq1-1:1:8      TCCAAGTCCGTTCCGCCTCCTCTCACACGGCACGAAACCGTGACGGGCACCGGCAGCACG
P-ANDge.Ubq1-1:1:11     TCCAAGTCCGTTCCGCCTCCTCTCACACGGCACGAAACCGTGACGGGCACCGGCAGCACG
P-ANDge.Ubq1-1:1:12     TCCAAGTCCGTTCCGCCTCCTCTCACACGGCACGAAACCGTGACGGGCACCGGCAGCACG
P-ANDge.Ubq1-1:1:13     TCCAAGTCCGTTCCGCCTCCTCTCACACGGCACGAAACCGTGACGGGCACCGGCAGCACG
P-ANDge.Ubq1-1:1:14     TCCAAGTCCGTTCCGCCTCCTCTCACACGGCACGAAACCGTGACGGGCACCGGCAGCACG
P-ANDge.Ubq1-1:1:10     TCCAAGTCCGTTCCGCCTCCTCTCACACGGCACGAAACCGTGACGGGCACCGGCAGCACG
                        ************************************************************

P-ANDge.Ubq1-1:1:9      GGGGGATTCCTTTCCCACCGCTCCTTCCCTTTCCCTTCCTCTCCCGCCGCTATAAATAGC
P-ANDge.Ubq1-1:1:8      GGGGGATTCCTTTCCCACCGCTCCTTCCCTTTCCCTTCCTCTCCCGCCGCTATAAATAGC
P-ANDge.Ubq1-1:1:11     GGGGGATTCCTTTCCCACCGCTCCTTCCCTTTCCCTTCCTCTCCCGCCGCTATAAATAGC
P-ANDge.Ubq1-1:1:12     GGGGGATTCCTTTCCCACCGCTCCTTCCCTTTCCCTTCCTCTCCCGCCGCTATAAATAGC
P-ANDge.Ubq1-1:1:13     GGGGGATTCCTTTCCCACCGCTCCTTCCCTTTCCCTTCCTCTCCCGCCGCTATAAATAGC
P-ANDge.Ubq1-1:1:14     GGGGGATTCCTTTCCCACCGCTCCTTCCCTTTCCCTTCCTCTCCCGCCGCTATAAATAGC
P-ANDge.Ubq1-1:1:10     GGGGGATTCCTTTCCCACCGCTCCTTCCCTTTCCCTTCCTCTCCCGCCGCTATAAATAGC
                        ************************************************************

P-ANDge.Ubq1-1:1:9      CAGCCCCATCCCCAGCTTCTTTC
P-ANDge.Ubq1-1:1:8      CAGCCCCATCCCCAGCTTCTTTC
P-ANDge.Ubq1-1:1:11     CAGCCCCATCCCCAGCTTCTTTC
P-ANDge.Ubq1-1:1:12     CAGCCCCATCCCCAGCTTCTTTC
P-ANDge.Ubq1-1:1:13     CAGCCCCATCCCCAGCTTCTTTC
P-ANDge.Ubq1-1:1:14     CAGCCCCATCCCCAGCTTCTTTC
P-ANDge.Ubq1-1:1:10     CAGCCCCATCCCCAGCTTCTTTC
                        ***********************
```

FIG. 1h

```
P-ERIra.Ubq1-1:1:9      ------------------------------------------------------------
P-ERIra.Ubq1-1:1:10     GTGGCCAGCTTTTGTTCTAGTTCAACGGCCCCGGCCTTCCGGGCACCTAATACCCTAATT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     AATCTATTGCAGCTAACCTCAAAAGAAATGCATTTGCAGTTGTCTGTCCCAATCAATCTA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     CTAGCAGACTTACATTATAGATGGAGGAAATTAAATTCAGCCTTTGACGTGGATGCAACA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     ACTGCACTGCACAGGATACCATCTTAGCCGTTGTGTCAAAGTTTGCTTTGCTAAACGTTT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     TGAGAAAACCAGCTTTGACCAACGCGAGATGAGCGCCTTACGTTTGGCACAATGTAATGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     AATCCGGCACGGCAAGTTAGACTCTGTAGTGTTAGCCGGCCTCTTTACGTTTGGCATAGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------
```

FIG. 2a

```
P-ERIra.Ubq1-1:1:9      ------------------------------------------------------------
P-ERIra.Ubq1-1:1:10     TTAATTGAATCCGGCATGGCAAGTTAGACCGTAGTGTGAGCCGGCCAACGCAAGTTATTA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      --------GTATAAGAGCAAGTGTATTGTCACGTGATATTTATGTTGAGATGAAGAAGAG
P-ERIra.Ubq1-1:1:10     TGACATATGTATAAGAGCAAGTGTATTGTCACGTGATATTTATGTTGAGATGAAGAAGAG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      AAAATAAACAGCCTGCAAATTTATAGCGAGTGATAGATGGGCACAAGGCTTCCTATTTCT
P-ERIra.Ubq1-1:1:10     AAAATAAACAGCCTGCAAATTTATAGCGAGTGATAGATGGGCACAAGGCTTCCTATTTCT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      TAAATCAGACTTTGTAAGAACAAAAAAAGGACTTATAAGAGAATGGGATAAACCATATAT
P-ERIra.Ubq1-1:1:10     TAAATCAGACTTTGTAAGAACAAAAAAAGGACTTATAAGAGAATGGGATAAACCATATAT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      CAATGGTGTAGTATGTTAGTATGCATTAAGATCTGACTATTATATGAGTGAGTTGTTAAA
P-ERIra.Ubq1-1:1:10     CAATGGTGTAGTATGTTAGTATGCATTAAGATCTGACTATTATATGAGTGAGTTGTTAAA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      TTCATTTTAGGTGACATGGCCCGGTTAAATTATTAGCCATACCCTAACAGCTCTAAAAAA
P-ERIra.Ubq1-1:1:10     TTCATTTTAGGTGACATGGCCCGGTTAAATTATTAGCCATACCCTAACAGCTCTAAAAAA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------
```

FIG. 2b

```
P-ERIra.Ubq1-1:1:9      GATATATTCGTTGAGGCACTTTTATGCAACCACATAGTCAACTTGAATGCCGCTTGAGTG
P-ERIra.Ubq1-1:1:10     GATATATTCGTTGAGGCACTTTTATGCAACCACATAGTCAACTTGAATGCCGCTTGAGTG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      CGTTCTCAAGTTTTTTTTCTTGCAAATTACGCTTTTTTAAGAAAGTATAATTTGGATCGT
P-ERIra.Ubq1-1:1:10     CGTTCTCAAGTTTTTTTTCTTGCAAATTACGCTTTTTTAAGAAAGTATAATTTGGATCGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      GCGATTTTTTTTCTCTAGGTGTGCGTGACTGTGTGAGTAACAATTTTGGATCTCAGAAAG
P-ERIra.Ubq1-1:1:10     GCGATTTTTTTTCTCTAGGTGTGCGTGACTGTGTGAGTAACAATTTTGGATCTCAGAAAG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      GTAATAAAAGAATAATACTGCTGCCTACTTTGAGGATTACAATATCTTTCTCTAAAATGT
P-ERIra.Ubq1-1:1:10     GTAATAAAAGAATAATACTGCTGCCTACTTTGAGGATTACAATATCTTTCTCTAAAATGT
P-ERIra.Ubq1-1:1:8      ------------------------------------------------------------
P-ERIra.Ubq1-1:1:11     -----------------CTGCTGCCTACTTTGAGGATTACAATATCTTTCTCTAAAATGT
P-ERIra.Ubq1-1:1:12     ------------------------------------------------------------
P-ERIra.Ubq1-1:1:13     ------------------------------------------------------------

P-ERIra.Ubq1-1:1:9      TTTGGTTTGTTATTTAAACCGTCTTTAAGGCCAATTGCTCAAGATTCATTCAACAATTGA
P-ERIra.Ubq1-1:1:10     TTTGGTTTGTTATTTAAACCGTCTTTAAGGCCAATTGCTCAAGATTCATTCAACAATTGA
P-ERIra.Ubq1-1:1:8      ------------------------------------------------------------
P-ERIra.Ubq1-1:1:11     TTTGGTTTGTTATTTAAACCGTCTTTAAGGCCAATTGCTCAAGATTCATTCAACAATTGA
P-ERIra.Ubq1-1:1:12     ------------------------------------------------------------
P-ERIra.Ubq1-1:1:13     ------------------------------------------------------------

P-ERIra.Ubq1-1:1:9      AACGTCTCACATGATTAAATCATATAAGGTTGCTAAGGTCTTGTTTGACAAGGTTTTTTT
P-ERIra.Ubq1-1:1:10     AACGTCTCACATGATTAAATCATATAAGGTTGCTAAGGTCTTGTTTGACAAGGTTTTTTT
P-ERIra.Ubq1-1:1:8      ------------------------------------------------------------
P-ERIra.Ubq1-1:1:11     AACGTCTCACATGATTAAATCATATAAGGTTGCTAAGGTCTTGTTTGACAAGGTTTTTTT
P-ERIra.Ubq1-1:1:12     ------------------------------------------------------------
P-ERIra.Ubq1-1:1:13     ------------------------------------------------------------
```

FIG. 2c

P-ERIra.Ubq1-1:1:9   TGTGGAAATTTCATCTAAATTTTTGAGTGAAACTATCAAATACTAATTTAAAAAAGGCAA
P-ERIra.Ubq1-1:1:10   TGTGGAAATTTCATCTAAATTTTTGAGTGAAACTATCAAATACTAATTTAAAAAAGGCAA
P-ERIra.Ubq1-1:1:8   ------------------------------------------------------------
P-ERIra.Ubq1-1:1:11   TGTGGAAATTTCATCTAAATTTTTGAGTGAAACTATCAAATACTAATTTAAAAAAGGCAA
P-ERIra.Ubq1-1:1:12   ------------------------------------------------------------
P-ERIra.Ubq1-1:1:13   ------------------------------------------------------------

P-ERIra.Ubq1-1:1:9   ATTTTGCTGGAGGACACTGCAGAAACGTGTAATTGGCCGGCACAAACCGCCAAACGGAGA
P-ERIra.Ubq1-1:1:10   ATTTTGCTGGAGGACACTGCAGAAACGTGTAATTGGCCGGCACAAACCGCCAAACGGAGA
P-ERIra.Ubq1-1:1:8   ------------------------------------------------------------
P-ERIra.Ubq1-1:1:11   ATTTTGCTGGAGGACACTGCAGAAACGTGTAATTGGCCGGCACAAACCGCCAAACGGAGA
P-ERIra.Ubq1-1:1:12   ------------------------------------------------------------
P-ERIra.Ubq1-1:1:13   ------------------------------------------------------------

P-ERIra.Ubq1-1:1:9   ATTTGCCCAGTACCATTATAAATTCATGATAAATTCATGGTTGTTTGCCAGTGGGGCTAG
P-ERIra.Ubq1-1:1:10   ATTTGCCCAGTACCATTATAAATTCATGATAAATTCATGGTTGTTTGCCAGTGGGGCTAG
P-ERIra.Ubq1-1:1:8   ------------------------------------------------------------
P-ERIra.Ubq1-1:1:11   ATTTGCCCAGTACCATTATAAATTCATGATAAATTCATGGTTGTTTGCCAGTGGGGCTAG
P-ERIra.Ubq1-1:1:12   ------------------------------------------------------------
P-ERIra.Ubq1-1:1:13   ------------------------------------------------------------

P-ERIra.Ubq1-1:1:9   GGTTCCTCGCGTATGGTGCGGAATGTGGTTTGGTTCGACCAACTCGAACTCAATCCGATC
P-ERIra.Ubq1-1:1:10   GGTTCCTCGCGTATGGTGCGGAATGTGGTTTGGTTCGACCAACTCGAACTCAATCCGATC
P-ERIra.Ubq1-1:1:8   ------------------------------------------------------------
P-ERIra.Ubq1-1:1:11   GGTTCCTCGCGTATGGTGCGGAATGTGGTTTGGTTCGACCAACTCGAACTCAATCCGATC
P-ERIra.Ubq1-1:1:12   ------------------------------------------------------------
P-ERIra.Ubq1-1:1:13   ------------------------------------------------------------

P-ERIra.Ubq1-1:1:9   CAAAGGGGCATCAATAGTCATTTTAGAAAGTTTCTCTCTCCCGAGCAGTGGAAATGATTA
P-ERIra.Ubq1-1:1:10   CAAAGGGGCATCAATAGTCATTTTAGAAAGTTTCTCTCTCCCGAGCAGTGGAAATGATTA
P-ERIra.Ubq1-1:1:8   ------------------------------------------------------------
P-ERIra.Ubq1-1:1:11   CAAAGGGGCATCAATAGTCATTTTAGAAAGTTTCTCTCTCCCGAGCAGTGGAAATGATTA
P-ERIra.Ubq1-1:1:12   ------------------------------------------------------------
P-ERIra.Ubq1-1:1:13   ------------------------------------------------------------

P-ERIra.Ubq1-1:1:9   TTCTATTTGGCGCGATGTCCACCGGCAAACAACCACGAATTTGTAATGGTACTAGGCAAA
P-ERIra.Ubq1-1:1:10   TTCTATTTGGCGCGATGTCCACCGGCAAACAACCACGAATTTGTAATGGTACTAGGCAAA
P-ERIra.Ubq1-1:1:8   ------------------CCACCGGCAAACAACCACGAATTTGTAATGGTACTAGGCAAA
P-ERIra.Ubq1-1:1:11   TTCTATTTGGCGCGATGTCCACCGGCAAACAACCACGAATTTGTAATGGTACTAGGCAAA
P-ERIra.Ubq1-1:1:12   ------------------------------------------------------------
P-ERIra.Ubq1-1:1:13   ------------------------------------------------------------

FIG. 2d

```
P-ERIra.Ubq1-1:1:9      TTCTCCGTTTGGCGGTGTGTGCCGGCCAATTACACGTTTTTGCGGTGTCCTCCGACAAAA
P-ERIra.Ubq1-1:1:10     TTCTCCGTTTGGCGGTGTGTGCCGGCCAATTACACGTTTTTGCGGTGTCCTCCGACAAAA
P-ERIra.Ubq1-1:1:8      TTCTCCGTTTGGCGGTGTGTGCCGGCCAATTACACGTTTTTGCGGTGTCCTCCGACAAAA
P-ERIra.Ubq1-1:1:11     TTCTCCGTTTGGCGGTGTGTGCCGGCCAATTACACGTTTTTGCGGTGTCCTCCGACAAAA
P-ERIra.Ubq1-1:1:12     ------------------------------------------------------------
P-ERIra.Ubq1-1:1:13     ------------------------------------------------------------

P-ERIra.Ubq1-1:1:9      TTTGCCTTTTAAAAACAATTTTATAAGAGAAGCTCCGGAGATAAAAGGCCGTCAATGTTA
P-ERIra.Ubq1-1:1:10     TTTGCCTTTTAAAAACAATTTTATAAGAGAAGCTCCGGAGATAAAAGGCCGTCAATGTTA
P-ERIra.Ubq1-1:1:8      TTTGCCTTTTAAAAACAATTTTATAAGAGAAGCTCCGGAGATAAAAGGCCGTCAATGTTA
P-ERIra.Ubq1-1:1:11     TTTGCCTTTTAAAAACAATTTTATAAGAGAAGCTCCGGAGATAAAAGGCCGTCAATGTTA
P-ERIra.Ubq1-1:1:12     ------------------------------------------------------------
P-ERIra.Ubq1-1:1:13     ------------------------------------------------------------

P-ERIra.Ubq1-1:1:9      CAAGAGTGAAGTCGTCTACTCCCTCCATCCCAAAAAATGTAATTCTAAGTATGAGTTGTA
P-ERIra.Ubq1-1:1:10     CAAGAGTGAAGTCGTCTACTCCCTCCATCCCAAAAAATGTAATTCTAAGTATGAGTTGTA
P-ERIra.Ubq1-1:1:8      CAAGAGTGAAGTCGTCTACTCCCTCCATCCCAAAAAATGTAATTCTAAGTATGAGTTGTA
P-ERIra.Ubq1-1:1:11     CAAGAGTGAAGTCGTCTACTCCCTCCATCCCAAAAAATGTAATTCTAAGTATGAGTTGTA
P-ERIra.Ubq1-1:1:12     ------------------------------------------------------------
P-ERIra.Ubq1-1:1:13     ------------------------------------------------------------

P-ERIra.Ubq1-1:1:9      TTATTATTTTTGGACAAAAGGAGTATACCACAAGAATGATATCATCGTCATGCTTAGATC
P-ERIra.Ubq1-1:1:10     TTATTATTTTTGGACAAAAGGAGTATACCACAAGAATGATATCATCGTCATGCTTAGATC
P-ERIra.Ubq1-1:1:8      TTATTATTTTTGGACAAAAGGAGTATACCACAAGAATGATATCATCGTCATGCTTAGATC
P-ERIra.Ubq1-1:1:11     TTATTATTTTTGGACAAAAGGAGTATACCACAAGAATGATATCATCGTCATGCTTAGATC
P-ERIra.Ubq1-1:1:12     --------------------------ACCACAAGAATGATATCATCGTCATGCTTAGATC
P-ERIra.Ubq1-1:1:13     ------------------------------------------------------------

P-ERIra.Ubq1-1:1:9      CTTTTTAGTAAAGCTTGAGCTTCTCTAAAAGTAGAGAAATTAGAAAAAAATCACGTTTTT
P-ERIra.Ubq1-1:1:10     CTTTTTAGTAAAGCTTGAGCTTCTCTAAAAGTAGAGAAATTAGAAAAAAATCACGTTTTT
P-ERIra.Ubq1-1:1:8      CTTTTTAGTAAAGCTTGAGCTTCTCTAAAAGTAGAGAAATTAGAAAAAAATCACGTTTTT
P-ERIra.Ubq1-1:1:11     CTTTTTAGTAAAGCTTGAGCTTCTCTAAAAGTAGAGAAATTAGAAAAAAATCACGTTTTT
P-ERIra.Ubq1-1:1:12     CTTTTTAGTAAAGCTTGAGCTTCTCTAAAAGTAGAGAAATTAGAAAAAAATCACGTTTTT
P-ERIra.Ubq1-1:1:13     ------------------------------------------------------------

P-ERIra.Ubq1-1:1:9      GTGGTCTTGATTTCTAGCCTCCACAAAATCTTTGGTTTTACATTTTTTGTTTGATTTTGG
P-ERIra.Ubq1-1:1:10     GTGGTCTTGATTTCTAGCCTCCACAAAATCTTTGGTTTTACATTTTTTGTTTGATTTTGG
P-ERIra.Ubq1-1:1:8      GTGGTCTTGATTTCTAGCCTCCACAAAATCTTTGGTTTTACATTTTTTGTTTGATTTTGG
P-ERIra.Ubq1-1:1:11     GTGGTCTTGATTTCTAGCCTCCACAAAATCTTTGGTTTTACATTTTTTGTTTGATTTTGG
P-ERIra.Ubq1-1:1:12     GTGGTCTTGATTTCTAGCCTCCACAAAATCTTTGGTTTTACATTTTTTGTTTGATTTTGG
P-ERIra.Ubq1-1:1:13     ------------------------------------------------------------
```

FIG. 2e

```
P-ERIra.Ubq1-1:1:9      TTTCAGAAGTCCTTATTTATATGTGCTAGTTTGGCAGCACTTAAAATCGTTAGAGAGAGC
P-ERIra.Ubq1-1:1:10     TTTCAGAAGTCCTTATTTATATGTGCTAGTTTGGCAGCACTTAAAATCGTTAGAGAGAGC
P-ERIra.Ubq1-1:1:8      TTTCAGAAGTCCTTATTTATATGTGCTAGTTTGGCAGCACTTAAAATCGTTAGAGAGAGC
P-ERIra.Ubq1-1:1:11     TTTCAGAAGTCCTTATTTATATGTGCTAGTTTGGCAGCACTTAAAATCGTTAGAGAGAGC
P-ERIra.Ubq1-1:1:12     TTTCAGAAGTCCTTATTTATATGTGCTAGTTTGGCAGCACTTAAAATCGTTAGAGAGAGC
P-ERIra.Ubq1-1:1:13     ------------------------------------------------------------

P-ERIra.Ubq1-1:1:9      CTAAACAAAAGCCTTTTCAAAACGACCTTGAGCCAGATTGGTTGATGGCCAAAATTTGAT
P-ERIra.Ubq1-1:1:10     CTAAACAAAAGCCTTTTCAAAACGACCTTGAGCCAGATTGGTTGATGGCCAAAATTTGAT
P-ERIra.Ubq1-1:1:8      CTAAACAAAAGCCTTTTCAAAACGACCTTGAGCCAGATTGGTTGATGGCCAAAATTTGAT
P-ERIra.Ubq1-1:1:11     CTAAACAAAAGCCTTTTCAAAACGACCTTGAGCCAGATTGGTTGATGGCCAAAATTTGAT
P-ERIra.Ubq1-1:1:12     CTAAACAAAAGCCTTTTCAAAACGACCTTGAGCCAGATTGGTTGATGGCCAAAATTTGAT
P-ERIra.Ubq1-1:1:13     ------------------------------------------------------------

P-ERIra.Ubq1-1:1:9      TGTCAAAACTTAGGCAAGCCAAGATTTTAGCAGCTATTTGGTTTGGTACCAAAATTTGCC
P-ERIra.Ubq1-1:1:10     TGTCAAAACTTAGGCAAGCCAAGATTTTAGCAGCTATTTGGTTTGGTACCAAAATTTGCC
P-ERIra.Ubq1-1:1:8      TGTCAAAACTTAGGCAAGCCAAGATTTTAGCAGCTATTTGGTTTGGTACCAAAATTTGCC
P-ERIra.Ubq1-1:1:11     TGTCAAAACTTAGGCAAGCCAAGATTTTAGCAGCTATTTGGTTTGGTACCAAAATTTGCC
P-ERIra.Ubq1-1:1:12     TGTCAAAACTTAGGCAAGCCAAGATTTTAGCAGCTATTTGGTTTGGTACCAAAATTTGCC
P-ERIra.Ubq1-1:1:13     -----------AGGCAAGCCAAGATTTTAGCAGCTATTTGGTTTGGTACCAAAATTTGCC
                                   *************************************************

P-ERIra.Ubq1-1:1:9      AATGATCTGTTCTTTTGCCTTTTCAACCGGTTTATCAGCCGTACTTCAGCTTATTCTCTC
P-ERIra.Ubq1-1:1:10     AATGATCTGTTCTTTTGCCTTTTCAACCGGTTTATCAGCCGTACTTCAGCTTATTCTCTC
P-ERIra.Ubq1-1:1:8      AATGATCTGTTCTTTTGCCTTTTCAACCGGTTTATCAGCCGTACTTCAGCTTATTCTCTC
P-ERIra.Ubq1-1:1:11     AATGATCTGTTCTTTTGCCTTTTCAACCGGTTTATCAGCCGTACTTCAGCTTATTCTCTC
P-ERIra.Ubq1-1:1:12     AATGATCTGTTCTTTTGCCTTTTCAACCGGTTTATCAGCCGTACTTCAGCTTATTCTCTC
P-ERIra.Ubq1-1:1:13     AATGATCTGTTCTTTTGCCTTTTCAACCGGTTTATCAGCCGTACTTCAGCTTATTCTCTC
                        ************************************************************

P-ERIra.Ubq1-1:1:9      TCACAGAACACTATTGAATCAGCCGAAAAGCCACCGCAGAACAGGACCAGTATCTCACAA
P-ERIra.Ubq1-1:1:10     TCACAGAACACTATTGAATCAGCCGAAAAGCCACCGCAGAACAGGACCAGTATCTCACAA
P-ERIra.Ubq1-1:1:8      TCACAGAACACTATTGAATCAGCCGAAAAGCCACCGCAGAACAGGACCAGTATCTCACAA
P-ERIra.Ubq1-1:1:11     TCACAGAACACTATTGAATCAGCCGAAAAGCCACCGCAGAACAGGACCAGTATCTCACAA
P-ERIra.Ubq1-1:1:12     TCACAGAACACTATTGAATCAGCCGAAAAGCCACCGCAGAACAGGACCAGTATCTCACAA
P-ERIra.Ubq1-1:1:13     TCACAGAACACTATTGAATCAGCCGAAAAGCCACCGCAGAACAGGACCAGTATCTCACAA
                        ************************************************************

P-ERIra.Ubq1-1:1:9      ATGGCATGCCAAATATACTCACCGTCAGTGAGCCCGTTTAACGGCGTCGACAAGTCTAAC
P-ERIra.Ubq1-1:1:10     ATGGCATGCCAAATATACTCACCGTCAGTGAGCCCGTTTAACGGCGTCGACAAGTCTAAC
P-ERIra.Ubq1-1:1:8      ATGGCATGCCAAATATACTCACCGTCAGTGAGCCCGTTTAACGGCGTCGACAAGTCTAAC
P-ERIra.Ubq1-1:1:11     ATGGCATGCCAAATATACTCACCGTCAGTGAGCCCGTTTAACGGCGTCGACAAGTCTAAC
P-ERIra.Ubq1-1:1:12     ATGGCATGCCAAATATACTCACCGTCAGTGAGCCCGTTTAACGGCGTCGACAAGTCTAAC
P-ERIra.Ubq1-1:1:13     ATGGCATGCCAAATATACTCACCGTCAGTGAGCCCGTTTAACGGCGTCGACAAGTCTAAC
                        ************************************************************
```

FIG. 2f

```
P-ERIra.Ubq1-1:1:9      GGCCACCAACCAGCGAACCACCAGCGTCAAGCTAGCCAAGCGAAGCAGACGGCCGAGACG
P-ERIra.Ubq1-1:1:10     GGCCACCAACCAGCGAACCACCAGCGTCAAGCTAGCCAAGCGAAGCAGACGGCCGAGACG
P-ERIra.Ubq1-1:1:8      GGCCACCAACCAGCGAACCACCAGCGTCAAGCTAGCCAAGCGAAGCAGACGGCCGAGACG
P-ERIra.Ubq1-1:1:11     GGCCACCAACCAGCGAACCACCAGCGTCAAGCTAGCCAAGCGAAGCAGACGGCCGAGACG
P-ERIra.Ubq1-1:1:12     GGCCACCAACCAGCGAACCACCAGCGTCAAGCTAGCCAAGCGAAGCAGACGGCCGAGACG
P-ERIra.Ubq1-1:1:13     GGCCACCAACCAGCGAACCACCAGCGTCAAGCTAGCCAAGCGAAGCAGACGGCCGAGACG
                        ************************************************************

P-ERIra.Ubq1-1:1:9      TTGACACCTTGGCGCGGGCATCTCTCTGGCCCCCTCTCGAGAGTTCCGCTCCACCTCCAC
P-ERIra.Ubq1-1:1:10     TTGACACCTTGGCGCGGGCATCTCTCTGGCCCCCTCTCGAGAGTTCCGCTCCACCTCCAC
P-ERIra.Ubq1-1:1:8      TTGACACCTTGGCGCGGGCATCTCTCTGGCCCCCTCTCGAGAGTTCCGCTCCACCTCCAC
P-ERIra.Ubq1-1:1:11     TTGACACCTTGGCGCGGGCATCTCTCTGGCCCCCTCTCGAGAGTTCCGCTCCACCTCCAC
P-ERIra.Ubq1-1:1:12     TTGACACCTTGGCGCGGGCATCTCTCTGGCCCCCTCTCGAGAGTTCCGCTCCACCTCCAC
P-ERIra.Ubq1-1:1:13     TTGACACCTTGGCGCGGGCATCTCTCTGGCCCCCTCTCGAGAGTTCCGCTCCACCTCCAC
                        ************************************************************

P-ERIra.Ubq1-1:1:9      TGGTGGCGGTTTCCAAGTCCGTTCCGCCTCCTGCTCCTCCTCACACGGCACGAAACCGTC
P-ERIra.Ubq1-1:1:10     TGGTGGCGGTTTCCAAGTCCGTTCCGCCTCCTGCTCCTCCTCACACGGCACGAAACCGTC
P-ERIra.Ubq1-1:1:8      TGGTGGCGGTTTCCAAGTCCGTTCCGCCTCCTGCTCCTCCTCACACGGCACGAAACCGTC
P-ERIra.Ubq1-1:1:11     TGGTGGCGGTTTCCAAGTCCGTTCCGCCTCCTGCTCCTCCTCACACGGCACGAAACCGTC
P-ERIra.Ubq1-1:1:12     TGGTGGCGGTTTCCAAGTCCGTTCCGCCTCCTGCTCCTCCTCACACGGCACGAAACCGTC
P-ERIra.Ubq1-1:1:13     TGGTGGCGGTTTCCAAGTCCGTTCCGCCTCCTGCTCCTCCTCACACGGCACGAAACCGTC
                        ************************************************************

P-ERIra.Ubq1-1:1:9      ACGGCACCGGCAGCACGGGGGATTCCTTTCCCACCGCTCCTTCCCTTTCCCTTCCTCGCC
P-ERIra.Ubq1-1:1:10     ACGGCACCGGCAGCACGGGGGATTCCTTTCCCACCGCTCCTTCCCTTTCCCTTCCTCGCC
P-ERIra.Ubq1-1:1:8      ACGGCACCGGCAGCACGGGGGATTCCTTTCCCACCGCTCCTTCCCTTTCCCTTCCTCGCC
P-ERIra.Ubq1-1:1:11     ACGGCACCGGCAGCACGGGGGATTCCTTTCCCACCGCTCCTTCCCTTTCCCTTCCTCGCC
P-ERIra.Ubq1-1:1:12     ACGGCACCGGCAGCACGGGGGATTCCTTTCCCACCGCTCCTTCCCTTTCCCTTCCTCGCC
P-ERIra.Ubq1-1:1:13     ACGGCACCGGCAGCACGGGGGATTCCTTTCCCACCGCTCCTTCCCTTTCCCTTCCTCGCC
                        ************************************************************

P-ERIra.Ubq1-1:1:9      CGCCGTTTTAAATAGCCAGCCCCATCCCCAGCTTCTCTCCCC
P-ERIra.Ubq1-1:1:10     CGCCGTTTTAAATAGCCAGCCCCATCCCCAGCTTCTCTCCCC
P-ERIra.Ubq1-1:1:8      CGCCGTTTTAAATAGCCAGCCCCATCCCCAGCTTCTCTCCCC
P-ERIra.Ubq1-1:1:11     CGCCGTTTTAAATAGCCAGCCCCATCCCCAGCTTCTCTCCCC
P-ERIra.Ubq1-1:1:12     CGCCGTTTTAAATAGCCAGCCCCATCCCCAGCTTCTCTCCCC
P-ERIra.Ubq1-1:1:13     CGCCGTTTTAAATAGCCAGCCCCATCCCCAGCTTCTCTCCCC
                        ******************************************
```

FIG. 2g

```
P-Sv.Ubq1-1:1:2     ------------------------------------------------------------
P-Sv.Ubq1-1:1:1     ACTGCCGCGACACGCCTCACTGGCGGGAGGGCTCCGAGCGCTCTCTCCCCGGCGGCCGGC
P-Sv.Ubq1-1:1:3     ------------------------------------------------------------

P-Sv.Ubq1-1:1:2     ------------------------------------------------------------
P-Sv.Ubq1-1:1:1     GGAGCAGCGATCTGGATTGGAGAGAATAGAGGAAAGAGAGGGAAAAGGAGAGAGATAGCG
P-Sv.Ubq1-1:1:3     ------------------------------------------------------------

P-Sv.Ubq1-1:1:2     ------------------------------------------------------------
P-Sv.Ubq1-1:1:1     CAAAGAGCTGAAAAGATAAGGTTGTGCGGGCTGTGGTGATTAGAGGACCACTAATCCCTC
P-Sv.Ubq1-1:1:3     ------------------------------------------------------------

P-Sv.Ubq1-1:1:2     ------------------------------------------------------------
P-Sv.Ubq1-1:1:1     CATCTCCTAATGACGCGGTGCCCAAGACCAGTGCCGCGGCACACCAGCGTCTAAGTGAAC
P-Sv.Ubq1-1:1:3     ------------------------------------------------------------

P-Sv.Ubq1-1:1:2     ------------------------------------------------------------
P-Sv.Ubq1-1:1:1     TTCCGCTAACCTTCCGGTCATTGCGCCTGAAAGATGTCATGTGGCGAGGCCCCCCTCTCA
P-Sv.Ubq1-1:1:3     ------------------------------------------------------------

P-Sv.Ubq1-1:1:2     ------------------------------------------------------------
P-Sv.Ubq1-1:1:1     GTAGATTGCCAACTGCCTACCGTGCCACTCTTCCATGCATGATTGCTCCCGTCTATCCCG
P-Sv.Ubq1-1:1:3     ------------------------------------------------------------

P-Sv.Ubq1-1:1:2     ------------------------------------------------------------
P-Sv.Ubq1-1:1:1     TTTCTCACAACAGATAGACAACAGTAAGCATCACTAAAGCAAGCATGTGTAGAACCTTAA
P-Sv.Ubq1-1:1:3     ------------------------------------------------------------

P-Sv.Ubq1-1:1:2     --------------------------------------GCCGTTTTTGAAGTATCCAGGA
P-Sv.Ubq1-1:1:1     AAAAAGGCTTATACTACCAGTATACTATCAACCAGCATGCCGTTTTTGAAGTATCCAGGA
P-Sv.Ubq1-1:1:3     ------------------------------------------------------------

P-Sv.Ubq1-1:1:2     TTAGAAGCTTCTACTGCGCTTTTATATTATAGCTGTGGACCTGTGGTAACCTTTCTCTTT
P-Sv.Ubq1-1:1:1     TTAGAAGCTTCTACTGCGCTTTTATATTATAGCTGTGGACCTGTGGTAACCTTTCTCTTT
P-Sv.Ubq1-1:1:3     ------------------------------------------------------------

P-Sv.Ubq1-1:1:2     TGGCGCTTGCTTAATCTCGGCCGTGCTGGTCCATGCTTAGGCACTAGGCAGAGATAGAGC
P-Sv.Ubq1-1:1:1     TGGCGCTTGCTTAATCTCGGCCGTGCTGGTCCATGCTTAGGCACTAGGCAGAGATAGAGC
P-Sv.Ubq1-1:1:3     ------------------------------------------------------------

P-Sv.Ubq1-1:1:2     CGGGGGTGAATGGGGCTAAAGCTCAGCTGCTCGAGGGGCCGTGGGCTGGTTTCCACTAGC
P-Sv.Ubq1-1:1:1     CGGGGGTGAATGGGGCTAAAGCTCAGCTGCTCGAGGGGCCGTGGGCTGGTTTCCACTAGC
P-Sv.Ubq1-1:1:3     ------------------------------------------------------------

P-Sv.Ubq1-1:1:2     CTACAGCTGTGCCACGTGCGGCCGCGCAAGCCGAAGCAAGCACGCTGAGCCGTTGGACAG
P-Sv.Ubq1-1:1:1     CTACAGCTGTGCCACGTGCGGCCGCGCAAGCCGAAGCAAGCACGCTGAGCCGTTGGACAG
P-Sv.Ubq1-1:1:3     ------------------------------------------------------------
```

FIG. 3a

```
P-Sv.Ubq1-1:1:2      CTTGTCATAATGCCATTACGTGGATTACAGGTAACTGGCCCTGTAACTACTCGTTCGGCC
P-Sv.Ubq1-1:1:1      CTTGTCATAATGCCATTACGTGGATTACAGGTAACTGGCCCTGTAACTACTCGTTCGGCC
P-Sv.Ubq1-1:1:3      ------------------------------------------------------------

P-Sv.Ubq1-1:1:2      ATCATCAAACGACGACGTCCGCTAGGCGACGACACGGGTAATGCACGCAGCCACCCAGGC
P-Sv.Ubq1-1:1:1      ATCATCAAACGACGACGTCCGCTAGGCGACGACACGGGTAATGCACGCAGCCACCCAGGC
P-Sv.Ubq1-1:1:3      --------------------------------CACGGGTAATGCACGCAGCCACCCAGGC
                                                     ****************************

P-Sv.Ubq1-1:1:2      GCGCGCGCTAGCGGAGCACGGTCAGGTGACACGGGCGTCGTGACGCTTCCGAGTTGAAGG
P-Sv.Ubq1-1:1:1      GCGCGCGCTAGCGGAGCACGGTCAGGTGACACGGGCGTCGTGACGCTTCCGAGTTGAAGG
P-Sv.Ubq1-1:1:3      GCGCGCGCTAGCGGAGCACGGTCAGGTGACACGGGCGTCGTGACGCTTCCGAGTTGAAGG
                     ************************************************************

P-Sv.Ubq1-1:1:2      GGTTAACGCCAGAAACAGTGTTTGGCCAGGGTATGAACATAACAAAAAATATTCACACGA
P-Sv.Ubq1-1:1:1      GGTTAACGCCAGAAACAGTGTTTGGCCAGGGTATGAACATAACAAAAAATATTCACACGA
P-Sv.Ubq1-1:1:3      GGTTAACGCCAGAAACAGTGTTTGGCCAGGGTATGAACATAACAAAAAATATTCACACGA
                     ************************************************************

P-Sv.Ubq1-1:1:2      AAGAATGGAAGTATGGAGCTGCTACTGTGTAAATGCCAAGCAGGAAACTCACGCCCGCTA
P-Sv.Ubq1-1:1:1      AAGAATGGAAGTATGGAGCTGCTACTGTGTAAATGCCAAGCAGGAAACTCACGCCCGCTA
P-Sv.Ubq1-1:1:3      AAGAATGGAAGTATGGAGCTGCTACTGTGTAAATGCCAAGCAGGAAACTCACGCCCGCTA
                     ************************************************************

P-Sv.Ubq1-1:1:2      ACATCCAACGGCCAACAGCTCGACGTGCCGGTCAGCAGAGACATCGGAACACTGGTGATT
P-Sv.Ubq1-1:1:1      ACATCCAACGGCCAACAGCTCGACGTGCCGGTCAGCAGAGACATCGGAACACTGGTGATT
P-Sv.Ubq1-1:1:3      ACATCCAACGGCCAACAGCTCGACGTGCCGGTCAGCAGAGACATCGGAACACTGGTGATT
                     ************************************************************

P-Sv.Ubq1-1:1:2      GGTGGAGCCGGCAGTATGCGCCCCAGCACGGCCGAGGTGGTGGTGGCCCGTGGCCCTGCT
P-Sv.Ubq1-1:1:1      GGTGGAGCCGGCAGTATGCGCCCCAGCACGGCCGAGGTGGTGGTGGCCCGTGGCCCTGCT
P-Sv.Ubq1-1:1:3      GGTGGAGCCGGCAGTATGCGCCCCAGCACGGCCGAGGTGGTGGTGGCCCGTGGCCCTGCT
                     ************************************************************

P-Sv.Ubq1-1:1:2      GTCTGCGCGGCTCGGGACAACTTGAAACTGGGCCACCGCCTCGTCGCAACTCGCAACCCG
P-Sv.Ubq1-1:1:1      GTCTGCGCGGCTCGGGACAACTTGAAACTGGGCCACCGCCTCGTCGCAACTCGCAACCCG
P-Sv.Ubq1-1:1:3      GTCTGCGCGGCTCGGGACAACTTGAAACTGGGCCACCGCCTCGTCGCAACTCGCAACCCG
                     ************************************************************

P-Sv.Ubq1-1:1:2      TTGGCGGAAGAAAGGAATGGCTCGTAGGGGCCCGGGTAGAATCCAAGAATGTTGCGCTGG
P-Sv.Ubq1-1:1:1      TTGGCGGAAGAAAGGAATGGCTCGTAGGGGCCCGGGTAGAATCCAAGAATGTTGCGCTGG
P-Sv.Ubq1-1:1:3      TTGGCGGAAGAAAGGAATGGCTCGTAGGGGCCCGGGTAGAATCCAAGAATGTTGCGCTGG
                     ************************************************************

P-Sv.Ubq1-1:1:2      GCTTCGATTCACATAACATGGGCCTGAAGCTCTAAAACGACGGCCCGGTCACCGGGCGAT
P-Sv.Ubq1-1:1:1      GCTTCGATTCACATAACATGGGCCTGAAGCTCTAAAACGACGGCCCGGTCACCGGGCGAT
P-Sv.Ubq1-1:1:3      GCTTCGATTCACATAACATGGGCCTGAAGCTCTAAAACGACGGCCCGGTCACCGGGCGAT
                     ************************************************************
```

FIG. 3b

```
P-Sv.Ubq1-1:1:2      GGAAAGAGACCGGATCCTCCTCGTGAATTCTGGAAGGCCACACGAGAGCGACCCACCACC
P-Sv.Ubq1-1:1:1      GGAAAGAGACCGGATCCTCCTCGTGAATTCTGGAAGGCCACACGAGAGCGACCCACCACC
P-Sv.Ubq1-1:1:3      GGAAAGAGACCGGATCCTCCTTGTGAATTCTGGAAGGCCACACGAGAGCGACCCACCACC
                     ********************* **************************************

P-Sv.Ubq1-1:1:2      GACGCGGAGGAGTCGTGCGTGGTCCAACACGGCCGGCGGGCTGGGCTGCGACCTTAACCA
P-Sv.Ubq1-1:1:1      GACGCGGAGGAGTCGTGCGTGGTCCAACACGGCCGGCGGGCTGGGCTGCGACCTTAACCA
P-Sv.Ubq1-1:1:3      GACGCGGAGGAGTCGTGCGTGGTCCAACACGGCCGGCGGGCTGGGCTGCGACCTTAACCA
                     ************************************************************

P-Sv.Ubq1-1:1:2      GCAAGGCACGCCACGACCCGCCTCGCCCTCGAGGCATAAATACCCTCCCATCC
P-Sv.Ubq1-1:1:1      GCAAGGCACGCCACGACCCGCCTCGCCCTCGAGGCATAAATACCCTCCCATCC
P-Sv.Ubq1-1:1:3      GCAAGGCACGCCACGACCCGCCTCGCCCTCGAGGCATAAATACCCTCCCATCC
                     *****************************************************
```

FIG. 3c

```
EXP-Zm.UbqM1:1:2      GTCGTGCCCCTCTCTAGAGATAAAGAGCATTGCATGTCTAAAGTATAAAAAATTACCACA
EXP-Zm.UbqM1:1:5      GTCGTGCCCCTCTCTAGAGATAAAGAGCATTGCATGTCTAAAGTATAAAAAATTACCACA
EXP-Zm.UbqM1:1:1      GTCGTGCCCCTCTCTAGAGATAATGAGCATTGCATGTCTAAGTTATAAAAAATTACCACA
EXP-Zm.UbqM1:1:4      GTCGTGCCCCTCTCTAGAGATAAAGAGCATTGCATGTCTAAGTTATAAAAAATTACCACA
                      *********************** *****************  *****************

EXP-Zm.UbqM1:1:2      TA--TTTTTTTGTCACACT--TATTTGAAGTGTAGTTTATCTATCTCTATACATATATTT
EXP-Zm.UbqM1:1:5      TA--TTTTTTTGTCACACT--TATTTGAAGTGTAGTTTATCTATCTCTATACATATATTT
EXP-Zm.UbqM1:1:1      TATTTTTTTTTGTCACACTTGTGTTTGAAGTGCAGTTTATCTATCTCTATACATATATTT
EXP-Zm.UbqM1:1:4      TA-TTTTTTTTGTCACACT--TGTTTGAAGTGCAGTTTATCTATCTTTATACATATATTT
                      **  ***************  * ********* ************* *************

EXP-Zm.UbqM1:1:2      AAACTTCACTCTACAAATAATATAGTCTATAATACTAAAATAATATTAGTGTTTTAGAGG
EXP-Zm.UbqM1:1:5      AAACTTCACTCTACAAATAATATAGTCTATAATACTAAAATAATATTAGTGTTTTAGAGG
EXP-Zm.UbqM1:1:1      AAACTTCACTATATGAATAATATAGTCTATAGTATTAAAATAATATCAATGTTTTAGATG
EXP-Zm.UbqM1:1:4      AAACTTTACTCTACGAATAATATAATCTATAGTACTACAATAATATCAGTGTTTTAGAGA
                      ****** *** **  ********* ****** ** ** ******** * *********

EXP-Zm.UbqM1:1:2      ATCATATAAATAAACTGCTAGACATGGTCTAAAGGATAATTGAATATTTTGACAA-----
EXP-Zm.UbqM1:1:5      ATCATATAAATAAACTGCTAGACATGGTCTAAAGGATAATTGAATATTTTGACAA-----
EXP-Zm.UbqM1:1:1      ATTATATAACTGAACTGCTAGACATGGTCTAAAGGACAACCGAGTATTTTGACAACATGA
EXP-Zm.UbqM1:1:4      ATCATATAAATGAACAGTTAGACATGGTCTAAAGGACAATTGAGTATTTTGACAACAGGA
                      ** ****** * *** * ****************** **  ** ***********

EXP-Zm.UbqM1:1:2      -TCTACAGTTTTATCTTTTTAGTGTGCATGTGATCTCTCTGTTTTTTTTGCAAATAGCTT
EXP-Zm.UbqM1:1:5      -TCTACAGTTTTATCTTTTTAGTGTGCATGTGATCTCTCTGTTTTTTTTGCAAATAGCTT
EXP-Zm.UbqM1:1:1      CTCTACAGTTTTATCTTTTTAGTGTGCATGTGTTCTTT---TTACTTTTGCAAATAGCTT
EXP-Zm.UbqM1:1:4      CTCTACAGTTTTATCTTTTTAGTGTGCATGTGTTCTCCTT-TTTTTTTTGCAAATAGCTT
                       ******************************* ***     **  ***************

EXP-Zm.UbqM1:1:2      GACCTATATAATACTTCATCCATTTTATTAGTACATCCATTTAGGATTTAGGGTTGATGG
EXP-Zm.UbqM1:1:5      GACCTATATAATACTTCATCCATTTTATTAGTACATCCATTTAGGATTTAGGGTTGATGG
EXP-Zm.UbqM1:1:1      CACCTATATAATACTTCATCCATTTTATTAGTACATCCATTT------------------
EXP-Zm.UbqM1:1:4      CACCTATATAATACTTCATCCATTTTATTAGTACATCCATTTAGGGTTTAGGGTTAATGG
                       *****************************************

EXP-Zm.UbqM1:1:2      TTTCTATAGACTAA--TTTTTAGTACATCCATTTTATTCT-TTTTAGTCTCTAAATTTTT
EXP-Zm.UbqM1:1:5      TTTCTATAGACTAA--TTTTTAGTACATCCATTTTATTCT-TTTTAGTCTCTAAATTTTT
EXP-Zm.UbqM1:1:1      ---------ACTAAA-TTTTTAGTACATCTATTTTATTCTATTTTAGCCTCTAAA-TTAA
EXP-Zm.UbqM1:1:4      TTTTTATAGACTAATTTTTTTAGTACATCTATTTTATTCTATTTTAGCCTCTAAA-TTAA
                               *****  ************* ********** ****** ******* **

EXP-Zm.UbqM1:1:2      TAAAACTAAAACTCTATTTTAG-TTTTTTATTTAATAATTTAGATATAAAATGAAATAAA
EXP-Zm.UbqM1:1:5      TAAAACTAAAACTCTATTTTAG-TTTTTTATTTAATAATTTAGATATAAAATGAAATAAA
EXP-Zm.UbqM1:1:1      GAAAACTTAAACTCTATTTTAG-TTTTTTATTTAATAATTTAGATATAAAATAGAATAAA
EXP-Zm.UbqM1:1:4      GAAAACTAAAACTCTATTTTAGTTTTTTTATTTAATAATTTAGATATAAAATAGAATAAA
                       ****** ************** *****************************  ******
```

FIG. 4a

```
EXP-Zm.UbqM1:1:2    ATAAATTGACTACAAATAAAACAAATACCCTTTAAGAAA-TAAAAAAACTAAGCAAACAT
EXP-Zm.UbqM1:1:5    ATAAATTGACTACAAATAAAACAAATACCCTTTAAGAAA-TAAAAAAACTAAGCAAACAT
EXP-Zm.UbqM1:1:1    ATAAAGTGACTAAAAAATAACTAAATACCTTTTAAGAAA-TAAAAAAACTAAGGAACCAT
EXP-Zm.UbqM1:1:4    ATAAAGTGACTAAAAATTAAACAAATACCCTTTAAGAAATTAAAAAAACTAAGGAAACAT
                    ***** ****** ***  **  ******* ********* ************* ** ***

EXP-Zm.UbqM1:1:2    TTTTCTTGTTTCGAGTAGATAATGACAGGCTGTTCAACGCCGTCGACGAGTCTAACGGAC
EXP-Zm.UbqM1:1:5    TTTTCTTGTTTCGAGTAGATAATGACAGGCTGTTCAACGCCGTCGACGAGTCTAACGGAC
EXP-Zm.UbqM1:1:1    TTTTCTTGTTCCGAGTAGATAATGACAGCCTGTTCAACGCCGTCGACGAGTCTAACGGAC
EXP-Zm.UbqM1:1:4    TTTTCTTGTTTCGAGTAGATAATGCCAGCCTGTTAAACGCCGTCGACGAGTCTAACGGAC
                    ********** ************* *** ***** *************************

EXP-Zm.UbqM1:1:2    ACCAACCAGCGAACCAGCAGCGTCGCGTCGGGCCAAGCGAAGCAGACGGCACGGCATCTC
EXP-Zm.UbqM1:1:5    ACCAACCAGCGAACCAGCAGCGTCGCGTCGGGCCAAGCGAAGCAGACGGCACGGCATCTC
EXP-Zm.UbqM1:1:1    ACCAACCAGCGAACCAGCAGCGTCGCGTCGGGCCAAGCGAAGCAGACGGCACGGCATCTC
EXP-Zm.UbqM1:1:4    ACCAACCAGCGAACCAGCAGCGTCGCGTCGGGCCAAGCGAAGCAGACGGCACGGCATCTC
                    ************************************************************

EXP-Zm.UbqM1:1:2    TGTAGCTGCCTCTGGACCCCTCTCGAGAGTTCCGCTCCACCGTTGGACTTGCTCCGCTGT
EXP-Zm.UbqM1:1:5    TGTAGCTGCCTCTGGACCCCTCTCGAGAGTTCCGCTCCACCGTTGGACTTGCTCCGCTGT
EXP-Zm.UbqM1:1:1    TGTAGCTGCCTCTGGACCCCTCTCGAGAGTTCCGCTCCACCGTTGGACTTGCTCCGCTGT
EXP-Zm.UbqM1:1:4    TGTCGCTGCCTCTGGACCCCTCTCGAGAGTTCCGCTCCACCGTTGGACTTGCTCCGCTGT
                    *** ********************************************************

EXP-Zm.UbqM1:1:2    CGGCATCCAGAAATTGCGTGGCGGAGCGGCAGACGTGAGGCGGCACGGCAGGCGGCCTCT
EXP-Zm.UbqM1:1:5    CGGCATCCAGAAATTGCGTGGCGGAGCGGCAGACGTGAGGCGGCACGGCAGGCGGCCTCT
EXP-Zm.UbqM1:1:1    CGGCATCCAGAAATTGCGTGGCGGAGCGGCAGACGTGAGCCGGCACGGCAGGCGG-----
EXP-Zm.UbqM1:1:4    CGGCATCCAGAAATTGCGTGGCGGAGCGGCAGACGTGAGCCGGCACGGCAGGCGGCCTCC
                    *************************************** ***************

EXP-Zm.UbqM1:1:2    TCCTCCTCTCACGGCACCGGCAGCTACGGGGGATTCCTTTCCCACCGCTCCTTCGCTTTC
EXP-Zm.UbqM1:1:5    TCCTCCTCTCACGGCACCGGCAGCTACGGGGGATTCCTTTCCCACCGCTCCTTCGCTTTC
EXP-Zm.UbqM1:1:1    -CCTCCTCTCACGGCACCGGCAGCTACGGGGGATTCCTTTCCCACCGCTCCTTCGCTTTC
EXP-Zm.UbqM1:1:4    TCCTCCTCTCACGGCACCGGCAGCTACGGGGGATTCCTTTCCCACCGCTCCTTCGCTTTC
                     ***********************************************************
EXP-Zm.UbqM1:1:2    CCTTCCTCGCCCGCCGTAATAAATAGACACCCCCTCCACACCCTCTTTCCCCAACCTCGT
EXP-Zm.UbqM1:1:5    CCTTCCTCGCCCGCCGTAATAAATAGACACCCCCTCCACACCCTCTTTCCCCAACCTCGT
EXP-Zm.UbqM1:1:1    CCTTCCTCGCCCGCCGTAATAAATAG--ACCCCCTCCACACCCTCTTTCCCCAACCTCGT
EXP-Zm.UbqM1:1:4    CCTTCCTCGCCCGCCGTAATAAATAGACACCCCCTCCACACCTTCTTTCCCCAACCTCGT
                    **************************  ************** *****************

EXP-Zm.UbqM1:1:2    GTTCGTTCGGAGCGCACACACACGCAACCAGATCTCCCCCAAATCCAGCCGTCGGCACCT
EXP-Zm.UbqM1:1:5    GTTCGTTCGGAGCGCACACACACGCAACCAGATCTCCCCCAAATCCAGCCGTCGGCACCT
EXP-Zm.UbqM1:1:1    GTTCGTTCGGAGCGCGCACACACACAACCAGATCTCCCCCAAATCCACCCGTCGGCACCT
EXP-Zm.UbqM1:1:4    GTT-GTTCGGAGCGCACACACACACAACCAGATCTCCCCCAAATCCACCCGTCGGCACCT
                    *** *********** ******* *********************** ************
```

FIG. 4b

```
EXP-Zm.UbqM1:1:2     CCGCTTCAAGGTACGCCGCTCATCCTCCCCCCCCCCCTCTCTCTACCTTCTCTAGATCGG
EXP-Zm.UbqM1:1:5     CCGCTTCAAGGTACGCCGCTCATCCTCCCCCCCCCCCTCTCTCTACCTTCTCTAGATCGG
EXP-Zm.UbqM1:1:1     CCGCTTCAAGGTACGCCGCTCATCCTCCTCCCCCCCCTCTCTCTACCTTCTCTAGATCGG
EXP-Zm.UbqM1:1:4     CCGCTTCAAGGTACGCCGCTCATCCTCCCCCCCCC---CTCTCTACCTTCTCTAGATCGG
                     **************************** ******   **********************

EXP-Zm.UbqM1:1:2     CGATCCGGTCCATGGTTAGGGCCCGGTAGTTCTACTTCTGTTCATGTTTGTGTTAGAGCA
EXP-Zm.UbqM1:1:5     CGATCCGGTCCATGGTTAGGGCCCGGTAGTTCTACTTCTGTTCATGTTTGTGTTAGAGCA
EXP-Zm.UbqM1:1:1     CGTTTCGGTCCATGGTTAGGGCCCGGTAGTTCTACTTCTGTTCATGTTTGTGTTAGATC-
EXP-Zm.UbqM1:1:4     CGTTCCGGTCCATGGTTAGGGCCCGGTAGTTCTACTTCTGTTCATGTTTGTGTTAGATC-
                     ** * **************************************************** *

EXP-Zm.UbqM1:1:2     AACATGTTCATGTT------------------------CATGTTTGTGAT----------
EXP-Zm.UbqM1:1:5     AACATGTTCATGTT------------------------CATGTTTGTGAT----------
EXP-Zm.UbqM1:1:1     --CGTGTTTGTGTTAGATCCGTGCTGCTAGATTTCGTACACGGATGCGACCTGTACATCA
EXP-Zm.UbqM1:1:4     --CGTGTTTGTGTTAGATCCGTGCTGCTAGCGTTCGTACACGGATGCGACCTGTACGTCA
                       * ****  ****                        ** *  ** **

EXP-Zm.UbqM1:1:2     GATGTGGTCTGGTTG-------GGCGGTCGTTCTAGATCGGAG----TAGGATACTGTTT
EXP-Zm.UbqM1:1:5     GATGTGGTCTGGTTG-------GGCGGTCGTTCTAGATCGGAG----TAGGATACTGTTT
EXP-Zm.UbqM1:1:1     GACATGTTCTGATTGCTAACTTGCCAGTGTTTCTCTTTGGGGAATCCTGGGA---TGGCT
EXP-Zm.UbqM1:1:4     GACACGTTCTGATTGCTAACTTGCCAGTGTTTCTCTTTGGGGAATCCTGGGA---TGGCT
                     **   * **** ***       * * **  ****   * **      * ***   **  *

EXP-Zm.UbqM1:1:2     CAAGCT---------ACCTGGTGGATTT-----ATTAATTTTGTATCTGTATGT------
EXP-Zm.UbqM1:1:5     CAAGCT---------ACCTGGTGGATTT-----ATTAATTTTGTATCTGTATGT------
EXP-Zm.UbqM1:1:1     CTAGCCGTTCCGCAGACGGGATCGATTTCATGAATTTTTTTTGTTTCGTTGCATAGGGTT
EXP-Zm.UbqM1:1:4     CTAGCCGTTCCGCAGACGGGATCGATTTCATG-ATTTTTTTTGTTTCGTTGCATAGGGTT
                     * ***          **  * * *****     ***  ****** **  *   *

EXP-Zm.UbqM1:1:2     --GTGTGCCATACATCTTCATAGTTACGAGTTTAAGATGATGGATGGAAATATCGATCTA
EXP-Zm.UbqM1:1:5     --GTGTGCCATACATCTTCATAGTTACGAGTTTAAGATGATGGATGGAAATATCGATCTA
EXP-Zm.UbqM1:1:1     TGGTTTGCCCTTTTCCTTTAT---------TTCAATAT-----------ATGCC------
EXP-Zm.UbqM1:1:4     TGGTTTGCCCTTTTCCTTTAT---------TTCAATAT-----------ATGCC------
                       ** **** *    *** **         ** ** **           **  *

EXP-Zm.UbqM1:1:2     GGATAGGTATACATGTTGATGCGGGT--TTTACTGATGCATATACAGAGATGCTTTTTTT
EXP-Zm.UbqM1:1:5     GGATAGGTATACATGTTGATGCGGGT--TTTACTGATGCATATACAGAGATGCTTTTTTT
EXP-Zm.UbqM1:1:1     ------GTGCACTTGTTTGT-CGGGTCATCTTTTCATG----------------TTTTTT
EXP-Zm.UbqM1:1:4     ------GTGCACTTGTTTGT-CGGGTCATCTTTTCATGC---------------TTTTTT
                           **  ** ****  * *****  * *  * ***                ******

EXP-Zm.UbqM1:1:2     CTCGCTTGGTTGTGATGATATGGTCTGGTTGGGCGGTCGTTCTAGATCGGAGTAGAATAC
EXP-Zm.UbqM1:1:5     CTCGCTTGGTTGTGATGATATGGTCTGGTTGGGCGGTCGTTCTAGATCGGAGTAGAATAC
EXP-Zm.UbqM1:1:1     TTGGCTTGGTTGTGATGATGTGGTCTGGTTGGGCGGTCGTTCTAGATCGGAGTAGAATAC
EXP-Zm.UbqM1:1:4     TTGTCTTGGTTGTGATGATGTGGTCTGGTTGGGCGGTCGTTCTAGATCGGAGAAGAATTC
                      *  *************** ******************************** ***** *
```

FIG. 4c

```
EXP-Zm.UbqM1:1:2     TGTTTCAAACTACCTGGTGGATTTATTAAAGGATAAAGGGTCGTTCTAGATCGGAGTAGA
EXP-Zm.UbqM1:1:5     TGTTTCAAACTACCTGGTGGATTTATTAAAGGATAAAGGGTCGTTCTAGATCGGAGTAGA
EXP-Zm.UbqM1:1:1     TGTTTCAAACTACCTGGTGGATTTATTAA-------------------------------
EXP-Zm.UbqM1:1:4     TGTTTCAAACTACCTGGTGGATTTATTAA-------------------------------
                     *****************************

EXP-Zm.UbqM1:1:2     ATACTGTTTCAAACTACCTGGTGGATTTATTAAAGGATCTGTATGTATGTGCC-TACATC
EXP-Zm.UbqM1:1:5     ATACTGTTTCAAACTACCTGGTGGATTTATTAAAGGATCTGTATGTATGTGCC-TACATC
EXP-Zm.UbqM1:1:1     ---------------------------------AGGATCTGTATGTATGTGCCATACATC
EXP-Zm.UbqM1:1:4     ------------------------------TTTTGGATCTGTATGTGTGTGCCATACATA
                                                       ************ ****** *****

EXP-Zm.UbqM1:1:2     TTCATAGTTACGAGTTTAAGATGATGGATGGAAATATCGATCTAGGATAGGTATACATGT
EXP-Zm.UbqM1:1:5     TTCATAGTTACGAGTTTAAGATGATGGATGGAAATATCGATCTAGGATAGGTATACATGT
EXP-Zm.UbqM1:1:1     TTCATAGTTACGAGTTTAAGATGATGGATGGAAATATCGATCTAGGATAGGTATACATGT
EXP-Zm.UbqM1:1:4     TTCATAGTTACGAATTGAAGATGATGGATGGAAATATCGATCTAGGATAGGTATACATGT
                     ************* ** *******************************************

EXP-Zm.UbqM1:1:2     TGATGCGGGTTTTACTGATGCATATACAGAGATGCTTTTT-TTCGCTTGGTTGTGATGAT
EXP-Zm.UbqM1:1:5     TGATGCGGGTTTTACTGATGCATATACAGAGATGCTTTTT-TTCGCTTGGTTGTGATGAT
EXP-Zm.UbqM1:1:1     TGATGCGGGTTTTACTGATGCATATACAGAGATGCTTTTTTTTCGCTTGGTTGTGATGAT
EXP-Zm.UbqM1:1:4     TGATGCGGGTTTTACTGATGCATATACAGAGATGCTTTTTGTTCGCTTGGTTGTGATGAT
                     **************************************** *******************

EXP-Zm.UbqM1:1:2     GTGGTCTGGTTGGGCGG--------TCGTTCTAGATCGGAGTAGAATACTGTTTCAAACT
EXP-Zm.UbqM1:1:5     GTGGTCTGGTTGGGCGG--------TCGTTCTAGATCGGAGTAGAATACTGTTTCAAACT
EXP-Zm.UbqM1:1:1     GTGGTCTGGTCGGGCGG--------TCGTTCTAGATCGGAGTAGAATACTGTTTCAAACT
EXP-Zm.UbqM1:1:4     GTGGTCTGGTTGGGCGGTCGTTCATTCGTTCTAGATCGGAGTAGAATACTGTTTCAAACT
                     ********** ******        ***********************************

EXP-Zm.UbqM1:1:2     ACCTGGTGGATTTATTAATTTTGTATCTTTATGTGTGTGCCATACATCTTCATAGTTACG
EXP-Zm.UbqM1:1:5     ACCTGGTGGATTTATTAATTTTGTATCTTTATGTGTGTGCCATACATCTTCATAGTTACG
EXP-Zm.UbqM1:1:1     ACCTGGTGGATTTATTAATTTTGGATCTGTATGTGTGT--CATACATCTTCATAGTTACG
EXP-Zm.UbqM1:1:4     ACCTGGTGTATTTATTAATTTTGGAACTGTATGTGTGTGTCATACATCTTCATAGTTACG
                     ******** ************** * ** *********  ********************

EXP-Zm.UbqM1:1:2     AGTTTAAGATGATGGATGGAAATATTGATCTAGGATAGGTATACATGTTGATGTGGGTTT
EXP-Zm.UbqM1:1:5     AGTTTAAGATGATGGATGGAAATATTGATCTAGGATAGGTATACATGTTGATGTGGGTTT
EXP-Zm.UbqM1:1:1     AGTTTAA---GATCGATGGAAATATCGATCTAGGATAGGTATACATGTTGATGTGGGTTT
EXP-Zm.UbqM1:1:4     AGTTTAA---GATGGATGGAAATATCGATCTAGGATAGGTATACATGTTGATGTGGGTTT
                     *******   *** *********** **********************************

EXP-Zm.UbqM1:1:2     TACTGATGCATATACATGATGGCATATGCGGCATCTATTCATATGCTCTAACCTTGAGTA
EXP-Zm.UbqM1:1:5     TACTGATGCATATACATGATGGCATATGCGGCATCTATTCATATGCTCTAACCTTGAGTA
EXP-Zm.UbqM1:1:1     TACTGATGCATATAC---ATGGCATATGCAGCATCTATTCATATGCTCTAACCTTGAGTA
EXP-Zm.UbqM1:1:4     TACTGATGCATATACATGATGGCATATGCAGCATCTATTCATATGCTCTAACCTTGAGTA
                     ***************   *********** ******************************
```

FIG. 4d

```
EXP-Zm.UbqM1:1:2      CCTATCTATTATAATAAACAAGTATGTTTTATAATTATTTTGATCTTGATATACTTGGAT
EXP-Zm.UbqM1:1:5      CCTATCTATTATAATAAACAAGTATGTTTTATAATTATTTTGATCTTGATATACTTGGAT
EXP-Zm.UbqM1:1:1      CCTATCTATTATAATAAACAAGTATGTTTTATAATTATTTTGATCTTGATATACTTGGAT
EXP-Zm.UbqM1:1:4      CCTATCTATTATAATAAACAAGTATGTTTTATAATTATTTTGATCTTGATATACTTGGAT
                      ************************************************************

EXP-Zm.UbqM1:1:2      GATGGCATATGCAGCAGCTATATGTGGA-TTTTTAGCCCTGCCTTCATACGCTATTTAT
EXP-Zm.UbqM1:1:5      GATGGCATATGCAGCAGCTATATGTGGA-TTTTTAGCCCTGCCTTCATACGCTATTTAT
EXP-Zm.UbqM1:1:1      GATGGCATATGCAGCAGCTATATGTGGATTTTTTAGCCCTGCCTTCATACGCTATTTAT
EXP-Zm.UbqM1:1:4      GATGGCATATGCAGCAGCTATATGTGGATTTTTTAGCCCTGCCTTCATACGCTATTTAT
                      **************************** *******************************

EXP-Zm.UbqM1:1:2      TTGCTTGGTACTGTTTCTTTTGTCCGATGCTCACCCTGTTGTTGGGTGATACTTCTGCAG
EXP-Zm.UbqM1:1:5      TTGCTTGGTACTGTTTCTTTTGTCCGATGCTCACCCTGTTGTTTGGTGATACTTCTGCAG
EXP-Zm.UbqM1:1:1      TTGCTTGGTACTGTTTCTTTTGT-CGATGCTCACCCTGTTGTTTGGTGATACTTCTGCAG
EXP-Zm.UbqM1:1:4      TTGCTTGGTACTGTTTCTTTTGT-CGATGCTCACCCTGTTGTTTGGTGATACTTCTGCAG
                      *********************** ******************* ****************
```

FIG. 4e

```
P-Sb.Ubq6-1:1:2      ------------------------------------------------------------
P-Sb.Ubq6-1:1:1      CATTAAAAGTCATTATGTGCATGCGTCGTAACTAACATGGATATGTTGCTGCACTATCTC

P-Sb.Ubq6-1:1:2      ----CACTAGCTGCGCATGATAAAGCCACAAGCCAAAATTAATTATTATGGGTGAGAATA
P-Sb.Ubq6-1:1:1      CTCGCACTAGCTGCGCATGATAAAGCCACAAGCCAAAATTAATTATTATGGGTGAGAATA
                         ********************************************************

P-Sb.Ubq6-1:1:2      AATACGTACCAGCACCGGCCATAGAAAAAGTACATTATTAAAGGTCTAATTTGGAAACAG
P-Sb.Ubq6-1:1:1      AATACGTACCAGCACCGGCCATAGAAAAAGTACATTATTAAAGGTCTAATTTGGAAACAG
                     ************************************************************

P-Sb.Ubq6-1:1:2      TCTGAAAACGACGTGCGCTGCAGAGGTAAATGTAATTTTCGGCACTAAAACCATTATCAA
P-Sb.Ubq6-1:1:1      TCTGAAAACGACGTGCGCTGCAGAGGTAAATGTAATTTTCGGCACTAAAACCATTATCAA
                     ************************************************************

P-Sb.Ubq6-1:1:2      CTAATTCATTCAATAACAGTTATTTAGAAAATGTATAGCTCGCTCTAAAAAAACAGTTTA
P-Sb.Ubq6-1:1:1      CTAATTCATTCAATAACAGTTATTTAGAAAATGTATAGCTCGCTCTAAAAAAACAGTTTA
                     ************************************************************

P-Sb.Ubq6-1:1:2      GAAAAACAGTCAAAATAATTCGACCAACAAACAGTTAATAAGGTTCATTAAATATATAAT
P-Sb.Ubq6-1:1:1      GAAAAACAGTCAAAATAATTCGACCAACAAACAGTTAATAAGGTTCATTAAATATATAAT
                     ************************************************************

P-Sb.Ubq6-1:1:2      GCACGGTGCTATTTGATCTTTTAAAGGAAAAAGAGGAATAGTCGTGGGCGCCAGGCGGGA
P-Sb.Ubq6-1:1:1      GCACGGTGCTATTTGATCTTTTAAAGGAAAAAGAGGAATAGTCGTGGGCGCCAGGCGGGA
                     ************************************************************

P-Sb.Ubq6-1:1:2      ATTGGGGCGCGGGAGTCTGCCGGACGACGCGTTCCGTCCGAACGGCCGGACCCGACGAGG
P-Sb.Ubq6-1:1:1      ATTGGGGCGCGGGAGTCTGCCGGACGACGCGTTCCGTCCGAACGGCCGGACCCGACGAGG
                     ************************************************************

P-Sb.Ubq6-1:1:2      CCCCCCCGCCGCCCCACGTCGCAGAACCGTCCGTGGGTGGTAATCTGGCCGGGTACACCA
P-Sb.Ubq6-1:1:1      CCCCCCCGCCGCCCCACGTCGCAGAACCGTCCGTGGGTGGTAATCTGGCCGGGTACACCA
                     ************************************************************

P-Sb.Ubq6-1:1:2      GCCGTCCCCTTGGGCGGCCTCACAGCACTGGGCTCACACGTGAGTTTTGTTCTGGGCTTC
P-Sb.Ubq6-1:1:1      GCCGTCCCCTTGGGCGGCCTCACAGCACTGGGCTCACACGTGAGTTTTGTTCTGGGCTTC
                     ************************************************************

P-Sb.Ubq6-1:1:2      GGATCGCACCATATGGGCCTCGGCATCAGAAAGACGGGGCCCGTCTGGGATAGAAGAGAC
P-Sb.Ubq6-1:1:1      GGATCGCACCATATGGGCCTCGGCATCAGAAAGACGGGGCCCGTCTGGGATAGAAGAGAC
                     ************************************************************
```

FIG. 5a

```
P-Sb.Ubq6-1:1:2      AGGAACCTCCTCGTGGATTCCAGAAGCCAGCCACGAGCGACCACCGACGCGGAGGATACT
P-Sb.Ubq6-1:1:1      AGGAACCTCCTCGTGGATTCCAGAAGCCAGCCACGAGCGACCACCGACGCGGAGGATACT
                     ************************************************************

P-Sb.Ubq6-1:1:2      CGTCGTCCAAGTCCAACACGGCGGGCGGGCGGGCGGACGCGTGGGCTGGGCTAACTGCCT
P-Sb.Ubq6-1:1:1      CGTCGTCCAAGTCCAACACGGCGGGCGGGCGGGCGGACGCGTGGGCTGGGCTAACTGCCT
                     ************************************************************

P-Sb.Ubq6-1:1:2      AACCTTAACCTCCAAGGCACGCCAAGGCCCGCTTCTCCCACCCGACATAAATATCCCCCC
P-Sb.Ubq6-1:1:1      AACCTTAACCTCCAAGGCACGCCAAGGCCCGCTTCTCCCACCCGACATAAATATCCCCCC
                     ************************************************************

P-Sb.Ubq6-1:1:2      ATCCAGGCAAGGCGC
P-Sb.Ubq6-1:1:1      ATCCAGGCAAGGCGC
                     ***************
```

FIG. 5b

```
P-SETit.Ubq1-1:1:4      ACTGCCGCGACACGCCTCACTGGCGGGAGGGCTCCGAGCGCTCTCTCCCCGGCGGCCGGC
P-SETit.Ubq1-1:1:3      ------------------------------------------------------------
P-SETit.Ubq1-1:1:1      ACTGCCGCGACACGCCTCACTGGCGGGAGGGCTCCGAGCGCTCTCTCCCCGGCGGCCGGC
P-SETit.Ubq1-1:1:2      ------------------------------------------------------------

P-SETit.Ubq1-1:1:4      GGAGCAGCGATCTGGATTGGAGAGAATAGAGGAAAGAGAGGGAAAAGGAGAGAGATAGCG
P-SETit.Ubq1-1:1:3      ------------------------------------------------------------
P-SETit.Ubq1-1:1:1      GGAGCAGCGATCTGGATTGGAGAGAATAGAGGAAAGAGAGGGAAAAGGAGAGAGATAGCG
P-SETit.Ubq1-1:1:2      ------------------------------------------------------------

P-SETit.Ubq1-1:1:4      CAAAGAGCTGAAAAGATAAGGTTGTGCGGGCTGTGGTGATTAGAGGACCACTAATCCCTC
P-SETit.Ubq1-1:1:3      ------------------------------------------------------------
P-SETit.Ubq1-1:1:1      CAAAGAGCTGAAAAGATAAGGTTGTGCGGGCTGTGGTGATTAGAGGACCACTAATCCCTC
P-SETit.Ubq1-1:1:2      ------------------------------------------------------------

P-SETit.Ubq1-1:1:4      CATCTCCTAATGACGCGGTGCCCAAGACCAGTGCCGCGGCACACCAGCGTCTAAGTGAAC
P-SETit.Ubq1-1:1:3      ------------------------------------------------------------
P-SETit.Ubq1-1:1:1      CATCTCCTAATGACGCGGTGCCCAAGACCAGTGCCGCGGCACACCAGCGTCTAAGTGAAC
P-SETit.Ubq1-1:1:2      ------------------------------------------------------------

P-SETit.Ubq1-1:1:4      TTCCGCTAACCTTCCGGTCATTGCGCCTGAAAGATGTCATGTGGCGAGGCCCCCCTCTCA
P-SETit.Ubq1-1:1:3      ------------------------------------------------------------
P-SETit.Ubq1-1:1:1      TTCCGCTAACCTTCCGGTCATTGCGCCTGAAAGATGTCATGTGGCGAGGCCCCCCTCTCA
P-SETit.Ubq1-1:1:2      ------------------------------------------------------------

P-SETit.Ubq1-1:1:4      GTAGATTGCCAACTGCCTACCGTGCCACTCTTCCATGCATGATTGCTCCCGTCTATCCCG
P-SETit.Ubq1-1:1:3      ------------------------------------------------------------
P-SETit.Ubq1-1:1:1      GTAGATTGCCAACTGCCTACCGTGCCACTCTTCCATGCATGATTGCTCCCGTCTATCCCG
P-SETit.Ubq1-1:1:2      ------------------------------------------------------------

P-SETit.Ubq1-1:1:4      TTTCTCACAACAGATAGACAACAGTAAGCATCACTAAAGCAAGCATGTGTAGAACCTTAA
P-SETit.Ubq1-1:1:3      ------------------------------------------------------------
P-SETit.Ubq1-1:1:1      TTTCTCACAACAGATAGACAACAGTAAGCATCACTAAAGCAAGCATGTGTAGAACCTTAA
P-SETit.Ubq1-1:1:2      ------------------------------------------------------------

P-SETit.Ubq1-1:1:4      AAAAAGGCTTATACTACCAGTATACTATCAACCAGCATGCCGTTTTTGAAGTATCCAGGA
P-SETit.Ubq1-1:1:3      ------------------------------------------------------------
P-SETit.Ubq1-1:1:1      AAAAAGGCTTATACTACCAGTATACTATCAACCAGCATGCCGTTTTTGAAGTATCCAGGA
P-SETit.Ubq1-1:1:2      --------------------------------------GCCGTTTTTGAAGTATCCAGGA

P-SETit.Ubq1-1:1:4      TTAGAAGCTTCTACTGCGCTTTTATATTATAGCTGTGGACCCGTGGTAACCTTTCTCTTT
P-SETit.Ubq1-1:1:3      ------------------------------------------------------------
P-SETit.Ubq1-1:1:1      TTAGAAGCTTCTACTGCGCTTTTATATTATAGCTGTGGACCTGTGGTAACCTTTCTCTTT
P-SETit.Ubq1-1:1:2      TTAGAAGCTTCTACTGCGCTTTTATATTATAGCTGTGGACCTGTGGTAACCTTTCTCTTT

P-SETit.Ubq1-1:1:4      TGGCGCTTGCTTAATCTCGGCCGTGCTGGTCCATGCTTAGGCACTAGGCAGAGATAGAGC
P-SETit.Ubq1-1:1:3      ------------------------------------------------------------
P-SETit.Ubq1-1:1:1      TGGCGCTTGCTTAATCTCGGCCGTGCTGGTCCATGCTTAGGCACTAGGCAGAGATAGAGC
P-SETit.Ubq1-1:1:2      TGGCGCTTGCTTAATCTCGGCCGTGCTGGTCCATGCTTAGGCACTAGGCAGAGATAGAGC
```

FIG. 6a

```
P-SETit.Ubq1-1:1:4     CGGGGGTGAATGGGGCTAAAGCTCAGCTGCTCGAGGGGCCGTGGGCTGGTTTCCACTAGC
P-SETit.Ubq1-1:1:3     ------------------------------------------------------------
P-SETit.Ubq1-1:1:1     CGGGGGTGAATGGGGCTAAAGCTCAGCTGCTCGAGGGGCCGTGGGCTGGTTTCCACTAGC
P-SETit.Ubq1-1:1:2     CGGGGGTGAATGGGGCTAAAGCTCAGCTGCTCGAGGGGCCGTGGGCTGGTTTCCACTAGC

P-SETit.Ubq1-1:1:4     CTACAGCTGTGCCACGTGCGGCCGCGCAAGCCGAAGCAAGCACGCTGAGCCGTTGGACAG
P-SETit.Ubq1-1:1:3     ------------------------------------------------------------
P-SETit.Ubq1-1:1:1     CTACAGCTGTGCCACGTGCGGCCGCGCAAGCCGAAGCAAGCACGCTGAGCCGTTGGACAG
P-SETit.Ubq1-1:1:2     CTACAGCTGTGCCACGTGCGGCCGCGCAAGCCGAAGCAAGCACGCTGAGCCGTTGGACAG

P-SETit.Ubq1-1:1:4     CTTGTCATAATGCCATTACGTGGATTACACGTAACTGGCCCTGTAACTACTCGTTCGGCC
P-SETit.Ubq1-1:1:3     ------------------------------------------------------------
P-SETit.Ubq1-1:1:1     CTTGTCATAATGCCATTACGTGGATTACACGTAACTGGCCCTGTAACTACTCGTTCGGCC
P-SETit.Ubq1-1:1:2     CTTGTCATAATGCCATTACGTGGATTACACGTAACTGGCCCTGTAACTACTCGTTCGGCC

P-SETit.Ubq1-1:1:4     ATCATCAAACGACGACGTCCGCTAGGCGACGACACGGGTAATGCACGCAGCCACCCAGGC
P-SETit.Ubq1-1:1:3     --------------------------------CACGGGTAATGCACGCAGCCACCCAGGC
P-SETit.Ubq1-1:1:1     ATCATCAAACGACGACGTCCGCTAGGCGACGACACGGGTAATGCACGCAGCCACCCAGGC
P-SETit.Ubq1-1:1:2     ATCATCAAACGACGACGTCCGCTAGGCGACGACACGGGTAATGCACGCAGCCACCCAGGC
                                                       ****************************

P-SETit.Ubq1-1:1:4     GCGCGCGCTAGCGGAGCACGGTCAGGTGACACGGGCGTCGTGACGCTTCCGAGTTGAAGG
P-SETit.Ubq1-1:1:3     GCGCGCGCTAGCGGAGCACGGTCAGGTGACACGGGCGTCGTGACGCTTCCGAGTTGAAGG
P-SETit.Ubq1-1:1:1     GCGCGCGCTAGCGGAGCACGGTCAGGTGACACGGGCGTCGTGACGCTTCCGAGTTGAAGG
P-SETit.Ubq1-1:1:2     GCGCGCGCTAGCGGAGCACGGTCAGGTGACACGGGCGTCGTGACGCTTCCGAGTTGAAGG
                       ************************************************************

P-SETit.Ubq1-1:1:4     GGTTAACGCCAGAAACAGTGTTTGGCCAGGGTATGAACATAACAAAAAATATTCACACGA
P-SETit.Ubq1-1:1:3     GGTTAACGCCAGAAACAGTGTTTGGCCAGGGTATGAACATAACAAAAAATATTCACACGA
P-SETit.Ubq1-1:1:1     GGTTAACGCCAGAAACAGTGTTTGGCCAGGGTATGAACATAACAAAAAATATTCACACGA
P-SETit.Ubq1-1:1:2     GGTTAACGCCAGAAACAGTGTTTGGCCAGGGTATGAACATAACAAAAAATATTCACACGA
                       ************************************************************

P-SETit.Ubq1-1:1:4     AAGAATGGAAGTATGGAGCTGCTACTGTGTAAATGCCAAGCAGGAAACTCACGCCCGCTA
P-SETit.Ubq1-1:1:3     AAGAATGGAAGTATGGAGCTGCTACTGTGTAAATGCCAAGCAGGAAACTCACGCCCGCTA
P-SETit.Ubq1-1:1:1     AAGAATGGAAGTATGGAGCTGCTACTGTGTAAATGCCAAGCAGGAAACTCACGCCCGCTA
P-SETit.Ubq1-1:1:2     AAGAATGGAAGTATGGAGCTGCTACTGTGTAAATGCCAAGCAGGAAACTCACGCCCGCTA
                       ************************************************************

P-SETit.Ubq1-1:1:4     ACATCCAACGGCCAACAGCTCGACGTGCCGGTCAGCAGAGCATCGGAACACTGGTGATTG
P-SETit.Ubq1-1:1:3     ACATCCAACGGCCAACAGCTCGACGTGCCGGTCAGCAGAGCATCGGAACACTGGTGATTG
P-SETit.Ubq1-1:1:1     ACATCCAACGGCCAACAGCTCGACGTGCCGGTCAGCAGAGCATCGGAACACTGGTGATTG
P-SETit.Ubq1-1:1:2     ACATCCAACGGCCAACAGCTCGACGTGCCGGTCAGCAGAGCATCGGAACACTGGTGATTG
                       ************************************************************

P-SETit.Ubq1-1:1:4     GTGGAGCCGGCAGTATGCGCCCCAGCACGGCCGAGGTGGTGGTGGCCCGTGGCCCTGCTG
P-SETit.Ubq1-1:1:3     GTGGAGCCGGCAGTATGCGCCCCAGCACGGCCGAGGTGGTGGTGGCCCGTGGCCCTGCTG
P-SETit.Ubq1-1:1:1     GTGGAGCCGGCAGTATGCGCCCCAGCACGGCCGAGGTGGTGGTGGCCCGTGGCCCTGCTG
P-SETit.Ubq1-1:1:2     GTGGAGCCGGCAGTATGCGCCCCAGCACGGCCGAGGTGGTGGTGGCCCGTGGCCCTGCTG
                       ************************************************************
```

FIG. 6b

```
P-SETit.Ubq1-1:1:4      TCTGCGCGGCTCGGGACAACTTGAAACTGGGCCACCGCCTCGTCGCAACTCGCAACCCGT
P-SETit.Ubq1-1:1:3      TCTGCGCGGCTCGGGACAACTTGAAACTGGGCCACCGCCTCGTCGCAACTCGCAACCCGT
P-SETit.Ubq1-1:1:1      TCTGCGCGGCTCGGGACAACTTGAAACTGGGCCACCGCCTCGTCGCAACTCGCAACCCGT
P-SETit.Ubq1-1:1:2      TCTGCGCGGCTCGGGACAACTTGAAACTGGGCCACCGCCTCGTCGCAACTCGCAACCCGT
                        ************************************************************

P-SETit.Ubq1-1:1:4      TGGCGGAAGAAAGGAATGGCTCGTAGGGGCCCGGGTAGAATCGAAGAATGTTGCGCTGGG
P-SETit.Ubq1-1:1:3      TGGCGGAAGAAAGGAATGGCTCGTAGGGGCCCGGGTAGAATCGAAGAATGTTGCGCTGGG
P-SETit.Ubq1-1:1:1      TGGCGGAAGAAAGGAATGGCTCGTAGGGGCCCGGGTAGAATCGAAGAATGTTGCGCTGGG
P-SETit.Ubq1-1:1:2      TGGCGGAAGAAAGGAATGGCTCGTAGGGGCCCGGGTAGAATCGAAGAATGTTGCGCTGGG
                        ************************************************************

P-SETit.Ubq1-1:1:4      CTTCGATTCACATAACATGGGCCTGAAGCTCTAAAACGACGGCCCGGTCGCCGCGCGATG
P-SETit.Ubq1-1:1:3      CTTCGATTCACATAACATGGGCCTGAAGCTCTAAAACGACGGCCCGGTCGCCGCGCGATG
P-SETit.Ubq1-1:1:1      CTTCGATTCACATAACATGGGCCTGAAGCTCTAAAACGACGGCCCGGTCGCCGCGCGATG
P-SETit.Ubq1-1:1:2      CTTCGATTCACATAACATGGGCCTGAAGCTCTAAAACGACGGCCCGGTCGCCGCGCGATG
                        ************************************************************

P-SETit.Ubq1-1:1:4      GAAAGAGACCGGATCCTCCTCGTGAATTCTGGAAGGCCACACGAGAGCGACCCACCACCG
P-SETit.Ubq1-1:1:3      GAAAGAGACCGGATCCTCCTCGTGAATTCTGGAAGGCCACACGAGAGCGACCCACCACCG
P-SETit.Ubq1-1:1:1      GAAAGAGACCGGATCCTCCTCGTGAATTCTGGAAGGCCACACGAGAGCGACCCACCACCG
P-SETit.Ubq1-1:1:2      GAAAGAGACCGGATCCTCCTCGTGAATTCTGGAAGGCCACACGAGAGCGACCCACCACCG
                        ************************************************************

P-SETit.Ubq1-1:1:4      ACGCGGAGGAGTCGTGCGTGGTCCAACACGGCCGGCGGGCTGGGCTGCGACCTTAACCAG
P-SETit.Ubq1-1:1:3      ACGCGGAGGAGTCGTGCGTGGTCCAACACGGCCGGCGGGCTGGGCTGCGACCTTAACCAG
P-SETit.Ubq1-1:1:1      ACGCGGAGGAGTCGTGCGTGGTCCAACACGGCCGGCGGGCTGGGCTGCGACCTTAACCAG
P-SETit.Ubq1-1:1:2      ACGCGGAGGAGTCGTGCGTGGTCCAACACGGCCGGCGGGCTGGGCTGCGACCTTAACCAG
                        ************************************************************

P-SETit.Ubq1-1:1:4      CAAGGCACGCCACGACCCGCCCCGCCCTCGAGGCATAAATACCCTCCCATCC
P-SETit.Ubq1-1:1:3      CAAGGCACGCCACGACCCGCCCCGCCCTCGAGGCATAAATACCCTCCCATCC
P-SETit.Ubq1-1:1:1      CAAGGCACGCCACGACCCGCCCCGCCCTCGAGGCATAAATACCCTCCCATCC
P-SETit.Ubq1-1:1:2      CAAGGCACGCCACGACCCGCCCCGCCCTCGAGGCATAAATACCCTCCCATCC
                        ****************************************************
```

FIG. 6c

```
E-Cl.Ubq1-1:1:1     AGCAGACTCGCATTATCGATGGAGCTCTACCAAACTGGCCCTAGGCATTAACCTACCATG
P-Cl.Ubq1-1:1:1     AGCAGACTCGCATTATCGATGGAGCTCTACCAAACTGGCCCTAGGCATTAACCTACCATG
P-Cl.Ubq1-1:1:3     ------------------------------------------------------------
P-Cl.Ubq1-1:1:4     ------------------------------------------------------------
P-Cl.Ubq1-1:1:5     ------------------------------------------------------------

E-Cl.Ubq1-1:1:1     GATCACATCGTAAAAAAAAAACCCTACCATGGATCCTATCTGTTTTCTTTTTGCCCTGAA
P-Cl.Ubq1-1:1:1     GATCACATCGTAAAAAAAAAACCCTACCATGGATCCTATCTGTTTTCTTTTTGCCCTGAA
P-Cl.Ubq1-1:1:3     ------------------------------------------------------------
P-Cl.Ubq1-1:1:4     -----------------------------------CTATCTGTTTTCTTTTTGCCCTGAA
P-Cl.Ubq1-1:1:5     ------------------------------------------------------------

E-Cl.Ubq1-1:1:1     AGAGTGAAGTCATCATCATATTTACCATGGCGCGCGTAGGAGCGCTTCGTCGAAGACCCA
P-Cl.Ubq1-1:1:1     AGAGTGAAGTCATCATCATATTTACCATGGCGCGCGTAGGAGCGCTTCGTCGAAGACCCA
P-Cl.Ubq1-1:1:3     ------------------------------------------------------------
P-Cl.Ubq1-1:1:4     AGAGTGAAGTCATCATCATATTTACCATGGCGCGCGTAGGAGCGCTTCGTCGAAGACCCA
P-Cl.Ubq1-1:1:5     ------------------------------------------------------------

E-Cl.Ubq1-1:1:1     TAGGGGGGCGGTACTCGCACCGTGGTTGTTTCCTGTTATGTAATATCGGATGGGGGAGCA
P-Cl.Ubq1-1:1:1     TAGGGGGGCGGTACTCGCACCGTGGTTGTTTCCTGTTATGTAATATCGGATGGGGGAGCA
P-Cl.Ubq1-1:1:3     ------------------------------------------------------------
P-Cl.Ubq1-1:1:4     TAGGGGGGCGGTACTCGCACCGTGGTTGTTTCCTGTTATGTAATATCGGATGGGGGAGCA
P-Cl.Ubq1-1:1:5     ------------------------------------------------------------

E-Cl.Ubq1-1:1:1     GTCGGCTAGGTTGGTCCCATCGGTACTGGTCGTCCCCTAGTGCGCTAGATGCGCGATGTT
P-Cl.Ubq1-1:1:1     GTCGGCTAGGTTGGTCCCATCGGTACTGGTCGTCCCCTAGTGCGCTAGATGCGCGATGTT
P-Cl.Ubq1-1:1:3     ------------------------------------------------------------
P-Cl.Ubq1-1:1:4     GTCGGCTAGGTTGGTCCCATCGGTACTGGTCGTCCCCTAGTGCGCTAGATGCGCGATGTT
P-Cl.Ubq1-1:1:5     ------------------------------------------------------------

E-Cl.Ubq1-1:1:1     TGTCCTCAAAAACTCTTTTCTTCTTAATAACAATCATACGCAAATTTTTTGCGTATTCGA
P-Cl.Ubq1-1:1:1     TGTCCTCAAAAACTCTTTTCTTCTTAATAACAATCATACGCAAATTTTTTGCGTATTCGA
P-Cl.Ubq1-1:1:3     ------------------------------------------------------------
P-Cl.Ubq1-1:1:4     TGTCCTCAAAAACTCTTTTCTTCTTAATAACAATCATACGCAAATTTTTTGCGTATTCGA
P-Cl.Ubq1-1:1:5     ------------------------------------------------------------

E-Cl.Ubq1-1:1:1     GAAAAAAAGAAGATTCTATCTGTTTTTTTTTTGAAATGGCTCCAATTTATAGGAGGAGCC
P-Cl.Ubq1-1:1:1     GAAAAAAAGAAGATTCTATCTGTTTTTTTTTTGAAATGGCTCCAATTTATAGGAGGAGCC
P-Cl.Ubq1-1:1:3     ------------------------------------------------------------
P-Cl.Ubq1-1:1:4     GAAAAAAAGAAGATTCTATCTGTTTTTTTTTTGAAATGGCTCCAATTTATAGGAGGAGCC
P-Cl.Ubq1-1:1:5     ------------------------------------------------------------

E-Cl.Ubq1-1:1:1     CGTTTAACGGCGTCGACAAATCTAACGGACACCAACCAGCGAATGAGCGAACCCACCAGC
P-Cl.Ubq1-1:1:1     CGTTTAACGGCGTCGACAAATCTAACGGACACCAACCAGCGAATGAGCGAACCCACCAGC
P-Cl.Ubq1-1:1:3     ----------------CAAATCTAACGGACACCAACCAGCGAATGAGCGAACCCACCAGC
P-Cl.Ubq1-1:1:4     CGTTTAACGGCGTCGACAAATCTAACGGACACCAACCAGCGAATGAGCGAACCCACCAGC
P-Cl.Ubq1-1:1:5     ------------------------------------------------------------
```

FIG. 7a

```
E-Cl.Ubq1-1:1:1      GCCAAGCTAGCCAAGCGAAGCAGACGGCCGAGACGCTGACACCCTTGCCTTGGCGCGGCA
P-Cl.Ubq1-1:1:1      GCCAAGCTAGCCAAGCGAAGCAGACGGCCGAGACGCTGACACCCTTGCCTTGGCGCGGCA
P-Cl.Ubq1-1:1:3      GCCAAGCTAGCCAAGCGAAGCAGACGGCCGAGACGCTGACACCCTTGCCTTGGCGCGGCA
P-Cl.Ubq1-1:1:4      GCCAAGCTAGCCAAGCGAAGCAGACGGCCGAGACGCTGACACCCTTGCCTTGGCGCGGCA
P-Cl.Ubq1-1:1:5      ------------------------------------------------------------

E-Cl.Ubq1-1:1:1      TCTCCGTCGCTGGCTCGCTGGCTCTGGCCCCTTCGCGAGAGTTCCGGTCCACCTCCACCT
P-Cl.Ubq1-1:1:1      TCTCCGTCGCTGGCTCGCTGGCTCTGGCCCCTTCGCGAGAGTTCCGGTCCACCTCCACCT
P-Cl.Ubq1-1:1:3      TCTCCGTCGCTGGCTCGCTGGCTCTGGCCCCTTCGCGAGAGTTCCGGTCCACCTCCACCT
P-Cl.Ubq1-1:1:4      TCTCCGTCGCTGGCTCGCTGGCTCTGGCCCCTTCGCGAGAGTTCCGGTCCACCTCCACCT
P-Cl.Ubq1-1:1:5      ------------------------------------------------------------

E-Cl.Ubq1-1:1:1      GTGTCGGTTTCCAACTCCGTTCCGCCTTCGCGTGGGACTTGTTCCGTTCATCCGTTGGCG
P-Cl.Ubq1-1:1:1      GTGTCGGTTTCCAACTCCGTTCCGCCTTCGCGTGGGACTTGTTCCGTTCATCCGTTGGCG
P-Cl.Ubq1-1:1:3      GTGTCGGTTTCCAACTCCGTTCCGCCTTCGCGTGGGACTTGTTCCGTTCATCCGTTGGCG
P-Cl.Ubq1-1:1:4      GTGTCGGTTTCCAACTCCGTTCCGCCTTCGCGTGGGACTTGTTCCGTTCATCCGTTGGCG
P-Cl.Ubq1-1:1:5      ------------------------------------------------------------

E-Cl.Ubq1-1:1:1      GCATCCGGAAATTGCGTGGCGTAGAGCACGGGGCCCTCCTCTCACACGGCACGGAACCGT
P-Cl.Ubq1-1:1:1      GCATCCGGAAATTGCGTGGCGTAGAGCACGGGGCCCTCCTCTCACACGGCACGGAACCGT
P-Cl.Ubq1-1:1:3      GCATCCGGAAATTGCGTGGCGTAGAGCACGGGGCCCTCCTCTCACACGGCACGGAACCGT
P-Cl.Ubq1-1:1:4      GCATCCGGAAATTGCGTGGCGTAGAGCACGGGGCCCTCCTCTCACACGGCACGGAACCGT
P-Cl.Ubq1-1:1:5      ------------------------------------------------------------

E-Cl.Ubq1-1:1:1      CACGAGCTCACGGCACCGGCAGCACGGCGGGGATTCCTTCCCCACCACCGCTCCTTCCCT
P-Cl.Ubq1-1:1:1      CACGAGCTCACGGCACCGGCAGCACGGCGGGGATTCCTTCCCCACCACCGCTCCTTCCCT
P-Cl.Ubq1-1:1:3      CACGAGCTCACGGCACCGGCAGCACGGCGGGGATTCCTTCCCCACCACCGCTCCTTCCCT
P-Cl.Ubq1-1:1:4      CACGAGCTCACGGCACCGGCAGCACGGCGGGGATTCCTTCCCCACCACCGCTCCTTCCCT
P-Cl.Ubq1-1:1:5      ------------------------------------------------------------

E-Cl.Ubq1-1:1:1      TTCCCTTCCTCGCCCGCC---------------------------------------
P-Cl.Ubq1-1:1:1      TTCCCTTCCTCGCCCGCCATCATAAATAGCCACCCCTCCCAGCTTCCTTCGCCACAT
P-Cl.Ubq1-1:1:3      TTCCCTTCCTCGCCCGCCATCATAAATAGCCACCCCTCCCAGCTTCCTTCGCCACAT
P-Cl.Ubq1-1:1:4      TTCCCTTCCTCGCCCGCCATCATAAATAGCCACCCCTCCCAGCTTCCTTCGCCACAT
P-Cl.Ubq1-1:1:5      ---CCTTCCTCGCCCGCCATCATAAATAGCCACCCCTCCCAGCTTCCTTCGCCACAT
                        ***************
```

FIG. 7b

Transgene Cassette Configuration 1

Promoter or chimeric promoter [A]    Leader [B]    Intron [C]    Coding Region [D]    3' UTR [E]

Transgene Cassette Configuration 2

Promoter or chimeric promoter [F]    Leader [G]    Intron [H]    Leader [I]    Coding Region [J]    3' UTR [K]

Transgene Cassette Configuration 3

Promoter or chimeric promoter [L]    Leader [M]    Coding Region [N]    Intron [O]    Coding Region [P]    3' UTR [Q]

SEQUENCE LISTING

```
<160> NUMBER OF SEQ ID NOS: 183

<210> SEQ ID NO 1
<211> LENGTH: 3741
<212> TYPE: DNA
<213> ORGANISM: Andropogon gerardii

<400> SEQUENCE: 1

agcagactcg cattatcgat ggaggggtgg gtttagaacc ctgaaaactg gtactgtttc      60

gaactgaaaa acactgtagc acttttcgtt tgtttgtggt aaatattatc ttactatggt     120

ctaactaggc tcaaaagaat cgtctcgcaa tgtacatcta aattatgcaa ttagttattt     180

tgtttacctg catttcatac tccgagcatg cgtcttttgg tacatttaat gcttcgatgt     240

gatgggaatt ttaaaaattt tggagaaaag ttggtttcta aacacccccg aggacgaaat     300

tggattcggt ctttgacgcg gatgcagcaa ctgcagtgcg caggatacca tcttagccgt     360

tgcgtcgaag ttcgctttgc taacgttttg agaaaattaa accagctttg accaacgtga     420

gacgagcgcc ttacgtggca gtgtaatgga accgggcacg gcaagtttga cgctgtagtg     480

ttagccggtc tcgttacgtt tggcacaact tagttgaatc cggcttccgg caaactatat     540

ggcaagttag acccaagtgt gagccggcca ccgcaagtta ttgggacatt atacgtagga     600

agcaagtgta taataagaat atgagataat gtaagcagct atatgaatca tcacgtcata     660
```

```
tttatgttaa gatgaagagg atagaataaa cggtatgtaa atttatagcg agtgatagac    720
gggcacaagg cctcctagct atttccataa atcggatttt gtaagaacaa aaaagaggac    780
ttattataag agaatgtggt aagtaagtat actctctccg tttcaaatta taagttgttt    840
tgattttttt ggtacatcta ttttactatg cattagatat aataatgtgt ctagatacat    900
aacaaaatgg atgaatcaaa aaagtcaaag tgatttacaa tttggaacgg agagagtaag    960
ttcaagccgt caaggcactt ctatgcaacc acagtcaact tgaatgccgc ttgagtgcct   1020
tctcaagttt tttttcttg caaaaatcat ttcttttttt taaaaaaagt ataatttgga   1080
tcgtgcaaat ttctctctag gtgtgtgtgt gactgtgtga gtaacaattt ctctagttgt   1140
gcgcgactgc tgcttacttt ggagattaca atatctttct aaaatgcttc gattacttat   1200
ttataaaccg tctctaaggc caattgctca agattcattc aacaattgaa acgtctcaca   1260
tgattaaatc atataaagtt tctaagtctt gtttgacaag atttttttag attttcatct   1320
aaattggatg aaactatcaa acactaattt taaaaaatat aagagaagct ccggagataa   1380
aaggtcgtct atgttattat aagagtaaag tcgtctattc tcttcgtccc aacatatata   1440
attctaagca tgaattgctt tctttttgga caaaaggagc atgccacaac acaagaatga   1500
tgtcaccgtc atgcttggat ccttttatgg taaagcttca ccttctataa tctaacaata   1560
gagaaatcag ggaaaaatca tgttttggtt gtttttattt ctaacctcca caataacttt   1620
ggtttaccat tttttgtttg attttagttt tagagaagcg tttataacag gacctaaaat   1680
ctttttttcag tacacagtac aacgcagacg ctcatacacg cacgcacact cacctctatg   1740
aacacacgta agaaaaccct acaccttgag caccttcgaa ggactgagcc ggtaaatata   1800
gagattctcg aagtcactat tagcgcctcg ttgtcaacgg gaatgtcgct taccacttaa   1860
agcataacgc cgagaaatcc cgtaataaat ccagtaaaat acgagcaccc gtgccaagtt   1920
gaatatttga acccgagtgg gtagattcca ccgcaaagga cctaaccaga tcatttcgca   1980
aacaggaact aaaatcggta gagagcccag acaaaagcct ttcctaagag ccactccagt   2040
ggaagcccct actttaggta taaaatgcaa tactagtggg gctcctaaat aaacttctat   2100
ttttcatggc cttctaaaat tcactcccaa accccctagct atagaagtct cttatccatc   2160
ctctaaataa aaatgggagt ctattttatt tcaccagagt tgatcgtaaa tttagtctct   2220
caaattttat aagttgaggg tagaggatga ctggagttgc tctaaacgga cctatcttca   2280
agtgacctca gtgagcccgt ttaacggcgt cgacaagttt aatctaacgg acaccaacca   2340
gagaagagaa ccaccgccag cgccgagcca agcgacgttg acatcttggc gcggcacggc   2400
atctccctgg cgtctggccc cctctcgaga cttccgctcc acctcccacc ggtggcggtt   2460
tccaagtccg ttccgcctcc tctcacacgg cacgaaaccg tgacgggcac cggcagcacg   2520
gggggattcc tttcccaccg ctccttccct ttcccttcct ctcccgccgc tataaatagc   2580
cagccccatc cccagcttct ttccccaacc tcatcttctc tcgtgttgtt cggcacaacc   2640
cgatcgatcc ccaactccct cgtcgtctct cctcgcgagc ctcgtcgatc ccccgcttca   2700
aggtacggcg atcgattatc ttccctctct ctaccttctc tctcttatag ggcctgctag   2760
ctctgttcct gtttttccat ggctgcgagg tacaatagat cggcgatcca tggttagggc   2820
ctgctagttg tgttcctgtt tttccatggc tgcgaggcac aatagatctg atggcgttat   2880
gatggttaac ttgtcatact cttgcgatct atggtccctt taggagttta ggacatctat   2940
ttaatttcgg atagttcgag atctgtgatc catggttagt accctaggca gtggggttag   3000
```

atccgtgctg ttatggttcg tagatggatt ctgattgctc agtaactggg aatcctggga 3060
tggttctagc tggttcgcag ataagatcga tttcatgata tgctatatct tgtttggttg 3120
ccgtggttcc gttaaatctg tctgttatga tcttagtctt tgataaggtt cggtcgtgct 3180
agctacgtcc tgtgcagcac ttaattgtca ggtcataatt tttagcatgc ctttttttta 3240
ttggtttggt tttgtctgac tgggctgtag atagtttcaa tctttgtctg actgggctgt 3300
agatagtttc aatctacctg tcggtttatt ttattaaatt tggatctgta tgtgtgtcat 3360
atatcttcat cttttagata tatcgatagg tttatatgtt gctgtcggtt ttttactgtt 3420
cctttatgag atatattcat gcttagatac atgaaacaac gtgctgttac agtttaatag 3480
ttcttgttta tctaataaac aaataaggat aggtatatgc tgcagttagt tttactggta 3540
ctttttttga catgaaccta cggcttaata attagtcttc atcaaataaa aagcatattt 3600
tttaattatt tcgatatact tgaatgatgt catatgcagc atctgtgtga atttttggcc 3660
ctgtcttcat atgctgttta tttgtttggg actgtttctt tggttgataa ctcatcctgt 3720
tgtttggtga tccttttgca g 3741

<210> SEQ ID NO 2
<211> LENGTH: 2603
<212> TYPE: DNA
<213> ORGANISM: Andropogon gerardii

<400> SEQUENCE: 2
agcagactcg cattatcgat ggaggggtgg gtttagaacc ctgaaaactg gtactgtttc 60
gaactgaaaa acactgtagc acttttcgtt tgtttgtggt aaatattatc ttactatggt 120
ctaactaggc tcaaaagaat cgtctcgcaa tgtacatcta aattatgcaa ttagttattt 180
tgtttacctg catttcatac tccgagcatg cgtcttttgg tacatttaat gcttcgatgt 240
gatgggaatt ttaaaaattt tggagaaaag ttggtttcta aacacccccg aggacgaaat 300
tggattcggt ctttgacgcg gatgcagcaa ctgcagtgcg caggatacca tcttagccgt 360
tgcgtcgaag ttcgctttgc taacgttttg agaaaattaa accagctttg accaacgtga 420
gacgagcgcc ttacgtggca gtgtaatgga accgggcacg gcaagtttga cgctgtagtg 480
ttagccggtc tcgttacgtt tggcacaact tagttgaatc cggcttccgg caaactatat 540
ggcaagttag acccaagtgt gagccggcca ccgcaagtta ttgggacatt atacgtagga 600
agcaagtgta taataagaat atgagataat gtaagcagct atatgaatca tcacgtcata 660
tttatgttaa gatgaagagg atagaataaa cggtatgtaa atttatagcg agtgatagac 720
gggcacaagg cctcctagct atttccataa atcggatttt gtaagaacaa aaaagaggac 780
ttattataag agaatgtggt aagtaagtat actctctccg tttcaaatta taagttgttt 840
tgattttttt ggtacatcta ttttactatg cattagatat aataatgtgt ctagatacat 900
aacaaaatgg atgaatcaaa aaagtcaaag tgatttacaa tttggaacgg agagagtaag 960
ttcaagccgt caaggcactt ctatgcaacc acagtcaact tgaatgccgc ttgagtgcct 1020
tctcaagttt ttttttcttg caaaaatcat ttcttttttt taaaaaaagt ataatttgga 1080
tcgtgcaaat ttctctctag gtgtgtgtgt gactgtgtga gtaacaattt ctctagttgt 1140
gcgcgactgc tgcttacttt ggagattaca atatctttct aaaatgcttc gattacttat 1200
ttataaaccg tctctaaggc caattgctca agattcattc aacaattgaa acgtctcaca 1260
tgattaaatc atataaagtt tctaagtctt gtttgacaag atttttttag attttcatct 1320
aaattggatg aaactatcaa acactaattt taaaaaatat aagagaagct ccggagataa 1380
aaggtcgtct atgttattat aagagtaaag tcgtctattc tcttcgtccc aacatatata 1440
attctaagca tgaattgctt tctttttgga caaaaggagc atgccacaac acaagaatga 1500
tgtcaccgtc atgcttggat ccttttatgg taaagcttca ccttctataa tctaacaata 1560
gagaaatcag ggaaaaatca tgttttggtt gtttttattt ctaacctcca caataacttt 1620
ggtttaccat tttttgtttg attttagttt tagagaagcg tttataacag gacctaaaat 1680 ctttttttcag tacacagtac aacgcagacg ctcatacacg cacgcacact cacctctatg 1740
aacacacgta agaaaaccct acaccttgag caccttcgaa ggactgagcc ggtaaatata 1800
gagattctcg aagtcactat tagcgcctcg ttgtcaacgg gaatgtcgct taccacttaa 1860
agcataacgc cgagaaatcc cgtaataaat ccagtaaaat acgagcaccc gtgccaagtt 1920
gaatatttga acccgagtgg gtagattcca ccgcaaagga cctaaccaga tcatttcgca 1980
aacaggaact aaaatcggta gagagcccag acaaaagcct ttcctaagag ccactccagt 2040
ggaagcccct actttaggta taaaatgcaa tactagtggg gctcctaaat aaacttctat 2100
ttttcatggc cttctaaaat tcactcccaa acccctagct atagaagtct cttatccatc 2160
ctctaaataa aaatgggagt ctattttatt tcaccagagt tgatcgtaaa tttagtctct 2220
caaattttat aagttgaggg tagaggatga ctggagttgc tctaaacgga cctatcttca 2280
agtgacctca gtgagcccgt ttaacggcgt cgacaagttt aatctaacgg acaccaacca 2340
gagaagagaa ccaccgccag cgccgagcca agcgacgttg acatcttggc gcggcacggc 2400
atctccctgg cgtctggccc cctctcgaga cttccgctcc acctcccacc ggtggcggtt 2460
tccaagtccg ttccgcctcc tctcacacgg cacgaaaccg tgacgggcac cggcagcacg 2520
gggggattcc tttcccaccg ctccttccct ttcccttcct ctcccgccgc tataaatagc 2580
cagccccatc cccagcttct ttc 2603

<210> SEQ ID NO 3
<211> LENGTH: 99
<212> TYPE: DNA
<213> ORGANISM: Andropogon gerardii

<400> SEQUENCE: 3
cccaacctca tcttctctcg tgttgttcgg cacaacccga tcgatcccca actccctcgt 60
cgtctctcct cgcgagcctc gtcgatcccc cgcttcaag 99

<210> SEQ ID NO 4
<211> LENGTH: 1039
<212> TYPE: DNA
<213> ORGANISM: Andropogon gerardii

<400> SEQUENCE: 4
gtacggcgat cgattatctt ccctctctct accttctctc tcttataggg cctgctagct 60
ctgttcctgt ttttccatgg ctgcgaggta caatagatcg gcgatccatg gttagggcct 120
gctagttgtg ttcctgtttt tccatggctg cgaggcacaa tagatctgat ggcgttatga 180
tggttaactt gtcatactct tgcgatctat ggtcccttta ggagtttagg acatctattt 240
aatttcggat agttcgagat ctgtgatcca tggttagtac cctaggcagt ggggttagat 300
ccgtgctgtt atggttcgta gatggattct gattgctcag taactgggaa tcctgggatg 360
gttctagctg gttcgcagat aagatcgatt tcatgatatg ctatatcttg tttggttgcc 420
gtggttccgt taaatctgtc tgttatgatc ttagtctttg ataaggttcg gtcgtgctag 480
ctacgtcctg tgcagcactt aattgtcagg tcataatttt tagcatgcct tttttttatt 540
ggtttggttt tgtctgactg ggctgtagat agtttcaatc tttgtctgac tgggctgtag 600
atagtttcaa tctacctgtc ggtttatttt attaaatttg gatctgtatg tgtgtcatat 660
atcttcatct tttagatata tcgataggtt tatatgttgc tgtcggtttt ttactgttcc 720
tttatgagat atattcatgc ttagatacat gaaacaacgt gctgttacag tttaatagtt 780
cttgtttatc taataaacaa ataaggatag gtatatgctg cagttagttt tactggtact 840 tttttgaca tgaacctacg gcttaataat tagtcttcat caaataaaaa gcatattttt 900
taattatttc gatatacttg aatgatgtca tatgcagcat ctgtgtgaat ttttggccct 960
gtcttcatat gctgtttatt tgtttgggac tgtttctttg gttgataact catcctgttg 1020
tttggtgatc cttttgcag 1039

<210> SEQ ID NO 5
<211> LENGTH: 3255
<212> TYPE: DNA
<213> ORGANISM: Andropogon gerardii

<400> SEQUENCE: 5
ctcgttacgt ttggcacaac ttagttgaat ccggcttccg gcaaactata tggcaagtta 60
gacccaagtg tgagccggcc accgcaagtt attgggacat tatacgtagg aagcaagtgt 120
ataataagaa tatgagataa tgtaagcagc tatatgaatc atcacgtcat atttatgtta 180
agatgaagag gatagaataa acggtatgta aatttatagc gagtgataga cgggcacaag 240
gcctcctagc tatttccata aatcggattt tgtaagaaca aaaaagagga cttattataa 300
gagaatgtgg taagtaagta tactctctcc gtttcaaatt ataagttgtt ttgatttttt 360
tggtacatct attttactat gcattagata taataatgtg tctagataca taacaaaatg 420
gatgaatcaa aaaagtcaaa gtgatttaca atttggaacg gagagagtaa gttcaagccg 480
tcaaggcact tctatgcaac cacagtcaac ttgaatgccg cttgagtgcc ttctcaagtt 540
tttttttctt gcaaaaatca tttctttttt ttaaaaaaag tataatttgg atcgtgcaaa 600
tttctctcta ggtgtgtgtg tgactgtgtg agtaacaatt tctctagttg tgcgcgactg 660
ctgcttactt tggagattac aatatctttc taaaatgctt cgattactta tttataaacc 720
gtctctaagg ccaattgctc aagattcatt caacaattga aacgtctcac atgattaaat 780
catataaagt ttctaagtct tgtttgacaa gattttttta gattttcatc taaattggat 840
gaaactatca aacactaatt ttaaaaaata taagagaagc tccggagata aaaggtcgtc 900
tatgttatta taagagtaaa gtcgtctatt ctcttcgtcc caacatatat aattctaagc 960
atgaattgct ttctttttgg acaaaaggag catgccacaa cacaagaatg atgtcaccgt 1020
catgcttgga tccttttatg gtaaagcttc accttctata atctaacaat agagaaatca 1080
gggaaaaatc atgttttggt tgtttttatt tctaacctcc acaataactt tggtttacca 1140 tttttttgttt gattttagtt ttagagaagc gtttataaca ggacctaaaa tcttttttca 1200
gtacacagta caacgcagac gctcatacac gcacgcacac tcacctctat gaacacacgt 1260
aagaaaaccc tacaccttga gcaccttcga aggactgagc cggtaaatat agagattctc 1320
gaagtcacta ttagcgcctc gttgtcaacg ggaatgtcgc ttaccactta aagcataacg 1380
ccgagaaatc ccgtaataaa tccagtaaaa tacgagcacc cgtgccaagt tgaatatttg 1440
aacccgagtg ggtagattcc accgcaaagg acctaaccag atcatttcgc aaacaggaac 1500
taaaatcggt agagagccca gacaaaagcc tttcctaaga gccactccag tggaagcccc 1560

```
tactttaggt ataaaatgca atactagtgg ggctcctaaa taaacttcta tttttcatgg   1620
ccttctaaaa ttcactccca aacccctagc tatagaagtc tcttatccat cctctaaata   1680
aaaatgggag tctattttat ttcaccagag ttgatcgtaa atttagtctc tcaaatttta   1740
taagttgagg gtagaggatg actggagttg ctctaaacgg acctatcttc aagtgacctc   1800
agtgagcccg tttaacggcg tcgacaagtt taatctaacg gacaccaacc agagaagaga   1860
accaccgcca gcgccgagcc aagcgacgtt gacatcttgg cgcggcacgg catctccctg   1920
gcgtctggcc ccctctcgag acttccgctc cacctcccac cggtggcggt ttccaagtcc   1980
gttccgcctc ctctcacacg gcacgaaacc gtgacgggca ccggcagcac ggggggattc   2040
ctttcccacc gctccttccc tttcccttcc tctcccgccg ctataaatag ccagccccat   2100
ccccagcttc tttccccaac ctcatcttct ctcgtgttgt tcggcacaac ccgatcgatc   2160
cccaactccc tcgtcgtctc tcctcgcgag cctcgtcgat cccccgcttc aaggtacggc   2220
gatcgattat cttccctctc tctaccttct ctctcttata gggcctgcta gctctgttcc   2280
tgtttttcca tggctgcgag gtacaataga tcggcgatcc atggttaggg cctgctagtt   2340
gtgttcctgt ttttccatgg ctgcgaggca caatagatct gatggcgtta tgatggttaa   2400
cttgtcatac tcttgcgatc tatggtccct ttaggagttt aggacatcta tttaatttcg   2460
gatagttcga gatctgtgat ccatggttag taccctaggc agtggggtta gatccgtgct   2520
gttatggttc gtagatggat tctgattgct cagtaactgg gaatcctggg atggttctag   2580
ctggttcgca gataagatcg atttcatgat atgctatatc ttgtttggtt gccgtggttc   2640
cgttaaatct gtctgttatg atcttagtct ttgataaggt tcggtcgtgc tagctacgtc   2700
ctgtgcagca cttaattgtc aggtcataat ttttagcatg ccttttttt attggtttgg   2760
ttttgtctga ctgggctgta gatagtttca atctttgtct gactgggctg tagatagttt   2820
caatctacct gtcggtttat tttattaaat ttggatctgt atgtgtgtca tatatcttca   2880
tcttttagat atatcgatag gtttatatgt tgctgtcggt tttttactgt tcctttatga   2940
gatatattca tgcttagata catgaaacaa cgtgctgtta cagtttaata gttcttgttt   3000
atctaataaa caaataagga taggtatatg ctgcagttag ttttactggt actttttttg   3060
acatgaacct acggcttaat aattagtctt catcaaataa aaagcatatt ttttaattat   3120
ttcgatatac ttgaatgatg tcatatgcag catctgtgtg aatttttggc cctgtcttca   3180
tatgctgttt atttgtttgg gactgtttct ttggttgata actcatcctg ttgtttggtg   3240
atccttttgc aggtg                                                     3255
```

<210> SEQ ID NO 6
<211> LENGTH: 2114
<212> TYPE: DNA
<213> ORGANISM: Andropogon gerardii

<400> SEQUENCE: 6

```
ctcgttacgt ttggcacaac ttagttgaat ccggcttccg gcaaactata tggcaagtta     60
gacccaagtg tgagccggcc accgcaagtt attgggacat tatacgtagg aagcaagtgt    120
ataataagaa tatgagataa tgtaagcagc tatatgaatc atcacgtcat atttatgtta    180
agatgaagag gatagaataa acggtatgta aatttatagc gagtgataga cgggcacaag    240
gcctcctagc tatttccata aatcggattt tgtaagaaca aaaaagagga cttattataa    300
gagaatgtgg taagtaagta tactctctcc gtttcaaatt ataagttgtt ttgatttttt    360
```

```
tggtacatct attttactat gcattagata taataatgtg tctagataca taacaaaatg    420

gatgaatcaa aaaagtcaaa gtgatttaca atttggaacg gagagagtaa gttcaagccg    480

tcaaggcact tctatgcaac cacagtcaac ttgaatgccg cttgagtgcc ttctcaagtt    540

tttttttctt gcaaaaatca tttctttttt ttaaaaaaag tataatttgg atcgtgcaaa    600

tttctctcta ggtgtgtgtg tgactgtgtg agtaacaatt tctctagttg tgcgcgactg    660

ctgcttactt tggagattac aatatctttc taaaatgctt cgattactta tttataaacc    720

gtctctaagg ccaattgctc aagattcatt caacaattga aacgtctcac atgattaaat    780

catataaagt ttctaagtct tgtttgacaa gattttttta gattttcatc taaattggat    840

gaaactatca aacactaatt ttaaaaaata taagagaagc tccggagata aaaggtcgtc    900

tatgttatta taagagtaaa gtcgtctatt ctcttcgtcc caacatatat aattctaagc    960

atgaattgct ttctttttgg acaaaaggag catgccacaa cacaagaatg atgtcaccgt   1020

catgcttgga tccttttatg gtaaagcttc accttctata atctaacaat agagaaatca   1080

gggaaaaatc atgttttggt tgtttttatt tctaacctcc acaataactt tggtttacca   1140

ttttttgttt gattttagtt ttagagaagc gtttataaca ggacctaaaa tctttttca    1200

gtacacagta caacgcagac gctcatacac gcacgcacac tcacctctat gaacacacgt   1260

aagaaaaccc tacaccttga gcaccttcga aggactgagc cggtaaatat agagattctc   1320

gaagtcacta ttagcgcctc gttgtcaacg ggaatgtcgc ttaccactta aagcataacg   1380

ccgagaaatc ccgtaataaa tccagtaaaa tacgagcacc cgtgccaagt tgaatatttg   1440

aacccgagtg ggtagattcc accgcaaagg acctaaccag atcatttcgc aaacaggaac   1500

taaaatcggt agagagccca gacaaaagcc tttcctaaga gccactccag tggaagcccc   1560

tactttaggt ataaaatgca atactagtgg ggctcctaaa taaacttcta tttttcatgg   1620

ccttctaaaa ttcactccca aaccccctagc tatagaagtc tcttatccat cctctaaata  1680

aaaatgggag tctattttat ttcaccagag ttgatcgtaa atttagtctc tcaaatttta   1740

taagttgagg gtagaggatg actggagttg ctctaaacgg acctatcttc aagtgacctc   1800

agtgagcccg tttaacggcg tcgacaagtt taatctaacg gacaccaacc agagaagaga   1860

accaccgcca gcgccgagcc aagcgacgtt gacatcttgg cgcggcacgg catctccctg   1920

gcgtctggcc ccctctcgag acttccgctc cacctcccac cggtggcggt ttccaagtcc   1980

gttccgcctc ctctcacacg gcacgaaacc gtgacgggca ccggcagcac ggggggattc   2040

ctttcccacc gctccttccc tttcccttcc tctcccgccg ctataaatag ccagccccat   2100

ccccagcttc tttc                                                     2114
```

```
<210> SEQ ID NO 7
<211> LENGTH: 1042
<212> TYPE: DNA
<213> ORGANISM: Andropogon gerardii

<400> SEQUENCE: 7

gtacggcgat cgattatctt ccctctctct accttctctc tcttataggg cctgctagct     60

ctgttcctgt ttttccatgg ctgcgaggta caatagatcg gcgatccatg gttagggcct    120

gctagttgtg ttcctgtttt tccatggctg cgaggcacaa tagatctgat ggcgttatga    180

tggttaactt gtcatactct tgcgatctat ggtcccttta ggagtttagg acatctattt    240

aatttcggat agttcgagat ctgtgatcca tggttagtac cctaggcagt ggggttagat    300

ccgtgctgtt atggttcgta gatggattct gattgctcag taactgggaa tcctgggatg    360
```

```
gttctagctg gttcgcagat aagatcgatt tcatgatatg ctatatcttg tttggttgcc    420

gtggttccgt taaatctgtc tgttatgatc ttagtctttg ataaggttcg gtcgtgctag    480

ctacgtcctg tgcagcactt aattgtcagg tcataatttt tagcatgcct tttttttatt    540

ggtttggttt tgtctgactg ggctgtagat agtttcaatc tttgtctgac tgggctgtag    600

atagtttcaa tctacctgtc ggtttatttt attaaatttg gatctgtatg tgtgtcatat    660

atcttcatct tttagatata tcgataggtt tatatgttgc tgtcggtttt ttactgttcc    720

tttatgagat atattcatgc ttagatacat gaaacaacgt gctgttacag tttaatagtt    780

cttgtttatc taataaacaa ataaggatag gtatatgctg cagttagttt tactggtact    840

tttttgaca tgaacctacg gcttaataat tagtcttcat caaataaaaa gcatattttt    900

taattatttc gatatacttg aatgatgtca tatgcagcat ctgtgtgaat ttttggccct    960

gtcttcatat gctgtttatt tgtttgggac tgtttctttg gttgataact catcctgttg   1020

tttggtgatc cttttgcagg tg                                            1042
```

<210> SEQ ID NO 8
<211> LENGTH: 2785
<212> TYPE: DNA
<213> ORGANISM: Andropogon gerardii

<400> SEQUENCE: 8

```
gttcaagccg tcaaggcact tctatgcaac cacagtcaac ttgaatgccg cttgagtgcc     60

ttctcaagtt tttttttctt gcaaaaatca tttctttttt ttaaaaaaag tataatttgg    120

atcgtgcaaa tttctctcta ggtgtgtgtg tgactgtgtg agtaacaatt tctctagttg    180

tgcgcgactg ctgcttactt tggagattac aatatctttc taaaatgctt cgattactta    240

tttataaacc gtctctaagg ccaattgctc aagattcatt caacaattga aacgtctcac    300

atgattaaat catataaagt ttctaagtct tgtttgacaa gattttttta gattttcatc    360

taaattggat gaaactatca aacactaatt ttaaaaaata taagagaagc tccggagata    420

aaaggtcgtc tatgttatta taagagtaaa gtcgtctatt ctcttcgtcc caacatatat    480

aattctaagc atgaattgct ttctttttgg acaaaaggag catgccacaa cacaagaatg    540

atgtcaccgt catgcttgga tccttttatg gtaaagcttc accttctata atctaacaat    600

agagaaatca gggaaaaatc atgttttggt tgtttttatt tctaacctcc acaataactt    660

tggtttacca tttttttgttt gattttagtt ttagagaagc gtttataaca ggacctaaaa    720

tctttttttca gtacacagta caacgcagac gctcatacac gcacgcacac tcacctctat    780

gaacacacgt aagaaaaccc tacaccttga gcaccttcga aggactgagc cggtaaatat    840

agagattctc gaagtcacta ttagcgcctc gttgtcaacg ggaatgtcgc ttaccactta    900

aagcataacg ccgagaaatc ccgtaataaa tccagtaaaa tacgagcacc cgtgccaagt    960

tgaatatttg aacccgagtg ggtagattcc accgcaaagg acctaaccag atcatttcgc   1020

aaacaggaac taaaatcggt agagagccca gacaaaagcc tttcctaaga gccactccag   1080

tggaagcccc tactttaggt ataaaatgca atactagtgg ggctcctaaa taaacttcta   1140

tttttcatgg ccttctaaaa ttcactccca aacccctagc tatagaagtc tcttatccat   1200

cctctaaata aaaatgggag tctattttat ttcaccagag ttgatcgtaa atttagtctc   1260

tcaaatttta taagttgagg gtagaggatg actggagttg ctctaaacgg acctatcttc   1320

aagtgacctc agtgagcccg tttaacggcg tcgacaagtt taatctaacg gacaccaacc   1380
```

```
agagaagaga accaccgcca gcgccgagcc aagcgacgtt gacatcttgg cgcggcacgg   1440

catctccctg gcgtctggcc ccctctcgag acttccgctc cacctcccac cggtggcggt   1500

ttccaagtcc gttccgcctc ctctcacacg gcacgaaacc gtgacgggca ccggcagcac   1560

ggggggattc ctttcccacc gctccttccc tttcccttcc tctcccgccg ctataaatag   1620

ccagccccat ccccagcttc tttccccaac ctcatcttct ctcgtgttgt tcggcacaac   1680

ccgatcgatc cccaactccc tcgtcgtctc tcctcgcgag cctcgtcgat cccccgcttc   1740

aaggtacggc gatcgattat cttccctctc tctaccttct ctctcttata gggcctgcta   1800

gctctgttcc tgtttttcca tggctgcgag gtacaataga tcggcgatcc atggttaggg   1860

cctgctagtt gtgttcctgt ttttccatgg ctgcgaggca caatagatct gatggcgtta   1920

tgatggttaa cttgtcatac tcttgcgatc tatggtccct ttaggagttt aggacatcta   1980

tttaatttcg gatagttcga gatctgtgat ccatggttag taccctaggc agtggggtta   2040

gatccgtgct gttatggttc gtagatggat tctgattgct cagtaactgg gaatcctggg   2100

atggttctag ctggttcgca gataagatcg atttcatgat atgctatatc ttgtttggtt   2160

gccgtggttc cgttaaatct gtctgttatg atcttagtct ttgataaggt tcggtcgtgc   2220

tagctacgtc ctgtgcagca cttaattgtc aggtcataat ttttagcatg cctttttttt   2280

attggtttgg ttttgtctga ctgggctgta gatagtttca atctttgtct gactgggctg   2340

tagatagttt caatctacct gtcggtttat tttattaaat ttggatctgt atgtgtgtca   2400

tatatcttca tcttttagat atatcgatag gtttatatgt tgctgtcggt tttttactgt   2460

tcctttatga gatatattca tgcttagata catgaaacaa cgtgctgtta cagtttaata   2520

gttcttgttt atctaataaa caaataagga taggtatatg ctgcagttag ttttactggt   2580

acttttttttg acatgaacct acggcttaat aattagtctt catcaaataa aaagcatatt   2640

ttttaattat ttcgatatac ttgaatgatg tcatatgcag catctgtgtg aatttttggc   2700

cctgtcttca tatgctgttt atttgtttgg gactgtttct ttggttgata actcatcctg   2760

ttgtttggtg atccttttgc aggtg                                          2785
```

<210> SEQ ID NO 9
<211> LENGTH: 1644
<212> TYPE: DNA
<213> ORGANISM: Andropogon gerardii

<400> SEQUENCE: 9

```
gttcaagccg tcaaggcact tctatgcaac cacagtcaac ttgaatgccg cttgagtgcc     60

ttctcaagtt ttttttcttt gcaaaaatca tttctttttt ttaaaaaaag tataatttgg    120

atcgtgcaaa tttctctcta ggtgtgtgtg tgactgtgtg agtaacaatt tctctagttg    180

tgcgcgactg ctgcttactt tggagattac aatatctttc taaaatgctt cgattactta    240

tttataaacc gtctctaagg ccaattgctc aagattcatt caacaattga aacgtctcac    300

atgattaaat catataaagt ttctaagtct tgtttgacaa gatttttta gattttcatc    360

taaattggat gaaactatca aacactaatt ttaaaaaata taagagaagc tccggagata    420

aaaggtcgtc tatgttatta taagagtaaa gtcgtctatt ctcttcgtcc caacatatat    480

aattctaagc atgaattgct ttctttttgg acaaaaggag catgccacaa cacaagaatg    540

atgtcaccgt catgcttgga tccttttatg gtaaagcttc accttctata atctaacaat    600

agagaaatca gggaaaaatc atgttttggt tgtttttatt tctaacctcc acaataactt    660

tggtttacca ttttttgttt gattttagtt ttagagaagc gtttataaca ggacctaaaa    720
```

```
tctttttca gtacacagta caacgcagac gctcatacac gcacgcacac tcacctctat    780

gaacacacgt aagaaaaccc tacaccttga gcaccttcga aggactgagc cggtaaatat    840

agagattctc gaagtcacta ttagcgcctc gttgtcaacg ggaatgtcgc ttaccactta    900

aagcataacg ccgagaaatc ccgtaataaa tccagtaaaa tacgagcacc cgtgccaagt    960

tgaatatttg aacccgagtg ggtagattcc accgcaaagg acctaaccag atcatttcgc   1020

aaacaggaac taaaatcggt agagagccca gacaaaagcc tttcctaaga gccactccag   1080

tggaagcccc tactttaggt ataaaatgca atactagtgg ggctcctaaa taaacttcta   1140

tttttcatgg ccttctaaaa ttcactccca aacccctagc tatagaagtc tcttatccat   1200

cctctaaata aaaatgggag tctattttat ttcaccagag ttgatcgtaa atttagtctc   1260

tcaaatttta taagttgagg gtagaggatg actggagttg ctctaaacgg acctatcttc   1320

aagtgacctc agtgagcccg tttaacggcg tcgacaagtt taatctaacg gacaccaacc   1380

agagaagaga accaccgcca gcgccgagcc aagcgacgtt gacatcttgg cgcggcacgg   1440

catctccctg gcgtctggcc ccctctcgag acttccgctc cacctcccac cggtggcggt   1500

ttccaagtcc gttccgcctc ctctcacacg gcacgaaacc gtgacgggca ccggcagcac   1560

ggggggattc ctttcccacc gctccttccc tttcccttcc tctcccgccg ctataaatag   1620

ccagccccat ccccagcttc tttc                                          1644
```

<210> SEQ ID NO 10
<211> LENGTH: 2613
<212> TYPE: DNA
<213> ORGANISM: Andropogon gerardii

<400> SEQUENCE: 10

```
tctagttgtg cgcgactgct gcttactttg gagattacaa tatctttcta aaatgcttcg     60

attacttatt tataaaccgt ctctaaggcc aattgctcaa gattcattca acaattgaaa    120

cgtctcacat gattaaatca tataaagttt ctaagtcttg tttgacaaga tttttttaga    180

ttttcatcta aattggatga aactatcaaa cactaatttt aaaaaatata agagaagctc    240

cggagataaa aggtcgtcta tgttattata agagtaaagt cgtctattct cttcgtccca    300

acatatataa ttctaagcat gaattgcttt ctttttggac aaaaggagca tgccacaaca    360

caagaatgat gtcaccgtca tgcttggatc cttttatggt aaagcttcac cttctataat    420

ctaacaatag agaaatcagg gaaaaatcat gttttggttg tttttatttc taacctccac    480

aataactttg gtttaccatt ttttgtttga ttttagtttt agagaagcgt ttataacagg    540

acctaaaatc tttttcagt acacagtaca acgcagacgc tcatacacgc acgcacactc    600

acctctatga acacacgtaa gaaaacccta caccttgagc accttcgaag gactgagccg    660

gtaaatatag agattctcga agtcactatt agcgcctcgt tgtcaacggg aatgtcgctt    720

accacttaaa gcataacgcc gagaaatccc gtaataaatc cagtaaaata cgagcacccg    780

tgccaagttg aatatttgaa cccgagtggg tagattccac cgcaaaggac ctaaccagat    840

catttcgcaa acaggaacta aaatcggtag agagcccaga caaaagcctt tcctaagagc    900

cactccagtg gaagcccccta ctttaggtat aaaatgcaat actagtgggg ctcctaaata    960

aacttctatt tttcatggcc ttctaaaatt cactcccaaa cccctagcta tagaagtctc   1020

ttatccatcc tctaaataaa aatgggagtc tattttattt caccagagtt gatcgtaaat   1080

ttagtctctc aaattttata agttgagggt agaggatgac tggagttgct ctaaacggac   1140
```

-continued

```
ctatcttcaa gtgacctcag tgagcccgtt taacggcgtc gacaagttta atctaacgga   1200
caccaaccag agaagagaac caccgccagc gccgagccaa gcgacgttga catcttggcg   1260
cggcacggca tctccctggc gtctggcccc ctctcgagac ttccgctcca cctcccaccg   1320
gtggcggttt ccaagtccgt tccgcctcct ctcacacggc acgaaaccgt gacgggcacc   1380
ggcagcacgg ggggattcct ttcccaccgc tccttccctt tcccttcctc tcccgccgct   1440
ataaatagcc agccccatcc ccagcttctt tccccaacct catcttctct cgtgttgttc   1500
ggcacaaccc gatcgatccc caactccctc gtcgtctctc ctcgcgagcc tcgtcgatcc   1560
cccgcttcaa ggtacggcga tcgattatct tccctctctc taccttctct ctcttatagg   1620
gcctgctagc tctgttcctg tttttccatg gctgcgaggt acaatagatc ggcgatccat   1680
ggttagggcc tgctagttgt gttcctgttt ttccatggct gcgaggcaca atagatctga   1740
tggcgttatg atggttaact tgtcatactc ttgcgatcta tggtcccttt aggagtttag   1800
gacatctatt taatttcgga tagttcgaga tctgtgatcc atggttagta ccctaggcag   1860
tggggttaga tccgtgctgt tatggttcgt agatggattc tgattgctca gtaactggga   1920
atcctgggat ggttctagct ggttcgcaga taagatcgat ttcatgatat gctatatctt   1980
gtttggttgc cgtggttccg ttaaatctgt ctgttatgat cttagtcttt gataaggttc   2040
ggtcgtgcta gctacgtcct gtgcagcact taattgtcag gtcataattt ttagcatgcc   2100
tttttttat tggtttggtt ttgtctgact gggctgtaga tagtttcaat ctttgtctga   2160
ctgggctgta gatagtttca atctacctgt cggtttattt tattaaattt ggatctgtat   2220
gtgtgtcata tatcttcatc ttttagatat atcgataggt ttatatgttg ctgtcggttt   2280
tttactgttc ctttatgaga tatattcatg cttagataca tgaaacaacg tgctgttaca   2340
gtttaatagt tcttgtttat ctaataaaca aataaggata ggtatatgct gcagttagtt   2400
ttactggtac ttttttgac atgaacctac ggcttaataa ttagtcttca tcaaataaaa   2460
agcatatttt ttaattattt cgatatactt gaatgatgtc atatgcagca tctgtgtgaa   2520
tttttggccc tgtcttcata tgctgtttat ttgtttggga ctgtttcttt ggttgataac   2580
tcatcctgtt gtttggtgat ccttttgcag gtg                              2613
```

<210> SEQ ID NO 11
<211> LENGTH: 1472
<212> TYPE: DNA
<213> ORGANISM: Andropogon gerardii

<400> SEQUENCE: 11

```
tctagttgtg cgcgactgct gcttactttg gagattacaa tatctttcta aaatgcttcg     60
attacttatt tataaaccgt ctctaaggcc aattgctcaa gattcattca acaattgaaa    120
cgtctcacat gattaaatca tataaagttt ctaagtcttg tttgacaaga tttttttaga    180
ttttcatcta aattggatga aactatcaaa cactaatttt aaaaaatata agagaagctc    240
cggagataaa aggtcgtcta tgttattata agagtaaagt cgtctattct cttcgtccca    300
acatatataa ttctaagcat gaattgcttt ctttttggac aaaaggagca tgccacaaca    360
caagaatgat gtcaccgtca tgcttggatc cttttatggt aaagcttcac cttctataat    420
ctaacaatag agaaatcagg gaaaaatcat gttttggttg tttttatttc taacctccac    480
aataactttg gtttaccatt ttttgtttga ttttagtttt agagaagcgt ttataacagg    540
acctaaaatc ttttttcagt acacagtaca acgcagacgc tcatacacgc acgcacactc    600
acctctatga acacacgtaa gaaaacccta caccttgagc accttcgaag gactgagccg    660
```

```
gtaaatatag agattctcga agtcactatt agcgcctcgt tgtcaacggg aatgtcgctt    720

accacttaaa gcataacgcc gagaaatccc gtaataaatc cagtaaaata cgagcacccg    780

tgccaagttg aatatttgaa cccgagtggg tagattccac cgcaaaggac ctaaccagat    840

catttcgcaa acaggaacta aaatcggtag agagcccaga caaaagcctt tcctaagagc    900

cactccagtg gaagccccta ctttaggtat aaaatgcaat actagtgggg ctcctaaata    960

aacttctatt tttcatggcc ttctaaaatt cactcccaaa cccctagcta tagaagtctc   1020

ttatccatcc tctaaataaa aatgggagtc tattttattt caccagagtt gatcgtaaat   1080

ttagtctctc aaattttata agttgagggt agaggatgac tggagttgct ctaaacggac   1140

ctatcttcaa gtgacctcag tgagcccgtt taacggcgtc gacaagttta atctaacgga   1200

caccaaccag agaagagaac caccgccagc gccgagccaa gcgacgttga catcttggcg   1260

cggcacggca tctccctggc gtctggcccc ctctcgagac ttccgctcca cctcccaccg   1320

gtggcggttt ccaagtccgt tccgcctcct ctcacacggc acgaaaccgt gacgggcacc   1380

ggcagcacgg ggggattcct ttcccaccgc tccttccctt tcccttcctc tcccgccgct   1440

ataaatagcc agccccatcc ccagcttctt tc                                 1472
```

<210> SEQ ID NO 12
<211> LENGTH: 2255
<212> TYPE: DNA
<213> ORGANISM: Andropogon gerardii

<400> SEQUENCE: 12

```
cacaagaatg atgtcaccgt catgcttgga tccttttatg gtaaagcttc accttctata     60

atctaacaat agagaaatca gggaaaaatc atgttttggt tgtttttatt tctaacctcc    120

acaataactt tggtttacca ttttttgttt gattttagtt ttagagaagc gtttataaca    180

ggacctaaaa tctttttttca gtacacagta caacgcagac gctcatacac gcacgcacac    240

tcacctctat gaacacacgt aagaaaaccc tacaccttga gcaccttcga aggactgagc    300

cggtaaatat agagattctc gaagtcacta ttagcgcctc gttgtcaacg ggaatgtcgc    360

ttaccactta aagcataacg ccgagaaatc ccgtaataaa tccagtaaaa tacgagcacc    420

cgtgccaagt tgaatatttg aacccgagtg ggtagattcc accgcaaagg acctaaccag    480

atcatttcgc aaacaggaac taaaatcggt agagagccca gacaaaagcc tttcctaaga    540

gccactccag tggaagcccc tactttaggt ataaaatgca atactagtgg ggctcctaaa    600

taaacttcta tttttcatgg ccttctaaaa ttcactccca aacccctagc tatagaagtc    660

tcttatccat cctctaaata aaaatgggag tctattttat ttcaccagag ttgatcgtaa    720

atttagtctc tcaaatttta taagttgagg gtagaggatg actggagttg ctctaaacgg    780

acctatcttc aagtgacctc agtgagcccg tttaacggcg tcgacaagtt taatctaacg    840

gacaccaacc agagaagaga accaccgcca gcgccgagcc aagcgacgtt gacatcttgg    900

cgcggcacgg catctccctg gcgtctggcc ccctctcgag acttccgctc cacctcccac    960

cggtggcggt ttccaagtcc gttccgcctc ctctcacacg gcacgaaacc gtgacgggca   1020

ccggcagcac ggggggattc ctttcccacc gctccttccc tttcccttcc tctcccgccg   1080

ctataaatag ccagccccat ccccagcttc tttccccaac ctcatcttct ctcgtgttgt   1140

tcggcacaac ccgatcgatc cccaactccc tcgtcgtctc tcctcgcgag cctcgtcgat   1200

cccccgcttc aaggtacggc gatcgattat cttccctctc tctaccttct ctctcttata   1260
```

gggcctgcta gctctgttcc tgtttttcca tggctgcgag gtacaataga tcggcgatcc 1320
atggttaggg cctgctagtt gtgttcctgt ttttccatgg ctgcgaggca caatagatct 1380
gatggcgtta tgatggttaa cttgtcatac tcttgcgatc tatggtccct ttaggagttt 1440
aggacatcta tttaatttcg gatagttcga gatctgtgat ccatggttag taccctaggc 1500
agtggggtta gatccgtgct gttatggttc gtagatggat tctgattgct cagtaactgg 1560
gaatcctggg atggttctag ctggttcgca gataagatcg atttcatgat atgctatatc 1620
ttgtttggtt gccgtggttc cgttaaatct gtctgttatg atcttagtct ttgataaggt 1680
tcggtcgtgc tagctacgtc ctgtgcagca cttaattgtc aggtcataat ttttagcatg 1740
cctttttttt attggtttgg ttttgtctga ctgggctgta gatagtttca atctttgtct 1800
gactgggctg tagatagttt caatctacct gtcggtttat tttattaaat ttggatctgt 1860
atgtgtgtca tatatcttca tcttttagat atatcgatag gtttatatgt tgctgtcggt 1920
tttttactgt tcctttatga gatatattca tgcttagata catgaaacaa cgtgctgtta 1980
cagtttaata gttcttgttt atctaataaa caaataagga taggtatatg ctgcagttag 2040
ttttactggt actttttttg acatgaacct acggcttaat aattagtctt catcaaataa 2100
aaagcatatt ttttaattat ttcgatatac ttgaatgatg tcatatgcag catctgtgtg 2160
aatttttggc cctgtcttca tatgctgttt atttgtttgg gactgtttct ttggttgata 2220
actcatcctg ttgtttggtg atccttttgc aggtg 2255

<210> SEQ ID NO 13
<211> LENGTH: 1114
<212> TYPE: DNA
<213> ORGANISM: Andropogon gerardii

<400> SEQUENCE: 13
cacaagaatg atgtcaccgt catgcttgga tccttttatg gtaaagcttc accttctata 60
atctaacaat agagaaatca gggaaaaatc atgttttggt tgtttttatt tctaacctcc 120
acaataactt tggtttacca ttttttgttt gattttagtt ttagagaagc gtttataaca 180
ggacctaaaa tcttttttca gtacacagta caacgcagac gctcatacac gcacgcacac 240
tcacctctat gaacacacgt aagaaaaccc tacaccttga gcaccttcga aggactgagc 300
cggtaaatat agagattctc gaagtcacta ttagcgcctc gttgtcaacg ggaatgtcgc 360
ttaccactta aagcataacg ccgagaaatc ccgtaataaa tccagtaaaa tacgagcacc 420
cgtgccaagt tgaatatttg aacccgagtg ggtagattcc accgcaaagg acctaaccag 480
atcatttcgc aaacaggaac taaaatcggt agagagccca gacaaaagcc tttcctaaga 540
gccactccag tggaagcccc tactttaggt ataaaatgca atactagtgg ggctcctaaa 600
taaacttcta tttttcatgg ccttctaaaa ttcactccca aacccctagc tatagaagtc 660
tcttatccat cctctaaata aaaatgggag tctattttat ttcaccagag ttgatcgtaa 720
atttagtctc tcaaatttta taagttgagg gtagaggatg actggagttg ctctaaacgg 780
acctatcttc aagtgacctc agtgagcccg tttaacggcg tcgacaagtt taatctaacg 840
gacaccaacc agagaagaga accaccgcca gcgccgagcc aagcgacgtt gacatcttgg 900
cgcggcacgg catctccctg gcgtctggcc ccctctcgag acttccgctc cacctcccac 960
cggtggcggt ttccaagtcc gttccgcctc ctctcacacg gcacgaaacc gtgacgggca 1020
ccggcagcac ggggggattc ctttcccacc gctccttccc tttcccttcc tctcccgccg 1080
ctataaatag ccagccccat ccccagcttc tttc 1114

<210> SEQ ID NO 14
<211> LENGTH: 1912
<212> TYPE: DNA
<213> ORGANISM: Andropogon gerardii

<400> SEQUENCE: 14
gtcaacggga atgtcgctta ccacttaaag cataacgccg agaaatcccg taataaatcc 60
agtaaaatac gagcacccgt gccaagttga atatttgaac ccgagtgggt agattccacc 120
gcaaaggacc taaccagatc atttcgcaaa caggaactaa aatcggtaga gagcccagac 180
aaaagccttt cctaagagcc actccagtgg aagcccctac tttaggtata aaatgcaata 240
ctagtggggc tcctaaataa acttctattt ttcatggcct tctaaaattc actcccaaac 300
ccctagctat agaagtctct tatccatcct ctaaataaaa atgggagtct attttatttc 360
accagagttg atcgtaaatt tagtctctca aattttataa gttgagggta gaggatgact 420
ggagttgctc taaacggacc tatcttcaag tgacctcagt gagcccgttt aacggcgtcg 480
acaagtttaa tctaacggac accaaccaga gaagagaacc accgccagcg ccgagccaag 540
cgacgttgac atcttggcgc ggcacggcat ctccctggcg tctggccccc tctcgagact 600
tccgctccac ctcccaccgg tggcggtttc caagtccgtt ccgcctcctc tcacacggca 660
cgaaaccgtg acgggcaccg gcagcacggg gggattcctt tcccaccgct ccttcccttt 720
cccttcctct cccgccgcta taaatagcca gccccatccc cagcttcttt ccccaacctc 780
atcttctctc gtgttgttcg gcacaacccg atcgatcccc aactccctcg tcgtctctcc 840
tcgcgagcct cgtcgatccc ccgcttcaag gtacggcgat cgattatctt ccctctctct 900
accttctctc tcttataggg cctgctagct ctgttcctgt ttttccatgg ctgcgaggta 960
caatagatcg gcgatccatg gttagggcct gctagttgtg ttcctgtttt tccatggctg 1020
cgaggcacaa tagatctgat ggcgttatga tggttaactt gtcatactct tgcgatctat 1080
ggtcccttta ggagtttagg acatctattt aatttcggat agttcgagat ctgtgatcca 1140
tggttagtac cctaggcagt ggggttagat ccgtgctgtt atggttcgta gatggattct 1200
gattgctcag taactgggaa tcctgggatg gttctagctg gttcgcagat aagatcgatt 1260
tcatgatatg ctatatcttg tttggttgcc gtggttccgt taaatctgtc tgttatgatc 1320
ttagtctttg ataaggttcg gtcgtgctag ctacgtcctg tgcagcactt aattgtcagg 1380
tcataatttt tagcatgcct ttttttatt ggtttggttt tgtctgactg ggctgtagat 1440
agtttcaatc tttgtctgac tgggctgtag atagtttcaa tctacctgtc ggtttatttt 1500
attaaatttg gatctgtatg tgtgtcatat atcttcatct tttagatata tcgataggtt 1560
tatatgttgc tgtcggtttt ttactgttcc tttatgagat atattcatgc ttagatacat 1620
gaaacaacgt gctgttacag tttaatagtt cttgtttatc taataaacaa ataaggatag 1680
gtatatgctg cagttagttt tactggtact ttttttgaca tgaacctacg gcttaataat 1740
tagtcttcat caaataaaaa gcatattttt taattatttc gatatacttg aatgatgtca 1800
tatgcagcat ctgtgtgaat ttttggccct gtcttcatat gctgtttatt tgtttgggac 1860
tgtttctttg gttgataact catcctgttg tttggtgatc cttttgcagg tg 1912

<210> SEQ ID NO 15
<211> LENGTH: 771
<212> TYPE: DNA
<213> ORGANISM: Andropogon gerardii

<400> SEQUENCE: 15
gtcaacggga atgtcgctta ccacttaaag cataacgccg agaaatcccg taataaatcc 60
agtaaaatac gagcacccgt gccaagttga atatttgaac ccgagtgggt agattccacc 120
gcaaaggacc taaccagatc atttcgcaaa caggaactaa aatcggtaga gagcccagac 180
aaaagccttt cctaagagcc actccagtgg aagcccctac tttaggtata aaatgcaata 240
ctagtggggc tcctaaataa acttctattt ttcatggcct tctaaaattc actcccaaac 300
ccctagctat agaagtctct tatccatcct ctaaataaaa atgggagtct attttatttc 360
accagagttg atcgtaaatt tagtctctca aattttataa gttgagggta gaggatgact 420
ggagttgctc taaacggacc tatcttcaag tgacctcagt gagcccgttt aacggcgtcg 480
acaagtttaa tctaacggac accaaccaga gaagagaacc accgccagcg ccgagccaag 540
cgacgttgac atcttggcgc ggcacggcat ctccctggcg tctggccccc tctcgagact 600
tccgctccac ctcccaccgg tggcggtttc caagtccgtt ccgcctcctc tcacacggca 660
cgaaaccgtg acgggcaccg gcagcacggg ggattccttt tcccaccgct ccttcccttt 720
cccttcctct cccgccgcta taaatagcca gccccatccc cagcttcttt c 771

<210> SEQ ID NO 16
<211> LENGTH: 1623
<212> TYPE: DNA
<213> ORGANISM: Andropogon gerardii

<400> SEQUENCE: 16
cactcccaaa cccctagcta tagaagtctc ttatccatcc tctaaataaa aatgggagtc 60
tattttattt caccagagtt gatcgtaaat ttagtctctc aaattttata agttgagggt 120
agaggatgac tggagttgct ctaaacggac ctatcttcaa gtgacctcag tgagcccgtt 180
taacggcgtc gacaagttta atctaacgga caccaaccag agaagagaac caccgccagc 240
gccgagccaa gcgacgttga catcttggcg cggcacggca tctccctggc gtctggcccc 300
ctctcgagac ttccgctcca cctcccaccg gtggcggttt ccaagtccgt tccgcctcct 360
ctcacacggc acgaaaccgt gacgggcacc ggcagcacgg ggggattcct ttcccaccgc 420
tccttccctt tcccttcctc tcccgccgct ataaatagcc agccccatcc ccagcttctt 480
tccccaacct catcttctct cgtgttgttc ggcacaaccc gatcgatccc caactccctc 540
gtcgtctctc ctcgcgagcc tcgtcgatcc cccgcttcaa ggtacggcga tcgattatct 600
tccctctctc taccttctct ctcttatagg gcctgctagc tctgttcctg tttttccatg 660
gctgcgaggt acaatagatc ggcgatccat ggttagggcc tgctagttgt gttcctgttt 720
ttccatggct gcgaggcaca atagatctga tggcgttatg atggttaact tgtcatactc 780
ttgcgatcta tggtcccttt aggagtttag gacatctatt taatttcgga tagttcgaga 840
tctgtgatcc atggttagta ccctaggcag tggggttaga tccgtgctgt tatggttcgt 900
agatggattc tgattgctca gtaactggga atcctgggat ggttctagct ggttcgcaga 960
taagatcgat ttcatgatat gctatatctt gtttggttgc cgtggttccg ttaaatctgt 1020
ctgttatgat cttagtcttt gataaggttc ggtcgtgcta gctacgtcct gtgcagcact 1080
taattgtcag gtcataattt ttagcatgcc ttttttttat tggtttggtt ttgtctgact 1140
gggctgtaga tagtttcaat ctttgtctga ctgggctgta gatagtttca atctacctgt 1200
cggtttattt tattaaattt ggatctgtat gtgtgtcata tatcttcatc ttttagatat 1260
atcgataggt ttatatgttg ctgtcggttt tttactgttc ctttatgaga tatattcatg 1320

-continued

```
cttagataca tgaaacaacg tgctgttaca gtttaatagt tcttgtttat ctaataaaca   1380

aataaggata ggtatatgct gcagttagtt ttactggtac tttttttgac atgaacctac   1440

ggcttaataa ttagtcttca tcaaataaaa agcatatttt ttaattattt cgatatactt   1500

gaatgatgtc atatgcagca tctgtgtgaa tttttggccc tgtcttcata tgctgtttat   1560

ttgtttggga ctgtttcttt ggttgataac tcatcctgtt gtttggtgat ccttttgcag   1620

gtg                                                                 1623


<210> SEQ ID NO 17
<211> LENGTH: 482
<212> TYPE: DNA
<213> ORGANISM: Andropogon gerardii

<400> SEQUENCE: 17

cactcccaaa cccctagcta tagaagtctc ttatccatcc tctaaataaa aatgggagtc     60

tattttattt caccagagtt gatcgtaaat ttagtctctc aaattttata agttgagggt    120

agaggatgac tggagttgct ctaaacggac ctatcttcaa gtgacctcag tgagcccgtt    180

taacggcgtc gacaagttta atctaacgga caccaaccag agaagagaac caccgccagc    240

gccgagccaa gcgacgttga catcttggcg cggcacggca tctccctggc gtctggcccc    300

ctctcgagac ttccgctcca cctcccaccg gtggcggttt ccaagtccgt tccgcctcct    360

ctcacacggc acgaaaccgt gacgggcacc ggcagcacgg ggggattcct ttcccaccgc    420

tccttccctt tcccttcctc tcccgccgct ataaatagcc agccccatcc ccagcttctt    480

tc                                                                   482


<210> SEQ ID NO 18
<211> LENGTH: 3483
<212> TYPE: DNA
<213> ORGANISM: Saccharum ravennae

<400> SEQUENCE: 18

gtggccagct tttgttctag ttcaacggcc ccggccttcc gggcacctaa taccctaatt     60

aatctattgc agctaacctc aaaagaaatg catttgcagt tgtctgtccc aatcaatcta    120

ctagcagact tacattatag atggaggaaa ttaaattcag cctttgacgt ggatgcaaca    180

actgcactgc acaggatacc atcttagccg ttgtgtcaaa gtttgctttg ctaaacgttt    240

tgagaaaacc agctttgacc aacgcgagat gagcgcctta cgtttggcac aatgtaatgt    300

aatccggcac ggcaagttag actctgtagt gttagccggc ctctttacgt ttggcatagt    360

ttaattgaat ccggcatggc aagttagacc gtagtgtgag ccggccaacg caagttatta    420

tgacatatgt ataagagcaa gtgtattgtc acgtgatatt tatgttgaga tgaagaagag    480

aaaataaaca gcctgcaaat ttatagcgag tgatagatgg gcacaaggct tcctatttct    540

taaatcagac tttgtaagaa caaaaaaagg acttataaga gaatgggata aaccatatat    600

caatggtgta gtatgttagt atgcattaag atctgactat tatatgagtg agttgttaaa    660

ttcattttag gtgacatggc ccggttaaat tattagccat accctaacag ctctaaaaaa    720

gatatattcg ttgaggcact tttatgcaac cacatagtca acttgaatgc cgcttgagtg    780

cgttctcaag tttttttct tgcaaattac gcttttttaa gaaagtataa tttggatcgt    840

gcgatttttt ttctctaggt gtgcgtgact gtgtgagtaa caattttgga tctcagaaag    900

gtaataaaag aataatactg ctgcctactt tgaggattac aatatctttc tctaaaatgt    960
```

-continued

```
tttggtttgt tatttaaacc gtctttaagg ccaattgctc aagattcatt caacaattga   1020
aacgtctcac atgattaaat catataaggt tgctaaggtc ttgtttgaca aggttttttt   1080
tgtggaaatt tcatctaaat ttttgagtga aactatcaaa tactaattta aaaaaggcaa   1140
attttgctgg aggacactgc agaaacgtgt aattggccgg cacaaaccgc caaacggaga   1200
atttgcccag taccattata aattcatgat aaattcatgg ttgtttgcca gtggggctag   1260
ggttcctcgc gtatggtgcg gaatgtggtt tggttcgacc aactcgaact caatccgatc   1320
caaaggggca tcaatagtca ttttagaaag tttctctctc ccgagcagtg gaaatgatta   1380
ttctatttgg cgcgatgtcc accggcaaac aaccacgaat ttgtaatggt actaggcaaa   1440
ttctccgttt ggcggtgtgt gccggccaat tacacgtttt tgcggtgtcc tccgacaaaa   1500
tttgcctttt aaaaacaatt ttataagaga agctccggag ataaaaggcc gtcaatgtta   1560
caagagtgaa gtcgtctact ccctccatcc caaaaaatgt aattctaagt atgagttgta   1620
ttattatttt tggacaaaag gagtatacca caagaatgat atcatcgtca tgcttagatc   1680
ctttttagta aagcttgagc ttctctaaaa gtagagaaat tagaaaaaaa tcacgttttt   1740
gtggtcttga tttctagcct ccacaaaatc tttggtttta catttttttgt ttgattttgg   1800
tttcagaagt ccttatttat atgtgctagt ttggcagcac ttaaaatcgt tagagagagc   1860
ctaaacaaaa gccttttcaa aacgaccttg agccagattg gttgatggcc aaaatttgat   1920
tgtcaaaact taggcaagcc aagattttag cagctatttg gtttggtacc aaaatttgcc   1980
aatgatctgt tcttttgcct tttcaaccgg tttatcagcc gtacttcagc ttattctctc   2040
tcacagaaca ctattgaatc agccgaaaag ccaccgcaga acaggaccag tatctcacaa   2100
atggcatgcc aaatatactc accgtcagtg agcccgttta acggcgtcga caagtctaac   2160
ggccaccaac cagcgaacca ccagcgtcaa gctagccaag cgaagcagac ggccgagacg   2220
ttgacacctt ggcgcgggca tctctctggc cccctctcga gagttccgct ccacctccac   2280
tggtggcggt ttccaagtcc gttccgcctc ctgctcctcc tcacacggca cgaaaccgtc   2340
acggcaccgg cagcacgggg gattcctttc ccaccgctcc ttccctttcc cttcctcgcc   2400
cgccgtttta aatagccagc cccatcccca gcttctctcc ccgtacggcg atcatcctcc   2460
ctttctctac cttctcttct ctagactagg tcggcgatcc atggttaggg cctgctagtt   2520
ctgttcctgt ttttccgtgg ctgcgaggta caatagatct gatggcgtta tgatggttaa   2580
cttgtcatac tcctgcggtg tgcggtctat agtgctttta ggacatcaat ttgacctggc   2640
tcgttcgaga tcggcgatcc atggttagga ccctaggcgg tggagtcggg ttagatccgc   2700
gctgtttgtg ttagtagatg gatgcgacct ttacttcaga cacgttctga ttgttaactt   2760
gtcagcacct gggagtcctg ggatggttct agctggttcg cagatgagat cgatttcatg   2820
atctgctgta tcttgtttcg ttaggttcct tttaatctat ccgtggtatt atgctaacct   2880
atgatatggt tcgatcgtgc tagctacgtc ctgtgtcata atttttagca tgcccttttt   2940
tgtttggttt tgtctgattg ggctgtagat cagagtatac tgtttcaaac tacctactgg   3000
atatatttat taaatttgaa tctgtatgtg tgtcacatat atcttcataa ttaaaatgga   3060
tggaaagata tatggatagg tacatgtgtt gctgtgggtt ttactggtac tttgttagat   3120
atacatgctt agatacatga agcaacatga tgttacagtt caataattct tgtttaccta   3180
ataaacaaat aaggataggt gtatgttgct gtgggttttg ctggtacttt gttagatata   3240
tatgcttaga tatatgaagc aacatcctgc tacggtttaa taattattgt ttatatctaa   3300
tagacaagcc tgctttttaa ttattttgat atacttggat gatggcatac agcagctatg   3360
```

tgtggatttt taaataccca gcatcatgag catgcatgac cctgccttag tatgctgttt 3420
atttgcttga gacttctttt tttgttggta ctcacctttt gtagtttggt gactcttctg 3480
cag 3483

<210> SEQ ID NO 19
<211> LENGTH: 2536
<212> TYPE: DNA
<213> ORGANISM: Saccharum ravennae

<400> SEQUENCE: 19
gtggccagct tttgttctag ttcaacggcc ccggccttcc gggcacctaa taccctaatt 60
aatctattgc agctaacctc aaaagaaatg catttgcagt tgtctgtccc aatcaatcta 120
ctagcagact tacattatag atggaggaaa ttaaattcag cctttgacgt ggatgcaaca 180
actgcactgc acaggatacc atcttagccg ttgtgtcaaa gtttgctttg ctaaacgttt 240
tgagaaaacc agctttgacc aacgcgagat gagcgcctta cgtttggcac aatgtaatgt 300
aatccggcac ggcaagttag actctgtagt gttagccggc ctctttacgt ttggcatagt 360
ttaattgaat ccggcatggc aagttagacc gtagtgtgag ccggccaacg caagttatta 420
tgacatatgt ataagagcaa gtgtattgtc acgtgatatt tatgttgaga tgaagaagag 480
aaaataaaca gcctgcaaat ttatagcgag tgatagatgg gcacaaggct tcctatttct 540
taaatcagac tttgtaagaa caaaaaaagg acttataaga gaatgggata aaccatatat 600
caatggtgta gtatgttagt atgcattaag atctgactat tatatgagtg agttgttaaa 660
ttcattttag gtgacatggc ccggttaaat tattagccat accctaacag ctctaaaaaa 720
gatatattcg ttgaggcact tttatgcaac cacatagtca acttgaatgc cgcttgagtg 780
cgttctcaag ttttttttct tgcaaattac gcttttttaa gaaagtataa tttggatcgt 840
gcgatttttt ttctctaggt gtgcgtgact gtgtgagtaa caattttgga tctcagaaag 900
gtaataaaag aataatactg ctgcctactt tgaggattac aatatctttc tctaaaatgt 960
tttggtttgt tatttaaacc gtctttaagg ccaattgctc aagattcatt caacaattga 1020
aacgtctcac atgattaaat catataaggt tgctaaggtc ttgtttgaca aggttttttt 1080
tgtggaaatt tcatctaaat ttttgagtga aactatcaaa tactaattta aaaaaggcaa 1140
attttgctgg aggacactgc agaaacgtgt aattggccgg cacaaaccgc caaacggaga 1200
atttgcccag taccattata aattcatgat aaattcatgg ttgtttgcca gtggggctag 1260
ggttcctcgc gtatggtgcg gaatgtggtt tggttcgacc aactcgaact caatccgatc 1320
caaaggggca tcaatagtca ttttagaaag tttctctctc ccgagcagtg gaaatgatta 1380
ttctatttgg cgcgatgtcc accggcaaac aaccacgaat ttgtaatggt actaggcaaa 1440
ttctccgttt ggcggtgtgt gccggccaat tacacgtttt tgcggtgtcc tccgacaaaa 1500
tttgcctttt aaaaacaatt ttataagaga agctccggag ataaaaggcc gtcaatgtta 1560
caagagtgaa gtcgtctact ccctccatcc caaaaaatgt aattctaagt atgagttgta 1620
ttattatttt tggacaaaag gagtatacca caagaatgat atcatcgtca tgcttagatc 1680
ctttttagta aagcttgagc ttctctaaaa gtagagaaat tagaaaaaaa tcacgttttt 1740
gtggtcttga tttctagcct ccacaaaatc tttggtttta catttttttgt ttgattttgg 1800 tttcagaagt ccttatttat atgtgctagt ttggcagcac ttaaaatcgt tagagagagc 1860
ctaaacaaaa gccttttcaa aacgaccttg agccagattg gttgatggcc aaaatttgat 1920
tgtcaaaact taggcaagcc aagattttag cagctatttg gtttggtacc aaaatttgcc 1980
aatgatctgt tcttttgcct tttcaaccgg tttatcagcc gtacttcagc ttattctctc 2040
tcacagaaca ctattgaatc agccgaaaag ccaccgcaga acaggaccag tatctcacaa 2100
atggcatgcc aaatatactc accgtcagtg agcccgttta acggcgtcga caagtctaac 2160
ggccaccaac cagcgaacca ccagcgtcaa gctagccaag cgaagcagac ggccgagacg 2220
ttgacacctt ggcgcgggca tctctctggc cccctctcga gagttccgct ccacctccac 2280
tggtggcggt ttccaagtcc gttccgcctc ctgctcctcc tcacacggca cgaaaccgtc 2340
acggcaccgg cagcacgggg gattcctttc ccaccgctcc ttccctttcc cttcctcgcc 2400
cgccgtttta aatagccagc cccatcccca gcttctctcc ccaacctcag cttctctcgt 2460
tgttcggagc gcacacacaa cccgatcccc aatcccctcg tctctcctcg cgagcctcgt 2520
cgatccccgc ttcaag 2536

<210> SEQ ID NO 20
<211> LENGTH: 94
<212> TYPE: DNA
<213> ORGANISM: Saccharum ravennae

<400> SEQUENCE: 20
aacctcagct tctctcgttg ttcggagcgc acacacaacc cgatccccaa tcccctcgtc 60
tctcctcgcg agcctcgtcg atccccgctt caag 94

<210> SEQ ID NO 21
<211> LENGTH: 1041
<212> TYPE: DNA
<213> ORGANISM: Saccharum ravennae

<400> SEQUENCE: 21
gtacggcgat catcctccct ttctctacct tctcttctct agactaggtc ggcgatccat 60
ggttagggcc tgctagttct gttcctgttt ttccgtggct gcgaggtaca atagatctga 120
tggcgttatg atggttaact tgtcatactc ctgcggtgtg cggtctatag tgcttttagg 180
acatcaattt gacctggctc gttcgagatc ggcgatccat ggttaggacc ctaggcggtg 240
gagtcgggtt agatccgcgc tgtttgtgtt agtagatgga tgcgaccttt acttcagaca 300
cgttctgatt gttaacttgt cagcacctgg gagtcctggg atggttctag ctggttcgca 360
gatgagatcg atttcatgat ctgctgtatc ttgtttcgtt aggttccttt taatctatcc 420
gtggtattat gctaacctat gatatggttc gatcgtgcta gctacgtcct gtgtcataat 480
ttttagcatg cccttttttg tttggttttg tctgattggg ctgtagatca gagtatactg 540
tttcaaacta cctactggat atatttatta aatttgaatc tgtatgtgtg tcacatatat 600
cttcataatt aaaatggatg gaaagatata tggataggta catgtgttgc tgtgggtttt 660
actggtactt tgttagatat acatgcttag atacatgaag caacatgatg ttacagttca 720
ataattcttg tttacctaat aaacaaataa ggataggtgt atgttgctgt gggttttgct 780
ggtactttgt tagatatata tgcttagata tatgaagcaa catcctgcta cggtttaata 840
attattgttt atatctaata gacaagcctg ctttttaatt attttgatat acttggatga 900
tggcatacag cagctatgtg tggattttta aatacccagc atcatgagca tgcatgaccc 960
tgccttagta tgctgtttat ttgcttgaga cttctttttt tgttggtact caccttttgt 1020
agtttggtga ctcttctgca g 1041

<210> SEQ ID NO 22
<211> LENGTH: 3152
<212> TYPE: DNA
<213> ORGANISM: Saccharum ravennae

<400> SEQUENCE: 22
gtataagagc aagtgtattg tcacgtgata tttatgttga gatgaagaag agaaaataaa 60
cagcctgcaa atttatagcg agtgatagat gggcacaagg cttcctattt cttaaatcag 120
actttgtaag aacaaaaaaa ggacttataa gagaatggga taaaccatat atcaatggtg 180
tagtatgtta gtatgcatta agatctgact attatatgag tgagttgtta aattcatttt 240
aggtgacatg gcccggttaa attattagcc ataccctaac agctctaaaa aagatatatt 300
cgttgaggca cttttatgca accacatagt caacttgaat gccgcttgag tgcgttctca 360
agtttttttt cttgcaaatt acgctttttt aagaaagtat aatttggatc gtgcgatttt 420
ttttctctag gtgtgcgtga ctgtgtgagt aacaattttg gatctcagaa aggtaataaa 480
agaataatac tgctgcctac tttgaggatt acaatatctt tctctaaaat gttttggttt 540
gttatttaaa ccgtctttaa ggccaattgc tcaagattca ttcaacaatt gaaacgtctc 600
acatgattaa atcatataag gttgctaagg tcttgtttga caaggttttt tttgtggaaa 660
tttcatctaa atttttgagt gaaactatca aatactaatt taaaaaaggc aaattttgct 720
ggaggacact gcagaaacgt gtaattggcc ggcacaaacc gccaaacgga gaatttgccc 780
agtaccatta taaattcatg ataaattcat ggttgtttgc cagtggggct agggttcctc 840
gcgtatggtg cggaatgtgg tttggttcga ccaactcgaa ctcaatccga tccaaagggg 900
catcaatagt cattttagaa agtttctctc tcccgagcag tggaaatgat tattctattt 960
ggcgcgatgt ccaccggcaa acaaccacga atttgtaatg gtactaggca aattctccgt 1020
ttggcggtgt gtgccggcca attacacgtt tttgcggtgt cctccgacaa aatttgcctt 1080
ttaaaaacaa ttttataaga gaagctccgg agataaaagg ccgtcaatgt tacaagagtg 1140
aagtcgtcta ctccctccat cccaaaaaat gtaattctaa gtatgagttg tattattatt 1200
tttggacaaa aggagtatac cacaagaatg atatcatcgt catgcttaga tcctttttag 1260
taaagcttga gcttctctaa aagtagagaa attagaaaaa aatcacgttt ttgtggtctt 1320
gatttctagc ctccacaaaa tctttggttt tacatttttt gtttgatttt ggtttcagaa 1380
gtccttattt atatgtgcta gtttggcagc acttaaaatc gttagagaga gcctaaacaa 1440
aagccttttc aaaacgacct tgagccagat tggttgatgg ccaaaatttg attgtcaaaa 1500
cttaggcaag ccaagatttt agcagctatt tggtttggta ccaaaatttg ccaatgatct 1560
gttcttttgc cttttcaacc ggtttatcag ccgtacttca gcttattctc tctcacagaa 1620
cactattgaa tcagccgaaa agccaccgca gaacaggacc agtatctcac aaatggcatg 1680
ccaaatatac tcaccgtcag tgagcccgtt taacggcgtc gacaagtcta acggccacca 1740
accagcgaac caccagcgtc aagctagcca agcgaagcag acggccgaga cgttgacacc 1800
ttggcgcggg catctctctg gccccctctc gagagttccg ctccacctcc actggtggcg 1860
gtttccaagt ccgttccgcc tcctgctcct cctcacacgg cacgaaaccg tcacggcacc 1920
ggcagcacgg gggattcctt tcccaccgct ccttcccttt cccttcctcg cccgccgttt 1980
taaatagcca gccccatccc cagcttctct ccccaacctc agcttctctc gttgttcgga 2040
gcgcacacac aacccgatcc ccaatcccct cgtctctcct cgcgagcctc gtcgatcccc 2100
gcttcaaggt acggcgatca tcctcccttt ctctaccttc tcttctctag actaggtcgg 2160

```
cgatccatgg ttagggcctg ctagttctgt tcctgttttt ccgtggctgc gaggtacaat   2220
agatctgatg gcgttatgat ggttaacttg tcatactcct gcggtgtgcg gtctatagtg   2280
cttttaggac atcaatttga cctggctcgt tcgagatcgg cgatccatgg ttaggaccct   2340
aggcggtgga gtcgggttag atccgcgctg tttgtgttag tagatggatg cgacctttac   2400
ttcagacacg ttctgattgt taacttgtca gcacctggga gtcctgggat ggttctagct   2460
ggttcgcaga tgagatcgat ttcatgatct gctgtatctt gtttcgttag gttcctttta   2520
atctatccgt ggtattatgc taacctatga tatggttcga tcgtgctagc tacgtcctgt   2580
gtcataattt ttagcatgcc ctttttttgtt tggttttgtc tgattgggct gtagatcaga   2640
gtatactgtt tcaaactacc tactggatat atttattaaa tttgaatctg tatgtgtgtc   2700
acatatatct tcataattaa aatggatgga aagatatatg gataggtaca tgtgttgctg   2760
tgggttttac tggtactttg ttagatatac atgcttagat acatgaagca acatgatgtt   2820
acagttcaat aattcttgtt tacctaataa acaaataagg ataggtgtat gttgctgtgg   2880
gttttgctgg tactttgtta gatatatatg cttagatata tgaagcaaca tcctgctacg   2940
gtttaataat tattgtttat atctaataga caagcctgct ttttaattat tttgatatac   3000
ttggatgatg gcatacagca gctatgtgtg gatttttaaa tacccagcat catgagcatg   3060
catgaccctg ccttagtatg ctgtttattt gcttgagact tcttttttttg ttggtactca   3120
ccttttgtag tttggtgact cttctgcagg tg                                 3152
```

<210> SEQ ID NO 23
<211> LENGTH: 2014
<212> TYPE: DNA
<213> ORGANISM: Saccharum ravennae

<400> SEQUENCE: 23

```
gtataagagc aagtgtattg tcacgtgata tttatgttga gatgaagaag agaaaataaa     60
cagcctgcaa atttatagcg agtgatagat gggcacaagg cttcctattt cttaaatcag    120
actttgtaag aacaaaaaaa ggacttataa gagaatggga taaaccatat atcaatggtg    180
tagtatgtta gtatgcatta agatctgact attatatgag tgagttgtta aattcatttt    240
aggtgacatg gcccggttaa attattagcc ataccctaac agctctaaaa aagatatatt    300
cgttgaggca cttttatgca accacatagt caacttgaat gccgcttgag tgcgttctca    360
agttttttttt cttgcaaatt acgctttttt aagaaagtat aatttggatc gtgcgatttt    420
ttttctctag gtgtgcgtga ctgtgtgagt aacaattttg gatctcagaa aggtaataaa    480
agaataatac tgctgcctac tttgaggatt acaatatctt tctctaaaat gttttggttt    540
gttatttaaa ccgtctttaa ggccaattgc tcaagattca ttcaacaatt gaaacgtctc    600
acatgattaa atcatataag gttgctaagg tcttgtttga caaggttttt tttgtggaaa    660
tttcatctaa atttttgagt gaaactatca aatactaatt taaaaaaggc aaattttgct    720
ggaggacact gcagaaacgt gtaattggcc ggcacaaacc gccaaacgga gaatttgccc    780
agtaccatta taaattcatg ataaattcat ggttgtttgc cagtggggct agggttcctc    840
gcgtatggtg cggaatgtgg tttggttcga ccaactcgaa ctcaatccga tccaaagggg    900
catcaatagt catttttagaa agtttctctc tcccgagcag tggaaatgat tattctattt    960
ggcgcgatgt ccaccggcaa acaaccacga atttgtaatg gtactaggca aattctccgt   1020
ttggcggtgt gtgccggcca attacacgtt tttgcggtgt cctccgacaa aatttgcctt   1080
ttaaaaacaa ttttataaga gaagctccgg agataaaagg ccgtcaatgt tacaagagtg   1140
```

aagtcgtcta ctccctccat cccaaaaaat gtaattctaa gtatgagttg tattattatt 1200
tttggacaaa aggagtatac cacaagaatg atatcatcgt catgcttaga tcctttttag 1260
taaagcttga gcttctctaa aagtagagaa attagaaaaa aatcacgttt ttgtggtctt 1320
gatttctagc ctccacaaaa tctttggttt tacatttttt gtttgatttt ggtttcagaa 1380
gtccttattt atatgtgcta gtttggcagc acttaaaatc gttagagaga gcctaaacaa 1440
aagccttttc aaaacgacct tgagccagat tggttgatgg ccaaaatttg attgtcaaaa 1500
cttaggcaag ccaagatttt agcagctatt tggtttggta ccaaaatttg ccaatgatct 1560
gttcttttgc cttttcaacc ggtttatcag ccgtacttca gcttattctc tctcacagaa 1620
cactattgaa tcagccgaaa agccaccgca gaacaggacc agtatctcac aaatggcatg 1680
ccaaatatac tcaccgtcag tgagcccgtt taacggcgtc gacaagtcta acggccacca 1740
accagcgaac caccagcgtc aagctagcca agcgaagcag acggccgaga cgttgacacc 1800
ttggcgcggg catctctctg gccccctctc gagagttccg ctccacctcc actggtggcg 1860
gtttccaagt ccgttccgcc tcctgctcct cctcacacgg cacgaaaccg tcacggcacc 1920
ggcagcacgg gggattcctt tcccaccgct ccttcccttt cccttcctcg cccgccgttt 1980
taaatagcca gccccatccc cagcttctct cccc 2014

<210> SEQ ID NO 24
<211> LENGTH: 1044
<212> TYPE: DNA
<213> ORGANISM: Saccharum ravennae

<400> SEQUENCE: 24
gtacggcgat catcctccct ttctctacct tctcttctct agactaggtc ggcgatccat 60
ggttagggcc tgctagttct gttcctgttt ttccgtggct gcgaggtaca atagatctga 120
tggcgttatg atggttaact tgtcatactc ctgcggtgtg cggtctatag tgcttttagg 180
acatcaattt gacctggctc gttcgagatc ggcgatccat ggttaggacc ctaggcggtg 240
gagtcgggtt agatccgcgc tgtttgtgtt agtagatgga tgcgaccttt acttcagaca 300
cgttctgatt gttaacttgt cagcacctgg gagtcctggg atggttctag ctggttcgca 360
gatgagatcg atttcatgat ctgctgtatc ttgtttcgtt aggttccttt taatctatcc 420
gtggtattat gctaacctat gatatggttc gatcgtgcta gctacgtcct gtgtcataat 480
ttttagcatg cccttttttg tttggttttg tctgattggg ctgtagatca gagtatactg 540
tttcaaacta cctactggat atatttatta aatttgaatc tgtatgtgtg tcacatatat 600
cttcataatt aaaatggatg gaaagatata tggataggta catgtgttgc tgtgggtttt 660
actggtactt tgttagatat acatgcttag atacatgaag caacatgatg ttacagttca 720
ataattcttg tttacctaat aaacaaataa ggataggtgt atgttgctgt gggttttgct 780
ggtactttgt tagatatata tgcttagata tatgaagcaa catcctgcta cggtttaata 840
attattgttt atatctaata gacaagcctg ctttttaatt attttgatat acttggatga 900
tggcatacag cagctatgtg tggattttta aatacccagc atcatgagca tgcatgaccc 960
tgccttagta tgctgtttat ttgcttgaga cttctttttt tgttggtact caccttttgt 1020
agtttggtga ctcttctgca ggtg 1044

<210> SEQ ID NO 25
<211> LENGTH: 2663
<212> TYPE: DNA

<213> ORGANISM: Saccharum ravennae

<400> SEQUENCE: 25

```
ctgctgccta ctttgaggat tacaatatct ttctctaaaa tgttttggtt tgttatttaa      60
accgtcttta aggccaattg ctcaagattc attcaacaat tgaaacgtct cacatgatta     120
aatcatataa ggttgctaag gtcttgtttg acaaggtttt ttttgtggaa atttcatcta     180
aatttttgag tgaaactatc aaatactaat ttaaaaaagg caaattttgc tggaggacac     240
tgcagaaacg tgtaattggc cggcacaaac cgccaaacgg agaatttgcc cagtaccatt     300
ataaattcat gataaattca tggttgtttg ccagtggggc tagggttcct cgcgtatggt     360
gcggaatgtg gtttggttcg accaactcga actcaatccg atccaaaggg gcatcaatag     420
tcattttaga aagtttctct ctcccgagca gtggaaatga ttattctatt tggcgcgatg     480
tccaccggca aacaaccacg aatttgtaat ggtactaggc aaattctccg tttggcggtg     540
tgtgccggcc aattacacgt ttttgcggtg tcctccgaca aaatttgcct tttaaaaaca     600
attttataag agaagctccg gagataaaag gccgtcaatg ttacaagagt gaagtcgtct     660
actccctcca tcccaaaaaa tgtaattcta agtatgagtt gtattattat ttttggacaa     720
aaggagtata ccacaagaat gatatcatcg tcatgcttag atccttttta gtaaagcttg     780
agcttctcta aaagtagaga aattagaaaa aaatcacgtt tttgtggtct tgatttctag     840
cctccacaaa atctttggtt ttacattttt tgtttgattt tggtttcaga agtccttatt     900
tatatgtgct agtttggcag cacttaaaat cgttagagag agcctaaaca aaagcctttt     960
caaaacgacc ttgagccaga ttggttgatg gccaaaattt gattgtcaaa acttaggcaa    1020
gccaagattt tagcagctat ttggtttggt accaaaattt gccaatgatc tgttcttttg    1080
ccttttcaac cggtttatca gccgtacttc agcttattct ctctcacaga acactattga    1140
atcagccgaa aagccaccgc agaacaggac cagtatctca caaatggcat gccaaatata    1200
ctcaccgtca gtgagcccgt ttaacggcgt cgacaagtct aacggccacc aaccagcgaa    1260
ccaccagcgt caagctagcc aagcgaagca gacggccgag acgttgacac cttggcgcgg    1320
gcatctctct ggcccccctct cgagagttcc gctccacctc cactggtggc ggtttccaag    1380
tccgttccgc ctcctgctcc tcctcacacg gcacgaaacc gtcacggcac cggcagcacg    1440
ggggattcct ttcccaccgc tccttccctt tcccttcctc gcccgccgtt ttaaatagcc    1500
agccccatcc ccagcttctc tccccaacct cagcttctct cgttgttcgg agcgcacaca    1560
caacccgatc cccaatcccc tcgtctctcc tcgcgagcct cgtcgatccc cgcttcaagg    1620
tacggcgatc atcctccctt tctctacctt ctcttctcta gactaggtcg gcgatccatg    1680
gttagggcct gctagttctg ttcctgtttt tccgtggctg cgaggtacaa tagatctgat    1740
ggcgttatga tggttaactt gtcatactcc tgcggtgtgc ggtctatagt gcttttagga    1800
catcaatttg acctggctcg ttcgagatcg gcgatccatg gttaggaccc taggcggtgg    1860
agtcgggtta gatccgcgct gtttgtgtta gtagatggat gcgaccttta cttcagacac    1920
gttctgattg ttaacttgtc agcacctggg agtcctggga tggttctagc tggttcgcag    1980
atgagatcga tttcatgatc tgctgtatct tgtttcgtta ggttcctttt aatctatccg    2040
tggtattatg ctaacctatg atatggttcg atcgtgctag ctacgtcctg tgtcataatt    2100
tttagcatgc cctttttttgt ttggttttgt ctgattgggc tgtagatcag agtatactgt    2160
ttcaaactac ctactggata tatttattaa atttgaatct gtatgtgtgt cacatatatc    2220
ttcataatta aaatggatgg aaagatatat ggataggtac atgtgttgct gtgggtttta    2280
```

```
ctggtacttt gttagatata catgcttaga tacatgaagc aacatgatgt tacagttcaa   2340

taattcttgt ttacctaata aacaaataag gataggtgta tgttgctgtg ggttttgctg   2400

gtactttgtt agatatatat gcttagatat atgaagcaac atcctgctac ggtttaataa   2460

ttattgttta tatctaatag acaagcctgc tttttaatta ttttgatata cttggatgat   2520

ggcatacagc agctatgtgt ggatttttaa atacccagca tcatgagcat gcatgaccct   2580

gccttagtat gctgtttatt tgcttgagac ttcttttttt gttggtactc accttttgta   2640

gtttggtgac tcttctgcag gtg                                           2663
```

```
<210> SEQ ID NO 26
<211> LENGTH: 1525
<212> TYPE: DNA
<213> ORGANISM: Saccharum ravennae

<400> SEQUENCE: 26

ctgctgccta ctttgaggat tacaatatct ttctctaaaa tgttttggtt tgttatttaa     60

accgtcttta aggccaattg ctcaagattc attcaacaat tgaaacgtct cacatgatta    120

aatcatataa ggttgctaag gtcttgtttg acaaggtttt ttttgtggaa atttcatcta    180

aatttttgag tgaaactatc aaatactaat ttaaaaaagg caaattttgc tggaggacac    240

tgcagaaacg tgtaattggc cggcacaaac cgccaaacgg agaatttgcc cagtaccatt    300

ataaattcat gataaattca tggttgtttg ccagtggggc tagggttcct cgcgtatggt    360

gcggaatgtg gtttggttcg accaactcga actcaatccg atccaaaggg gcatcaatag    420

tcattttaga aagtttctct ctcccgagca gtggaaatga ttattctatt tggcgcgatg    480

tccaccggca aacaaccacg aatttgtaat ggtactaggc aaattctccg tttggcggtg    540

tgtgccggcc aattacacgt ttttgcggtg tcctccgaca aaatttgcct tttaaaaaca    600

attttataag agaagctccg gagataaaag gccgtcaatg ttacaagagt gaagtcgtct    660

actccctcca tcccaaaaaa tgtaattcta agtatgagtt gtattattat ttttggacaa    720

aaggagtata ccacaagaat gatatcatcg tcatgcttag atccttttta gtaaagcttg    780

agcttctcta aaagtagaga aattagaaaa aaatcacgtt tttgtggtct tgatttctag    840

cctccacaaa atctttggtt ttacattttt tgtttgattt tggtttcaga agtccttatt    900

tatatgtgct agtttggcag cacttaaaat cgttagagag agcctaaaca aaagcctttt    960

caaaacgacc ttgagccaga ttggttgatg gccaaaattt gattgtcaaa acttaggcaa   1020

gccaagattt tagcagctat ttggtttggt accaaaattt gccaatgatc tgttcttttg   1080

ccttttcaac cggtttatca gccgtacttc agcttattct ctctcacaga acactattga   1140

atcagccgaa aagccaccgc agaacaggac cagtatctca caaatggcat gccaaatata   1200

ctcaccgtca gtgagcccgt ttaacggcgt cgacaagtct aacggccacc aaccagcgaa   1260

ccaccagcgt caagctagcc aagcgaagca gacggccgag acgttgacac cttggcgcgg   1320

gcatctctct ggccccctct cgagagttcc gctccacctc cactggtggc ggtttccaag   1380

tccgttccgc ctcctgctcc tcctcacacg gcacgaaacc gtcacggcac cggcagcacg   1440

ggggattcct ttcccaccgc tccttccctt tcccttcctc gcccgccgtt ttaaatagcc   1500

agccccatcc ccagcttctc tcccc                                         1525
```

```
<210> SEQ ID NO 27
<211> LENGTH: 2182
<212> TYPE: DNA
```

-continued

<213> ORGANISM: Saccharum ravennae

<400> SEQUENCE: 27

```
ccaccggcaa acaaccacga atttgtaatg gtactaggca aattctccgt ttggcggtgt     60
gtgccggcca attacacgtt tttgcggtgt cctccgacaa aatttgcctt ttaaaaacaa    120
ttttataaga gaagctccgg agataaaagg ccgtcaatgt tacaagagtg aagtcgtcta    180
ctccctccat cccaaaaaat gtaattctaa gtatgagttg tattattatt tttggacaaa    240
aggagtatac cacaagaatg atatcatcgt catgcttaga tcctttttag taaagcttga    300
gcttctctaa aagtagagaa attagaaaaa aatcacgttt ttgtggtctt gatttctagc    360
ctccacaaaa tctttggttt tacatttttt gtttgatttt ggtttcagaa gtccttattt    420
atatgtgcta gtttggcagc acttaaaatc gttagagaga gcctaaacaa aagccttttc    480
aaaacgacct tgagccagat tggttgatgg ccaaaatttg attgtcaaaa cttaggcaag    540
ccaagatttt agcagctatt tggtttggta ccaaaatttg ccaatgatct gttcttttgc    600
cttttcaacc ggtttatcag ccgtacttca gcttattctc tctcacagaa cactattgaa    660
tcagccgaaa agccaccgca gaacaggacc agtatctcac aaatggcatg ccaaatatac    720
tcaccgtcag tgagcccgtt taacggcgtc gacaagtcta acggccacca accagcgaac    780
caccagcgtc aagctagcca agcgaagcag acggccgaga cgttgacacc ttggcgcggg    840
catctctctg gccccctctc gagagttccg ctccacctcc actggtggcg gtttccaagt    900
ccgttccgcc tcctgctcct cctcacacgg cacgaaaccg tcacggcacc ggcagcacgg    960
gggattcctt tcccaccgct ccttcccttt cccttcctcg cccgccgttt taaatagcca   1020
gccccatccc cagcttctct ccccaacctc agcttctctc gttgttcgga gcgcacacac   1080
aacccgatcc ccaatcccct cgtctctcct cgcgagcctc gtcgatcccc gcttcaaggt   1140
acggcgatca tcctcccttt ctctaccttc tcttctctag actaggtcgg cgatccatgg   1200
ttagggcctg ctagttctgt tcctgttttt ccgtggctgc gaggtacaat agatctgatg   1260
gcgttatgat ggttaacttg tcatactcct gcggtgtgcg gtctatagtg cttttaggac   1320
atcaatttga cctggctcgt tcgagatcgg cgatccatgg ttaggaccct aggcggtgga   1380
gtcgggttag atccgcgctg tttgtgttag tagatggatg cgacctttac ttcagacacg   1440
ttctgattgt taacttgtca gcacctggga gtcctgggat ggttctagct ggttcgcaga   1500
tgagatcgat ttcatgatct gctgtatctt gtttcgttag gttcctttta atctatccgt   1560
ggtattatgc taacctatga tatggttcga tcgtgctagc tacgtcctgt gtcataattt   1620
ttagcatgcc ctttttttgtt tggttttgtc tgattgggct gtagatcaga gtatactgtt   1680
tcaaactacc tactggatat atttattaaa tttgaatctg tatgtgtgtc acatatatct   1740
tcataattaa aatggatgga aagatatatg gataggtaca tgtgttgctg tgggttttac   1800
tggtactttg ttagatatac atgcttagat acatgaagca acatgatgtt acagttcaat   1860
aattcttgtt tacctaataa acaaataagg ataggtgtat gttgctgtgg gttttgctgg   1920
tactttgtta gatatatatg cttagatata tgaagcaaca tcctgctacg gtttaataat   1980
tattgtttat atctaataga caagcctgct ttttaattat tttgatatac ttggatgatg   2040
gcatacagca gctatgtgtg gatttttaaa tacccagcat catgagcatg catgaccctg   2100
ccttagtatg ctgtttattt gcttgagact tctttttttg ttggtactca ccttttgtag   2160
tttggtgact cttctgcagg tg                                            2182
```

<210> SEQ ID NO 28
<211> LENGTH: 1044
<212> TYPE: DNA
<213> ORGANISM: Saccharum ravennae

<400> SEQUENCE: 28
ccaccggcaa acaaccacga atttgtaatg gtactaggca aattctccgt ttggcggtgt 60
gtgccggcca attacacgtt tttgcggtgt cctccgacaa aatttgcctt ttaaaaacaa 120
ttttataaga gaagctccgg agataaaagg ccgtcaatgt tacaagagtg aagtcgtcta 180
ctccctccat cccaaaaaat gtaattctaa gtatgagttg tattattatt tttggacaaa 240
aggagtatac cacaagaatg atatcatcgt catgcttaga tcctttttag taaagcttga 300
gcttctctaa aagtagagaa attagaaaaa aatcacgttt ttgtggtctt gatttctagc 360
ctccacaaaa tctttggttt tacatttttt gtttgatttt ggtttcagaa gtccttattt 420
atatgtgcta gtttggcagc acttaaaatc gttagagaga gcctaaacaa aagccttttc 480
aaaacgacct tgagccagat tggttgatgg ccaaaatttg attgtcaaaa cttaggcaag 540
ccaagatttt agcagctatt tggtttggta ccaaaatttg ccaatgatct gttcttttgc 600
cttttcaacc ggtttatcag ccgtacttca gcttattctc tctcacagaa cactattgaa 660
tcagccgaaa agccaccgca gaacaggacc agtatctcac aaatggcatg ccaaatatac 720
tcaccgtcag tgagcccgtt taacggcgtc gacaagtcta acggccacca accagcgaac 780
caccagcgtc aagctagcca agcgaagcag acggccgaga cgttgacacc ttggcgcggg 840
catctctctg gccccctctc gagagttccg ctccacctcc actggtggcg gtttccaagt 900
ccgttccgcc tcctgctcct cctcacacgg cacgaaaccg tcacggcacc ggcagcacgg 960
gggattcctt tcccaccgct ccttcccttt cccttcctcg cccgccgttt taaatagcca 1020
gccccatccc cagcttctct cccc 1044

<210> SEQ ID NO 29
<211> LENGTH: 1934
<212> TYPE: DNA
<213> ORGANISM: Saccharum ravennae

<400> SEQUENCE: 29
accacaagaa tgatatcatc gtcatgctta gatccttttt agtaaagctt gagcttctct 60
aaaagtagag aaattagaaa aaaatcacgt ttttgtggtc ttgatttcta gcctccacaa 120
aatctttggt tttacatttt ttgtttgatt ttggtttcag aagtccttat ttatatgtgc 180
tagtttggca gcacttaaaa tcgttagaga gagcctaaac aaaagccttt tcaaaacgac 240
cttgagccag attggttgat ggccaaaatt tgattgtcaa aacttaggca agccaagatt 300
ttagcagcta tttggtttgg taccaaaatt tgccaatgat ctgttctttt gccttttcaa 360
ccggtttatc agccgtactt cagcttattc tctctcacag aacactattg aatcagccga 420
aaagccaccg cagaacagga ccagtatctc acaaatggca tgccaaatat actcaccgtc 480
agtgagcccg tttaacggcg tcgacaagtc taacggccac caaccagcga accaccagcg 540
tcaagctagc caagcgaagc agacggccga gacgttgaca ccttggcgcg ggcatctctc 600
tggccccctc tcgagagttc cgctccacct ccactggtgg cggtttccaa gtccgttccg 660
cctcctgctc ctcctcacac ggcacgaaac cgtcacggca ccggcagcac gggggattcc 720
tttcccaccg ctccttccct ttcccttcct cgcccgccgt tttaaatagc cagccccatc 780
cccagcttct ctccccaacc tcagcttctc tcgttgttcg gagcgcacac acaacccgat 840
ccccaatccc ctcgtctctc ctcgcgagcc tcgtcgatcc ccgcttcaag gtacggcgat 900
catcctccct ttctctacct tctcttctct agactaggtc ggcgatccat ggttagggcc 960
tgctagttct gttcctgttt ttccgtggct gcgaggtaca atagatctga tggcgttatg 1020
atggttaact tgtcatactc ctgcggtgtg cggtctatag tgcttttagg acatcaattt 1080
gacctggctc gttcgagatc ggcgatccat ggttaggacc ctaggcggtg gagtcgggtt 1140
agatccgcgc tgtttgtgtt agtagatgga tgcgaccttt acttcagaca cgttctgatt 1200
gttaacttgt cagcacctgg gagtcctggg atggttctag ctggttcgca gatgagatcg 1260
atttcatgat ctgctgtatc ttgtttcgtt aggttccttt taatctatcc gtggtattat 1320
gctaacctat gatatggttc gatcgtgcta gctacgtcct gtgtcataat ttttagcatg 1380
cccttttttg tttggttttg tctgattggg ctgtagatca gagtatactg tttcaaacta 1440
cctactggat atatttatta aatttgaatc tgtatgtgtg tcacatatat cttcataatt 1500
aaaatggatg gaaagatata tggataggta catgtgttgc tgtgggtttt actggtactt 1560
tgttagatat acatgcttag atacatgaag caacatgatg ttacagttca ataattcttg 1620
tttacctaat aaacaaataa ggataggtgt atgttgctgt gggttttgct ggtactttgt 1680
tagatatata tgcttagata tatgaagcaa catcctgcta cggtttaata attattgttt 1740
atatctaata gacaagcctg ctttttaatt attttgatat acttggatga tggcatacag 1800
cagctatgtg tggattttta aatacccagc atcatgagca tgcatgaccc tgccttagta 1860
tgctgtttat ttgcttgaga cttctttttt tgttggtact caccttttgt agtttggtga 1920
ctcttctgca ggtg 1934

<210> SEQ ID NO 30
<211> LENGTH: 796
<212> TYPE: DNA
<213> ORGANISM: Saccharum ravennae

<400> SEQUENCE: 30
accacaagaa tgatatcatc gtcatgctta gatccttttt agtaaagctt gagcttctct 60
aaaagtagag aaattagaaa aaaatcacgt ttttgtggtc ttgatttcta gcctccacaa 120
aatctttggt tttacatttt ttgtttgatt ttggtttcag aagtccttat ttatatgtgc 180
tagtttggca gcacttaaaa tcgttagaga gagcctaaac aaaagccttt tcaaaacgac 240
cttgagccag attggttgat ggccaaaatt tgattgtcaa aacttaggca agccaagatt 300
ttagcagcta tttggtttgg taccaaaatt tgccaatgat ctgttctttt gccttttcaa 360
ccggtttatc agccgtactt cagcttattc tctctcacag aacactattg aatcagccga 420
aaagccaccg cagaacagga ccagtatctc acaaatggca tgccaaatat actcaccgtc 480
agtgagcccg tttaacggcg tcgacaagtc taacggccac caaccagcga accaccagcg 540
tcaagctagc caagcgaagc agacggccga gacgttgaca ccttggcgcg ggcatctctc 600
tggccccctc tcgagagttc cgctccacct ccactggtgg cggtttccaa gtccgttccg 660
cctcctgctc ctcctcacac ggcacgaaac cgtcacggca ccggcagcac gggggattcc 720
tttcccaccg ctccttccct ttcccttcct cgcccgccgt tttaaatagc cagccccatc 780
cccagcttct ctcccc 796

<210> SEQ ID NO 31
<211> LENGTH: 1649
<212> TYPE: DNA
<213> ORGANISM: Saccharum ravennae -continued

<400> SEQUENCE: 31
aggcaagcca agattttagc agctatttgg tttggtacca aaatttgcca atgatctgtt 60
cttttgcctt ttcaaccggt ttatcagccg tacttcagct tattctctct cacagaacac 120
tattgaatca gccgaaaagc caccgcagaa caggaccagt atctcacaaa tggcatgcca 180
aatatactca ccgtcagtga gcccgtttaa cggcgtcgac aagtctaacg gccaccaacc 240
agcgaaccac cagcgtcaag ctagccaagc gaagcagacg gccgagacgt tgacaccttg 300
gcgcgggcat ctctctggcc ccctctcgag agttccgctc cacctccact ggtggcggtt 360
tccaagtccg ttccgcctcc tgctcctcct cacacggcac gaaaccgtca cggcaccggc 420
agcacggggg attcctttcc caccgctcct tccctttccc ttcctcgccc gccgttttaa 480
atagccagcc ccatccccag cttctctccc caacctcagc ttctctcgtt gttcggagcg 540
cacacacaac ccgatcccca atcccctcgt ctctcctcgc gagcctcgtc gatccccgct 600
tcaaggtacg gcgatcatcc tccctttctc taccttctct tctctagact aggtcggcga 660
tccatggtta gggcctgcta gttctgttcc tgtttttccg tggctgcgag gtacaataga 720
tctgatggcg ttatgatggt taacttgtca tactcctgcg gtgtgcggtc tatagtgctt 780
ttaggacatc aatttgacct ggctcgttcg agatcggcga tccatggtta ggaccctagg 840
cggtggagtc gggttagatc cgcgctgttt gtgttagtag atggatgcga cctttacttc 900
agacacgttc tgattgttaa cttgtcagca cctgggagtc ctgggatggt tctagctggt 960
tcgcagatga gatcgatttc atgatctgct gtatcttgtt tcgttaggtt ccttttaatc 1020
tatccgtggt attatgctaa cctatgatat ggttcgatcg tgctagctac gtcctgtgtc 1080
ataattttta gcatgccctt ttttgtttgg ttttgtctga ttgggctgta gatcagagta 1140
tactgtttca aactacctac tggatatatt tattaaattt gaatctgtat gtgtgtcaca 1200
tatatcttca taattaaaat ggatggaaag atatatggat aggtacatgt gttgctgtgg 1260
gttttactgg tactttgtta gatatacatg cttagataca tgaagcaaca tgatgttaca 1320
gttcaataat tcttgtttac ctaataaaca aataaggata ggtgtatgtt gctgtgggtt 1380
ttgctggtac tttgttagat atatatgctt agatatatga agcaacatcc tgctacggtt 1440
taataattat tgtttatatc taatagacaa gcctgctttt taattatttt gatatacttg 1500
gatgatggca tacagcagct atgtgtggat ttttaaatac ccagcatcat gagcatgcat 1560
gaccctgcct tagtatgctg tttatttgct tgagacttct ttttttgttg gtactcacct 1620
tttgtagttt ggtgactctt ctgcaggtg 1649

<210> SEQ ID NO 32
<211> LENGTH: 511
<212> TYPE: DNA
<213> ORGANISM: Saccharum ravennae

<400> SEQUENCE: 32
aggcaagcca agattttagc agctatttgg tttggtacca aaatttgcca atgatctgtt 60
cttttgcctt ttcaaccggt ttatcagccg tacttcagct tattctctct cacagaacac 120
tattgaatca gccgaaaagc caccgcagaa caggaccagt atctcacaaa tggcatgcca 180
aatatactca ccgtcagtga gcccgtttaa cggcgtcgac aagtctaacg gccaccaacc 240
agcgaaccac cagcgtcaag ctagccaagc gaagcagacg gccgagacgt tgacaccttg 300
gcgcgggcat ctctctggcc ccctctcgag agttccgctc cacctccact ggtggcggtt 360
tccaagtccg ttccgcctcc tgctcctcct cacacggcac gaaaccgtca cggcaccggc 420
agcacggggg attcctttcc caccgctcct tccctttccc ttcctcgccc gccgttttaa 480
atagccagcc ccatccccag cttctctccc c 511

<210> SEQ ID NO 33
<211> LENGTH: 2631
<212> TYPE: DNA
<213> ORGANISM: Setaria viridis

<400> SEQUENCE: 33
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgagggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcccgttgcc 1500
gcaagactca gatcagattc cgatccccag ttcttcccca atcaccttgt ggtctctcgt 1560
gtcgcggttc ccagggacgc ctccggctcg tcgctcgaca gcgatctccg ccccagcaag 1620
gtatagattc agttccttgc tccgatccca atctggttga gatgttgctc cgatgcgact 1680
tgattatgtc atatatctgc ggtttgcacc gatctgaagc ctagggtttc tcgagcgacc 1740
cagttgtttg caatttgcga tttgctcgtt tgttgcgcat cgtagtttat gtttggagta 1800
atcgaggatt tgtatgcggc gtcggcgcta cctgcttaat cacgccatgt gacgcggtta 1860
cttgcagagg ctgggttagt gggttctgtt atgtcgtgat ctaagaatct agattaggct 1920
cagtcgttct tgctgtcgac tagtttgttt tgatatccat gtagtacaag ttacttaaaa 1980
tttaggtcca atatattttg catgcttttg gcctgttatt cttgccaaca agttgtcctg 2040
gtaaaaagta gatgtgaaag tcacgtattg ggacaaattg atggttaagt gctatagttc 2100
tatagttctg tgatacatct atctgatttt ttttggtcta ttggtgccta acttatctga 2160
aaatcatgga acatgaggct agtttgatca tggtttagtt cattgtgatt aataatgtat 2220
gatttagtag ctattttggt gatcgtgtca ttttatttgt gaatggaatc attgtatgta 2280
aatgaagcta gttcaggggt tatgatgtag ctggctttgt attctaaagg ctgctattat 2340
tcatccatcg atttcaccta tatgtaatcc agagctttcg atgtgaaatt tgtctgatcc 2400
ttcactagga aggacagaac attgttaata ttttggcaca tctgtcttat tctcatcctt 2460
tgtttgaaca tgttagcctg ttcaaacaga tactgttgta atgtcctagt tatataggta 2520
catatgtgtt ctctattgag tttatggact tttgtgtgtg aagttatatt tcattttgct 2580
caaaactcat gtttgcaagc tttctgacat tattctattg ttctgaaaca g 2631

<210> SEQ ID NO 34
<211> LENGTH: 1493
<212> TYPE: DNA
<213> ORGANISM: Setaria viridis

<400> SEQUENCE: 34
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440

```
gcaaggcacg ccacgacccg cctcgccctc gaggcataaa taccctccca tcc          1493

<210> SEQ ID NO 35
<211> LENGTH: 127
<212> TYPE: DNA
<213> ORGANISM: Setaria viridis

<400> SEQUENCE: 35
cgttgccgca agactcagat cagattccga tccccagttc ttccccaatc accttgtggt     60
ctctcgtgtc gcggttccca gggacgcctc cggctcgtcg ctcgacagcg atctccgccc    120
cagcaag                                                              127

<210> SEQ ID NO 36
<211> LENGTH: 1011
<212> TYPE: DNA
<213> ORGANISM: Setaria viridis

<400> SEQUENCE: 36
gtatagattc agttccttgc tccgatccca atctggttga gatgttgctc cgatgcgact     60
tgattatgtc atatatctgc ggtttgcacc gatctgaagc ctagggtttc tcgagcgacc    120
cagttgtttg caatttgcga tttgctcgtt tgttgcgcat cgtagtttat gtttggagta    180
atcgaggatt tgtatgcggc gtcggcgcta cctgcttaat cacgccatgt gacgcggtta    240
cttgcagagg ctgggttagt gggttctgtt atgtcgtgat ctaagaatct agattaggct    300
cagtcgttct tgctgtcgac tagtttgttt tgatatccat gtagtacaag ttacttaaaa    360
tttaggtcca atatattttg catgcttttg gcctgttatt cttgccaaca agttgtcctg    420
gtaaaaagta gatgtgaaag tcacgtattg ggacaaattg atggttaagt gctatagttc    480
tatagttctg tgatacatct atctgatttt ttttggtcta ttggtgccta acttatctga    540
aaatcatgga acatgaggct agtttgatca tggtttagtt cattgtgatt aataatgtat    600
gatttagtag ctattttggt gatcgtgtca ttttatttgt gaatggaatc attgtatgta    660
aatgaagcta gttcaggggt tatgatgtag ctggctttgt attctaaagg ctgctattat    720
tcatccatcg atttcaccta tatgtaatcc agagctttcg atgtgaaatt tgtctgatcc    780
ttcactagga aggacagaac attgttaata ttttggcaca tctgtcttat tctcatcctt    840
tgtttgaaca tgttagcctg ttcaaacaga tactgttgta atgtcctagt tatataggta    900
catatgtgtt ctctattgag tttatggact tttgtgtgtg aagttatatt tcattttgct    960
caaaactcat gtttgcaagc tttctgacat tattctattg ttctgaaaca g            1011

<210> SEQ ID NO 37
<211> LENGTH: 2173
<212> TYPE: DNA
<213> ORGANISM: Setaria viridis

<400> SEQUENCE: 37
gccgtttttg aagtatccag gattagaagc ttctactgcg cttttatatt atagctgtgg     60
acctgtggta acctttctct tttggcgctt gcttaatctc ggccgtgctg gtccatgctt    120
aggcactagg cagagataga gccgggggtg aatggggcta aagctcagct gctcgagggg    180
ccgtgggctg gtttccacta gcctacagct gtgccacgtg cggccgcgca agccgaagca    240
agcacgctga gccgttggac agcttgtcat aatgccatta cgtggattac aggtaactgg    300
ccctgtaact actcgttcgg ccatcatcaa acgacgacgt ccgctaggcg acgacacggg    360
taatgcacgc agccacccag gcgcgcgcgc tagcggagca cggtcaggtg acacgggcgt    420
```

cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcccgttg ccgcaagact cagatcagat tccgatcccc agttcttccc 1080
caatcacctt gtggtctctc gtgtcgcggt tcccagggac gcctccggct cgtcgctcga 1140
cagcgatctc cgccccagca aggtatagat tcagttcctt gctccgatcc caatctggtt 1200
gagatgttgc tccgatgcga cttgattatg tcatatatct gcggtttgca ccgatctgaa 1260
gcctagggtt tctcgagcga cccagttgtt tgcaatttgc gatttgctcg tttgttgcgc 1320
atcgtagttt atgtttggag taatcgagga tttgtatgcg gcgtcggcgc tacctgctta 1380
atcacgccat gtgacgcggt tacttgcaga ggctgggtta gtgggttctg ttatgtcgtg 1440
atctaagaat ctagattagg ctcagtcgtt cttgctgtcg actagtttgt tttgatatcc 1500
atgtagtaca agttacttaa aatttaggtc caatatattt tgcatgcttt tggcctgtta 1560
ttcttgccaa caagttgtcc tggtaaaaag tagatgtgaa agtcacgtat tgggacaaat 1620
tgatggttaa gtgctatagt tctatagttc tgtgatacat ctatctgatt ttttttggtc 1680
tattggtgcc taacttatct gaaaatcatg gaacatgagg ctagtttgat catggtttag 1740
ttcattgtga ttaataatgt atgatttagt agctattttg gtgatcgtgt cattttattt 1800
gtgaatggaa tcattgtatg taaatgaagc tagttcaggg gttatgatgt agctggcttt 1860
gtattctaaa ggctgctatt attcatccat cgatttcacc tatatgtaat ccagagcttt 1920
cgatgtgaaa tttgtctgat ccttcactag gaaggacaga acattgttaa tattttggca 1980
catctgtctt attctcatcc tttgtttgaa catgttagcc tgttcaaaca gatactgttg 2040
taatgtccta gttatatagg tacatatgtg ttctctattg agtttatgga cttttgtgtg 2100
tgaagttata tttcattttg ctcaaaactc atgtttgcaa gctttctgac attattctat 2160
tgttctgaaa cag 2173

<210> SEQ ID NO 38
<211> LENGTH: 1035
<212> TYPE: DNA
<213> ORGANISM: Setaria viridis

<400> SEQUENCE: 38
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300

```
ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420

cgtgacgctt ccgagttgaa ggggttaacg ccagaaacag tgtttggcca gggtatgaac    480

ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agacatcgga acactggtga ttggtggagc cggcagtatg cgccccagca cggccgaggt    660

ggtggtggcc cgtggccctg ctgtctgcgc ggctcgggac aacttgaaac tgggccaccg    720

cctcgtcgca actcgcaacc cgttggcgga agaaaggaat ggctcgtagg ggcccgggta    780

gaatccaaga atgttgcgct gggcttcgat tcacataaca tgggcctgaa gctctaaaac    840

gacggcccgg tcaccgggcg atggaaagag accggatcct cctcgtgaat tctggaaggc    900

cacacgagag cgacccacca ccgacgcgga ggagtcgtgc gtggtccaac acggccggcg    960

ggctgggctg cgaccttaac cagcaaggca cgccacgacc cgcctcgccc tcgaggcata   1020

aataccctcc catcc                                                    1035
```

```
<210> SEQ ID NO 39
<211> LENGTH: 1819
<212> TYPE: DNA
<213> ORGANISM: Setaria viridis

<400> SEQUENCE: 39

cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctt gtgaattctg    540

gaaggccaca cgagagcgac ccaccaccga cgcggaggag tcgtgcgtgg tccaacacgg    600

ccggcgggct gggctgcgac cttaaccagc aaggcacgcc acgacccgcc tcgccctcga    660

ggcataaata ccctcccatc ccgttgccgc aagactcaga tcagattccg atccccagtt    720

cttccccaat caccttgtgg tctctcgtgt cgcggttccc agggacgcct ccggctcgtc    780

gctcgacagc gatctccgcc ccagcaaggt atagattcag ttccttgctc cgatcccaat    840

ctggttgaga tgttgctccg atgcgacttg attatgtcat atatctgcgg tttgcaccga    900

tctgaagcct agggtttctc gagcgaccca gttgtttgca atttgcgatt tgctcgtttg    960

ttgcgcatcg tagtttatgt ttggagtaat cgaggatttg tatgcggcgt cggcgctacc   1020

tgcttaatca cgccatgtga cgcggttact tgcagaggct gggttagtgg gttctgttat   1080

gtcgtgatct aagaatctag attaggctca gtcgttcttg ctgtcgacta gtttgttttg   1140

atatccatgt agtacaagtt acttaaaatt taggtccaat atattttgca tgcttttggc   1200

ctgttattct tgccaacaag ttgtcctggt aaaaagtaga tgtgaaagtc acgtattggg   1260

acaaattgat ggttaagtgc tatagttcta tagttctgtg atacatctat ctgatttttt   1320

ttggtctatt ggtgcctaac ttatctgaaa atcatggaac atgaggctag tttgatcatg   1380
```

gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacag 1819

<210> SEQ ID NO 40
<211> LENGTH: 681
<212> TYPE: DNA
<213> ORGANISM: Setaria viridis

<400> SEQUENCE: 40
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 41
<211> LENGTH: 1922
<212> TYPE: DNA
<213> ORGANISM: Zea mays subsp. Mexicana

<400> SEQUENCE: 41
gtcgtgcccc tctctagaga taatgagcat tgcatgtcta agttataaaa aattaccaca 60
tatttttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag ttttttattt 420
aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660

-continued ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc ccccctctct 960
ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg attttttag ccctgccttc atacgctatt 1860
tatttgcttg gtactgtttc ttttgtcgat gctcaccctg ttgtttggtg atacttctgc 1920
ag 1922

<210> SEQ ID NO 42
<211> LENGTH: 850
<212> TYPE: DNA
<213> ORGANISM: Zea mays subsp. Mexicana

<400> SEQUENCE: 42
gtcgtgcccc tctctagaga taatgagcat tgcatgtcta agttataaaa aattaccaca 60
tatttttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttttattt 420 aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc 850

<210> SEQ ID NO 43
<211> LENGTH: 78
<212> TYPE: DNA
<213> ORGANISM: Zea mays subsp. Mexicana

<400> SEQUENCE: 43
aacctcgtgt tcgttcggag cgcgcacaca cacaaccaga tctcccccaa atccacccgt 60
cggcacctcc gcttcaag 78

<210> SEQ ID NO 44
<211> LENGTH: 994
<212> TYPE: DNA
<213> ORGANISM: Zea mays subsp. Mexicana

<400> SEQUENCE: 44
gtacgccgct catcctcctc cccccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gcccttttcc 300
tttatttcaa tatatgccgt gcacttgttt gtcgggtcat cttttcatgt ttttttggc 360 ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcag 994

<210> SEQ ID NO 45
<211> LENGTH: 1971
<212> TYPE: DNA
<213> ORGANISM: Zea mays subsp. Mexicana

<400> SEQUENCE: 45
gtcgtgcccc tctctagaga taaagagcat tgcatgtcta agttataaaa aattaccaca 60 tattttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa tttttttagt acatctattt tattctattt tagcctctaa attaagaaaa 420

```
ctaaaactct attttagttt ttttatttaa taatttagat ataaaataga ataaaataaa    480
gtgactaaaa attaaacaaa taccctttaa gaaattaaaa aaactaagga aacatttttc    540
ttgtttcgag tagataatgc cagcctgtta aacgccgtcg acgagtctaa cggacaccaa    600
ccagcgaacc agcagcgtcg cgtcgggcca agcgaagcag acggcacggc atctctgtcg    660
ctgcctctgg acccctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacacccct ccacaccttc tttccccaac ctcgtgttgt     900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gccctttttcc  1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga tttttttagc cctgccttca tacgctattt atttgcttgg   1920
tactgtttct tttgtcgatg ctcaccctgt tgtttggtga tacttctgca g             1971
```

<210> SEQ ID NO 46
<211> LENGTH: 887
<212> TYPE: DNA
<213> ORGANISM: Zea mays subsp. Mexicana

<400> SEQUENCE: 46

```
gtcgtgcccc tctctagaga taaagagcat tgcatgtcta agttataaaa aattaccaca     60
tatttttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tctttttagt gtgcatgtgt tctccttttt tttttgcaaa tagcttcacc    300
tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt ttttatttaa taatttagat ataaaataga ataaaataaa    480
gtgactaaaa attaaacaaa taccctttaa gaaattaaaa aaactaagga aacatttttc    540
ttgtttcgag tagataatgc cagcctgtta aacgccgtcg acgagtctaa cggacaccaa    600
```

ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720
tccagaaatt gcgtggcgga gcggcagacg tgagccggca cggcaggcgg cctcctcctc 780
ctctcacggc accggcagct acgggggatt cctttcccac cgctccttcg ctttcccttc 840
ctcgcccgcc gtaataaata gacacccccct ccacaccttc tttcccc 887

<210> SEQ ID NO 47
<211> LENGTH: 77
<212> TYPE: DNA
<213> ORGANISM: Zea mays subsp. Mexicana

<400> SEQUENCE: 47
aacctcgtgt tgttcggagc gcacacacac acaaccagat ctcccccaaa tccacccgtc 60
ggcacctccg cttcaag 77

<210> SEQ ID NO 48
<211> LENGTH: 1007
<212> TYPE: DNA
<213> ORGANISM: Zea mays subsp. Mexicana

<400> SEQUENCE: 48
gtacgccgct catcctcccc ccccccctctc taccttctct agatcggcgt tccggtccat 60
ggttagggcc cggtagttct acttctgttc atgtttgtgt tagatccgtg tttgtgttag 120
atccgtgctg ctagcgttcg tacacggatg cgacctgtac gtcagacacg ttctgattgc 180
taacttgcca gtgtttctct ttggggaatc ctgggatggc tctagccgtt ccgcagacgg 240
gatcgatttc atgatttttt ttgtttcgtt gcatagggtt tggtttgccc ttttccttta 300
tttcaatata tgccgtgcac ttgtttgtcg ggtcatcttt tcatgctttt ttttgtcttg 360
gttgtgatga tgtggtctgg ttgggcggtc gttctagatc ggagaagaat tctgtttcaa 420
actacctggt ggatttatta attttggatc tgtatgtgtg tgccatacat attcatagtt 480
acgaattgaa gatgatggat ggaaatatcg atctaggata ggtatacatg ttgatgcggg 540
ttttactgat gcatatacag agatgctttt tgttcgcttg gttgtgatga tgtggtctgg 600
ttgggcggtc gttcattcgt tctagatcgg agtagaatac tgtttcaaac tacctggtgt 660
atttattaat tttggaactg tatgtgtgtg tcatacatct tcatagttac gagtttaaga 720
tggatggaaa tatcgatcta ggataggtat acatgttgat gtgggtttta ctgatgcata 780
tacatgatgg catatgcagc atctattcat atgctctaac cttgagtacc tatctattat 840
aataaacaag tatgttttat aattattttg atcttgatat acttggatga tggcatatgc 900
agcagctata tgtggatttt tttagccctg ccttcatacg ctatttattt gcttggtact 960
gtttcttttg tcgatgctca ccctgttgtt tggtgatact tctgcag 1007

<210> SEQ ID NO 49
<211> LENGTH: 2005
<212> TYPE: DNA
<213> ORGANISM: Zea mays subsp. Mexicana

<400> SEQUENCE: 49
gtcgtgcccc tctctagaga taaagagcat tgcatgtcta aagtataaaa aattaccaca 60
tatttttttg tcacacttat ttgaagtgta gtttatctat ctctatacat atatttaaac 120
ttcactctac aaataatata gtctataata ctaaaataat attagtgttt tagaggatca 180

-continued

```
tataaataaa ctgctagaca tggtctaaag gataattgaa tattttgaca atctacagtt    240
ttatcttttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aattttttaa aactaaaact    420
ctattttagt tttttattta ataatttaga tataaaatga aataaaataa attgactaca    480
aataaaacaa ataccccttta agaaataaaa aaactaagca aacatttttc ttgtttcgag   540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaata gacacccccct ccacaccctc tttccccaac ctcgtgttcg ttcggagcgc   900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttttcgc ttggttgtga tgatgtggtc tggttgggcg gtcgttctag  1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta tttatttgct tggtactgtt tcttttgtcc gatgctcacc   1980
ctgttgttgg gtgatacttc tgcag                                          2005
```

<210> SEQ ID NO 50
<211> LENGTH: 877
<212> TYPE: DNA
<213> ORGANISM: Zea mays subsp. Mexicana

<400> SEQUENCE: 50

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
```

```
atacttcatc cattttatta gtacatccat ttaggattta gggttgatgg tttctataga    360

ctaattttta gtacatccat tttattcttt ttagtctcta aatttttttaa aactaaaact    420

ctattttagt tttttattta ataatttaga tataaaatga aataaaataa attgactaca    480

aataaaacaa ataccccttta agaaataaaa aaactaagca aacatttttc ttgtttcgag    540

tagataatga caggctgttc aacgccgtcg acgagtctaa cggacaccaa ccagcgaacc    600

agcagcgtcg cgtcgggcca agcgaagcag acggcacggc atctctgtag ctgcctctgg    660

acccctctcg agagttccgc tccaccgttg gacttgctcc gctgtcggca tccagaaatt    720

gcgtggcgga gcggcagacg tgaggcggca cggcaggcgg cctcttcctc ctctcacggc    780

accggcagct acgggggatt cctttcccac cgctccttcg ctttcccttc ctcgcccgcc    840

gtaataaata gacaccccct ccacaccctc tttcccc                             877
```

<210> SEQ ID NO 51
<211> LENGTH: 78
<212> TYPE: DNA
<213> ORGANISM: Zea mays subsp. Mexicana

<400> SEQUENCE: 51

```
aacctcgtgt tcgttcggag cgcacacaca cgcaaccaga tctcccccaa atccagccgt     60

cggcacctcc gcttcaag                                                   78
```

<210> SEQ ID NO 52
<211> LENGTH: 1050
<212> TYPE: DNA
<213> ORGANISM: Zea mays subsp. Mexicana

<400> SEQUENCE: 52

```
gtacgccgct catcctcccc cccccccctct ctctaccttc tctagatcgg cgatccggtc     60

catggttagg gcccggtagt tctacttctg ttcatgtttg tgttagagca aacatgttca    120

tgttcatgtt tgtgatgatg tggtctggtt gggcggtcgt tctagatcgg agtaggatac    180

tgtttcaagc tacctggtgg atttattaat tttgtatctg tatgtgtgtg ccatacatct    240

tcatagttac gagtttaaga tgatggatgg aaatatcgat ctaggatagg tatacatgtt    300

gatgcgggtt ttactgatgc atatacagag atgctttttt tctcgcttgg ttgtgatgat    360

atggtctggt tgggcggtcg ttctagatcg gagtagaata ctgtttcaaa ctacctggtg    420

gatttattaa aggataaagg gtcgttctag atcggagtag aatactgttt caaactacct    480

ggtggattta ttaaaggatc tgtatgtatg tgcctacatc ttcatagtta cgagtttaag    540

atgatggatg gaaatatcga tctaggatag gtatacatgt tgatgcgggt tttactgatg    600

catatacaga gatgcttttt ttcgcttggt tgtgatgatg tggtctggtt gggcggtcgt    660

tctagatcgg agtagaatac tgtttcaaac tacctggtgg atttattaat tttgtatctt    720

tatgtgtgtg ccatacatct tcatagttac gagtttaaga tgatggatgg aaatattgat    780

ctaggatagg tatacatgtt gatgtgggtt ttactgatgc atatacatga tggcatatgc    840

ggcatctatt catatgctct aaccttgagt acctatctat tataataaac aagtatgttt    900

tataattatt ttgatcttga tatacttgga tgatggcata tgcagcagct atatgtggat    960

tttttagccc tgccttcata cgctatttat ttgcttggta ctgtttcttt tgtccgatgc   1020

tcaccctgtt gttgggtgat acttctgcag                                    1050
```

<210> SEQ ID NO 53

<211> LENGTH: 2005
<212> TYPE: DNA
<213> ORGANISM: Zea mays subsp. Mexicana

<400> SEQUENCE: 53
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aatttttttaa aactaaaact 420 ctattttagt tttttattta ataatttaga tataaaatga aataaaataa attgactaca 480
aataaaacaa ataccettta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccccct ccacaccctc tttccccaac ctcgtgttcg ttcggagcgc 900
acacacacgc aaccagatct cccccaaatc cagccgtcgg cacctccgct tcaaggtacg 960
ccgctcatcc tcccccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc tttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgtttg gtgatacttc tgcag 2005

<210> SEQ ID NO 54
<211> LENGTH: 1050
<212> TYPE: DNA
<213> ORGANISM: Zea mays subsp. Mexicana

<400> SEQUENCE: 54
gtacgccgct catcctcccc cccccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gtttggtgat acttctgcag 1050

<210> SEQ ID NO 55
<211> LENGTH: 1632
<212> TYPE: DNA
<213> ORGANISM: Sorghum bicolor

<400> SEQUENCE: 55
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga cgtaaccctc cgttgcccac 420
gataaaagct ccaccccega ccccggcccc ccgatttccc ctacggacca gtctcccccc 480
gatcgcaatc gcgaattcgt cgcaccatcg gcacgcagac gaacgaagca aggctctccc 540
catcggctcg tcaaggtatg cgttccctag atttgttccc ttcctctctc ggtttgtcta 600
tatatatgca tgtatggtcg attcccgatc tcgtcgattc tcggtttcgc cttccgtacg 660
aagattcgtt tagattgttc atatgttctg ttgtgttacc agattgatcg gatcaacttg 720
atccagttat cttcgctcct ccgattagat ccgtttctat ttcagtatat atatactagt 780
atagtatcta gggttcacac tgttgaccga ctggttactt ggaattgatc cgtgctgagt 840
tcagttgttg ccgtccataa aggcccgtgc tattgtctgt tctgaaacga aatcctgtag 900
atttcttagg gttagtgttc aattcatcaa aaggttgatt agtgaattat caaatttgag 960
agggttaaat cattctcatc atgttgtctc gaatgtaatc ccaaagatat tatagactgt 1020
gtttcgattt gatggattga tttgtgtatc atctaaatca acaaggctaa gtcatcagtt 1080
catagaatca tgtttaggtt tccgttcaat agactagttt tatcaatata taaaattata 1140
agaagggtag ggtaaatcac gttgcctcaa atgccatcct gtatggtttg gtttcaattc 1200
aattagtttg gttgattagg gtatgctctg gattaagatg gttaaatctt ccctagcatc 1260
ttccctgcct atccttactt gatccgtttc ggatatgttg gaagtacagc gagcttattt 1320
catgttgata gtgacccctt tcagattata ctattgaata ttgtatgttt gccacttctg 1380
tatgttgaat tatcctgcta aattagcaat ggaattagca tattggcaat tggtatgcat 1440
ggacctaatc aggacggatg tggttatgtt agtttcaatt cattgtcaat tcattgttca 1500
cctgcgttag atatatatga tgatttttac gtgtagttca tagttcttga gttttggatc 1560
tttcttatct gatatatgct ttcctgtgcc tgtgctttat tgtgtcttac catgcgattt 1620
ttgtctatgc ag 1632

<210> SEQ ID NO 56
<211> LENGTH: 401
<212> TYPE: DNA
<213> ORGANISM: Sorghum bicolor

<400> SEQUENCE: 56
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga c 401

<210> SEQ ID NO 57
<211> LENGTH: 154
<212> TYPE: DNA
<213> ORGANISM: Sorghum bicolor

<400> SEQUENCE: 57
gtaaccctcc gttgcccacg ataaaagctc cacccccgac cccggccccc cgatttcccc 60
tacggaccag tctccccccg atcgcaatcg cgaattcgtc gcaccatcgg cacgcagacg 120
aacgaagcaa ggctctcccc atcggctcgt caag 154

<210> SEQ ID NO 58
<211> LENGTH: 1077
<212> TYPE: DNA
<213> ORGANISM: Sorghum bicolor

<400> SEQUENCE: 58
gtatgcgttc cctagatttg ttcccttcct ctctcggttt gtctatatat atgcatgtat 60
ggtcgattcc cgatctcgtc gattctcggt ttcgccttcc gtacgaagat tcgtttagat 120
tgttcatatg ttctgttgtg ttaccagatt gatcggatca acttgatcca gttatcttcg 180
ctcctccgat tagatccgtt tctatttcag tatatatata ctagtatagt atctagggtt 240
cacactgttg accgactggt tacttggaat tgatccgtgc tgagttcagt tgttgccgtc 300
cataaaggcc cgtgctattg tctgttctga aacgaaatcc tgtagatttc ttagggttag 360
tgttcaattc atcaaaaggt tgattagtga attatcaaat ttgagagggt taaatcattc 420
tcatcatgtt gtctcgaatg taatcccaaa gatattatag actgtgtttc gatttgatgg 480
attgatttgt gtatcatcta aatcaacaag gctaagtcat cagttcatag aatcatgttt 540
aggtttccgt tcaatagact agttttatca atatataaaa ttataagaag ggtagggtaa 600
atcacgttgc ctcaaatgcc atcctgtatg gtttggtttc aattcaatta gtttggttga 660
ttagggtatg ctctggatta agatggttaa atcttcccta gcatcttccc tgcctatcct 720
tacttgatcc gtttcggata tgttggaagt acagcgagct tatttcatgt tgatagtgac 780
ccctttcaga ttatactatt gaatattgta tgtttgccac ttctgtatgt tgaattatcc 840
tgctaaatta gcaatggaat tagcatattg gcaattggta tgcatggacc taatcaggac 900
ggatgtggtt atgttagttt caattcattg tcaattcatt gttcacctgc gttagatata 960
tatgatgatt tttacgtgta gttcatagtt cttgagtttt ggatctttct tatctgatat 1020
atgctttcct gtgcctgtgc tttattgtgt cttaccatgc gatttttgtc tatgcag 1077

<210> SEQ ID NO 59
<211> LENGTH: 2000
<212> TYPE: DNA
<213> ORGANISM: Sorghum bicolor

<400> SEQUENCE: 59
cactagctgc gcatgataaa gccacaagcc aaaattaatt attatgggtg agaataaata 60
cgtaccagca ccggccatag aaaaagtaca ttattaaagg tctaatttgg aaacagtctg 120
aaaacgacgt gcgctgcaga ggtaaatgta attttcggca ctaaaaccat tatcaactaa 180
ttcattcaat aacagttatt tagaaaatgt atagctcgct ctaaaaaaac agtttagaaa 240
aacagtcaaa ataattcgac caacaaacag ttaataaggt tcattaaata tataatgcac 300
ggtgctattt gatcttttaa aggaaaaaga ggaatagtcg tgggcgccag gcgggaattg 360
gggcgcggga gtctgccgga cgacgcgttc cgtccgaacg gccggacccg acgaggcccc 420
cccgccgccc cacgtcgcag aaccgtccgt gggtggtaat ctggccgggt acaccagccg 480
tccccttggg cggcctcaca gcactgggct cacacgtgag ttttgttctg ggcttcggat 540
cgcaccatat gggcctcggc atcagaaaga cggggcccgt ctgggataga agagacagga 600
acctcctcgt ggattccaga agccagccac gagcgaccac cgacgcggag gatactcgtc 660
gtccaagtcc aacacggcgg gcgggcgggc ggacgcgtgg gctgggctaa ctgcctaacc 720
ttaacctcca aggcacgcca aggcccgctt ctcccacccg acataaatat ccccccatcc 780
aggcaaggcg cagagcctca gaccagattc cgatcaatca cccataagct ccccccaaat 840
ctgttcctcg tctcccgtct cgcggtttcc tacttccctc ggacgcctcc ggcaagtcgc 900
tcgaccgcgc gattccgccc gctcaaggta tcaactcggt tcaccactcc aatctacgtc 960
tgatttagat gttacttcca tctatgtcta atttagatgt tactccgatg cgattggatt 1020
atgtttatgc ggtttgcact gctctggaaa ctggaatcta gggtttcgag tgatttgatc 1080
gatcgcgatc tgtgatttcg ttgcgccttg tgtatgcttg gagtgatcta ggcttgtata 1140
tgcggcatcg cgatctgacg cggttgcttt gtagaggctg ggggtctagg ctgtgatttt 1200
agaatcaaat aaagctgttc cttaccgtag atgtttccta catgttctgt ccagtactcc 1260
agtgctatat tcacattgtt tgaggcttga gttttgtcga tcagtggtca tgagaaaaat 1320
atatctcatg attttagagg cacctattgg gaaaggtaga tggttccgtt ttacatgttt 1380

```
tatagacctt gtggcatggc tcctttgttc tatgggtgct ttattttcct gaataacagt   1440

aatgcgagac tggtctatgg gtgctttgac cagtaatgcg agactagtta tttgatcatg   1500

gtgcagttcc tagtgattac gaacaacaat ttggtagctc agttcattca gcattggttt   1560

ctacgatcct tatcatttta cttctgaatg aatttattta tttaagatat tacagtgcaa   1620

taaactgctg tataatatca gtaacaaact gctattacta gtaaatgcct agattcataa   1680

taattcatta ttctacttga aaatgatctt aggccttttt atgcggtcct acgcatcctt   1740

ccacaggact tgctgtttgt ttgtttttttg taatccctcg ctgggacgca gaatggttca   1800

tctgtgctaa taattttttt gcatatataa gtttatagtt ctcattattc atgtggctat   1860

ggtagcctgt aaaatctatt gtaataacat attagtcagc catacatctg ttccaacttg   1920

ctcaattgca aatcatatct ccacttaaag cacatgtttg caagctttct gacaagtttc   1980

tttgtgtttg attgaaacag                                               2000


<210> SEQ ID NO 60
<211> LENGTH: 791
<212> TYPE: DNA
<213> ORGANISM: Sorghum bicolor

<400> SEQUENCE: 60

cactagctgc gcatgataaa gccacaagcc aaaattaatt attatgggtg agaataaata     60

cgtaccagca ccggccatag aaaaagtaca ttattaaagg tctaatttgg aaacagtctg    120

aaaacgacgt gcgctgcaga ggtaaatgta attttcggca ctaaaaccat tatcaactaa    180

ttcattcaat aacagttatt tagaaaatgt atagctcgct ctaaaaaaac agtttagaaa    240

aacagtcaaa ataattcgac caacaaacag ttaataaggt tcattaaata tataatgcac    300

ggtgctattt gatcttttaa aggaaaaaga ggaatagtcg tgggcgccag gcgggaattg    360

gggcgcggga gtctgccgga cgacgcgttc cgtccgaacg gccggacccg acgaggcccc    420

cccgccgccc cacgtcgcag aaccgtccgt gggtggtaat ctggccgggt acaccagccg    480

tccccttggg cggcctcaca gcactgggct cacacgtgag ttttgttctg ggcttcggat    540

cgcaccatat gggcctcggc atcagaaaga cggggcccgt ctgggataga agagacagga    600

acctcctcgt ggattccaga agccagccac gagcgaccac cgacgcggag gatactcgtc    660

gtccaagtcc aacacggcgg gcgggcgggc ggacgcgtgg gctgggctaa ctgcctaacc    720

ttaacctcca aggcacgcca aggcccgctt ctcccacccg acataaatat ccccccatcc    780

aggcaaggcg c                                                         791


<210> SEQ ID NO 61
<211> LENGTH: 136
<212> TYPE: DNA
<213> ORGANISM: Sorghum bicolor

<400> SEQUENCE: 61

agagcctcag accagattcc gatcaatcac ccataagctc cccccaaatc tgttcctcgt     60

ctcccgtctc gcggtttcct acttccctcg gacgcctccg gcaagtcgct cgaccgcgcg    120

attccgcccg ctcaag                                                    136


<210> SEQ ID NO 62
<211> LENGTH: 1073
<212> TYPE: DNA
<213> ORGANISM: Sorghum bicolor

<400> SEQUENCE: 62
```

```
gtatcaactc ggttcaccac tccaatctac gtctgattta gatgttactt ccatctatgt     60
ctaatttaga tgttactccg atgcgattgg attatgttta tgcggtttgc actgctctgg    120
aaactggaat ctagggtttc gagtgatttg atcgatcgcg atctgtgatt tcgttgcgcc    180
ttgtgtatgc ttggagtgat ctaggcttgt atatgcggca tcgcgatctg acgcggttgc    240
tttgtagagg ctgggggtct aggctgtgat tttagaatca aataaagctg ttccttaccg    300
tagatgtttc ctacatgttc tgtccagtac tccagtgcta tattcacatt gtttgaggct    360
tgagttttgt cgatcagtgg tcatgagaaa aatatatctc atgattttag aggcacctat    420
tgggaaaggt agatggttcc gttttacatg ttttatagac cttgtggcat ggctcctttg    480
ttctatgggt gctttatttt cctgaataac agtaatgcga gactggtcta tgggtgcttt    540
gaccagtaat gcgagactag ttatttgatc atggtgcagt tcctagtgat tacgaacaac    600
aatttggtag ctcagttcat tcagcattgg tttctacgat ccttatcatt ttacttctga    660
atgaatttat ttatttaaga tattacagtg caataaactg ctgtataata tcagtaacaa    720
actgctatta ctagtaaatg cctagattca taataattca ttattctact tgaaaatgat    780
cttaggcctt tttatgcggt cctacgcatc cttccacagg acttgctgtt tgtttgtttt    840
ttgtaatccc tcgctgggac gcagaatggt tcatctgtgc taataatttt tttgcatata    900
taagtttata gttctcatta ttcatgtggc tatggtagcc tgtaaaatct attgtaataa    960
catattagtc agccatacat ctgttccaac ttgctcaatt gcaaatcata tctccactta   1020
aagcacatgt ttgcaagctt tctgacaagt ttctttgtgt ttgattgaaa cag          1073
```

<210> SEQ ID NO 63
<211> LENGTH: 2064
<212> TYPE: DNA
<213> ORGANISM: Sorghum bicolor

<400> SEQUENCE: 63

```
cattaaaagt cattatgtgc atgcgtcgta actaacatgg atatgttgct gcactatctc     60
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attggggcgc gggagtctgc cggacgacgc gttccgtccg aacggccgga cccgacgagg    480
cccccccgcc gccccacgtc gcagaaccgt ccgtgggtgg taatctggcc gggtacacca    540
gccgtcccct tgggcggcct cacagcactg ggctcacacg tgagttttgt tctgggcttc    600
ggatcgcacc atatgggcct cggcatcaga aagacggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggccc gcttctccca cccgacataa atatcccccc    840
atccaggcaa ggcgcagagc ctcagaccag attccgatca atcacccata agctcccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta   1020
```

cgtctgattt agatgttact tccatctatg tctaatttag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcggc atcgcgatct gacgcggttg ctttgtagag gctgggggtc taggctgtga 1260
ttttagaatc aaataaagct gttccttacc gtagatgttt cctacatgtt ctgtccagta 1320
ctccagtgct atattcacat tgtttgaggc ttgagttttg tcgatcagtg gtcatgagaa 1380
aaatatatct catgatttta gaggcaccta ttgggaaagg tagatggttc cgttttacat 1440
gttttataga ccttgtggca tggctccttt gttctatggg tgctttattt tcctgaataa 1500
cagtaatgcg agactggtct atgggtgctt tgaccagtaa tgcgagacta gttatttgat 1560
catggtgcag ttcctagtga ttacgaacaa caatttggta gctcagttca ttcagcattg 1620
gtttctacga tccttatcat tttacttctg aatgaattta tttatttaag atattacagt 1680
gcaataaact gctgtataat atcagtaaca aactgctatt actagtaaat gcctagattc 1740
ataataattc attattctac ttgaaaatga tcttaggcct ttttatgcgg tcctacgcat 1800
ccttccacag gacttgctgt ttgtttgttt tttgtaatcc ctcgctggga cgcagaatgg 1860
ttcatctgtg ctaataattt ttttgcatat ataagtttat agttctcatt attcatgtgg 1920
ctatggtagc ctgtaaaatc tattgtaata acatattagt cagccataca tctgttccaa 1980
cttgctcaat tgcaaatcat atctccactt aaagcacatg tttgcaagct ttctgacaag 2040
tttctttgtg tttgattgaa acag 2064

<210> SEQ ID NO 64
<211> LENGTH: 855
<212> TYPE: DNA
<213> ORGANISM: Sorghum bicolor

<400> SEQUENCE: 64
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480 ccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgc 855

<210> SEQ ID NO 65
<211> LENGTH: 2000
<212> TYPE: DNA
<213> ORGANISM: Sorghum bicolor

<400> SEQUENCE: 65

```
agaagtaaaa aaaaagttcg tttcagaatc ataaaggtaa gttaaaaaaa gaccatacaa     60
aaaagaggta tttaatgata aactataatc cagaatttgt taggatagta tataagaata    120
agaccttgtt tagtttcaaa aaaatttgca aaattttcca gattcctcgt cacatcaaat    180
ctttagaggt atgcatggag tattaaatat agacaagacc taaataagaa aacatgaaat    240
gttcacgaaa aaaatcaagc caatgcatga tcgaagcaaa cggtatagta acggtgttaa    300
cctgatccat tgatctttgt aatctttaac ggccacctac cgcgggcagc aaacggcgtc    360
cccctcctcg atatctccgc ggcggcctct ggctttttcc gcggaattgc gcggtgggga    420
cggattccac gagaccgcaa cgcaaccgcc tctcgccgct gggccccaca ccgctcggtg    480
ccgtagcccg tagcctcacg ggattctttc tccctcctcc cccgtgtata aattggcttc    540
atcccctccc tgcctcatcc atccaaatcc cactccccaa tcccatcccg tcggagaaat    600
tcatcgaagc gaagcgaagc gaatcctccc gatcctctca aggtacgcga gttttcgaat    660
cccctccaga cccctcgtat gctttccctg ttcgttttcg tcgtagcgtt tgattaggta    720
tgctttccct gttcgtgttc gtcgtagggt tcgattaggt cgtgtgaggc catggcctgc    780
tgtgataaat ttatttgttg ttatatcgga tctgtagtcg atttgggggt cgtggtgtag    840
atccgcgggc tgtgatgaag ttatttggtg tgattgtgct cgcgtgattc tgcgcgttga    900
gctcgagtag atctgatggt tggacgaccg attggttcgt tggctggctg cgctaaggtt    960
gggctgggct catgttgcgt tcgctgttgc gcgtgattcc gcggatggac ttgcgcttga   1020
ttgccgccag atcacgttac gattatgtga tttcgtttgg aactttttag atttgtagct   1080
tctgcttatt atatgacaga tgcgcctact gctcatatgc ctgtggtaaa taatggatgg   1140
ctgtgggtca aactagttga ttgtcgagtc atgtatcata tacaggtgta tagacttgcg   1200
tctaattgtt tgcatgttgc agttatatga tttgttttag attgtttgtt ccactcatct   1260
aggctgtaaa agggacacta cttattagct tgttgtttaa tctttttatt agtagattat   1320
attggtaatg ttttactaat tattattatg ttatatgtga cttctgctca tgcctgatta   1380
taatcataga tcactgtagt tgattgttga atcatgtgtc aaatacccgt atacataaca   1440
ctacacattt gcttagttgt ttccttaact catgcaaatt gaacaccatg tatgatttgc   1500
atggtgctgt aatgttaaat actacagtcc tgttggtact tgtttagtaa gaatctgctt   1560
catacaacta tatgctatgc ctgatgataa tcatatatct ttgtgtaatt aataattagt   1620
tgactgttga ataatgtatc gagtacatac catggcacaa ttgcttagtc acttccttaa   1680
ccatgcatat tgaactgacc ccttcatgtt ctgctgaatt gttctattct gattagacca   1740
tacatcatgt attgcaatct ttatttgcaa ttgtaatgta atggttcggt tctcaaatgt   1800
taaatgctat agttgtgcta ctttctaatg ttaaatgcta tagctgtgct acttgtaaga   1860
tctgcttcat agtttagtta aattaggatg atgagctttg atgctgtaac tttgtttgat   1920
tatgttcata gttgatcagt ttttgttaga ctcacagtaa cttatggtct cactcttctt   1980
ctggtctttg atgtttgcag                                                2000
```

<210> SEQ ID NO 66
<211> LENGTH: 565
<212> TYPE: DNA
<213> ORGANISM: Sorghum bicolor

<400> SEQUENCE: 66
agaagtaaaa aaaaagttcg tttcagaatc ataaaggtaa gttaaaaaaa gaccatacaa 60
aaaagaggta tttaatgata aactataatc cagaatttgt taggatagta tataagaata 120
agaccttgtt tagtttcaaa aaaatttgca aaattttcca gattcctcgt cacatcaaat 180
ctttagaggt atgcatggag tattaaatat agacaagacc taaataagaa aacatgaaat 240
gttcacgaaa aaaatcaagc caatgcatga tcgaagcaaa cggtatagta acggtgttaa 300
cctgatccat tgatctttgt aatctttaac ggccacctac cgcgggcagc aaacggcgtc 360
cccctcctcg atatctccgc ggcggcctct ggctttttcc gcggaattgc gcggtgggga 420
cggattccac gagaccgcaa cgcaaccgcc tctcgccgct gggccccaca ccgctcggtg 480
ccgtagcccg tagcctcacg ggattctttc tccctcctcc cccgtgtata aattggcttc 540
atcccctccc tgcctcatcc atcca 565

<210> SEQ ID NO 67
<211> LENGTH: 77
<212> TYPE: DNA
<213> ORGANISM: Sorghum bicolor

<400> SEQUENCE: 67
aatcccactc cccaatccca tcccgtcgga gaaattcatc gaagcgaagc gaagcgaatc 60
ctcccgatcc tctcaag 77

<210> SEQ ID NO 68
<211> LENGTH: 1358
<212> TYPE: DNA
<213> ORGANISM: Sorghum bicolor

<400> SEQUENCE: 68
gtacgcgagt tttcgaatcc cctccagacc cctcgtatgc tttccctgtt cgttttcgtc 60
gtagcgtttg attaggtatg ctttccctgt tcgtgttcgt cgtagggttc gattaggtcg 120
tgtgaggcca tggcctgctg tgataaattt atttgttgtt atatcggatc tgtagtcgat 180
ttgggggtcg tggtgtagat ccgcgggctg tgatgaagtt atttggtgtg attgtgctcg 240
cgtgattctg cgcgttgagc tcgagtagat ctgatggttg gacgaccgat tggttcgttg 300
gctggctgcg ctaaggttgg gctgggctca tgttgcgttc gctgttgcgc gtgattccgc 360
ggatggactt gcgcttgatt gccgccagat cacgttacga ttatgtgatt tcgtttggaa 420
ctttttagat ttgtagcttc tgcttattat atgacagatg cgcctactgc tcatatgcct 480
gtggtaaata atggatggct gtgggtcaaa ctagttgatt gtcgagtcat gtatcatata 540
caggtgtata gacttgcgtc taattgtttg catgttgcag ttatatgatt tgttttagat 600
tgtttgttcc actcatctag gctgtaaaag ggacactact tattagcttg ttgtttaatc 660
tttttattag tagattatat tggtaatgtt ttactaatta ttattatgtt atatgtgact 720
tctgctcatg cctgattata atcatagatc actgtagttg attgttgaat catgtgtcaa 780
atacccgtat acataacact acacatttgc ttagttgttt ccttaactca tgcaaattga 840
acaccatgta tgatttgcat ggtgctgtaa tgttaaatac tacagtcctg ttggtacttg 900
tttagtaaga atctgcttca tacaactata tgctatgcct gatgataatc atatatcttt 960
gtgtaattaa taattagttg actgttgaat aatgtatcga gtacatacca tggcacaatt 1020
gcttagtcac ttccttaacc atgcatattg aactgacccc ttcatgttct gctgaattgt 1080
tctattctga ttagaccata catcatgtat tgcaatcttt atttgcaatt gtaatgtaat 1140
ggttcggttc tcaaatgtta aatgctatag ttgtgctact ttctaatgtt aaatgctata 1200
gctgtgctac ttgtaagatc tgcttcatag tttagttaaa ttaggatgat gagctttgat 1260
gctgtaactt tgtttgatta tgttcatagt tgatcagttt ttgttagact cacagtaact 1320
tatggtctca ctcttcttct ggtctttgat gtttgcag 1358

<210> SEQ ID NO 69
<211> LENGTH: 2622
<212> TYPE: DNA
<213> ORGANISM: Setaria italica

<400> SEQUENCE: 69
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920

-continued ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220
gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac ag 2622

<210> SEQ ID NO 70
<211> LENGTH: 1492
<212> TYPE: DNA
<213> ORGANISM: Setaria italica

<400> SEQUENCE: 70
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 71
<211> LENGTH: 127
<212> TYPE: DNA
<213> ORGANISM: Setaria italica

<400> SEQUENCE: 71
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 72
<211> LENGTH: 1003
<212> TYPE: DNA
<213> ORGANISM: Setaria italica

<400> SEQUENCE: 72
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa cag 1003

<210> SEQ ID NO 73
<211> LENGTH: 2622
<212> TYPE: DNA
<213> ORGANISM: Setaria italica

<400> SEQUENCE: 73
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360

```
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ccgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacac gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aaggaatggc tcgtaggggc ccgggtagaa tcgaagaatg ttgcgctggg   1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cccgttgccg   1500
caagactcag atcagattcc gatccccagt tcttccccaa tcaccttgtg gtctctcgtg   1560
tcgcggttcc cagggacgcc tccggctcgt cgctcgacag cgatctccgc cccagcaagg   1620
tatagattca gttccttgct ccgatcccaa tctggttgag atgttgctcc gatgcgactt   1680
gattatgtca tatatctgcg gtttgcaccg atctgaagcc tagggtttct cgagcgaccc   1740
agttatttgc aatttgcgat ttgctcgttt gttgcgcagc gtagtttatg tttggagtaa   1800
tcgaggattt gtatgcggcg tcggcgctac ctgcttaatc acgccatgtg acgcggttac   1860
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt tttttggtct attggtgcct aacttatctg aaaatcatgg   2160
aacatgaggc tagtttgatc atggtttagt tcattgtgat taataatgta tgatttagta   2220
gctattttgg tgatcgtgtc attttatttg tgaatggaat cattgtatgt aaatgaagct   2280
agttcagggg ttacgatgta gctggctttg tattctaaag gctgctatta ttcatccatc   2340
gatttcacct atatgtaatc cagagctttt gatgtgaaat ttgtctgatc cttcactagg   2400
aaggacagaa cattgttaat attttggcac atctgtctta ttctcatcct ttgtttgaac   2460
atgttagcct gttcaaacag atactgttgt aatgtcctag ttatataggt acatatgtgt   2520
tctctattga gtttatggac ttttgtgtgt gaagttatat ttcattttgc tcaaaactca   2580
tgtttgcaag ctttctgaca ttattctatt gttctgaaac ag                      2622
```

<210> SEQ ID NO 74
<211> LENGTH: 1492

<212> TYPE: DNA
<213> ORGANISM: Setaria italica

<400> SEQUENCE: 74
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 75
<211> LENGTH: 2164
<212> TYPE: DNA
<213> ORGANISM: Setaria italica

<400> SEQUENCE: 75
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480

```
ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agcatcggaa cactggtgat tggtggagcc ggcagtatgc gccccagcac ggccgaggtg    660

gtggtggccc gtggccctgc tgtctgcgcg gctcgggaca acttgaaact gggccaccgc    720

ctcgtcgcaa ctcgcaaccc gttggcggaa gaaaggaatg gctcgtaggg gcccgggtag    780

aatcgaagaa tgttgcgctg ggcttcgatt cacataacat gggcctgaag ctctaaaacg    840

acggcccggt cgccgcgcga tggaaagaga ccggatcctc ctcgtgaatt ctggaaggcc    900

acacgagagc gacccaccac cgacgcggag gagtcgtgcg tggtccaaca cggccggcgg    960

gctgggctgc gaccttaacc agcaaggcac gccacgaccc gccccgccct cgaggcataa   1020

ataccctccc atcccgttgc cgcaagactc agatcagatt ccgatcccca gttcttcccc   1080

aatcaccttg tggtctctcg tgtcgcggtt cccagggacg cctccggctc gtcgctcgac   1140

agcgatctcc gccccagcaa ggtatagatt cagttccttg ctccgatccc aatctggttg   1200

agatgttgct ccgatgcgac ttgattatgt catatatctg cggtttgcac cgatctgaag   1260

cctagggttt ctcgagcgac ccagttattt gcaatttgcg atttgctcgt ttgttgcgca   1320

gcgtagttta tgtttggagt aatcgaggat ttgtatgcgg cgtcggcgct acctgcttaa   1380

tcacgccatg tgacgcggtt acttgcagag gctgggttct gttatgtcgt gatctaagaa   1440

tctagattag gctcagtcgt tcttgctgtc gactagtttg ttttgatatc catgtagtac   1500

aagttactta aaatttaggt ccaatatatt ttgcatgctt ttggcctgtt attcttgcca   1560

acaagttgtc ctggtaaaaa gtagatgtga aagtcacgta ttgggacaaa ttgatggttt   1620

agtgctatag ttctatagtt ctgtgataca tctatctgat ttttttggt ctattggtgc   1680

ctaacttatc tgaaaatcat ggaacatgag gctagtttga tcatggttta gttcattgtg   1740

attaataatg tatgatttag tagctatttt ggtgatcgtg tcattttatt tgtgaatgga   1800

atcattgtat gtaaatgaag ctagttcagg ggttacgatg tagctggctt tgtattctaa   1860

aggctgctat tattcatcca tcgatttcac ctatatgtaa tccagagctt ttgatgtgaa   1920

atttgtctga tccttcacta ggaaggacag aacattgtta atattttggc acatctgtct   1980

tattctcatc ctttgtttga acatgttagc ctgttcaaac agatactgtt gtaatgtcct   2040

agttatatag gtacatatgt gttctctatt gagtttatgg acttttgtgt gtgaagttat   2100

atttcatttt gctcaaaact catgtttgca agctttctga cattattcta ttgttctgaa   2160

acag                                                                2164
```

<210> SEQ ID NO 76
<211> LENGTH: 1034
<212> TYPE: DNA
<213> ORGANISM: Setaria italica

<400> SEQUENCE: 76

```
gccgtttttg aagtatccag gattagaagc ttctactgcg cttttatatt atagctgtgg     60

acctgtggta acctttctct tttggcgctt gcttaatctc ggccgtgctg gtccatgctt    120

aggcactagg cagagataga gccgggggtg aatggggcta aagctcagct gctcgagggg    180

ccgtgggctg gtttccacta gcctacagct gtgccacgtg cggccgcgca agccgaagca    240

agcacgctga gccgttggac agcttgtcat aatgccatta cgtggattac acgtaactgg    300

ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420
```

cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960
gctgggctgc gaccttaacc agcaaggcac gccacgaccc gccccgccct cgaggcataa 1020
ataccctccc atcc 1034

<210> SEQ ID NO 77
<211> LENGTH: 1810
<212> TYPE: DNA
<213> ORGANISM: Setaria italica

<400> SEQUENCE: 77
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag 1810

<210> SEQ ID NO 78
<211> LENGTH: 680
<212> TYPE: DNA
<213> ORGANISM: Setaria italica

<400> SEQUENCE: 78
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc 680

<210> SEQ ID NO 79
<211> LENGTH: 1940
<212> TYPE: DNA
<213> ORGANISM: Coix lacryma-jobi

<400> SEQUENCE: 79
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc cacccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag 1940

<210> SEQ ID NO 80
<211> LENGTH: 837
<212> TYPE: DNA
<213> ORGANISM: Coix lacryma-jobi

<400> SEQUENCE: 80
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc cacccctccc agcttccttc gccacat 837

<210> SEQ ID NO 81

<211> LENGTH: 86
<212> TYPE: DNA
<213> ORGANISM: Coix lacryma-jobi

<400> SEQUENCE: 81
cctctcatca tcttctctcg tgtagcacgc gcagcccgat ccccaatccc ctctcctcgc 60
gagcctcgtc gatccctcgc ttcaag 86

<210> SEQ ID NO 82
<211> LENGTH: 1017
<212> TYPE: DNA
<213> ORGANISM: Coix lacryma-jobi

<400> SEQUENCE: 82
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tacttttttta gacggaatat 660 tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcag 1017

<210> SEQ ID NO 83
<211> LENGTH: 1845
<212> TYPE: DNA
<213> ORGANISM: Coix lacryma-jobi

<400> SEQUENCE: 83
ctatctgttt tctttttgcc ctgaaagagt gaagtcatca tcatatttac catggcgcgc 60
gtaggagcgc ttcgtcgaag acccataggg gggcggtact cgcaccgtgg ttgtttcctg 120
ttatgtaata tcggatgggg gagcagtcgg ctaggttggt cccatcggta ctggtcgtcc 180
cctagtgcgc tagatgcgcg atgtttgtcc tcaaaaactc ttttcttctt aataacaatc 240
atacgcaaat tttttgcgta ttcgagaaaa aaagaagatt ctatctgttt tttttttgaa 300
atggctccaa tttataggag gagcccgttt aacggcgtcg acaaatctaa cggacaccaa 360
ccagcgaatg agcgaaccca ccagcgccaa gctagccaag cgaagcagac ggccgagacg 420
ctgacaccct tgccttggcg cggcatctcc gtcgctggct cgctggctct ggccccttcg 480
cgagagttcc ggtccacctc cacctgtgtc ggtttccaac tccgttccgc cttcgcgtgg 540
gacttgttcc gttcatccgt tggcggcatc cggaaattgc gtggcgtaga gcacggggcc 600

```
ctcctctcac acggcacgga accgtcacga gctcacggca ccggcagcac ggcggggatt    660
ccttccccac caccgctcct tccctttccc ttcctcgccc gccatcataa atagccaccc    720
ctcccagctt ccttcgccac atcctctcat catcttctct cgtgtagcac gcgcagcccg    780
atccccaatc ccctctcctc gcgagcctcg tcgatccctc gcttcaaggt atggctatcg    840
tccttcctct ctctctcttt accttatcta gatcggcgat ccatggttag ggcctgctag    900
ttctccgttc gtgtttgtcg atggctgtga ggcacaatag atccgtcggc gttatgatgg    960
ttagcctgtc atgctcttgc gatctgtggt tcctttagga aaggcattaa tttaatccct   1020
gatggttcga gatcggtgat ccatggttag taccctaagc tgtggagtcg ggtttagatc   1080
cgcgctgttc gtaggcgatc tgttctgatt gttaacttgt cagtacctgc gaatcctcgg   1140
tggttctagc tggttcggag atcagatcga ttccattatc tgctatacat cttgtttcgt   1200
tgcctaggct ccgtttaatc tatccatcgt atgatgttag cctttgatat gattcgatcg   1260
tgctagctat gtcctgtgga cttaattgtc aggtcctaat tttaggaag actgttccaa    1320
accatctgct ggatttatta aatttggatc tggatgtgtc acatacacct tcataattaa   1380
aatggatgga aatatctctt atcttttaga tatggatagg catttatatg atgctgtgag   1440
ttttactagt actttcttag aatatatgta ctttttttaga cggaatattg atatgtatac   1500
atgtgtagat acatgaagca acatgctgct gtagtctaat aattcctgtt catctaataa   1560
tcaagtatgt atatgttctg tgtgttttat tggtatttga ttagatatat acatgcttag   1620
atacatacat gaagcagcat gctgctacag tttaatcatt attgtttatc caataaacaa   1680
acatgctttt taatttatct tgatatgctt ggatgacgga atatgcagag attttaagta   1740
cccagcatca tgagcatgca tgaccctgcg ttagtatgct gtttatttgc ttgagactct   1800
ttcttttgta gatactcacc ctgttttctg gtgatcctac tgcag                   1845
```

<210> SEQ ID NO 84
<211> LENGTH: 742
<212> TYPE: DNA
<213> ORGANISM: Coix lacryma-jobi

<400> SEQUENCE: 84

```
ctatctgttt tctttttgcc ctgaaagagt gaagtcatca tcatatttac catggcgcgc     60
gtaggagcgc ttcgtcgaag acccataggg gggcggtact cgcaccgtgg ttgtttcctg    120
ttatgtaata tcggatgggg gagcagtcgg ctaggttggt cccatcggta ctggtcgtcc    180
cctagtgcgc tagatgcgcg atgtttgtcc tcaaaaactc ttttcttctt aataacaatc    240
atacgcaaat tttttgcgta ttcgagaaaa aaagaagatt ctatctgttt tttttttgaa    300
atggctccaa tttataggag gagcccgttt aacggcgtcg acaaatctaa cggacaccaa    360
ccagcgaatg agcgaaccca ccagcgccaa gctagccaag cgaagcagac ggccgagacg    420
ctgacaccct tgccttggcg cggcatctcc gtcgctggct cgctggctct ggccccttcg    480
cgagagttcc ggtccacctc cacctgtgtc ggtttccaac tccgttccgc cttcgcgtgg    540
gacttgttcc gttcatccgt tggcggcatc cggaaattgc gtggcgtaga gcacggggcc    600
ctcctctcac acggcacgga accgtcacga gctcacggca ccggcagcac ggcggggatt    660
ccttccccac caccgctcct tccctttccc ttcctcgccc gccatcataa atagccaccc    720
ctcccagctt ccttcgccac at                                             742
```

<210> SEQ ID NO 85

<211> LENGTH: 1504
<212> TYPE: DNA
<213> ORGANISM: Coix lacryma-jobi

<400> SEQUENCE: 85
caaatctaac ggacaccaac cagcgaatga gcgaacccac cagcgccaag ctagccaagc 60
gaagcagacg gccgagacgc tgacaccctt gccttggcgc ggcatctccg tcgctggctc 120
gctggctctg gccccttcgc gagagttccg gtccacctcc acctgtgtcg gtttccaact 180
ccgttccgcc ttcgcgtggg acttgttccg ttcatccgtt ggcggcatcc ggaaattgcg 240
tggcgtagag cacggggccc tcctctcaca cggcacggaa ccgtcacgag ctcacggcac 300
cggcagcacg gcggggattc cttccccacc accgctcctt ccctttccct tcctcgcccg 360
ccatcataaa tagccacccc tcccagcttc cttcgccaca tcctctcatc atcttctctc 420
gtgtagcacg cgcagcccga tccccaatcc cctctcctcg cgagcctcgt cgatccctcg 480
cttcaaggta tggctatcgt ccttcctctc tctctcttta ccttatctag atcggcgatc 540
catggttagg gcctgctagt tctccgttcg tgtttgtcga tggctgtgag gcacaataga 600
tccgtcggcg ttatgatggt tagcctgtca tgctcttgcg atctgtggtt cctttaggaa 660
aggcattaat ttaatccctg atggttcgag atcggtgatc catggttagt accctaagct 720
gtggagtcgg gtttagatcc gcgctgttcg taggcgatct gttctgattg ttaacttgtc 780
agtacctgcg aatcctcggt ggttctagct ggttcggaga tcagatcgat tccattatct 840
gctatacatc ttgtttcgtt gcctaggctc cgtttaatct atccatcgta tgatgttagc 900
ctttgatatg attcgatcgt gctagctatg tcctgtggac ttaattgtca ggtcctaatt 960
tttaggaaga ctgttccaaa ccatctgctg gatttattaa atttggatct ggatgtgtca 1020
catacacctt cataattaaa atggatggaa atatctctta tcttttagat atggataggc 1080
atttatatga tgctgtgagt tttactagta ctttcttaga atatatgtac ttttttagac 1140
ggaatattga tatgtataca tgtgtagata catgaagcaa catgctgctg tagtctaata 1200
attcctgttc atctaataat caagtatgta tatgttctgt gtgttttatt ggtatttgat 1260
tagatatata catgcttaga tacatacatg aagcagcatg ctgctacagt ttaatcatta 1320
ttgtttatcc aataaacaaa catgcttttt aatttatctt gatatgcttg gatgacggaa 1380
tatgcagaga ttttaagtac ccagcatcat gagcatgcat gaccctgcgt tagtatgctg 1440
tttatttgct tgagactctt tcttttgtag atactcaccc tgttttctgg tgatcctact 1500
gcag 1504

<210> SEQ ID NO 86
<211> LENGTH: 401
<212> TYPE: DNA
<213> ORGANISM: Coix lacryma-jobi

<400> SEQUENCE: 86
caaatctaac ggacaccaac cagcgaatga gcgaacccac cagcgccaag ctagccaagc 60
gaagcagacg gccgagacgc tgacaccctt gccttggcgc ggcatctccg tcgctggctc 120
gctggctctg gccccttcgc gagagttccg gtccacctcc acctgtgtcg gtttccaact 180
ccgttccgcc ttcgcgtggg acttgttccg ttcatccgtt ggcggcatcc ggaaattgcg 240
tggcgtagag cacggggccc tcctctcaca cggcacggaa ccgtcacgag ctcacggcac 300
cggcagcacg gcggggattc cttccccacc accgctcctt ccctttccct tcctcgcccg 360
ccatcataaa tagccacccc tcccagcttc cttcgccaca t 401

<210> SEQ ID NO 87
<211> LENGTH: 1157
<212> TYPE: DNA
<213> ORGANISM: Coix lacryma-jobi

<400> SEQUENCE: 87
ccttcctcgc ccgccatcat aaatagccac ccctcccagc ttccttcgcc acatcctctc 60
atcatcttct ctcgtgtagc acgcgcagcc cgatccccaa tcccctctcc tcgcgagcct 120
cgtcgatccc tcgcttcaag gtatggctat cgtccttcct ctctctctct ttaccttatc 180
tagatcggcg atccatggtt agggcctgct agttctccgt tcgtgtttgt cgatggctgt 240
gaggcacaat agatccgtcg gcgttatgat ggttagcctg tcatgctctt gcgatctgtg 300
gttcctttag gaaaggcatt aatttaatcc ctgatggttc gagatcggtg atccatggtt 360
agtaccctaa gctgtggagt cgggtttaga tccgcgctgt tcgtaggcga tctgttctga 420
ttgttaactt gtcagtacct gcgaatcctc ggtggttcta gctggttcgg agatcagatc 480
gattccatta tctgctatac atcttgtttc gttgcctagg ctccgtttaa tctatccatc 540
gtatgatgtt agcctttgat atgattcgat cgtgctagct atgtcctgtg gacttaattg 600
tcaggtccta atttttagga agactgttcc aaaccatctg ctggatttat taaatttgga 660
tctggatgtg tcacatacac cttcataatt aaaatggatg gaaatatctc ttatctttta 720
gatatggata ggcatttata tgatgctgtg agttttacta gtactttctt agaatatatg 780
tactttttta gacggaatat tgatatgtat acatgtgtag atacatgaag caacatgctg 840
ctgtagtcta ataattcctg ttcatctaat aatcaagtat gtatatgttc tgtgtgtttt 900
attggtattt gattagatat atacatgctt agatacatac atgaagcagc atgctgctac 960
agtttaatca ttattgttta tccaataaac aaacatgctt tttaatttat cttgatatgc 1020
ttggatgacg gaatatgcag agattttaag tacccagcat catgagcatg catgaccctg 1080
cgttagtatg ctgtttattt gcttgagact ctttcttttg tagatactca ccctgttttc 1140
tggtgatcct actgcag 1157

<210> SEQ ID NO 88
<211> LENGTH: 54
<212> TYPE: DNA
<213> ORGANISM: Coix lacryma-jobi

<400> SEQUENCE: 88
ccttcctcgc ccgccatcat aaatagccac ccctcccagc ttccttcgcc acat 54

<210> SEQ ID NO 89
<211> LENGTH: 798
<212> TYPE: DNA
<213> ORGANISM: Coix lacryma-jobi

<400> SEQUENCE: 89
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360

-continued

```
gaaaaaaaga agattctatc tgttttttttt ttgaaatggc tccaatttat aggaggagcc    420

cgtttaacgg cgtcgacaaa tctaacggac accaaccagc gaatgagcga acccaccagc    480

gccaagctag ccaagcgaag cagacggccg agacgctgac acccttgcct tggcgcggca    540

tctccgtcgc tggctcgctg gctctggccc cttcgcgaga gttccggtcc acctccacct    600

gtgtcggttt ccaactccgt tccgccttcg cgtgggactt gttccgttca tccgttggcg    660

gcatccggaa attgcgtggc gtagagcacg gggccctcct ctcacacggc acggaaccgt    720

cacgagctca cggcaccggc agcacggcgg ggattccttc cccaccaccg ctccttccct    780

ttcccttcct cgcccgcc                                                  798
```

<210> SEQ ID NO 90
<211> LENGTH: 3393
<212> TYPE: DNA
<213> ORGANISM: Coix lacryma-jobi

<400> SEQUENCE: 90

```
ggttctatac aacaccacac actgtgtgag tgtgtgacca gtggccaact tttgttcagt     60

tcaacgatcc tggcctttcc gggcacccaa tacactaatt aatctattgc agctaacctc    120

aaaagaaatg catttgcagt tgtctgtcct aatcaatcta ctagcagact cacattattg    180

atgtaggaaa taaaattcag cctgtgacgt ggatgcaaca actgcactgc acaggatacc    240

atcttagccg ttgtgtcaca atttgctttg ctaatgtttt gagaaaccca gctttgacaa    300

acgtaagatc gatgagggcc ttacgtttgg cacaatatgt attgtaatcc ggcacggcaa    360

gttagactcg gtagtgttta gccggcatct ttatgtttgg cacaatttaa tttaattcgg    420

catggtaggt tagactgcag cgtgagccgg tcattgcaag ttattatgac atgttagagc    480

atctccaaca agttggaaaa aatgacttgg tatatcatgg tatatcatga gttttagcaa    540

cttattaatt catttgacaa gtaaaaaaaa gatccctctt caacaatttg ctattccaac    600

tcgctaaaat aaaaaaaaat taggctcacc taggccgatc tgcgttgccg cgggagagga    660

gggtaaaaga ttttgcgcta ggagaggtgg aggaacaggg cgcgggagcc ggccacggtg    720

aaatcacggg atagcaacct cacccgcgcg cgcaaattta cgcgtgtggc atggaggaat    780

agaaagttgg aaaagatagc aagttcattt agggagttgt tggagaagaa tatttgtgct    840

tttaccaaat ttataagaat agcaagtgag aatagagagt tgttggagat gctcaacaaa    900

tatacacaat aaagtggtat aataagcggc aagttattat gacatatata agagcaagta    960

tacaataagg tgaactgtta tatcgatcga tttttttttg agcacatatc gatcgaattt   1020

attgtaagat agaaaagaga agatataaaa acttatagtg atgaacaata ataatataaa   1080

gattattttt aaactatgaa aacaataacc gaactactcg ctctcttcta attagtaaag   1140

taaaggcttc tcattgtata tatataaaaa aattcgttct gatttcttat attcaagacg   1200

gggagagtgc tgagtgctaa cttactagtc tacgagagaa gcttcaaatc aaacagtgta   1260

ctatagggct tacacaattt ttctgaggga agcgattgtc tgaaatgaac taaaaggctg   1320

agagctggaa aaagtagctt attctgattc tgtgaagtga ttctccatgc tgattttaaa   1380

agtttatgat aaaaaatcaa agagaataac tttcagccac agaatcactt ctctcagaga   1440

atcaacttat atggagaatc agaatcagat ggagctctac caaactggcc ctaggcatta   1500

acctaccatg gatcacatcg taaaaaaaaa accctaccat ggatcctatc tgttttcttt   1560

ttgccctgaa agagtgaagt catcatcata tttaccatgg cgcgcgtagg agcgcttcgt   1620

cgaagaccca tagggggggcg gtactcgcac cgtggttgtt tcctgttatg taatatcgga   1680
```

```
tgggggagca gtcggctagg ttggtcccat cggtactggt cgtcccctag tgcgctagat   1740
gcgcgatgtt tgtcctcaaa aactcttttc ttcttaataa caatcatacg caaatttttt   1800
gcgtattcga gaaaaaaaga agattctatc tgtttttttt ttgaaatggc tccaatttat   1860
aggaggagcc cgtttaacgg cgtcgacaaa tctaacggac accaaccagc gaatgagcga   1920
acccaccagc gccaagctag ccaagcgaag cagacggccg agacgctgac acccttgcct   1980
tggcgcggca tctccgtcgc tggctcgctg gctctggccc cttcgcgaga gttccggtcc   2040
acctccacct gtgtcggttt ccaactccgt tccgccttcg cgtgggactt gttccgttca   2100
tccgttggcg gcatccggaa attgcgtggc gtagagcacg gggccctcct ctcacacggc   2160
acggaaccgt cacgagctca cggcaccggc agcacggcgg ggattccttc cccaccaccg   2220
ctccttccct ttcccttcct cgcccgccat cataaatagc cacccctccc agcttccttc   2280
gccacatcct ctcatcatct tctctcgtgt agcacgcgca gcccgatccc caatcccctc   2340
tcctcgcgag cctcgtcgat ccctcgcttc aaggtatggc tatcgtcctt cctctctctc   2400
tctttacctt atctagatcg gcgatccatg gttagggcct gctagttctc cgttcgtgtt   2460
tgtcgatggc tgtgaggcac aatagatccg tcggcgttat gatggttagc ctgtcatgct   2520
cttgcgatct gtggttcctt taggaaaggc attaatttaa tccctgatgg ttcgagatcg   2580
gtgatccatg gttagtaccc taagctgtgg agtcgggttt agatccgcgc tgttcgtagg   2640
cgatctgttc tgattgttaa cttgtcagta cctgcgaatc ctcggtggtt ctagctggtt   2700
cggagatcag atcgattcca ttatctgcta tacatcttgt ttcgttgcct aggctccgtt   2760
taatctatcc atcgtatgat gttagccttt gatatgattc gatcgtgcta gctatgtcct   2820
gtggacttaa ttgtcaggtc ctaattttta ggaagactgt tccaaaccat ctgctggatt   2880
tattaaattt ggatctggat gtgtcacata caccttcata attaaaatgg atggaaatat   2940
ctcttatctt ttagatatgg ataggcattt atatgatgct gtgagtttta ctagtacttt   3000
cttagaatat atgtactttt ttagacggaa tattgatatg tatacatgtg tagatacatg   3060
aagcaacatg ctgctgtagt ctaataattc ctgttcatct aataatcaag tatgtatatg   3120
ttctgtgtgt tttattggta tttgattaga tatatacatg cttagataca tacatgaagc   3180
agcatgctgc tacagtttaa tcattattgt ttatccaata aacaaacatg ctttttaatt   3240
tatcttgata tgcttggatg acggaatatg cagagatttt aagtacccag catcatgagc   3300
atgcatgacc ctgcgttagt atgctgttta tttgcttgag actctttctt ttgtagatac   3360
tcaccctgtt ttctggtgat cctactgcag gtg                                3393
```

<210> SEQ ID NO 91
<211> LENGTH: 2287
<212> TYPE: DNA
<213> ORGANISM: Coix lacryma-jobi

<400> SEQUENCE: 91

```
ggttctatac aacaccacac actgtgtgag tgtgtgacca gtggccaact tttgttcagt     60
tcaacgatcc tggcctttcc gggcacccaa tacactaatt aatctattgc agctaacctc    120
aaaagaaatg catttgcagt tgtctgtcct aatcaatcta ctagcagact cacattattg    180
atgtaggaaa taaaattcag cctgtgacgt ggatgcaaca actgcactgc acaggatacc    240
atcttagccg ttgtgtcaca atttgctttg ctaatgtttt gagaaaccca gctttgacaa    300
acgtaagatc gatgagggcc ttacgtttgg cacaatatgt attgtaatcc ggcacggcaa    360
```

```
gttagactcg gtagtgttta gccggcatct ttatgtttgg cacaatttaa tttaattcgg    420

catggtaggt tagactgcag cgtgagccgg tcattgcaag ttattatgac atgttagagc    480

atctccaaca agttggaaaa aatgacttgg tatatcatgg tatatcatga gttttagcaa    540

cttattaatt catttgacaa gtaaaaaaaa gatccctctt caacaatttg ctattccaac    600

tcgctaaaat aaaaaaaaat taggctcacc taggccgatc tgcgttgccg cgggagagga    660

gggtaaaaga ttttgcgcta ggagaggtgg aggaacaggg cgcgggagcc ggccacggtg    720

aaatcacggg atagcaacct cacccgcgcg cgcaaattta cgcgtgtggc atggaggaat    780

agaaagttgg aaaagatagc aagttcattt agggagttgt tggagaagaa tatttgtgct    840

tttaccaaat ttataagaat agcaagtgag aatagagagt tgttggagat gctcaacaaa    900

tatacacaat aaagtggtat aataagcggc aagttattat gacatatata agagcaagta    960

tacaataagg tgaactgtta tatcgatcga tttttttttg agcacatatc gatcgaattt   1020

attgtaagat agaaaagaga agatataaaa acttatagtg atgaacaata ataatataaa   1080

gattattttt aaactatgaa aacaataacc gaactactcg ctctcttcta attagtaaag   1140

taaaggcttc tcattgtata tatataaaaa aattcgttct gatttcttat attcaagacg   1200

gggagagtgc tgagtgctaa cttactagtc tacgagagaa gcttcaaatc aaacagtgta   1260

ctatagggct tacacaattt ttctgaggga agcgattgtc tgaaatgaac taaaaggctg   1320

agagctggaa aaagtagctt attctgattc tgtgaagtga ttctccatgc tgattttaaa   1380

agtttatgat aaaaaatcaa agagaataac tttcagccac agaatcactt ctctcagaga   1440

atcaacttat atggagaatc agaatcagat ggagctctac caaactggcc ctaggcatta   1500

acctaccatg gatcacatcg taaaaaaaaa accctaccat ggatcctatc tgtttttcttt   1560

ttgccctgaa agagtgaagt catcatcata tttaccatgg cgcgcgtagg agcgcttcgt   1620

cgaagaccca taggggggcg gtactcgcac cgtggttgtt tcctgttatg taatatcgga   1680

tgggggagca gtcggctagg ttggtcccat cggtactggt cgtcccctag tgcgctagat   1740

gcgcgatgtt tgtcctcaaa aactcttttc ttcttaataa caatcatacg caaatttttt   1800

gcgtattcga gaaaaaaaga agattctatc tgtttttttt ttgaaatggc tccaatttat   1860

aggaggagcc cgtttaacgg cgtcgacaaa tctaacggac accaaccagc gaatgagcga   1920

acccaccagc gccaagctag ccaagcgaag cagacggccg agacgctgac acccttgcct   1980

tggcgcggca tctccgtcgc tggctcgctg gctctggccc cttcgcgaga gttccggtcc   2040

acctccacct gtgtcggttt ccaactccgt tccgccttcg cgtgggactt gttccgttca   2100

tccgttggcg gcatccggaa attgcgtggc gtagagcacg gggccctcct ctcacacggc   2160

acggaaccgt cacgagctca cggcaccggc agcacggcgg ggattccttc cccaccaccg   2220

ctccttccct ttcccttcct cgcccgccat cataaatagc cacccctccc agcttccttc   2280

gccacat                                                              2287
```

<210> SEQ ID NO 92
<211> LENGTH: 1020
<212> TYPE: DNA
<213> ORGANISM: Coix lacryma-jobi

<400> SEQUENCE: 92

```
gtatggctat cgtccttcct ctctctctct ttaccttatc tagatcggcg atccatggtt     60

agggcctgct agttctccgt tcgtgtttgt cgatggctgt gaggcacaat agatccgtcg    120

gcgttatgat ggttagcctg tcatgctctt gcgatctgtg gttcctttag gaaaggcatt    180
```

aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tactttttta gacggaatat 660
tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttctttg tagatactca ccctgtttc tggtgatcct actgcaggtg 1020

<210> SEQ ID NO 93
<211> LENGTH: 3393
<212> TYPE: DNA
<213> ORGANISM: Coix lacryma-jobi

<400> SEQUENCE: 93
ggttctatac aacaccacac actgtgtgag tgtgtgacca gtggccaact tttgttcagt 60
tcaacgatcc tggcctttcc gggcacccaa tacactaatt aatctattgc agctaacctc 120
aaaagaaatg catttgcagt tgtctgtcct aatcaatcta ctagcagact cacattattg 180
atgtaggaaa taaaattcag cctgtgacgt ggatgcaaca actgcactgc acaggatacc 240
atcttagccg ttgtgtcaca atttgctttg ctaatgtttt gagaaaccca gctttgacaa 300
acgtaagatc gatgagggcc ttacgtttgg cacaatatgt attgtaatcc ggcacggcaa 360
gttagactcg gtagtgttta gccggcatct ttatgtttgg cacaatttaa tttaattcgg 420
catggtaggt tagactgcag cgtgagccgg tcattgcaag ttattatgac atgttagagc 480
atctccaaca agttggaaaa aatgacttgg tatatcatgg tatatcatga gttttagcaa 540
cttattaatt catttgacaa gtaaaaaaaa gatccctctt caacaatttg ctattccaac 600
tcgctaaaat aaaaaaaaat taggctcacc taggccgatc tgcgttgccg cgggagagga 660
gggtaaaaga ttttgcgcta ggagaggtgg aggaacaggg cgcgggagcc ggccacggtg 720
aaatcacggg atagcaacct cacccgcgcg cgcaaattta cgcgtgtggc atggaggaat 780
agaaagttgg aaaagatagc aagttcattt agggagttgt tggagaagaa tatttgtgct 840
tttaccaaat ttataagaat agcaagtgag aatagagagt tgttggagat gctcaacaaa 900
tatacacaat aaagtggtat aataagcggc aagttattat gacatatata agagcaagta 960
tacaataagg tgaactgtta tatcgatcga tttttttttg agcacatatc gatcgaattt 1020
attgtaagat agaaaagaga agatataaaa acttatagtg atgaacaata ataatataaa 1080
gattattttt aaactatgaa aacaataacc gaactactcg ctctcttcta attagtaaag 1140
taaaggcttc tcattgtata tatataaaaa aattcgttct gatttcttat attcaagacg 1200
gggagagtgc tgagtgctaa cttactagtc tacgagagaa gcttcaaatc aaacagtgta 1260

```
ctatagggct tacacaattt ttctgaggga agcgattgtc tgaaatgaac taaaaggctg   1320

agagctggaa aaagtagctt attctgattc tgtgaagtga ttctccatgc tgattttaaa   1380

agtttatgat aaaaaatcaa agagaataac tttcagccac agaatcactt ctctcagaga   1440

atcaacttat atggagaatc agaatcagat ggagctctac caaactggcc ctaggcatta   1500

acctaccatg gatcacatcg taaaaaaaaa accctaccat ggatcctatc tgttttcttt   1560

ttgccctgaa agagtgaagt catcatcata tttaccatgg cgcgcgtagg agcgcttcgt   1620

cgaagaccca tagggggcg gtactcgcac cgtggttgtt tcctgttatg taatatcgga   1680

tgggggagca gtcggctagg ttggtcccat cggtactggt cgtcccctag tgcgctagat   1740

gcgcgatgtt tgtcctcaaa aactcttttc ttcttaataa caatcatacg caaatttttt   1800

gcgtattcga gaaaaaaaga agattctatc tgtttttttt ttgaaatggc tccaatttat   1860

aggaggagcc cgtttaacgg cgtcgacaaa tctaacggac accaaccagc gaatgagcga   1920

acccaccagc gccaagctag ccaagcgaag cagacggccg agacgctgac acccttgcct   1980

tggcgcggca tctccgtcgc tggctcgctg gctctggccc cttcgcgaga gttccggtcc   2040

acctccacct gtgtcggttt ccaactccgt tccgccttcg cgtgggactt gttccgttca   2100

tccgttggcg gcatccggaa attgcgtggc gtagagcacg gggccctcct ctcacacggc   2160

acggaaccgt cacgagctca cggcaccggc agcacggcgg ggattccttc cccaccaccg   2220

ctccttccct ttcccttcct cgcccgccat cataaatagc caccccctccc agcttccttc   2280

gccacatcct ctcatcatct tctctcgtgt agcacgcgca gcccgatccc caatcccctc   2340

tcctcgcgag cctcgtcgat ccctcgcttc aaggtatggc tatcgtcctt cctctctctc   2400

tctttacctt atctagatcg gcgatccatg gttagggcct gctagttctc cgttcgtgtt   2460

tgtcgatggc tgtgaggcac aatagatccg tcggcgttat gatggttagc ctgtcatgct   2520

cttgcgatct gtggttcctt taggaaaggc attaatttaa tccctgatgg ttcgagatcg   2580

gtgatccatg gttagtaccc taagctgtgg agtcgggttt agatccgcgc tgttcgtagg   2640

cgatctgttc tgattgttaa cttgtcagta cctgcgaatc ctcggtggtt ctagctggtt   2700

cggagatcag atcgattcca ttatctgcta tacatcttgt ttcgttgcct aggctccgtt   2760

taatctatcc atcgtatgat gttagccttt gatatgattc gatcgtgcta gctatgtcct   2820

gtggacttaa ttgtcaggtc ctaatttta ggaagactgt tccaaaccat ctgctggatt   2880

tattaaattt ggatctggat gtgtcacata caccttcata attaaaatgg atggaaatat   2940

ctcttatctt ttagatatgg ataggcattt atatgatgct gtgagtttta ctagtacttt   3000

cttagaatat atgtactttt ttagacggaa tattgatatg tatacatgtg tagatacatg   3060

aagcaacatg ctgctgtagt ctaataattc ctgttcatct aataatcaag tatgtatatg   3120

ttctgtgtgt tttattggta tttgattaga tatatacatg cttagataca tacatgaagc   3180

agcatgctgc tacagtttaa tcattattgt ttatccaata aacaaacatg ctttttaatt   3240

tatcttgata tgcttggatg acggaatatg cagagatttt aagtacccag catcatgagc   3300

atgcatgacc ctgcgttagt atgctgttta tttgcttgag actctttctt ttgtagatac   3360

tcaccctgtt ttctggtgat cctactgcag gtc                                3393
```

<210> SEQ ID NO 94
<211> LENGTH: 1020
<212> TYPE: DNA
<213> ORGANISM: Coix lacryma-jobi

<400> SEQUENCE: 94
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tacttttttta gacggaatat 660 tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcaggtc 1020

<210> SEQ ID NO 95
<211> LENGTH: 2166
<212> TYPE: DNA
<213> ORGANISM: Coix lacryma-jobi

<400> SEQUENCE: 95
gtctacgaga gaagcttcaa atcaaacagt gtactatagg gcttacacaa tttttctgag 60
ggaagcgatt gtctgaaatg aactaaaagg ctgagagctg gaaaaagtag cttattctga 120
ttctgtgaag tgattctcca tgctgatttt aaaagtttat gataaaaaat caaagagaat 180
aactttcagc cacagaatca cttctctcag agaatcaact tatatggaga atcagaatca 240
gatggagctc taccaaactg gccctaggca ttaacctacc atggatcaca tcgtaaaaaa 300
aaaaccctac catggatcct atctgttttc tttttgccct gaaagagtga agtcatcatc 360
atatttacca tggcgcgcgt aggagcgctt cgtcgaagac ccataggggg gcggtactcg 420
caccgtggtt gtttcctgtt atgtaatatc ggatggggga gcagtcggct aggttggtcc 480
catcggtact ggtcgtcccc tagtgcgcta gatgcgcgat gtttgtcctc aaaaactctt 540
ttcttcttaa taacaatcat acgcaaattt tttgcgtatt cgagaaaaaa agaagattct 600
atctgttttt tttttgaaat ggctccaatt tataggagga gcccgtttaa cggcgtcgac 660
aaatctaacg gacaccaacc agcgaatgag cgaacccacc agcgccaagc tagccaagcg 720
aagcagacgg ccgagacgct gacacccttg ccttggcgcg gcatctccgt cgctggctcg 780
ctggctctgg ccccttcgcg agagttccgg tccacctcca cctgtgtcgg tttccaactc 840
cgttccgcct tcgcgtggga cttgttccgt tcatccgttg gcggcatccg gaaattgcgt 900
ggcgtagagc acggggccct cctctcacac ggcacggaac cgtcacgagc tcacggcacc 960
ggcagcacgg cggggattcc ttccccacca ccgctccttc cctttccctt cctcgcccgc 1020
catcataaat agccacccct cccagcttcc ttcgccacat cctctcatca tcttctctcg 1080
tgtagcacgc gcagcccgat ccccaatccc ctctcctcgc gagcctcgtc gatccctcgc 1140
ttcaaggtat ggctatcgtc cttcctctct ctctctttac cttatctaga tcggcgatcc 1200
atggttaggg cctgctagtt ctccgttcgt gtttgtcgat ggctgtgagg cacaatagat 1260
ccgtcggcgt tatgatggtt agcctgtcat gctcttgcga tctgtggttc ctttaggaaa 1320
ggcattaatt taatccctga tggttcgaga tcggtgatcc atggttagta ccctaagctg 1380
tggagtcggg tttagatccg cgctgttcgt aggcgatctg ttctgattgt taacttgtca 1440
gtacctgcga atcctcggtg gttctagctg gttcggagat cagatcgatt ccattatctg 1500
ctatacatct tgtttcgttg cctaggctcc gtttaatcta tccatcgtat gatgttagcc 1560
tttgatatga ttcgatcgtg ctagctatgt cctgtggact taattgtcag gtcctaattt 1620
ttaggaagac tgttccaaac catctgctgg atttattaaa tttggatctg gatgtgtcac 1680
atacaccttc ataattaaaa tggatggaaa tatctcttat cttttagata tggataggca 1740
tttatatgat gctgtgagtt ttactagtac tttcttagaa tatatgtact tttttagacg 1800
gaatattgat atgtatacat gtgtagatac atgaagcaac atgctgctgt agtctaataa 1860
ttcctgttca tctaataatc aagtatgtat atgttctgtg tgttttattg gtatttgatt 1920
agatatatac atgcttagat acatacatga agcagcatgc tgctacagtt taatcattat 1980
tgtttatcca ataaacaaac atgcttttta atttatcttg atatgcttgg atgacggaat 2040
atgcagagat tttaagtacc cagcatcatg agcatgcatg accctgcgtt agtatgctgt 2100
ttatttgctt gagactcttt cttttgtaga tactcaccct gttttctggt gatcctactg 2160
caggtg 2166

<210> SEQ ID NO 96
<211> LENGTH: 1060
<212> TYPE: DNA
<213> ORGANISM: Coix lacryma-jobi

<400> SEQUENCE: 96
gtctacgaga gaagcttcaa atcaaacagt gtactatagg gcttacacaa tttttctgag 60
ggaagcgatt gtctgaaatg aactaaaagg ctgagagctg gaaaaagtag cttattctga 120
ttctgtgaag tgattctcca tgctgatttt aaaagtttat gataaaaaat caaagagaat 180
aactttcagc cacagaatca cttctctcag agaatcaact tatatggaga atcagaatca 240
gatggagctc taccaaactg gccctaggca ttaacctacc atggatcaca tcgtaaaaaa 300
aaaaccctac catggatcct atctgttttc tttttgccct gaaagagtga agtcatcatc 360
atatttacca tggcgcgcgt aggagcgctt cgtcgaagac ccataggggg gcggtactcg 420
caccgtggtt gtttcctgtt atgtaatatc ggatggggga gcagtcggct aggttggtcc 480
catcggtact ggtcgtcccc tagtgcgcta gatgcgcgat gtttgtcctc aaaaactctt 540
ttcttcttaa taacaatcat acgcaaattt tttgcgtatt cgagaaaaaa agaagattct 600
atctgttttt tttttgaaat ggctccaatt tataggagga gcccgtttaa cggcgtcgac 660
aaatctaacg gacaccaacc agcgaatgag cgaacccacc agcgccaagc tagccaagcg 720
aagcagacgg ccgagacgct gacacccttg ccttggcgcg gcatctccgt cgctggctcg 780
ctggctctgg ccccttcgcg agagttccgg tccacctcca cctgtgtcgg tttccaactc 840
cgttccgcct tcgcgtggga cttgttccgt tcatccgttg gcggcatccg gaaattgcgt 900
ggcgtagagc acggggccct cctctcacac ggcacggaac cgtcacgagc tcacggcacc 960
ggcagcacgg cggggattcc ttccccacca ccgctccttc cctttccctt cctcgcccgc 1020
catcataaat agccacccct cccagcttcc ttcgccacat 1060

<210> SEQ ID NO 97
<211> LENGTH: 2166
<212> TYPE: DNA
<213> ORGANISM: Coix lacryma-jobi

<400> SEQUENCE: 97
gtctacgaga gaagcttcaa atcaaacagt gtactatagg gcttacacaa tttttctgag 60
ggaagcgatt gtctgaaatg aactaaaagg ctgagagctg gaaaaagtag cttattctga 120
ttctgtgaag tgattctcca tgctgatttt aaaagtttat gataaaaaat caaagagaat 180
aactttcagc cacagaatca cttctctcag agaatcaact tatatggaga atcagaatca 240
gatggagctc taccaaactg gccctaggca ttaacctacc atggatcaca tcgtaaaaaa 300
aaaaccctac catggatcct atctgttttc tttttgccct gaaagagtga agtcatcatc 360
atatttacca tggcgcgcgt aggagcgctt cgtcgaagac ccataggggg gcggtactcg 420
caccgtggtt gtttcctgtt atgtaatatc ggatggggga gcagtcggct aggttggtcc 480
catcggtact ggtcgtcccc tagtgcgcta gatgcgcgat gtttgtcctc aaaaactctt 540
ttcttcttaa taacaatcat acgcaaattt tttgcgtatt cgagaaaaaa agaagattct 600
atctgttttt tttttgaaat ggctccaatt tataggagga gcccgtttaa cggcgtcgac 660
aaatctaacg gacaccaacc agcgaatgag cgaacccacc agcgccaagc tagccaagcg 720
aagcagacgg ccgagacgct gacacccttg ccttggcgcg gcatctccgt cgctggctcg 780
ctggctctgg ccccttcgcg agagttccgg tccacctcca cctgtgtcgg tttccaactc 840
cgttccgcct tcgcgtggga cttgttccgt tcatccgttg gcggcatccg gaaattgcgt 900
ggcgtagagc acggggccct cctctcacac ggcacggaac cgtcacgagc tcacggcacc 960
ggcagcacgg cggggattcc ttccccacca ccgctccttc cctttccctt cctcgcccgc 1020
catcataaat agccacccct cccagcttcc ttcgccacat cctctcatca tcttctctcg 1080
tgtagcacgc gcagcccgat ccccaatccc ctctcctcgc gagcctcgtc gatccctcgc 1140
ttcaaggtat ggctatcgtc cttcctctct ctctctttac cttatctaga tcggcgatcc 1200
atggttaggg cctgctagtt ctccgttcgt gtttgtcgat ggctgtgagg cacaatagat 1260
ccgtcggcgt tatgatggtt agcctgtcat gctcttgcga tctgtggttc ctttaggaaa 1320
ggcattaatt taatccctga tggttcgaga tcggtgatcc atggttagta ccctaagctg 1380
tggagtcggg tttagatccg cgctgttcgt aggcgatctg ttctgattgt taacttgtca 1440
gtacctgcga atcctcggtg gttctagctg gttcggagat cagatcgatt ccattatctg 1500
ctatacatct tgtttcgttg cctaggctcc gtttaatcta tccatcgtat gatgttagcc 1560
tttgatatga ttcgatcgtg ctagctatgt cctgtggact taattgtcag gtcctaattt 1620
ttaggaagac tgttccaaac catctgctgg atttattaaa tttggatctg gatgtgtcac 1680
atacaccttc ataattaaaa tggatggaaa tatctcttat cttttagata tggataggca 1740
tttatatgat gctgtgagtt ttactagtac tttcttagaa tatatgtact tttttagacg 1800
gaatattgat atgtatacat gtgtagatac atgaagcaac atgctgctgt agtctaataa 1860
ttcctgttca tctaataatc aagtatgtat atgttctgtg tgttttattg gtatttgatt 1920
agatatatac atgcttagat acatacatga agcagcatgc tgctacagtt taatcattat 1980
tgtttatcca ataaacaaac atgcttttta atttatcttg atatgcttgg atgacggaat 2040
atgcagagat tttaagtacc cagcatcatg agcatgcatg accctgcgtt agtatgctgt 2100
ttatttgctt gagactcttt cttttgtaga tactcaccct gttttctggt gatcctactg 2160
caggtc 2166

<210> SEQ ID NO 98
<211> LENGTH: 1943
<212> TYPE: DNA
<213> ORGANISM: Coix lacryma-jobi

<400> SEQUENCE: 98
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc cacccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag gtc 1943

<210> SEQ ID NO 99
<211> LENGTH: 1943
<212> TYPE: DNA
<213> ORGANISM: Coix lacryma-jobi

<400> SEQUENCE: 99

```
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
taggggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaatttttt gcgtattcga    360
gaaaaaaaga agattctatc tgtttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc cacccctccc agcttccttc gccacatcct    840
ctcatcatct tctctcgtgt agcacgcgca gcccgatccc caatcccctc tcctcgcgag    900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata caccttcata attaaaatgg atggaaatat ctcttatctt   1500
ttagatatgg ataggcattt atatgatgct gtgagtttta ctagtacttt cttagaatat   1560
atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag gtg                                           1943
```

<210> SEQ ID NO 100
<211> LENGTH: 1943
<212> TYPE: DNA

<213> ORGANISM: Coix lacryma-jobi

<400> SEQUENCE: 100
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc cacccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag gcg 1943

<210> SEQ ID NO 101
<211> LENGTH: 1020
<212> TYPE: DNA
<213> ORGANISM: Coix lacryma-jobi

<400> SEQUENCE: 101
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tactttttta gacggaatat 660
tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcaggcg 1020

<210> SEQ ID NO 102
<211> LENGTH: 1943
<212> TYPE: DNA
<213> ORGANISM: Coix lacryma-jobi

<400> SEQUENCE: 102
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc cacccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag gac 1943

<210> SEQ ID NO 103
<211> LENGTH: 1020
<212> TYPE: DNA
<213> ORGANISM: Coix lacryma-jobi

<400> SEQUENCE: 103
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tacttttttta gacggaatat 660 tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcaggac 1020

<210> SEQ ID NO 104
<211> LENGTH: 1943
<212> TYPE: DNA
<213> ORGANISM: Coix lacryma-jobi

<400> SEQUENCE: 104
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc caccccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag acc 1943

<210> SEQ ID NO 105
<211> LENGTH: 1020
<212> TYPE: DNA
<213> ORGANISM: Coix lacryma-jobi

<400> SEQUENCE: 105
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180

-continued

```
aatttaatcc ctgatggttc gagatcggtg atccatggtt agtaccctaa gctgtggagt    240

cgggtttaga tccgcgctgt tcgtaggcga tctgttctga ttgttaactt gtcagtacct    300

gcgaatcctc ggtggttcta gctggttcgg agatcagatc gattccatta tctgctatac    360

atcttgtttc gttgcctagg ctccgtttaa tctatccatc gtatgatgtt agcctttgat    420

atgattcgat cgtgctagct atgtcctgtg gacttaattg tcaggtccta atttttagga    480

agactgttcc aaaccatctg ctggatttat taaatttgga tctggatgtg tcacatacac    540

cttcataatt aaaatggatg gaaatatctc ttatctttta gatatggata ggcatttata    600

tgatgctgtg agttttacta gtactttctt agaatatatg tactttttta gacggaatat    660

tgatatgtat acatgtgtag atacatgaag caacatgctg ctgtagtcta ataattcctg    720

ttcatctaat aatcaagtat gtatatgttc tgtgtgtttt attggtattt gattagatat    780

atacatgctt agatacatac atgaagcagc atgctgctac agtttaatca ttattgttta    840

tccaataaac aaacatgctt tttaatttat cttgatatgc ttggatgacg gaatatgcag    900

agattttaag tacccagcat catgagcatg catgaccctg cgttagtatg ctgtttattt    960

gcttgagact ctttcttttg tagatactca ccctgttttc tggtgatcct actgcagacc   1020
```

<210> SEQ ID NO 106
<211> LENGTH: 1943
<212> TYPE: DNA
<213> ORGANISM: Coix lacryma-jobi

<400> SEQUENCE: 106

```
agcagactcg cattatcgat ggagctctac caaactggcc ctaggcatta acctaccatg     60

gatcacatcg taaaaaaaaa accctaccat ggatcctatc tgttttcttt ttgccctgaa    120

agagtgaagt catcatcata tttaccatgg cgcgcgtagg agcgcttcgt cgaagaccca    180

taggggggcg gtactcgcac cgtggttgtt tcctgttatg taatatcgga tgggggagca    240

gtcggctagg ttggtcccat cggtactggt cgtcccctag tgcgctagat gcgcgatgtt    300

tgtcctcaaa aactcttttc ttcttaataa caatcatacg caaatttttt gcgtattcga    360

gaaaaaaaga agattctatc tgtttttttt ttgaaatggc tccaatttat aggaggagcc    420

cgtttaacgg cgtcgacaaa tctaacggac accaaccagc gaatgagcga acccaccagc    480

gccaagctag ccaagcgaag cagacggccg agacgctgac acccttgcct tggcgcggca    540

tctccgtcgc tggctcgctg gctctggccc cttcgcgaga gttccggtcc acctccacct    600

gtgtcggttt ccaactccgt tccgccttcg cgtgggactt gttccgttca tccgttggcg    660

gcatccggaa attgcgtggc gtagagcacg gggccctcct ctcacacggc acggaaccgt    720

cacgagctca cggcaccggc agcacggcgg ggattccttc cccaccaccg ctccttccct    780

ttcccttcct cgcccgccat cataaatagc cacccctccc agcttccttc gccacatcct    840

ctcatcatct tctctcgtgt agcacgcgca gcccgatccc caatcccctc tcctcgcgag    900

cctcgtcgat ccctcgcttc aaggtatggc tatcgtcctt cctctctctc tctttacctt    960

atctagatcg gcgatccatg gttagggcct gctagttctc cgttcgtgtt tgtcgatggc   1020

tgtgaggcac aatagatccg tcggcgttat gatggttagc ctgtcatgct cttgcgatct   1080

gtggttcctt taggaaaggc attaatttaa tccctgatgg ttcgagatcg gtgatccatg   1140

gttagtaccc taagctgtgg agtcgggttt agatccgcgc tgttcgtagg cgatctgttc   1200

tgattgttaa cttgtcagta cctgcgaatc ctcggtggtt ctagctggtt cggagatcag   1260

atcgattcca ttatctgcta tacatcttgt ttcgttgcct aggctccgtt taatctatcc   1320
```

-continued atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag ggg 1943

<210> SEQ ID NO 107
<211> LENGTH: 1020
<212> TYPE: DNA
<213> ORGANISM: Coix lacryma-jobi

<400> SEQUENCE: 107
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tactttttta gacggaatat 660
tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcagggg 1020

<210> SEQ ID NO 108
<211> LENGTH: 1943
<212> TYPE: DNA
<213> ORGANISM: Coix lacryma-jobi

<400> SEQUENCE: 108
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180

-continued

```
taggggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaatttttt gcgtattcga    360
gaaaaaaaga agattctatc tgtttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccccctccc agcttccttc gccacatcct    840
ctcatcatct tctctcgtgt agcacgcgca gcccgatccc caatcccctc tcctcgcgag    900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata caccttcata attaaaatgg atggaaatat ctcttatctt   1500
ttagatatgg ataggcattt atatgatgct gtgagtttta ctagtacttt cttagaatat   1560
atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag ggt                                           1943
```

<210> SEQ ID NO 109
<211> LENGTH: 1020
<212> TYPE: DNA
<213> ORGANISM: Coix lacryma-jobi

<400> SEQUENCE: 109

```
gtatggctat cgtccttcct ctctctctct ttaccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
```

atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tactttttta gacggaatat 660
tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttctttg tagatactca ccctgttttc tggtgatcct actgcagggt 1020

<210> SEQ ID NO 110
<211> LENGTH: 1943
<212> TYPE: DNA
<213> ORGANISM: Coix lacryma-jobi

<400> SEQUENCE: 110
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360
gaaaaaaaga agattctatc tgtttttttt ttgaaatggc tccaatttat aggaggagcc 420
cgtttaacgg cgtcgacaaa tctaacggac accaaccagc gaatgagcga acccaccagc 480
gccaagctag ccaagcgaag cagacggccg agacgctgac acccttgcct tggcgcggca 540
tctccgtcgc tggctcgctg gctctggccc cttcgcgaga gttccggtcc acctccacct 600
gtgtcggttt ccaactccgt tccgccttcg cgtgggactt gttccgttca tccgttggcg 660
gcatccggaa attgcgtggc gtagagcacg gggccctcct ctcacacggc acggaaccgt 720
cacgagctca cggcaccggc agcacggcgg ggattccttc cccaccaccg ctccttccct 780
ttcccttcct cgcccgccat cataaatagc caccccctccc agcttccttc gccacatcct 840
ctcatcatct tctctcgtgt agcacgcgca gcccgatccc caatcccctc tcctcgcgag 900
cctcgtcgat ccctcgcttc aaggtatggc tatcgtcctt cctctctctc tctttacctt 960
atctagatcg gcgatccatg gttagggcct gctagttctc cgttcgtgtt tgtcgatggc 1020
tgtgaggcac aatagatccg tcggcgttat gatggttagc ctgtcatgct cttgcgatct 1080
gtggttcctt taggaaaggc attaatttaa tccctgatgg ttcgagatcg gtgatccatg 1140
gttagtaccc taagctgtgg agtcgggttt agatccgcgc tgttcgtagg cgatctgttc 1200
tgattgttaa cttgtcagta cctgcgaatc ctcggtggtt ctagctggtt cggagatcag 1260
atcgattcca ttatctgcta tacatcttgt ttcgttgcct aggctccgtt taatctatcc 1320
atcgtatgat gttagccttt gatatgattc gatcgtgcta gctatgtcct gtggacttaa 1380
ttgtcaggtc ctaattttta ggaagactgt tccaaaccat ctgctggatt tattaaattt 1440
ggatctggat gtgtcacata caccttcata attaaaatgg atggaaatat ctcttatctt 1500
ttagatatgg ataggcattt atatgatgct gtgagtttta ctagtacttt cttagaatat 1560
atgtactttt ttagacggaa tattgatatg tatacatgtg tagatacatg aagcaacatg 1620
ctgctgtagt ctaataattc ctgttcatct aataatcaag tatgtatatg ttctgtgtgt 1680
tttattggta tttgattaga tatatacatg cttagataca tacatgaagc agcatgctgc 1740
tacagtttaa tcattattgt ttatccaata aacaaacatg ctttttaatt tatcttgata 1800
tgcttggatg acggaatatg cagagatttt aagtacccag catcatgagc atgcatgacc 1860
ctgcgttagt atgctgttta tttgcttgag actctttctt ttgtagatac tcaccctgtt 1920
ttctggtgat cctactgcag cgt 1943

<210> SEQ ID NO 111
<211> LENGTH: 1020
<212> TYPE: DNA
<213> ORGANISM: Coix lacryma-jobi

<400> SEQUENCE: 111
gtatggctat cgtccttcct ctctctctct ttaccttatc tagatcggcg atccatggtt 60
agggcctgct agttctccgt tcgtgtttgt cgatggctgt gaggcacaat agatccgtcg 120
gcgttatgat ggttagcctg tcatgctctt gcgatctgtg gttcctttag gaaaggcatt 180
aatttaatcc ctgatggttc gagatcggtg atccatggtt agtaccctaa gctgtggagt 240
cgggtttaga tccgcgctgt tcgtaggcga tctgttctga ttgttaactt gtcagtacct 300
gcgaatcctc ggtggttcta gctggttcgg agatcagatc gattccatta tctgctatac 360
atcttgtttc gttgcctagg ctccgtttaa tctatccatc gtatgatgtt agcctttgat 420
atgattcgat cgtgctagct atgtcctgtg gacttaattg tcaggtccta atttttagga 480
agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tacttttttta gacggaatat 660 tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttcttttg tagatactca ccctgttttc tggtgatcct actgcagcgt 1020

<210> SEQ ID NO 112
<211> LENGTH: 1943
<212> TYPE: DNA
<213> ORGANISM: Coix lacryma-jobi

<400> SEQUENCE: 112
agcagactcg cattatcgat ggagctctac caaactggcc ctaggcatta acctaccatg 60
gatcacatcg taaaaaaaaa accctaccat ggatcctatc tgttttcttt ttgccctgaa 120
agagtgaagt catcatcata tttaccatgg cgcgcgtagg agcgcttcgt cgaagaccca 180
taggggggcg gtactcgcac cgtggttgtt tcctgttatg taatatcgga tgggggagca 240
gtcggctagg ttggtcccat cggtactggt cgtcccctag tgcgctagat gcgcgatgtt 300
tgtcctcaaa aactcttttc ttcttaataa caatcatacg caaatttttt gcgtattcga 360

```
gaaaaaaaga agattctatc tgtttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc cacccctccc agcttccttc gccacatcct    840
ctcatcatct tctctcgtgt agcacgcgca gcccgatccc caatcccctc tcctcgcgag    900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata caccttcata attaaaatgg atggaaatat ctcttatctt   1500
ttagatatgg ataggcattt atatgatgct gtgagtttta ctagtacttt cttagaatat   1560
atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag tgt                                           1943
```

<210> SEQ ID NO 113
<211> LENGTH: 1020
<212> TYPE: DNA
<213> ORGANISM: Coix lacryma-jobi

<400> SEQUENCE: 113

```
gtatggctat cgtccttcct ctctctctct ttaccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta atttttagga    480
```

-continued agactgttcc aaaccatctg ctggatttat taaatttgga tctggatgtg tcacatacac 540
cttcataatt aaaatggatg gaaatatctc ttatctttta gatatggata ggcatttata 600
tgatgctgtg agttttacta gtactttctt agaatatatg tacttttttta gacggaatat 660 tgatatgtat acatgtgtag atacatgaag caacatgctg ctgtagtcta ataattcctg 720
ttcatctaat aatcaagtat gtatatgttc tgtgtgtttt attggtattt gattagatat 780
atacatgctt agatacatac atgaagcagc atgctgctac agtttaatca ttattgttta 840
tccaataaac aaacatgctt tttaatttat cttgatatgc ttggatgacg gaatatgcag 900
agattttaag tacccagcat catgagcatg catgaccctg cgttagtatg ctgtttattt 960
gcttgagact ctttctttg tagatactca ccctgttttc tggtgatcct actgcagtgt 1020

<210> SEQ ID NO 114
<211> LENGTH: 1848
<212> TYPE: DNA
<213> ORGANISM: Coix lacryma-jobi

<400> SEQUENCE: 114
ctatctgttt tctttttgcc ctgaaagagt gaagtcatca tcatatttac catggcgcgc 60
gtaggagcgc ttcgtcgaag acccataggg gggcggtact cgcaccgtgg ttgtttcctg 120
ttatgtaata tcggatgggg gagcagtcgg ctaggttggt cccatcggta ctggtcgtcc 180
cctagtgcgc tagatgcgcg atgtttgtcc tcaaaaactc ttttcttctt aataacaatc 240
atacgcaaat tttttgcgta ttcgagaaaa aaagaagatt ctatctgttt ttttttgaa 300 atggctccaa tttataggag gagcccgttt aacggcgtcg acaaatctaa cggacaccaa 360
ccagcgaatg agcgaaccca ccagcgccaa gctagccaag cgaagcagac ggccgagacg 420
ctgacaccct tgccttggcg cggcatctcc gtcgctggct cgctggctct ggccccttcg 480
cgagagttcc ggtccacctc cacctgtgtc ggtttccaac tccgttccgc cttcgcgtgg 540
gacttgttcc gttcatccgt tggcggcatc cggaaattgc gtggcgtaga gcacggggcc 600
ctcctctcac acggcacgga accgtcacga gctcacggca ccggcagcac ggcggggatt 660
ccttccccac caccgctcct tccctttccc ttcctcgccc gccatcataa atagccaccc 720
ctcccagctt ccttcgccac atcctctcat catcttctct cgtgtagcac gcgcagcccg 780
atccccaatc ccctctcctc gcgagcctcg tcgatccctc gcttcaaggt atggctatcg 840
tccttcctct ctctctcttt accttatcta gatcggcgat ccatggttag ggcctgctag 900
ttctccgttc gtgtttgtcg atggctgtga ggcacaatag atccgtcggc gttatgatgg 960
ttagcctgtc atgctcttgc gatctgtggt tcctttagga aaggcattaa tttaatccct 1020
gatggttcga gatcggtgat ccatggttag taccctaagc tgtggagtcg ggtttagatc 1080
cgcgctgttc gtaggcgatc tgttctgatt gttaacttgt cagtacctgc gaatcctcgg 1140
tggttctagc tggttcggag atcagatcga ttccattatc tgctatacat cttgtttcgt 1200
tgcctaggct ccgtttaatc tatccatcgt atgatgttag cctttgatat gattcgatcg 1260
tgctagctat gtcctgtgga cttaattgtc aggtcctaat ttttaggaag actgttccaa 1320
accatctgct ggatttatta aatttggatc tggatgtgtc acatacacct tcataattaa 1380
aatggatgga aatatctctt atcttttaga tatggatagg catttatatg atgctgtgag 1440
ttttactagt actttcttag aatatatgta cttttttaga cggaatattg atatgtatac 1500
atgtgtagat acatgaagca acatgctgct gtagtctaat aattcctgtt catctaataa 1560
tcaagtatgt atatgttctg tgtgttttat tggtatttga ttagatatat acatgcttag 1620
atacatacat gaagcagcat gctgctacag tttaatcatt attgtttatc caataaacaa 1680
acatgctttt taatttatct tgatatgctt ggatgacgga atatgcagag attttaagta 1740
cccagcatca tgagcatgca tgaccctgcg ttagtatgct gtttatttgc ttgagactct 1800
ttcttttgta gatactcacc ctgttttctg gtgatcctac tgcaggtc 1848

<210> SEQ ID NO 115
<211> LENGTH: 1507
<212> TYPE: DNA
<213> ORGANISM: Coix lacryma-jobi

<400> SEQUENCE: 115
caaatctaac ggacaccaac cagcgaatga gcgaacccac cagcgccaag ctagccaagc 60
gaagcagacg gccgagacgc tgacaccctt gccttggcgc ggcatctccg tcgctggctc 120
gctggctctg gccccttcgc gagagttccg gtccacctcc acctgtgtcg gtttccaact 180
ccgttccgcc ttcgcgtggg acttgttccg ttcatccgtt ggcggcatcc ggaaattgcg 240
tggcgtagag cacggggccc tcctctcaca cggcacggaa ccgtcacgag ctcacggcac 300
cggcagcacg gcggggattc cttccccacc accgctcctt ccctttccct tcctcgcccg 360
ccatcataaa tagccacccc tcccagcttc cttcgccaca tcctctcatc atcttctctc 420
gtgtagcacg cgcagcccga tccccaatcc cctctcctcg cgagcctcgt cgatccctcg 480
cttcaaggta tggctatcgt ccttcctctc tctctcttta ccttatctag atcggcgatc 540
catggttagg gcctgctagt tctccgttcg tgtttgtcga tggctgtgag gcacaataga 600
tccgtcggcg ttatgatggt tagcctgtca tgctcttgcg atctgtggtt cctttaggaa 660
aggcattaat ttaatccctg atggttcgag atcggtgatc catggttagt accctaagct 720
gtggagtcgg gtttagatcc gcgctgttcg taggcgatct gttctgattg ttaacttgtc 780
agtacctgcg aatcctcggt ggttctagct ggttcggaga tcagatcgat tccattatct 840
gctatacatc ttgtttcgtt gcctaggctc cgtttaatct atccatcgta tgatgttagc 900
ctttgatatg attcgatcgt gctagctatg tcctgtggac ttaattgtca ggtcctaatt 960
tttaggaaga ctgttccaaa ccatctgctg gatttattaa atttggatct ggatgtgtca 1020
catacacctt cataattaaa atggatggaa atatctctta tcttttagat atggataggc 1080
atttatatga tgctgtgagt tttactagta ctttcttaga atatatgtac ttttttagac 1140
ggaatattga tatgtataca tgtgtagata catgaagcaa catgctgctg tagtctaata 1200
attcctgttc atctaataat caagtatgta tatgttctgt gtgttttatt ggtatttgat 1260
tagatatata catgcttaga tacatacatg aagcagcatg ctgctacagt ttaatcatta 1320
ttgtttatcc aataaacaaa catgcttttt aatttatctt gatatgcttg gatgacggaa 1380
tatgcagaga ttttaagtac ccagcatcat gagcatgcat gaccctgcgt tagtatgctg 1440
tttatttgct tgagactctt tcttttgtag atactcaccc tgttttctgg tgatcctact 1500
gcaggtc 1507

<210> SEQ ID NO 116
<211> LENGTH: 1160
<212> TYPE: DNA
<213> ORGANISM: Coix lacryma-jobi

<400> SEQUENCE: 116
ccttcctcgc ccgccatcat aaatagccac ccctcccagc ttccttcgcc acatcctctc 60
atcatcttct ctcgtgtagc acgcgcagcc cgatccccaa tcccctctcc tcgcgagcct 120
cgtcgatccc tcgcttcaag gtatggctat cgtccttcct ctctctctct ttaccttatc 180
tagatcggcg atccatggtt agggcctgct agttctccgt tcgtgtttgt cgatggctgt 240
gaggcacaat agatccgtcg gcgttatgat ggttagcctg tcatgctctt gcgatctgtg 300
gttcctttag gaaaggcatt aatttaatcc ctgatggttc gagatcggtg atccatggtt 360
agtaccctaa gctgtggagt cgggtttaga tccgcgctgt tcgtaggcga tctgttctga 420
ttgttaactt gtcagtacct gcgaatcctc ggtggttcta gctggttcgg agatcagatc 480
gattccatta tctgctatac atcttgtttc gttgcctagg ctccgtttaa tctatccatc 540
gtatgatgtt agcctttgat atgattcgat cgtgctagct atgtcctgtg gacttaattg 600
tcaggtccta atttttagga agactgttcc aaaccatctg ctggatttat taaatttgga 660
tctggatgtg tcacatacac cttcataatt aaaatggatg gaaatatctc ttatctttta 720
gatatggata ggcatttata tgatgctgtg agttttacta gtactttctt agaatatatg 780 tacttttttta gacggaatat tgatatgtat acatgtgtag atacatgaag caacatgctg 840
ctgtagtcta ataattcctg ttcatctaat aatcaagtat gtatatgttc tgtgtgtttt 900
attggtattt gattagatat atacatgctt agatacatac atgaagcagc atgctgctac 960
agtttaatca ttattgttta tccaataaac aaacatgctt tttaatttat cttgatatgc 1020
ttggatgacg gaatatgcag agattttaag tacccagcat catgagcatg catgaccctg 1080
cgttagtatg ctgtttattt gcttgagact ctttcttttg tagatactca ccctgttttc 1140
tggtgatcct actgcaggtc 1160

<210> SEQ ID NO 117
<211> LENGTH: 2625
<212> TYPE: DNA
<213> ORGANISM: Setaria italica

<400> SEQUENCE: 117
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220
gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac aggtg 2625

<210> SEQ ID NO 118
<211> LENGTH: 1006
<212> TYPE: DNA
<213> ORGANISM: Setaria italica

<400> SEQUENCE: 118
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa caggtg 1006

<210> SEQ ID NO 119
<211> LENGTH: 2625
<212> TYPE: DNA
<213> ORGANISM: Setaria italica

<400> SEQUENCE: 119
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620

```
tatagattca gttccttgct ccgatcccaa tctggttgag atgttgctcc gatgcgactt   1680
gattatgtca tatatctgcg gtttgcaccg atctgaagcc tagggtttct cgagcgaccc   1740
agttatttgc aatttgcgat ttgctcgttt gttgcgcagc gtagtttatg tttggagtaa   1800
tcgaggattt gtatgcggcg tcggcgctac ctgcttaatc acgccatgtg acgcggttac   1860
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt tttttggtct attggtgcct aacttatctg aaaatcatgg   2160
aacatgaggc tagtttgatc atggtttagt tcattgtgat taataatgta tgatttagta   2220
gctattttgg tgatcgtgtc attttatttg tgaatggaat cattgtatgt aaatgaagct   2280
agttcagggg ttacgatgta gctggctttg tattctaaag gctgctatta ttcatccatc   2340
gatttcacct atatgtaatc cagagctttt gatgtgaaat ttgtctgatc cttcactagg   2400
aaggacagaa cattgttaat attttggcac atctgtctta ttctcatcct ttgtttgaac   2460
atgttagcct gttcaaacag atactgttgt aatgtcctag ttatataggt acatatgtgt   2520
tctctattga gtttatggac ttttgtgtgt gaagttatat ttcattttgc tcaaaactca   2580
tgtttgcaag ctttctgaca ttattctatt gttctgaaac agggt                    2625
```

<210> SEQ ID NO 120
<211> LENGTH: 1006
<212> TYPE: DNA
<213> ORGANISM: Setaria italica

<400> SEQUENCE: 120

```
gtatagattc agttccttgc tccgatccca atctggttga gatgttgctc cgatgcgact     60
tgattatgtc atatatctgc ggtttgcacc gatctgaagc ctagggtttc tcgagcgacc    120
cagttatttg caatttgcga tttgctcgtt tgttgcgcag cgtagtttat gtttggagta    180
atcgaggatt tgtatgcggc gtcggcgcta cctgcttaat cacgccatgt gacgcggtta    240
cttgcagagg ctgggttctg ttatgtcgtg atctaagaat ctagattagg ctcagtcgtt    300
cttgctgtcg actagtttgt tttgatatcc atgtagtaca agttacttaa aatttaggtc    360
caatatattt tgcatgcttt tggcctgtta ttcttgccaa caagttgtcc tggtaaaaag    420
tagatgtgaa agtcacgtat tgggacaaat tgatggttta gtgctatagt tctatagttc    480
tgtgatacat ctatctgatt ttttttggtc tattggtgcc taacttatct gaaaatcatg    540
gaacatgagg ctagtttgat catggtttag ttcattgtga ttaataatgt atgatttagt    600
agctattttg gtgatcgtgt cattttattt gtgaatggaa tcattgtatg taaatgaagc    660
tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tattttggca catctgtctt attctcatcc tttgtttgaa    840
catgttagcc tgttcaaaca gatactgttg taatgtccta gttatatagg tacatatgtg    900
ttctctattg agtttatgga cttttgtgtg tgaagttata tttcattttg ctcaaaactc    960
atgtttgcaa gctttctgac attattctat tgttctgaaa cagggt                  1006
```

<210> SEQ ID NO 121

<211> LENGTH: 2625
<212> TYPE: DNA
<213> ORGANISM: Setaria italica

<400> SEQUENCE: 121

```
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc ccccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ccgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacac gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aaggaatggc tcgtaggggc ccgggtagaa tcgaagaatg ttgcgctggg   1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cccgttgccg   1500
caagactcag atcagattcc gatccccagt tcttccccaa tcaccttgtg gtctctcgtg   1560
tcgcggttcc cagggacgcc tccggctcgt cgctcgacag cgatctccgc cccagcaagg   1620
tatagattca gttccttgct ccgatcccaa tctggttgag atgttgctcc gatgcgactt   1680
gattatgtca tatatctgcg gtttgcaccg atctgaagcc tagggtttct cgagcgaccc   1740
agttatttgc aatttgcgat ttgctcgttt gttgcgcagc gtagtttatg tttggagtaa   1800
tcgaggattt gtatgcggcg tcggcgctac ctgcttaatc acgccatgtg acgcggttac   1860
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt tttttggtct attggtgcct aacttatctg aaaatcatgg   2160
aacatgaggc tagtttgatc atggtttagt tcattgtgat taataatgta tgatttagta   2220
```

gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac agacc 2625

<210> SEQ ID NO 122
<211> LENGTH: 1006
<212> TYPE: DNA
<213> ORGANISM: Setaria italica

<400> SEQUENCE: 122
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa cagacc 1006

<210> SEQ ID NO 123
<211> LENGTH: 2167
<212> TYPE: DNA
<213> ORGANISM: Setaria italica

<400> SEQUENCE: 123
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960
gctgggctgc gaccttaacc agcaaggcac gccacgaccc gccccgccct cgaggcataa 1020
ataccctccc atcccgttgc cgcaagactc agatcagatt ccgatcccca gttcttcccc 1080
aatcaccttg tggtctctcg tgtcgcggtt cccagggacg cctccggctc gtcgctcgac 1140
agcgatctcc gccccagcaa ggtatagatt cagttccttg ctccgatccc aatctggttg 1200
agatgttgct ccgatgcgac ttgattatgt catatatctg cggtttgcac cgatctgaag 1260
cctagggttt ctcgagcgac ccagttattt gcaatttgcg atttgctcgt ttgttgcgca 1320
gcgtagttta tgtttggagt aatcgaggat ttgtatgcgg cgtcggcgct acctgcttaa 1380
tcacgccatg tgacgcggtt acttgcagag gctgggttct gttatgtcgt gatctaagaa 1440
tctagattag gctcagtcgt tcttgctgtc gactagtttg ttttgatatc catgtagtac 1500
aagttactta aaatttaggt ccaatatatt ttgcatgctt ttggcctgtt attcttgcca 1560
acaagttgtc ctggtaaaaa gtagatgtga aagtcacgta ttgggacaaa ttgatggttt 1620
agtgctatag ttctatagtt ctgtgataca tctatctgat ttttttggt ctattggtgc 1680 ctaacttatc tgaaaatcat ggaacatgag gctagtttga tcatggttta gttcattgtg 1740
attaataatg tatgatttag tagctatttt ggtgatcgtg tcattttatt tgtgaatgga 1800
atcattgtat gtaaatgaag ctagttcagg ggttacgatg tagctggctt tgtattctaa 1860
aggctgctat tattcatcca tcgatttcac ctatatgtaa tccagagctt ttgatgtgaa 1920
atttgtctga tccttcacta ggaaggacag aacattgtta atattttggc acatctgtct 1980
tattctcatc ctttgtttga acatgttagc ctgttcaaac agatactgtt gtaatgtcct 2040
agttatatag gtacatatgt gttctctatt gagtttatgg acttttgtgt gtgaagttat 2100
atttcatttt gctcaaaact catgtttgca agctttctga cattattcta ttgttctgaa 2160
acaggtg 2167

<210> SEQ ID NO 124
<211> LENGTH: 1813
<212> TYPE: DNA
<213> ORGANISM: Setaria italica

<400> SEQUENCE: 124
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag gtg 1813

<210> SEQ ID NO 125
<211> LENGTH: 1813
<212> TYPE: DNA
<213> ORGANISM: Setaria italica

<400> SEQUENCE: 125
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag ggt 1813

<210> SEQ ID NO 126
<211> LENGTH: 1813
<212> TYPE: DNA
<213> ORGANISM: Setaria italica

<400> SEQUENCE: 126
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag ggc 1813

<210> SEQ ID NO 127
<211> LENGTH: 1006
<212> TYPE: DNA
<213> ORGANISM: Setaria italica

<400> SEQUENCE: 127
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa cagggc 1006

<210> SEQ ID NO 128
<211> LENGTH: 2634
<212> TYPE: DNA

<213> ORGANISM: Setaria viridis

<400> SEQUENCE: 128
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcccgttgcc 1500
gcaagactca gatcagattc cgatccccag ttcttcccca atcaccttgt ggtctctcgt 1560
gtcgcggttc ccagggacgc ctccggctcg tcgctcgaca gcgatctccg ccccagcaag 1620
gtatagattc agttccttgc tccgatccca atctggttga gatgttgctc cgatgcgact 1680
tgattatgtc atatatctgc ggtttgcacc gatctgaagc ctagggtttc tcgagcgacc 1740
cagttgtttg caatttgcga tttgctcgtt tgttgcgcat cgtagtttat gtttggagta 1800
atcgaggatt tgtatgcggc gtcggcgcta cctgcttaat cacgccatgt gacgcggtta 1860
cttgcagagg ctgggttagt gggttctgtt atgtcgtgat ctaagaatct agattaggct 1920
cagtcgttct tgctgtcgac tagtttgttt tgatatccat gtagtacaag ttacttaaaa 1980
tttaggtcca atatattttg catgcttttg gcctgttatt cttgccaaca agttgtcctg 2040
gtaaaaagta gatgtgaaag tcacgtattg ggacaaattg atggttaagt gctatagttc 2100
tatagttctg tgatacatct atctgatttt ttttggtcta ttggtgccta acttatctga 2160
aaatcatgga acatgaggct agtttgatca tggtttagtt cattgtgatt aataatgtat 2220
gatttagtag ctattttggt gatcgtgtca ttttatttgt gaatggaatc attgtatgta 2280
aatgaagcta gttcaggggt tatgatgtag ctggctttgt attctaaagg ctgctattat 2340
tcatccatcg atttcaccta tatgtaatcc agagctttcg atgtgaaatt tgtctgatcc 2400
ttcactagga aggacagaac attgttaata ttttggcaca tctgtcttat tctcatcctt 2460
tgtttgaaca tgttagcctg ttcaaacaga tactgttgta atgtcctagt tatataggta 2520
catatgtgtt ctctattgag tttatggact tttgtgtgtg aagttatatt tcattttgct 2580
caaaactcat gtttgcaagc tttctgacat tattctattg ttctgaaaca ggtg 2634

<210> SEQ ID NO 129
<211> LENGTH: 1014
<212> TYPE: DNA
<213> ORGANISM: Setaria viridis

<400> SEQUENCE: 129
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttgtttg caatttgcga tttgctcgtt tgttgcgcat cgtagtttat gtttggagta 180
atcgaggatt tgtatgcggc gtcggcgcta cctgcttaat cacgccatgt gacgcggtta 240
cttgcagagg ctgggttagt gggttctgtt atgtcgtgat ctaagaatct agattaggct 300
cagtcgttct tgctgtcgac tagtttgttt tgatatccat gtagtacaag ttacttaaaa 360
tttaggtcca atatattttg catgcttttg gcctgttatt cttgccaaca agttgtcctg 420
gtaaaaagta gatgtgaaag tcacgtattg ggacaaattg atggttaagt gctatagttc 480
tatagttctg tgatacatct atctgatttt ttttggtcta ttggtgccta acttatctga 540
aaatcatgga acatgaggct agtttgatca tggtttagtt cattgtgatt aataatgtat 600
gatttagtag ctattttggt gatcgtgtca ttttatttgt gaatggaatc attgtatgta 660
aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca ggtg 1014

<210> SEQ ID NO 130
<211> LENGTH: 2634
<212> TYPE: DNA
<213> ORGANISM: Setaria viridis

<400> SEQUENCE: 130
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480

```
ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag acatcggaac actggtgatt   1080
ggtggagccg gcagtatgcg ccccagcacg gccgaggtgg tggtggcccg tggccctgct   1140
gtctgcgcgg ctcgggacaa cttgaaactg ggccaccgcc tcgtcgcaac tcgcaacccg   1200
ttggcggaag aaaggaatgg ctcgtagggg cccgggtaga atccaagaat gttgcgctgg   1260
gcttcgattc acataacatg ggcctgaagc tctaaaacga cggcccggtc accgggcgat   1320
ggaaagagac cggatcctcc tcgtgaattc tggaaggcca cacgagagcg acccaccacc   1380
gacgcggagg agtcgtgcgt ggtccaacac ggccggcggg ctgggctgcg accttaacca   1440
gcaaggcacg ccacgacccg cctcgccctc gaggcataaa taccctccca tcccgttgcc   1500
gcaagactca gatcagattc cgatccccag ttcttcccca atcaccttgt ggtctctcgt   1560
gtcgcggttc ccagggacgc ctccggctcg tcgctcgaca gcgatctccg ccccagcaag   1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
cagttgtttg caatttgcga tttgctcgtt tgttgcgcat cgtagtttat gtttggagta   1800
atcgaggatt tgtatgcggc gtcggcgcta cctgcttaat cacgccatgt gacgcggtta   1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatattttg catgcttttg gcctgttatt cttgccaaca agttgtcctg   2040
gtaaaaagta gatgtgaaag tcacgtattg ggacaaattg atggttaagt gctatagttc   2100
tatagttctg tgatacatct atctgatttt ttttggtcta ttggtgccta acttatctga   2160
aaatcatgga acatgaggct agtttgatca tggtttagtt cattgtgatt aataatgtat   2220
gatttagtag ctattttggt gatcgtgtca ttttatttgt gaatggaatc attgtatgta   2280
aatgaagcta gttcaggggt tatgatgtag ctggctttgt attctaaagg ctgctattat   2340
tcatccatcg atttcaccta tatgtaatcc agagctttcg atgtgaaatt tgtctgatcc   2400
ttcactagga aggacagaac attgttaata ttttggcaca tctgtcttat tctcatcctt   2460
tgtttgaaca tgttagcctg ttcaaacaga tactgttgta atgtcctagt tatataggta   2520
catatgtgtt ctctattgag tttatggact tttgtgtgtg aagttatatt tcattttgct   2580
caaaactcat gtttgcaagc tttctgacat tattctattg ttctgaaaca gggt         2634
```

<210> SEQ ID NO 131
<211> LENGTH: 1014
<212> TYPE: DNA
<213> ORGANISM: Setaria viridis

<400> SEQUENCE: 131
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttgtttg caatttgcga tttgctcgtt tgttgcgcat cgtagtttat gtttggagta 180
atcgaggatt tgtatgcggc gtcggcgcta cctgcttaat cacgccatgt gacgcggtta 240
cttgcagagg ctgggttagt gggttctgtt atgtcgtgat ctaagaatct agattaggct 300
cagtcgttct tgctgtcgac tagtttgttt tgatatccat gtagtacaag ttacttaaaa 360
tttaggtcca atatatttg catgcttttg gcctgttatt cttgccaaca agttgtcctg 420
gtaaaaagta gatgtgaaag tcacgtattg ggacaaattg atggttaagt gctatagttc 480
tatagttctg tgatacatct atctgatttt ttttggtcta ttggtgccta acttatctga 540
aaatcatgga acatgaggct agtttgatca tggtttagtt cattgtgatt aataatgtat 600
gatttagtag ctattttggt gatcgtgtca ttttatttgt gaatggaatc attgtatgta 660
aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca gggt 1014

<210> SEQ ID NO 132
<211> LENGTH: 2176
<212> TYPE: DNA
<213> ORGANISM: Setaria viridis

<400> SEQUENCE: 132
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcccgttg ccgcaagact cagatcagat tccgatcccc agttcttccc 1080
caatcacctt gtggtctctc gtgtcgcggt tcccagggac gcctccggct cgtcgctcga 1140
cagcgatctc cgccccagca aggtatagat tcagttcctt gctccgatcc caatctggtt 1200
gagatgttgc tccgatgcga cttgattatg tcatatatct gcggtttgca ccgatctgaa 1260
gcctagggtt tctcgagcga cccagttgtt tgcaatttgc gatttgctcg tttgttgcgc 1320
atcgtagttt atgtttggag taatcgagga tttgtatgcg gcgtcggcgc tacctgctta 1380
atcacgccat gtgacgcggt tacttgcaga ggctgggtta gtgggttctg ttatgtcgtg 1440
atctaagaat ctagattagg ctcagtcgtt cttgctgtcg actagtttgt tttgatatcc 1500
atgtagtaca agttacttaa aatttaggtc caatatattt tgcatgcttt tggcctgtta 1560
ttcttgccaa caagttgtcc tggtaaaaag tagatgtgaa agtcacgtat tgggacaaat 1620
tgatggttaa gtgctatagt tctatagttc tgtgatacat ctatctgatt ttttttggtc 1680
tattggtgcc taacttatct gaaaatcatg gaacatgagg ctagtttgat catggtttag 1740
ttcattgtga ttaataatgt atgatttagt agctattttg gtgatcgtgt cattttattt 1800
gtgaatggaa tcattgtatg taaatgaagc tagttcaggg gttatgatgt agctggcttt 1860
gtattctaaa ggctgctatt attcatccat cgatttcacc tatatgtaat ccagagcttt 1920
cgatgtgaaa tttgtctgat ccttcactag gaaggacaga acattgttaa tattttggca 1980
catctgtctt attctcatcc tttgtttgaa catgttagcc tgttcaaaca gatactgttg 2040
taatgtccta gttatatagg tacatatgtg ttctctattg agtttatgga cttttgtgtg 2100
tgaagttata tttcattttg ctcaaaactc atgtttgcaa gctttctgac attattctat 2160
tgttctgaaa caggtg 2176

<210> SEQ ID NO 133
<211> LENGTH: 1822
<212> TYPE: DNA
<213> ORGANISM: Setaria viridis

<400> SEQUENCE: 133
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260
acaaattgat ggttaagtgc tatagttcta tagttctgtg atacatctat ctgatttttt 1320
ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg tg 1822

<210> SEQ ID NO 134
<211> LENGTH: 1822
<212> TYPE: DNA
<213> ORGANISM: Setaria viridis

<400> SEQUENCE: 134
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctc gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260

-continued

```
acaaattgat ggttaagtgc tatagttcta tagttctgtg atacatctat ctgatttttt   1320

ttggtctatt ggtgcctaac ttatctgaaa atcatggaac atgaggctag tttgatcatg   1380

gtttagttca ttgtgattaa taatgtatga tttagtagct attttggtga tcgtgtcatt   1440

ttatttgtga atggaatcat tgtatgtaaa tgaagctagt tcaggggtta tgatgtagct   1500

ggctttgtat tctaaaggct gctattattc atccatcgat ttcacctata tgtaatccag   1560

agctttcgat gtgaaatttg tctgatcctt cactaggaag gacagaacat tgttaatatt   1620

ttggcacatc tgtcttattc tcatcctttg tttgaacatg ttagcctgtt caaacagata   1680

ctgttgtaat gtcctagtta tataggtaca tatgtgttct ctattgagtt tatggacttt   1740

tgtgtgtgaa gttatatttc attttgctca aaactcatgt ttgcaagctt tctgacatta   1800

ttctattgtt ctgaaacagg tg                                             1822


<210> SEQ ID NO 135
<211> LENGTH: 681
<212> TYPE: DNA
<213> ORGANISM: Setaria viridis

<400> SEQUENCE: 135

cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctc gtgaattctg    540

gaaggccaca cgagagcgac ccaccaccga cgcggaggag tcgtgcgtgg tccaacacgg    600

ccggcgggct gggctgcgac cttaaccagc aaggcacgcc acgacccgcc tcgccctcga    660

ggcataaata ccctcccatc c                                              681


<210> SEQ ID NO 136
<211> LENGTH: 1822
<212> TYPE: DNA
<213> ORGANISM: Setaria viridis

<400> SEQUENCE: 136

cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctt gtgaattctg    540

gaaggccaca cgagagcgac ccaccaccga cgcggaggag tcgtgcgtgg tccaacacgg    600
```

```
ccggcgggct gggctgcgac cttaaccagc aaggcacgcc acgacccgcc tcgccctcga    660
ggcataaata ccctcccatc ccgttgccgc aagactcaga tcagattccg atccccagtt    720
cttccccaat caccttgtgg tctctcgtgt cgcggttccc agggacgcct ccggctcgtc    780
gctcgacagc gatctccgcc ccagcaaggt atagattcag ttccttgctc cgatcccaat    840
ctggttgaga tgttgctccg atgcgacttg attatgtcat atatctgcgg tttgcaccga    900
tctgaagcct agggtttctc gagcgaccca gttgtttgca atttgcgatt tgctcgtttg    960
ttgcgcatcg tagtttatgt ttggagtaat cgaggatttg tatgcggcgt cggcgctacc   1020
tgcttaatca cgccatgtga cgcggttact tgcagaggct gggttagtgg gttctgttat   1080
gtcgtgatct aagaatctag attaggctca gtcgttcttg ctgtcgacta gtttgttttg   1140
atatccatgt agtacaagtt acttaaaatt taggtccaat atattttgca tgcttttggc   1200
ctgttattct tgccaacaag ttgtcctggt aaaaagtaga tgtgaaagtc acgtattggg   1260
acaaattgat ggttaagtgc tatagttcta tagttctgtg atacatctat ctgatttttt   1320
ttggtctatt ggtgcctaac ttatctgaaa atcatggaac atgaggctag tttgatcatg   1380
gtttagttca ttgtgattaa taatgtatga tttagtagct attttggtga tcgtgtcatt   1440
ttatttgtga atggaatcat tgtatgtaaa tgaagctagt tcaggggtta tgatgtagct   1500
ggctttgtat tctaaaggct gctattattc atccatcgat ttcacctata tgtaatccag   1560
agctttcgat gtgaaatttg tctgatcctt cactaggaag gacagaacat tgttaatatt   1620
ttggcacatc tgtcttattc tcatcctttg tttgaacatg ttagcctgtt caaacagata   1680
ctgttgtaat gtcctagtta tataggtaca tatgtgttct ctattgagtt tatggacttt   1740
tgtgtgtgaa gttatatttc attttgctca aaactcatgt ttgcaagctt tctgacatta   1800
ttctattgtt ctgaaacagg gt                                            1822
```

<210> SEQ ID NO 137
<211> LENGTH: 1925
<212> TYPE: DNA
<213> ORGANISM: Zea mays subsp. Mexicana

<400> SEQUENCE: 137

```
gtcgtgcccc tctctagaga taatgagcat tgcatgtcta agttataaaa aattaccaca     60
tatttttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtatttt gacaacatga    240
ctctacagtt ttatcttttt agtgtgcatg tgttcttttt acttttgcaa atagcttcac    300
ctatataata cttcatccat tttattagta catccattta ctaaattttt agtacatcta    360
ttttattcta ttttagcctc taaattaaga aaacttaaac tctattttag tttttttattt    420
aataatttag atataaaata gaataaaata aagtgactaa aaaataacta aatacctttt    480
aagaaataaa aaaactaagg aaccattttt cttgttccga gtagataatg acagcctgtt    540
caacgccgtc gacgagtcta acggacacca accagcgaac cagcagcgtc gcgtcgggcc    600
aagcgaagca gacggcacgg catctctgta gctgcctctg gacccctctc gagagttccg    660
ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgctttc ccttcctcgc ccgccgtaat aaatagaccc cctccacacc    840
```

```
ctctttcccc aacctcgtgt tcgttcggag cgcgcacaca cacaaccaga tctcccccaa    900

atccacccgt cggcacctcc gcttcaaggt acgccgctca tcctcctccc ccccctctct    960

ctaccttctc tagatcggcg tttcggtcca tggttagggc ccggtagttc tacttctgtt   1020

catgtttgtg ttagatccgt gtttgtgtta gatccgtgct gctagatttc gtacacggat   1080

gcgacctgta catcagacat gttctgattg ctaacttgcc agtgtttctc tttggggaat   1140

cctgggatgg ctctagccgt tccgcagacg ggatcgattt catgaatttt ttttgtttcg   1200

ttgcataggg tttggtttgc ccttttcctt tatttcaata tatgccgtgc acttgtttgt   1260

cgggtcatct tttcatgttt tttttggctt ggttgtgatg atgtggtctg gttgggcggt   1320

cgttctagat cggagtagaa tactgtttca aactacctgg tggatttatt aaaggatctg   1380

tatgtatgtg ccatacatct tcatagttac gagtttaaga tgatggatgg aaatatcgat   1440

ctaggatagg tatacatgtt gatgcgggtt ttactgatgc atatacagag atgctttttt   1500

ttcgcttggt tgtgatgatg tggtctggtc gggcggtcgt tctagatcgg agtagaatac   1560

tgtttcaaac tacctggtgg atttattaat tttggatctg tatgtgtgtc atacatcttc   1620

atagttacga gtttaagatc gatggaaata tcgatctagg ataggtatac atgttgatgt   1680

gggttttact gatgcatata catggcatat gcagcatcta ttcatatgct ctaaccttga   1740

gtacctatct attataataa acaagtatgt tttataatta ttttgatctt gatatacttg   1800

gatgatggca tatgcagcag ctatatgtgg attttttttag ccctgccttc atacgctatt   1860

tatttgcttg gtactgtttc ttttgtcgat gctcaccctg ttgtttggtg atacttctgc   1920

aggtc                                                               1925
```

<210> SEQ ID NO 138
<211> LENGTH: 997
<212> TYPE: DNA
<213> ORGANISM: Zea mays subsp. Mexicana

<400> SEQUENCE: 138

```
gtacgccgct catcctcctc cccccccctct ctctaccttc tctagatcgg cgtttcggtc     60

catggttagg gcccggtagt tctacttctg ttcatgtttg tgttagatcc gtgtttgtgt    120

tagatccgtg ctgctagatt tcgtacacgg atgcgacctg tacatcagac atgttctgat    180

tgctaacttg ccagtgtttc tctttgggga atcctgggat ggctctagcc gttccgcaga    240

cgggatcgat ttcatgaatt ttttttgttt cgttgcatag ggtttggttt gcccttttcc    300

tttatttcaa tatatgccgt gcacttgttt gtcgggtcat cttttcatgt ttttttggc    360

ttggttgtga tgatgtggtc tggttgggcg gtcgttctag atcggagtag aatactgttt    420

caaactacct ggtggattta ttaaaggatc tgtatgtatg tgccatacat cttcatagtt    480

acgagtttaa gatgatggat ggaaatatcg atctaggata ggtatacatg ttgatgcggg    540

ttttactgat gcatatacag agatgctttt ttttcgcttg gttgtgatga tgtggtctgg    600

tcgggcggtc gttctagatc ggagtagaat actgtttcaa actacctggt ggatttatta    660

attttggatc tgtatgtgtg tcatacatct tcatagttac gagtttaaga tcgatggaaa    720

tatcgatcta ggataggtat acatgttgat gtgggtttta ctgatgcata tacatggcat    780

atgcagcatc tattcatatg ctctaacctt gagtacctat ctattataat aaacaagtat    840

gttttataat tattttgatc ttgatatact tggatgatgg catatgcagc agctatatgt    900

ggattttttt agccctgcct tcatacgcta tttatttgct tggtactgtt tcttttgtcg    960

atgctcaccc tgttgtttgg tgatacttct gcaggtc                             997
```

<210> SEQ ID NO 139
<211> LENGTH: 1925
<212> TYPE: DNA
<213> ORGANISM: Zea mays subsp. Mexicana

<400> SEQUENCE: 139

| | | | | | |
|---|---|---|---|---|---|
| gtcgtgcccc | tctctagaga | taatgagcat | tgcatgtcta | agttataaaa | aattaccaca | 60 |
| tatttttttt | tgtcacactt | gtgtttgaag | tgcagtttat | ctatctctat | acatatattt | 120 |
| aaacttcact | atatgaataa | tatagtctat | agtattaaaa | taatatcaat | gttttagatg | 180 |
| attatataac | tgaactgcta | gacatggtct | aaaggacaac | cgagtatttt | gacaacatga | 240 |
| ctctacagtt | ttatcttttt | agtgtgcatg | tgttcttttt | acttttgcaa | atagcttcac | 300 |
| ctatataata | cttcatccat | tttattagta | catccattta | ctaaattttt | agtacatcta | 360 |
| ttttattcta | ttttagcctc | taaattaaga | aaacttaaac | tctattttag | ttttttattt | 420 |
| aataatttag | atataaaata | gaataaaata | aagtgactaa | aaaataacta | aatacccttt | 480 |
| aagaaataaa | aaaactaagg | aaccattttt | cttgttccga | gtagataatg | acagcctgtt | 540 |
| caacgccgtc | gacgagtcta | acggacacca | accagcgaac | cagcagcgtc | gcgtcgggcc | 600 |
| aagcgaagca | gacggcacgg | catctctgta | gctgcctctg | gacccctctc | gagagttccg | 660 |
| ctccaccgtt | ggacttgctc | cgctgtcggc | atccagaaat | tgcgtggcgg | agcggcagac | 720 |
| gtgagccggc | acggcaggcg | gcctcctctc | acggcaccgg | cagctacggg | ggattccttt | 780 |
| cccaccgctc | cttcgctttc | ccttcctcgc | ccgccgtaat | aaatagaccc | cctccacacc | 840 |
| ctctttcccc | aacctcgtgt | tcgttcggag | cgcgcacaca | cacaaccaga | tctcccccaa | 900 |
| atccacccgt | cggcacctcc | gcttcaaggt | acgccgctca | tcctcctccc | cccctctct | 960 |
| ctaccttctc | tagatcggcg | tttcggtcca | tggttagggc | ccggtagttc | tacttctgtt | 1020 |
| catgtttgtg | ttagatccgt | gtttgtgtta | gatccgtgct | gctagatttc | gtacacggat | 1080 |
| gcgacctgta | catcagacat | gttctgattg | ctaacttgcc | agtgtttctc | tttggggaat | 1140 |
| cctgggatgg | ctctagccgt | tccgcagacg | ggatcgattt | catgaatttt | ttttgtttcg | 1200 |
| ttgcataggg | tttggtttgc | ccttttcctt | tatttcaata | tatgccgtgc | acttgtttgt | 1260 |
| cgggtcatct | tttcatgttt | tttttggctt | ggttgtgatg | atgtggtctg | gttgggcggt | 1320 |
| cgttctagat | cggagtagaa | tactgtttca | aactacctgg | tggatttatt | aaaggatctg | 1380 |
| tatgtatgtg | ccatacatct | tcatagttac | gagtttaaga | tgatggatgg | aaatatcgat | 1440 |
| ctaggatagg | tatacatgtt | gatgcgggtt | ttactgatgc | atatacagag | atgctttttt | 1500 |
| ttcgcttggt | tgtgatgatg | tggtctggtc | gggcggtcgt | tctagatcgg | agtagaatac | 1560 |
| tgtttcaaac | tacctggtgg | atttattaat | tttggatctg | tatgtgtgtc | atacatcttc | 1620 |
| atagttacga | gtttaagatc | gatggaaata | tcgatctagg | ataggtatac | atgttgatgt | 1680 |
| gggttttact | gatgcatata | catggcatat | gcagcatcta | ttcatatgct | ctaaccttga | 1740 |
| gtacctatct | attataataa | acaagtatgt | tttataatta | ttttgatctt | gatatacttg | 1800 |
| gatgatggca | tatgcagcag | ctatatgtgg | atttttttag | ccctgccttc | atacgctatt | 1860 |
| tatttgcttg | gtactgtttc | ttttgtcgat | gctcaccctg | ttgtttggtg | atacttctgc | 1920 |
| agggt | | | | | | 1925 |

<210> SEQ ID NO 140
<211> LENGTH: 997
<212> TYPE: DNA

<213> ORGANISM: Zea mays subsp. Mexicana

<400> SEQUENCE: 140
gtacgccgct catcctcctc ccccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gccctttttcc 300
tttatttcaa tatatgccgt gcacttgttt gtcgggtcat cttttcatgt ttttttggc 360
ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcagggt 997

<210> SEQ ID NO 141
<211> LENGTH: 1974
<212> TYPE: DNA
<213> ORGANISM: Zea mays subsp. Mexicana

<400> SEQUENCE: 141
gtcgtgcccc tctctagaga taaagagcat tgcatgtcta agttataaaa aattaccaca 60
tatttttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa tttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720
tccagaaatt gcgtggcgga gcggcagacg tgagccggca cggcaggcgg cctcctcctc 780
ctctcacggc accggcagct acgggggatt cctttcccac cgctccttcg ctttcccttc 840
ctcgcccgcc gtaataaata gacacccccct ccacaccttc tttccccaac ctcgtgttgt 900
tcggagcgca cacacacaca accagatctc ccccaaatcc acccgtcggc acctccgctt 960
caaggtacgc cgctcatcct cccccccccc tctctacctt ctctagatcg gcgttccggt 1020
ccatggttag ggcccggtag ttctacttct gttcatgttt gtgttagatc cgtgtttgtg 1080
ttagatccgt gctgctagcg ttcgtacacg gatgcgacct gtacgtcaga cacgttctga 1140
ttgctaactt gccagtgttt ctctttgggg aatcctggga tggctctagc cgttccgcag 1200
acgggatcga tttcatgatt ttttttgttt cgttgcatag ggtttggttt gccctttttcc 1260 tttatttcaa tatatgccgt gcacttgttt gtcgggtcat cttttcatgc ttttttttgt 1320
cttggttgtg atgatgtggt ctggttgggc ggtcgttcta gatcggagaa gaattctgtt 1380
tcaaactacc tggtggattt attaattttg gatctgtatg tgtgtgccat acatattcat 1440
agttacgaat tgaagatgat ggatggaaat atcgatctag gataggtata catgttgatg 1500
cgggttttac tgatgcatat acagagatgc tttttgttcg cttggttgtg atgatgtggt 1560
ctggttgggc ggtcgttcat tcgttctaga tcggagtaga atactgtttc aaactacctg 1620
gtgtatttat taattttgga actgtatgtg tgtgtcatac atcttcatag ttacgagttt 1680
aagatggatg gaaatatcga tctaggatag gtatacatgt tgatgtgggt tttactgatg 1740
catatacatg atggcatatg cagcatctat tcatatgctc taaccttgag tacctatcta 1800
ttataataaa caagtatgtt ttataattat tttgatcttg atatacttgg atgatggcat 1860
atgcagcagc tatatgtgga tttttttagc cctgccttca tacgctattt atttgcttgg 1920
tactgtttct tttgtcgatg ctcaccctgt tgtttggtga tacttctgca ggtc 1974

<210> SEQ ID NO 142
<211> LENGTH: 1010
<212> TYPE: DNA
<213> ORGANISM: Zea mays subsp. Mexicana

<400> SEQUENCE: 142
gtacgccgct catcctcccc ccccctctc taccttctct agatcggcgt tccggtccat 60
ggttagggcc cggtagttct acttctgttc atgtttgtgt tagatccgtg tttgtgttag 120
atccgtgctg ctagcgttcg tacacggatg cgacctgtac gtcagacacg ttctgattgc 180
taacttgcca gtgtttctct ttggggaatc ctgggatggc tctagccgtt ccgcagacgg 240
gatcgatttc atgatttttt ttgtttcgtt gcatagggtt tggtttgccc ttttccttta 300
tttcaatata tgccgtgcac ttgtttgtcg ggtcatcttt tcatgctttt ttttgtcttg 360
gttgtgatga tgtggtctgg ttgggcggtc gttctagatc ggagaagaat tctgtttcaa 420
actacctggt ggatttatta attttggatc tgtatgtgtg tgccatacat attcatagtt 480
acgaattgaa gatgatggat ggaaatatcg atctaggata ggtatacatg ttgatgcggg 540
ttttactgat gcatatacag agatgctttt tgttcgcttg gttgtgatga tgtggtctgg 600
ttgggcggtc gttcattcgt tctagatcgg agtagaatac tgtttcaaac tacctggtgt 660
atttattaat tttggaactg tatgtgtgtg tcatacatct tcatagttac gagtttaaga 720
tggatggaaa tatcgatcta ggataggtat acatgttgat gtgggtttta ctgatgcata 780
tacatgatgg catatgcagc atctattcat atgctctaac cttgagtacc tatctattat 840
aataaacaag tatgttttat aattattttg atcttgatat acttggatga tggcatatgc 900
agcagctata tgtggatttt tttagccctg ccttcatacg ctatttattt gcttggtact 960
gtttcttttg tcgatgctca ccctgttgtt tggtgatact tctgcaggtc 1010

<210> SEQ ID NO 143
<211> LENGTH: 1974
<212> TYPE: DNA

<213> ORGANISM: Zea mays subsp. Mexicana

<400> SEQUENCE: 143

```
gtcgtgcccc tctctagaga taaagagcat tgcatgtcta agttataaaa aattaccaca     60
tattttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tctttttagt gtgcatgtgt tctccttttt tttttgcaaa tagcttcacc    300
tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt ttttatttaa taatttagat ataaaataga ataaaataaa    480
gtgactaaaa attaaacaaa taccctttaa gaaattaaaa aaactaagga aacatttttc    540
ttgtttcgag tagataatgc cagcctgtta aacgccgtcg acgagtctaa cggacaccaa    600
ccagcgaacc agcagcgtcg cgtcgggcca agcgaagcag acggcacggc atctctgtcg    660
ctgcctctgg acccctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacacccccct ccacaccttc tttccccaac ctcgtgttgt    900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gccctttttcc  1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga tttttttagc cctgccttca tacgctattt atttgcttgg   1920
tactgtttct tttgtcgatg ctcaccctgt tgtttggtga tacttctgca gggt         1974
```

<210> SEQ ID NO 144
<211> LENGTH: 1010
<212> TYPE: DNA
<213> ORGANISM: Zea mays subsp. Mexicana

<400> SEQUENCE: 144

```
gtacgccgct catcctcccc cccccctctc taccttctct agatcggcgt tccggtccat     60
```

```
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatttc atgatttttt ttgtttcgtt gcatagggtt tggtttgccc ttttccttta    300
tttcaatata tgccgtgcac ttgtttgtcg ggtcatcttt tcatgctttt ttttgtcttg    360
gttgtgatga tgtggtctgg ttgggcggtc gttctagatc ggagaagaat tctgtttcaa    420
actacctggt ggatttatta attttggatc tgtatgtgtg tgccatacat attcatagtt    480
acgaattgaa gatgatggat ggaaatatcg atctaggata ggtatacatg ttgatgcggg    540
ttttactgat gcatatacag agatgctttt tgttcgcttg gttgtgatga tgtggtctgg    600
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgatat acttggatga tggcatatgc    900
agcagctata tgtggatttt tttagccctg ccttcatacg ctatttattt gcttggtact    960
gtttcttttg tcgatgctca ccctgttgtt tggtgatact tctgcagggt              1010
```

<210> SEQ ID NO 145
<211> LENGTH: 2008
<212> TYPE: DNA
<213> ORGANISM: Zea mays subsp. Mexicana

<400> SEQUENCE: 145

```
gtcgtgcccc tctctagaga taaagagcat tgcatgtcta aagtataaaa aattaccaca     60
tattttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gtttttttg caaatagctt gacctatata    300
atacttcatc cattttatta gtacatccat ttaggattta gggttgatgg tttctataga    360
ctaattttta gtacatccat tttattcttt ttagtctcta aattttttaa aactaaaact    420
ctattttagt tttttattta ataatttaga tataaaatga aataaaataa attgactaca    480
aataaaacaa ataccctta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaata gacaccccct ccacaccctc tttccccaac ctcgtgttcg ttcggagcgc    900
acacacacgc aaccagatct cccccaaatc cagccgtcgg cacctccgct tcaaggtacg    960
ccgctcatcc tcccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
```

caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcaggtc 2008

<210> SEQ ID NO 146
<211> LENGTH: 1053
<212> TYPE: DNA
<213> ORGANISM: Zea mays subsp. Mexicana

<400> SEQUENCE: 146
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag gtc 1053

<210> SEQ ID NO 147
<211> LENGTH: 2008
<212> TYPE: DNA
<213> ORGANISM: Zea mays subsp. Mexicana

<400> SEQUENCE: 147
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gtttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccctta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccct ccacaccctc tttccccaac ctcgtgttcg ttcggagcgc 900
acacacacgc aaccagatct cccccaaatc cagccgtcgg cacctccgct tcaaggtacg 960
ccgctcatcc tcccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc tttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgtttg gtgatacttc tgcaggtc 2008

<210> SEQ ID NO 148
<211> LENGTH: 1053
<212> TYPE: DNA
<213> ORGANISM: Zea mays subsp. Mexicana

<400> SEQUENCE: 148

-continued

```
gtacgccgct catcctcccc cccccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt tttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataataaac aagtatgttt    900
tataattatt ttgatcttga tatacttgga tgatggcata tgcagcagct atatgtggat    960
tttttagccc tgccttcata cgctatttat ttgcttggta ctgtttcttt tgtccgatgc   1020
tcaccctgtt gtttggtgat acttctgcag gtc                                 1053
```

<210> SEQ ID NO 149
<211> LENGTH: 2008
<212> TYPE: DNA
<213> ORGANISM: Zea mays subsp. Mexicana

<400> SEQUENCE: 149

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gtttttttttg caaatagctt gacctatata    300
atacttcatc cattttatta gtacatccat ttaggattta gggttgatgg tttctataga    360
ctaattttta gtacatccat tttattcttt ttagtctcta aatttttttaa aactaaaact    420
ctattttagt tttttattta ataatttaga tataaaatga aataaaataa attgactaca    480
aataaaacaa ataccctttta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaata gacaccccct ccacaccctc tttccccaac ctcgtgttcg ttcggagcgc    900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
```

atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcagggt 2008

<210> SEQ ID NO 150
<211> LENGTH: 1053
<212> TYPE: DNA
<213> ORGANISM: Zea mays subsp. Mexicana

<400> SEQUENCE: 150
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag ggt 1053

<210> SEQ ID NO 151

<211> LENGTH: 1635
<212> TYPE: DNA
<213> ORGANISM: Sorghum bicolor

<400> SEQUENCE: 151
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga cgtaaccctc cgttgcccac 420
gataaaagct ccacccccga ccccggcccc ccgatttccc ctacggacca gtctcccccc 480
gatcgcaatc gcgaattcgt cgcaccatcg gcacgcagac gaacgaagca aggctctccc 540
catcggctcg tcaaggtatg cgttccctag atttgttccc ttcctctctc ggtttgtcta 600
tatatatgca tgtatggtcg attcccgatc tcgtcgattc tcggtttcgc cttccgtacg 660
aagattcgtt tagattgttc atatgttctg ttgtgttacc agattgatcg gatcaacttg 720
atccagttat cttcgctcct ccgattagat ccgtttctat ttcagtatat atatactagt 780
atagtatcta gggttcacac tgttgaccga ctggttactt ggaattgatc cgtgctgagt 840
tcagttgttg ccgtccataa aggcccgtgc tattgtctgt tctgaaacga aatcctgtag 900
atttcttagg gttagtgttc aattcatcaa aaggttgatt agtgaattat caaatttgag 960
agggttaaat cattctcatc atgttgtctc gaatgtaatc ccaaagatat tatagactgt 1020
gtttcgattt gatggattga tttgtgtatc atctaaatca acaaggctaa gtcatcagtt 1080
catagaatca tgtttaggtt tccgttcaat agactagttt tatcaatata taaaattata 1140
agaagggtag ggtaaatcac gttgcctcaa atgccatcct gtatggtttg gtttcaattc 1200
aattagtttg gttgattagg gtatgctctg gattaagatg gttaaatctt ccctagcatc 1260
ttccctgcct atccttactt gatccgtttc ggatatgttg gaagtacagc gagcttattt 1320
catgttgata gtgacccctt tcagattata ctattgaata ttgtatgttt gccacttctg 1380
tatgttgaat tatcctgcta aattagcaat ggaattagca tattggcaat tggtatgcat 1440
ggacctaatc aggacggatg tggttatgtt agtttcaatt cattgtcaat tcattgttca 1500
cctgcgttag atatatatga tgatttttac gtgtagttca tagttcttga gttttggatc 1560
tttcttatct gatatatgct ttcctgtgcc tgtgctttat tgtgtcttac catgcgattt 1620
ttgtctatgc aggtc 1635

<210> SEQ ID NO 152
<211> LENGTH: 1080
<212> TYPE: DNA
<213> ORGANISM: Sorghum bicolor

<400> SEQUENCE: 152
gtatgcgttc cctagatttg ttcccttcct ctctcggttt gtctatatat atgcatgtat 60
ggtcgattcc cgatctcgtc gattctcggt ttcgccttcc gtacgaagat tcgtttagat 120
tgttcatatg ttctgttgtg ttaccagatt gatcggatca acttgatcca gttatcttcg 180
ctcctccgat tagatccgtt tctatttcag tatatatata ctagtatagt atctagggtt 240
cacactgttg accgactggt tacttggaat tgatccgtgc tgagttcagt tgttgccgtc 300
cataaaggcc cgtgctattg tctgttctga aacgaaatcc tgtagatttc ttagggttag 360
tgttcaattc atcaaaaggt tgattagtga attatcaaat ttgagagggt taaatcattc 420
tcatcatgtt gtctcgaatg taatcccaaa gatattatag actgtgtttc gatttgatgg 480
attgatttgt gtatcatcta aatcaacaag gctaagtcat cagttcatag aatcatgttt 540
aggtttccgt tcaatagact agttttatca atatataaaa ttataagaag ggtagggtaa 600
atcacgttgc ctcaaatgcc atcctgtatg gtttggtttc aattcaatta gtttggttga 660
ttagggtatg ctctggatta agatggttaa atcttcccta gcatcttccc tgcctatcct 720
tacttgatcc gtttcggata tgttggaagt acagcgagct tatttcatgt tgatagtgac 780
ccctttcaga ttatactatt gaatattgta tgtttgccac ttctgtatgt tgaattatcc 840
tgctaaatta gcaatggaat tagcatattg gcaattggta tgcatggacc taatcaggac 900
ggatgtggtt atgttagttt caattcattg tcaattcatt gttcacctgc gttagatata 960
tatgatgatt tttacgtgta gttcatagtt cttgagtttt ggatctttct tatctgatat 1020
atgctttcct gtgcctgtgc tttattgtgt cttaccatgc gatttttgtc tatgcaggtc 1080

<210> SEQ ID NO 153
<211> LENGTH: 2067
<212> TYPE: DNA
<213> ORGANISM: Sorghum bicolor

<400> SEQUENCE: 153
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480
cccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgcagagc ctcagaccag attccgatca atcacccata agctcccccc 900
aaatctgttc ctcgtctccc gtctcgcggt ttcctacttc cctcggacgc ctccggcaag 960
tcgctcgacc gcgcgattcc gcccgctcaa ggtatcaact cggttcacca ctccaatcta 1020
cgtctgattt agatgttact tccatctatg tctaatttag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcggc atcgcgatct gacgcggttg ctttgtagag gctgggggtc taggctgtga 1260
ttttagaatc aaataaagct gttccttacc gtagatgttt cctacatgtt ctgtccagta 1320

```
ctccagtgct atattcacat tgtttgaggc ttgagttttg tcgatcagtg gtcatgagaa   1380

aaatatatct catgatttta gaggcaccta ttgggaaagg tagatggttc cgttttacat   1440

gttttataga ccttgtggca tggctccttt gttctatggg tgctttattt tcctgaataa   1500

cagtaatgcg agactggtct atgggtgctt tgaccagtaa tgcgagacta gttatttgat   1560

catggtgcag ttcctagtga ttacgaacaa caatttggta gctcagttca ttcagcattg   1620

gtttctacga tccttatcat tttacttctg aatgaattta tttatttaag atattacagt   1680

gcaataaact gctgtataat atcagtaaca aactgctatt actagtaaat gcctagattc   1740

ataataattc attattctac ttgaaaatga tcttaggcct tttatgcgg tcctacgcat    1800

ccttccacag gacttgctgt ttgtttgttt tttgtaatcc ctcgctggga cgcagaatgg   1860

ttcatctgtg ctaataattt ttttgcatat ataagtttat agttctcatt attcatgtgg   1920

ctatggtagc ctgtaaaatc tattgtaata acatattagt cagccataca tctgttccaa   1980

cttgctcaat tgcaaatcat atctccactt aaagcacatg tttgcaagct ttctgacaag   2040

tttctttgtg tttgattgaa acaggtg                                       2067
```

<210> SEQ ID NO 154
<211> LENGTH: 1076
<212> TYPE: DNA
<213> ORGANISM: Sorghum bicolor

<400> SEQUENCE: 154

```
gtatcaactc ggttcaccac tccaatctac gtctgattta gatgttactt ccatctatgt     60

ctaatttaga tgttactccg atgcgattgg attatgttta tgcggtttgc actgctctgg    120

aaactggaat ctagggtttc gagtgatttg atcgatcgcg atctgtgatt tcgttgcgcc    180

ttgtgtatgc ttggagtgat ctaggcttgt atatgcggca tcgcgatctg acgcggttgc    240

tttgtagagg ctgggggtct aggctgtgat tttagaatca aataaagctg ttccttaccg    300

tagatgtttc ctacatgttc tgtccagtac tccagtgcta tattcacatt gtttgaggct    360

tgagttttgt cgatcagtgg tcatgagaaa aatatatctc atgattttag aggcacctat    420

tgggaaaggt agatggttcc gttttacatg ttttatagac cttgtggcat ggctcctttg    480

ttctatgggt gctttatttt cctgaataac agtaatgcga gactggtcta tgggtgcttt    540

gaccagtaat gcgagactag ttatttgatc atggtgcagt tcctagtgat tacgaacaac    600

aatttggtag ctcagttcat tcagcattgg tttctacgat ccttatcatt ttacttctga    660

atgaatttat ttatttaaga tattacagtg caataaactg ctgtataata tcagtaacaa    720

actgctatta ctagtaaatg cctagattca taataattca ttattctact tgaaaatgat    780

cttaggcctt tttatgcggt cctacgcatc cttccacagg acttgctgtt tgtttgtttt    840

ttgtaatccc tcgctgggac gcagaatggt tcatctgtgc taataatttt tttgcatata    900

taagtttata gttctcatta ttcatgtggc tatggtagcc tgtaaaatct attgtaataa    960

catattagtc agccatacat ctgttccaac ttgctcaatt gcaaatcata tctccactta   1020

aagcacatgt ttgcaagctt tctgacaagt ttctttgtgt ttgattgaaa caggtg       1076
```

<210> SEQ ID NO 155
<211> LENGTH: 2067
<212> TYPE: DNA
<213> ORGANISM: Sorghum bicolor

<400> SEQUENCE: 155

```
cattaaaagt cattatgtgc atgcgtcgta actaacatgg atatgttgct gcactatctc     60
```

```
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attggggcgc gggagtctgc cggacgacgc gttccgtccg aacggccgga cccgacgagg    480
cccccccgcc gccccacgtc gcagaaccgt ccgtgggtgg taatctggcc gggtacacca    540
gccgtcccct tgggcggcct cacagcactg ggctcacacg tgagttttgt tctgggcttc    600
ggatcgcacc atatgggcct cggcatcaga aagacggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggccc gcttctccca cccgacataa atatcccccc    840
atccaggcaa ggcgcagagc ctcagaccag attccgatca atcacccata agctcccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta   1020
cgtctgattt agatgttact tccatctatg tctaatttag atgttactcc gatgcgattg   1080
gattatgttt atgcggtttg cactgctctg gaaactggaa tctagggttt cgagtgattt   1140
gatcgatcgc gatctgtgat ttcgttgcgc cttgtgtatg cttggagtga tctaggcttg   1200
tatatgcggc atcgcgatct gacgcggttg ctttgtagag gctgggggtc taggctgtga   1260
ttttagaatc aaataaagct gttccttacc gtagatgttt cctacatgtt ctgtccagta   1320
ctccagtgct atattcacat tgtttgaggc ttgagttttg tcgatcagtg gtcatgagaa   1380
aaatatatct catgatttta gaggcaccta ttgggaaagg tagatggttc cgttttacat   1440
gttttataga ccttgtggca tggctccttt gttctatggg tgctttattt tcctgaataa   1500
cagtaatgcg agactggtct atgggtgctt tgaccagtaa tgcgagacta gttatttgat   1560
catggtgcag ttcctagtga ttacgaacaa caatttggta gctcagttca ttcagcattg   1620
gtttctacga tccttatcat tttacttctg aatgaattta tttatttaag atattacagt   1680
gcaataaact gctgtataat atcagtaaca aactgctatt actagtaaat gcctagattc   1740
ataataattc attattctac ttgaaaatga tcttaggcct ttttatgcgg tcctacgcat   1800
ccttccacag gacttgctgt ttgtttgttt tttgtaatcc ctcgctggga cgcagaatgg   1860
ttcatctgtg ctaataattt ttttgcatat ataagtttat agttctcatt attcatgtgg   1920
ctatggtagc ctgtaaaatc tattgtaata acatattagt cagccataca tctgttccaa   1980
cttgctcaat tgcaaatcat atctccactt aaagcacatg tttgcaagct ttctgacaag   2040
tttctttgtg tttgattgaa acagggt                                      2067
```

<210> SEQ ID NO 156
<211> LENGTH: 1076
<212> TYPE: DNA
<213> ORGANISM: Sorghum bicolor

<400> SEQUENCE: 156

```
gtatcaactc ggttcaccac tccaatctac gtctgattta gatgttactt ccatctatgt     60
```

ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360
tgagttttgt cgatcagtgg tcatgagaaa aatatatctc atgattttag aggcacctat 420
tgggaaaggt agatggttcc gttttacatg ttttatagac cttgtggcat ggctcctttg 480
ttctatgggt gctttatttt cctgaataac agtaatgcga gactggtcta tgggtgcttt 540
gaccagtaat gcgagactag ttatttgatc atggtgcagt tcctagtgat tacgaacaac 600
aatttggtag ctcagttcat tcagcattgg tttctacgat ccttatcatt ttacttctga 660
atgaatttat ttatttaaga tattacagtg caataaactg ctgtataata tcagtaacaa 720
actgctatta ctagtaaatg cctagattca taataattca ttattctact tgaaaatgat 780
cttaggcctt tttatgcggt cctacgcatc cttccacagg acttgctgtt tgtttgtttt 840
ttgtaatccc tcgctgggac gcagaatggt tcatctgtgc taataatttt tttgcatata 900
taagtttata gttctcatta ttcatgtggc tatggtagcc tgtaaaatct attgtaataa 960
catattagtc agccatacat ctgttccaac ttgctcaatt gcaaatcata tctccactta 1020
aagcacatgt ttgcaagctt tctgacaagt ttctttgtgt ttgattgaaa cagggt 1076

<210> SEQ ID NO 157
<211> LENGTH: 2003
<212> TYPE: DNA
<213> ORGANISM: Sorghum bicolor

<400> SEQUENCE: 157
agaagtaaaa aaaaagttcg tttcagaatc ataaaggtaa gttaaaaaaa gaccatacaa 60
aaaagaggta tttaatgata aactataatc cagaatttgt taggatagta tataagaata 120
agaccttgtt tagtttcaaa aaaatttgca aaattttcca gattcctcgt cacatcaaat 180
ctttagaggt atgcatggag tattaaatat agacaagacc taaataagaa aacatgaaat 240
gttcacgaaa aaaatcaagc caatgcatga tcgaagcaaa cggtatagta acggtgttaa 300
cctgatccat tgatctttgt aatctttaac ggccacctac cgcgggcagc aaacggcgtc 360
cccctcctcg atatctccgc ggcggcctct ggctttttcc gcggaattgc gcggtgggga 420
cggattccac gagaccgcaa cgcaaccgcc tctcgccgct gggccccaca ccgctcggtg 480
ccgtagcccg tagcctcacg ggattctttc tccctcctcc cccgtgtata aattggcttc 540
atcccctccc tgcctcatcc atccaaatcc cactccccaa tcccatcccg tcggagaaat 600
tcatcgaagc gaagcgaagc gaatcctccc gatcctctca aggtacgcga gttttcgaat 660
cccctccaga cccctcgtat gctttccctg ttcgttttcg tcgtagcgtt tgattaggta 720
tgctttccct gttcgtgttc gtcgtagggt tcgattaggt cgtgtgaggc catggcctgc 780
tgtgataaat ttatttgttg ttatatcgga tctgtagtcg atttgggggt cgtggtgtag 840
atccgcgggc tgtgatgaag ttatttggtg tgattgtgct cgcgtgattc tgcgcgttga 900
gctcgagtag atctgatggt tggacgaccg attggttcgt tggctggctg cgctaaggtt 960
gggctgggct catgttgcgt tcgctgttgc gcgtgattcc gcggatggac ttgcgcttga 1020
ttgccgccag atcacgttac gattatgtga tttcgtttgg aactttttag atttgtagct 1080
tctgcttatt atatgacaga tgcgcctact gctcatatgc ctgtggtaaa taatggatgg 1140
ctgtgggtca aactagttga ttgtcgagtc atgtatcata tacaggtgta tagacttgcg 1200
tctaattgtt tgcatgttgc agttatatga tttgttttag attgtttgtt ccactcatct 1260
aggctgtaaa agggacacta cttattagct tgttgtttaa tctttttatt agtagattat 1320
attggtaatg ttttactaat tattattatg ttatatgtga cttctgctca tgcctgatta 1380
taatcataga tcactgtagt tgattgttga atcatgtgtc aaatacccgt atacataaca 1440
ctacacattt gcttagttgt ttccttaact catgcaaatt gaacaccatg tatgatttgc 1500
atggtgctgt aatgttaaat actacagtcc tgttggtact tgtttagtaa gaatctgctt 1560
catacaacta tatgctatgc ctgatgataa tcatatatct ttgtgtaatt aataattagt 1620
tgactgttga ataatgtatc gagtacatac catggcacaa ttgcttagtc acttccttaa 1680
ccatgcatat tgaactgacc ccttcatgtt ctgctgaatt gttctattct gattagacca 1740
tacatcatgt attgcaatct ttatttgcaa ttgtaatgta atggttcggt tctcaaatgt 1800
taaatgctat agttgtgcta ctttctaatg ttaaatgcta tagctgtgct acttgtaaga 1860
tctgcttcat agtttagtta aattaggatg atgagctttg atgctgtaac tttgtttgat 1920
tatgttcata gttgatcagt ttttgttaga ctcacagtaa cttatggtct cactcttctt 1980
ctggtctttg atgtttgcag cgg 2003

<210> SEQ ID NO 158
<211> LENGTH: 1361
<212> TYPE: DNA
<213> ORGANISM: Sorghum bicolor

<400> SEQUENCE: 158
gtacgcgagt tttcgaatcc cctccagacc cctcgtatgc tttccctgtt cgttttcgtc 60
gtagcgtttg attaggtatg ctttccctgt tcgtgttcgt cgtagggttc gattaggtcg 120
tgtgaggcca tggcctgctg tgataaattt atttgttgtt atatcggatc tgtagtcgat 180
ttgggggtcg tggtgtagat ccgcgggctg tgatgaagtt atttggtgtg attgtgctcg 240
cgtgattctg cgcgttgagc tcgagtagat ctgatggttg gacgaccgat tggttcgttg 300
gctggctgcg ctaaggttgg gctgggctca tgttgcgttc gctgttgcgc gtgattccgc 360
ggatggactt gcgcttgatt gccgccagat cacgttacga ttatgtgatt tcgtttggaa 420
ctttttagat ttgtagcttc tgcttattat atgacagatg cgcctactgc tcatatgcct 480
gtggtaaata atggatggct gtgggtcaaa ctagttgatt gtcgagtcat gtatcatata 540
caggtgtata gacttgcgtc taattgtttg catgttgcag ttatatgatt tgttttagat 600
tgtttgttcc actcatctag gctgtaaaag ggacactact tattagcttg ttgtttaatc 660
tttttattag tagattatat tggtaatgtt ttactaatta ttattatgtt atatgtgact 720
tctgctcatg cctgattata atcatagatc actgtagttg attgttgaat catgtgtcaa 780
atacccgtat acataacact acacatttgc ttagttgttt ccttaactca tgcaaattga 840
acaccatgta tgatttgcat ggtgctgtaa tgttaaatac tacagtcctg ttggtacttg 900
tttagtaaga atctgcttca tacaactata tgctatgcct gatgataatc atatatcttt 960
gtgtaattaa taattagttg actgttgaat aatgtatcga gtacatacca tggcacaatt 1020
gcttagtcac ttccttaacc atgcatattg aactgacccc ttcatgttct gctgaattgt 1080
tctattctga ttagaccata catcatgtat tgcaatcttt atttgcaatt gtaatgtaat 1140
ggttcggttc tcaaatgtta aatgctatag ttgtgctact ttctaatgtt aaatgctata 1200

```
gctgtgctac ttgtaagatc tgcttcatag tttagttaaa ttaggatgat gagctttgat   1260

gctgtaactt tgtttgatta tgttcatagt tgatcagttt ttgttagact cacagtaact   1320

tatggtctca ctcttcttct ggtctttgat gtttgcagcg g                        1361
```

<210> SEQ ID NO 159
<211> LENGTH: 1812
<212> TYPE: DNA
<213> ORGANISM: Artificial sequence
<220> FEATURE:
<221> NAME/KEY: misc_feature
<222> LOCATION: (1)..(1812)
<223> OTHER INFORMATION: Codon redesigned coding sequence.

<400> SEQUENCE: 159

```
atggtccgtc ctgtagaaac cccaacccgt gaaatcaaaa aactcgacgg cctgtgggca     60

ttcagtctgg atcgcgaaaa ctgtggaatt gatcagcgtt ggtgggaaag cgcgttacaa    120

gaaagccggg caattgctgt gccaggcagt tttaacgatc agttcgccga tgcagatatt    180

cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtatc accgtttgtg tgaacaacga actgaactgg    420

cagactatcc cgccgggaat ggtgattacc gacgaaaacg gcaagaaaaa gcagtcttac    480

ttccatgatt tctttaacta tgccggaatc catcgcagcg taatgctcta caccacgccg    540

aacacctggg tggacgatat caccgtggtg acgcatgtcg cgcaagactg taaccacgcg    600

tctgttgact ggcaggtggt ggccaatggt gatgtcagcg ttgaactgcg tgatgcggat    660

caacaggtgg ttgcaactgg acaaggcact agcgggactt tgcaagtggt gaatccgcac    720

ctctggcaac cgggtgaagg ttatctctat gaactgtgcg tcacagccaa aagccagaca    780

gagtgtgata tctacccgct tcgcgtcggc atccggtcag tggcagtgaa gggcgaacag    840

ttcctgatta accacaaacc gttctacttt actggctttg gtcgtcatga agatgcggac    900

ttgcgtggca aaggattcga taacgtgctg atggtgcacg accacgcatt aatggactgg    960

attggggcca actcctaccg tacctcgcat tacccttacg ctgaagagat gctcgactgg   1020

gcagatgaac atggcatcgt ggtgattgat gaaactgctg ctgtcggctt taacctctct   1080

ttaggcattg gtttcgaagc gggcaacaag ccgaaagaac tgtacagcga agaggcagtc   1140

aacggggaaa ctcagcaagc gcacttacag gcgattaaag agctgatagc gcgtgacaaa   1200

aaccacccaa gcgtggtgat gtggagtatt gccaacgaac cggatacccg tccgcaaggt   1260

gcacgggaat atttcgcgcc actggcggaa gcaacgcgta aactcgaccc gacgcgtccg   1320

atcacctgcg tcaatgtaat gttctgcgac gctcacaccg ataccatcag cgatctcttt   1380

gatgtgctgt gcctgaaccg ttattacgga tggtatgtcc aaagcggcga tttggaaacg   1440

gcagagaagg tactggaaaa agaacttctg gcctggcagg agaaactgca tcagccgatt   1500

atcatcaccg aatacggcgt ggatacgtta gccgggctgc actcaatgta caccgacatg   1560

tggagtgaag agtatcagtg tgcatggctg gatatgtatc accgcgtctt tgatcgcgtc   1620

agcgccgtcg tcggtgaaca ggtatggaat ttcgccgatt ttgcgacctc gcaaggcata   1680

ttgcgcgttg gcggtaacaa gaaagggatc ttcactcgcg accgcaaacc gaagtcggcg   1740

gcttttctgc tgcaaaaacg ctggactggc atgaacttcg gtgaaaaacc gcagcaggga   1800

ggcaaacaat ga                                                        1812
```

<210> SEQ ID NO 160
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 160
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtaag tttctgcttc tacctttgat atatatataa 420
taattatcat taattagtag taatataata tttcaaatat ttttttcaaa ataaaagaat 480
gtagtatata gcaattgctt ttctgtagtt tataagtgtg tatattttaa tttataactt 540
ttctaatata tgaccaaaat ttgttgatgt gcaggtatca ccgtttgtgt gaacaacgaa 600
ctgaactggc agactatccc gccgggaatg gtgattaccg acgaaaacgg caagaaaaag 660
cagtcttact tccatgattt ctttaactat gccggaatcc atcgcagcgt aatgctctac 720
accacgccga acacctgggt ggacgatatc accgtggtga cgcatgtcgc gcaagactgt 780
aaccacgcgt ctgttgactg gcaggtggtg gccaatggtg atgtcagcgt tgaactgcgt 840
gatgcggatc aacaggtggt tgcaactgga caaggcacta gcgggacttt gcaagtggtg 900
aatccgcacc tctggcaacc gggtgaaggt tatctctatg aactgtgcgt cacagccaaa 960
agccagacag agtgtgatat ctacccgctt cgcgtcggca tccggtcagt ggcagtgaag 1020
ggcgaacagt tcctgattaa ccacaaaccg ttctacttta ctggctttgg tcgtcatgaa 1080
gatgcggact tgcgtggcaa aggattcgat aacgtgctga tggtgcacga ccacgcatta 1140
atggactgga ttggggccaa ctcctaccgt acctcgcatt acccttacgc tgaagagatg 1200
ctcgactggg cagatgaaca tggcatcgtg gtgattgatg aaactgctgc tgtcggcttt 1260
aacctctctt taggcattgg tttcgaagcg ggcaacaagc cgaaagaact gtacagcgaa 1320
gaggcagtca acggggaaac tcagcaagcg cacttacagg cgattaaaga gctgatagcg 1380
cgtgacaaaa accacccaag cgtggtgatg tggagtattg ccaacgaacc ggatacccgt 1440
ccgcaaggtg cacgggaata tttcgcgcca ctggcggaag caacgcgtaa actcgacccg 1500
acgcgtccga tcacctgcgt caatgtaatg ttctgcgacg ctcacaccga taccatcagc 1560
gatctctttg atgtgctgtg cctgaaccgt tattacggat ggtatgtcca aagcggcgat 1620
ttggaaacgg cagagaaggt actggaaaaa gaacttctgg cctggcagga gaaactgcat 1680
cagccgatta tcatcaccga atacggcgtg gatacgttag ccgggctgca ctcaatgtac 1740
accgacatgt ggagtgaaga gtatcagtgt gcatggctgg atatgtatca ccgcgtcttt 1800
gatcgcgtca gcgccgtcgt cggtgaacag gtatggaatt tcgccgattt tgcgacctcg 1860
caaggcatat tgcgcgttgg cggtaacaag aaagggatct tcactcgcga ccgcaaaccg 1920
aagtcggcgg cttttctgct gcaaaaacgc tggactggca tgaacttcgg tgaaaaaccg 1980
cagcagggag gcaaacaatg a 2001

<210> SEQ ID NO 161
<211> LENGTH: 253
<212> TYPE: DNA
<213> ORGANISM: Agrobacterium tumefaciens

<400> SEQUENCE: 161
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 162
<211> LENGTH: 210
<212> TYPE: DNA
<213> ORGANISM: Triticum aestivum

<400> SEQUENCE: 162
ctgcatgcgt ttggacgtat gctcattcag gttggagcca atttggttga tgtgtgtgcg 60
agttcttgcg agtctgatga gacatctctg tattgtgttt ctttccccag tgttttctgt 120
acttgtgtaa tcggctaatc gccaacagat tcggcgatga ataaatgaga aataaattgt 180
tctgattttg agtgcaaaaa aaaaggaatt 210

<210> SEQ ID NO 163
<211> LENGTH: 1204
<212> TYPE: DNA
<213> ORGANISM: Artificial sequence
<220> FEATURE:
<221> NAME/KEY: misc_feature
<222> LOCATION: (1)..(1204)
<223> OTHER INFORMATION: Chimeric transcriptional regulatory expression element group.

<400> SEQUENCE: 163
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tccttcgcaa gacccttcct ctatataagg aagttcattt 600
catttggaga ggacacgctg acaagctgac tctagcagat cctctagaac catcttccac 660
acactcaagc cacactattg gagaacacac agggacaaca caccataaga tccaagggag 720
gcctccgccg ccgccggtaa ccaccccgcc cctctcctct ttctttctcc gttttttttt 780
ccgtctcggt ctcgatcttt ggccttggta gtttgggtgg gcgagaggcg gcttcgtgcg 840
cgcccagatc ggtgcgcggg aggggcggga tctcgcggct ggggctctcg ccggcgtgga 900

-continued tccggcccgg atctcgcggg gaatggggct ctcggatgta gatctgcgat ccgccgttgt 960
tgggggagat gatgggggt ttaaaatttc cgccgtgcta aacaagatca ggaagagggg 1020
aaaagggcac tatggtttat atttttatat atttctgctg cttcgtcagg cttagatgtg 1080
ctagatcttt ctttcttctt tttgtgggta gaatttgaat ccctcagcat tgttcatcgg 1140
tagtttttct tttcatgatt tgtgacaaat gcagcctcgt gcggagcttt tttgtaggta 1200
gaag 1204

<210> SEQ ID NO 164
<211> LENGTH: 1399
<212> TYPE: DNA
<213> ORGANISM: Oryza sativa

<400> SEQUENCE: 164
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccaacc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata cccccccctc tcctcccatc cccccaaccc 840
taccaccacc accaccacca cctccacctc ctccccccctc gctgccggac gacgagctcc 900 tccccccctcc ccctccgccg ccgccgcgcc ggtaaccacc ccgcccctct cctctttctt 960
tctccgtttt tttttccgtc tcggtctcga tctttggcct tggtagtttg ggtgggcgag 1020
aggcggcttc gtgcgcgccc agatcggtgc gcgggagggg cgggatctcg cggctggggc 1080
tctcgccggc gtggatccgg cccggatctc gcggggaatg gggctctcgg atgtagatct 1140
gcgatccgcc gttgttgggg gagatgatgg ggggtttaaa atttccgccg tgctaaacaa 1200
gatcaggaag aggggaaaag ggcactatgg tttatatttt tatatatttc tgctgcttcg 1260
tcaggcttag atgtgctaga tctttctttc ttctttttgt gggtagaatt tgaatccctc 1320
agcattgttc atcggtagtt tttcttttca tgatttgtga caaatgcagc ctcgtgcgga 1380 gctttttgt aggtagaag 1399

<210> SEQ ID NO 165
<211> LENGTH: 2181
<212> TYPE: DNA
<213> ORGANISM: Oryza sativa

<400> SEQUENCE: 165
gacaacaaca tgcttctcat caacatggag ggaagaggga gggagaaagt gtcgcctggt 60
cacctccatt gtcacactag ccactggcca gctctcccac accaccaatg ccaggggcga 120

```
gctttagcac agccaccgct tcacctccac caccgcacta ccctagcttc gcccaacagc    180
caccgtcaac gcctcctctc cgtcaacata agagagagag agaagaggag agtagccatg    240
tggggaggag gaatagtaca tggggcctac cgtttggcaa gttattttgg gttgccaagt    300
taggccaata aggggaggga tttggccatc cggttggaaa ggttattggg gtagtatctt    360
tttactagaa ttgtcaaaaa aaaatagttt gagagccatt tggagaggat gttgcctgtt    420
agaggtgctc ttaggacatc aaattccata aaaacatcag aaaaattctc tcgatgaaga    480
tttataacca ctaaaactgc cctcaattcg aagggagttc aaaacaatta aaatcatgtt    540
cgaattgagt ttcaatttca ctttaacccc tttgaaatct caatggtaaa acatcaaccc    600
gtcaggtagc atggttcttt ttattccttt caaaaagagt taattacaaa cagaatcaaa    660
actaacagtt aggcccaagg cccatccgag caaacaatag atcatgggcc aggcctgcca    720
ccaccctccc cctcctggct cccgctcttg aatttcaaaa tccaaaaata tcggcacgac    780
tggccgccga cggagcgggc ggaaaatgac ggaacaaccc ctcgaattct accccaacta    840
cgcccaccaa cccacacgcc actgacaatc cggtcccacc cttgtgggcc cacctacaag    900
cgagacgtca gtcgctcgca gcaaccagtg ggcccacctc ccagtgagcg gcgggtagat    960
ctggactctt acccacccac actaaacaaa acggcatgaa tattttgcac taaaaccctc   1020
agaaaaattc cgatattcca aaccagtaca gttcctgacc gttggaggag ccaaagtgga   1080
gcggagtgta aaattgggaa acttaatcga gggggttaaa cgcaaaaacg ccgaggcgcc   1140
tcccgctcta tagaaagggg aggagtggga ggtggaaacc ctaccacacc gcagagaaag   1200
gcgtcttcgt actcgcctct ctccgcgccc tcctccgccg ccgctcgccg ccgttcgtct   1260
ccgccgccac cggctagcca tccaggtaaa acaaacaaaa acggatctga tgcttccatt   1320
cctccgtttc tcgtagtagc gcgcttcgat ctgtgggtgg atctgggtga tcctggggtg   1380
tggttcgttc tgtttgatag atctgtcggt ggatctggcc ttctgtggtt gtcgatgtcc   1440
ggatctgcgt tttgatcagt ggtagttcgt ggatctggcg aaatgttttg gatctggcag   1500
tgagacgcta agaatcggga aatgatgcaa tattaggggg gtttcggatg gggatccact   1560
gaattagtct gtctccctgc tgataatctg ttcctttttg gtagatctgg ttagtgtatg   1620
tttgtttcgg atagatctga tcaatgcttg tttgtttttt caaattttct acctaggttg   1680
tataggaatg gcatgcggat ctggttggat tgccatgatc cgtgctgaaa tgcccctttg   1740
gttgatggat cttgatattt tactgctgtt cacctagatt tgtactcccg tttatactta   1800
atttgttgct tattatgaat agatctgtaa cttaggcaca tgtatggacg gagtatgtgg   1860
atctgtagta tgtacattgc tgcgagctaa gaactatttc agagcaagca cagaaaaaaa   1920
tatttagaca gattgggcaa ctatttgatg gtctttggta tcatgctttg tagtgctcgt   1980
ttctgcgtag taatcttttg atctgatctg aagataggtg ctattatatt cttaaaggtc   2040
attagaacgc tatctgaaag gctgtattat gtggattggt tcacctgtga ctccctgttc   2100
gtcttgtctt gataaatcct gtgataaaaa aaattcttaa ggcgtaattt gttgaaatct   2160
tgttttgtcc tatgcagcct g                                             2181
```

<210> SEQ ID NO 166
<211> LENGTH: 1653
<212> TYPE: DNA
<213> ORGANISM: Artificial sequence
<220> FEATURE:
<221> NAME/KEY: misc_feature
<222> LOCATION: (1)..(1653)

<223> OTHER INFORMATION: Codon redesigned coding sequence.

<400> SEQUENCE: 166

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggccctt ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacacccg aggggggatga taaaccgggc    1080
gcggtcggta aagttgttcc atttttttgaa gcgaaggttg tggatctgga taccgggaaa   1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653
```

<210> SEQ ID NO 167
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 167

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gatttttctg catggtaacg ctgcctccag ctacctgtgg     180
aggcacgtcg tgcctcacat cgagcccgtg gctagatgca tcatccctga tctgatcgga     240
```

```
atgggtaagt ccggcaagag cgggaatggc tcatatcgcc tcctggatca ctacaagtac    300

ctcaccgctt ggttcgagct gctgaacctt ccaaagaaaa tcatctttgt gggccacgac    360

tggggggctt gtctggcctt tcactactcc tacgagcacc aagacaagat caaggccatc    420

gtccatgctg agagtgtcgt ggacgtgatc gagtcctggg acgagtggcc tgacatcgag    480

gaggatatcg ccctgatcaa gagcgaagag ggcgagaaaa tggtgcttga gaataacttc    540

ttcgtcgaga ccatgctccc aagcaagatc atgcggaaac tggagcctga ggagttcgct    600

gcctacctgg agccattcaa ggagaagggc gaggttagac ggcctaccct ctcctggcct    660

cgcgagatcc ctctcgttaa gggaggcaag cccgacgtcg tccagattgt ccgcaactac    720

aacgcctacc ttcgggccag cgacgatctg cctaagatgt tcatcgagtc cgaccctggg    780

ttcttttcca acgctattgt cgagggagct aagaagttcc ctaacaccga gttcgtgaag    840

gtgaagggcc tccacttcag ccaggaggac gctccagatg aaatgggtaa gtacatcaag    900

agcttcgtgg agcgcgtgct gaagaacgag cagtaa                              936
```

```
<210> SEQ ID NO 168
<211> LENGTH: 675
<212> TYPE: DNA
<213> ORGANISM: Artificial sequence
<220> FEATURE:
<221> NAME/KEY: misc_feature
<222> LOCATION: (1)..(675)
<223> OTHER INFORMATION: Chimeric transcriptional regulatory expression
      element group.

<400> SEQUENCE: 168

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggaaccat cttccacaca ctcaagccac actattggag aacacacagg    660

gacaacacac cataa                                                     675
```

```
<210> SEQ ID NO 169
<211> LENGTH: 622
<212> TYPE: DNA
<213> ORGANISM: Cauliflower mosaic virus

<400> SEQUENCE: 169

ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300
```

```
aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tctagacgca agacccttcc tctatataag gaagttcatt    600

tcatttggag aggacacgct ga                                              622
```

<210> SEQ ID NO 170
<211> LENGTH: 1446
<212> TYPE: DNA
<213> ORGANISM: Artificial sequence
<220> FEATURE:
<221> NAME/KEY: misc_feature
<222> LOCATION: (1)..(1446)
<223> OTHER INFORMATION: Chimeric transcriptional regulatory expression element group.

<400> SEQUENCE: 170

```
ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga ggacacgctg acaagctgac tctagcagat ctaccgtctt cggtacgcgc    660

tcactccgcc ctctgccttt gttactgcca cgtttctctg aatgctctct tgtgtggtga    720

ttgctgagag tggtttagct ggatctagaa ttacactctg aaatcgtgtt ctgcctgtgc    780

tgattacttg ccgtcctttg tagcagcaaa atatagggac atggtagtac gaaacgaaga    840

tagaacctac acagcaatac gagaaatgtg taatttggtg cttagcggta tttatttaag    900

cacatgttgg tgttataggg cacttggatt cagaagtttg ctgttaattt aggcacaggc    960

ttcatactac atgggtcaat agtataggga ttcatattat aggcgatact ataataattt   1020

gttcgtctgc agagcttatt atttgccaaa attagatatt cctattctgt ttttgtttgt   1080

gtgctgttaa attgttaacg cctgaaggaa taaatataaa tgacgaaatt ttgatgttta   1140

tctctgctcc tttattgtga ccataagtca agatcagatg cacttgtttt aaatattgtt   1200

gtctgaagaa ataagtactg acagtatttt gatgcattga tctgcttgtt tgttgtaaca   1260

aaatttaaaa ataaagagtt tcctttttgt tgctctcctt acctcctgat ggtatctagt   1320

atctaccaac tgacactata ttgcttctct ttacatacgt atcttgctcg atgccttctc   1380

cctagtgttg accagtgtta ctcacatagt ctttgctcat ttcattgtaa tgcagatacc   1440

aagcgg                                                               1446
```

<210> SEQ ID NO 171
<211> LENGTH: 1165

```
<212> TYPE: DNA
<213> ORGANISM: Artificial sequence
<220> FEATURE:
<221> NAME/KEY: misc_feature
<222> LOCATION: (1)..(1165)
<223> OTHER INFORMATION: Chimeric transcriptional regulatory expression
      element group.

<400> SEQUENCE: 171

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggacacgc tgacaagctg actctagcag atcctctaga accatcttcc    660

acacactcaa gccacactat tggagaacac acagggacaa cacaccataa gatccaaggg    720

aggcctccgc cgccgccggt aaccaccccg cccctctcct ctttctttct ccgttttttt    780

ttccgtctcg gtctcgatct ttggccttgg tagtttgggt gggcgagagg cggcttcgtg    840

cgcgcccaga tcggtgcgcg ggaggggcgg gatctcgcgg ggaatggggc tctcggatgt    900

agatctgcga tccgccgttg ttgggggaga tgatgggggg tttaaaattt gcgccgtgct    960

aaacaagatc aggaagaggg gaaaagggca ctatggttta tatttttata tatttctgct   1020

gcttcgtcag gcttagatgt gctagatctt tctttcttct ttttgtgggt agaatttgaa   1080

tccctcagca ttgttcatcg gtagtttttc ttttcatgat ttgtgacaaa tgcagcctcg   1140

tgcggagctt ttttgtaggt agaag                                         1165


<210> SEQ ID NO 172
<211> LENGTH: 1751
<212> TYPE: DNA
<213> ORGANISM: Artificial sequence
<220> FEATURE:
<221> NAME/KEY: misc_feature
<222> LOCATION: (1)..(1751)
<223> OTHER INFORMATION: Chimeric transcriptional regulatory expression
      element group.

<400> SEQUENCE: 172

tcgaggtcat tcatatgctt gagaagagag tcgggatagt ccaaaataaa acaaaggtaa     60

gattacctgg tcaaaagtga aaacatcagt taaaaggtgg tataaagtaa aatatcggta    120

ataaaaggtg gcccaaagtg aaatttactc ttttctacta ttataaaaat tgaggatgtt    180

tttgtcggta ctttgatacg tcatttttgt atgaattggt ttttaagttt attcgctttt    240

ggaaatgcat atctgtattt gagtcgggtt ttaagttcgt ttgcttttgt aaatacagag    300

ggatttgtat aagaaatatc tttagaaaaa cccatatgct aatttgacat aatttttgag    360

aaaaatatat attcaggcga attagcttag gcctcatcgt tgaagatgcc tctgccgaca    420

gtggtcccaa agatggaccc ccacccacga ggagcatcgt ggaaaaagaa gacgttccaa    480
```

```
ccacgtcttc aaagcaagtg gattgatgtg atatctccac tgacgtaagg gatgacgcac    540

aatcccacta tccttcgagg cctcatcgtt gaagatgcct ctgccgacag tggtcccaaa    600

gatggacccc cacccacgag gagcatcgtg gaaaaagaag acgttccaac cacgtcttca    660

aagcaagtgg attgatgtga tatctccact gacgtaaggg atgacgcaca atcccactat    720

ccttcgaagc taattctcac aatgaacaat aataagatta aaatagcttt cccccgttgc    780

agcgcatggg tattttttct agtaaaaata aaagataaac ttagactcaa aacatttaca    840

aaaacaaccc ctaaagttcc taaagcccaa agtgctatcc acgatccata gcaagcccag    900

cccaacccaa cccaacccaa cccaccccag tccagccaac tggacaatag tctccacacc    960

cccccactat caccgtgagt tgtccgcacg caccgcacgt ctcgcagcca aaaaaaaaaa   1020

gaaagaaaaa aaagaaaaag aaaaaacagc aggtgggtcc gggtcgtggg ggccggaaac   1080

gcgaggagga tcgcgagcca gcgacgaggc cggccctccc tccgcttcca aagaaacgcc   1140

ccccatcgcc actatataca taccccccc tctcctccca tccccccaac cctaccacca   1200

ccaccaccac cacctccacc tcctccccc tcgctgccgg acgacgagct cctcccccct   1260

ccccctccgc cgccgccgcg ccggtaacca ccccgcccct ctcctctttc tttctccgtt   1320

tttttttccg tctcggtctc gatctttggc cttggtagtt tgggtgggcg agaggcggct   1380

tcgtgcgcgc ccagatcggt gcgcgggagg ggcgggatct cgcggctggg gctctcgccg   1440

gcgtggatcc ggcccggatc tcgcggggaa tggggctctc ggatgtagat ctgcgatccg   1500

ccgttgttgg gggagatgat gggggtttta aaatttccgc cgtgctaaac aagatcagga   1560

agaggggaaa agggcactat ggtttatatt tttatatatt tctgctgctt cgtcaggctt   1620

agatgtgcta gatctttctt tcttcttttt gtgggtagaa tttgaatccc tcagcattgt   1680

tcatcggtag tttttctttt catgatttgt gacaaatgca gcctcgtgcg gagctttttt   1740

gtaggtagaa g                                                          1751
```

```
<210> SEQ ID NO 173
<211> LENGTH: 1101
<212> TYPE: DNA
<213> ORGANISM: Artificial sequence
<220> FEATURE:
<221> NAME/KEY: misc_feature
<222> LOCATION: (1)..(1101)
<223> OTHER INFORMATION: Chimeric transcriptional regulatory expression
      element group.

<400> SEQUENCE: 173
```

```
ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga ggacacgctg accgccgccg ccggtaacca ccccgcccct ctcctctttc    660
```

```
tttctccgtt ttttttttccg tctcggtctc gatctttggc cttggtagtt tgggtgggcg    720

agaggcggct tcgtgcgcgc ccagatcggt gcgcgggagg ggcgggatct cgcggctggg    780

gctctcgccg gcgtggatcc ggcccggatc tcgcggggaa tggggctctc ggatgtagat    840

ctgcgatccg ccgttgttgg gggagatgat ggggggttta aaatttccgc cgtgctaaac    900

aagatcagga agaggggaaa agggcactat ggtttatatt tttatatatt tctgctgctt    960

cgtcaggctt agatgtgcta gatctttctt tcttcttttt gtgggtagaa tttgaatccc   1020

tcagcattgt tcatcggtag tttttctttt catgatttgt gacaaatgca gcctcgtgcg   1080

gagctttttt gtaggtagaa g                                             1101


<210> SEQ ID NO 174
<211> LENGTH: 200
<212> TYPE: DNA
<213> ORGANISM: Cauliflower mosaic virus

<400> SEQUENCE: 174

aaatcaccag tctctctcta caaatctatc tctctctatt tttctccaga ataatgtgtg     60

agtagttccc agataaggga attagggttc ttatagggtt tcgctcatgt gttgagcata    120

taagaaaccc ttagtatgta tttgtatttg taaaatactt ctatcaataa aatttctaat    180

tcctaaaacc aaaatccagt                                                200


<210> SEQ ID NO 175
<211> LENGTH: 300
<212> TYPE: DNA
<213> ORGANISM: Oryza sativa

<400> SEQUENCE: 175

attaatcgat cctccgatcc cttaattacc ataccattac accatgcatc aatatccata     60

tatatataaa ccctttcgca cgtacttata ctatgttttg tcatacatat atatgtgtcg    120

aacgatcgat ctatcactga tatgatatga ttgatccatc agcctgatct ctgtatcttg    180

ttatttgtat accgtcaaat aaaagtttct tccacttgtg ttaataatta gctactctca    240

tctcatgaac cctatatata actagtttaa tttgctgtca attgaacatg atgatcgatg    300


<210> SEQ ID NO 176
<211> LENGTH: 623
<212> TYPE: DNA
<213> ORGANISM: Cauliflower mosaic virus

<400> SEQUENCE: 176

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggacacgc tga                                            623
```

<210> SEQ ID NO 177
<211> LENGTH: 8
<212> TYPE: DNA
<213> ORGANISM: Cauliflower mosaic virus

<400> SEQUENCE: 177 acacgctg 8

<210> SEQ ID NO 178
<211> LENGTH: 804
<212> TYPE: DNA
<213> ORGANISM: Zea mays

<400> SEQUENCE: 178
accgtcttcg gtacgcgctc actccgccct ctgcctttgt tactgccacg tttctctgaa 60
tgctctcttg tgtggtgatt gctgagagtg gtttagctgg atctagaatt acactctgaa 120
atcgtgttct gcctgtgctg attacttgcc gtcctttgta gcagcaaaat atagggacat 180
ggtagtacga aacgaagata gaacctacac agcaatacga gaaatgtgta atttggtgct 240
tagcggtatt tatttaagca catgttggtg ttatagggca cttggattca gaagtttgct 300
gttaatttag gcacaggctt catactacat gggtcaatag tatagggatt catattatag 360
gcgatactat aataatttgt tcgtctgcag agcttattat ttgccaaaat tagatattcc 420
tattctgttt ttgtttgtgt gctgttaaat tgttaacgcc tgaaggaata aatataaatg 480
acgaaatttt gatgtttatc tctgctcctt tattgtgacc ataagtcaag atcagatgca 540
cttgttttaa atattgttgt ctgaagaaat aagtactgac agtattttga tgcattgatc 600
tgcttgtttg ttgtaacaaa atttaaaaat aaagagtttc ctttttgttg ctctccttac 660
ctcctgatgg tatctagtat ctaccaactg acactatatt gcttctcttt acatacgtat 720
cttgctcgat gccttctccc tagtgttgac cagtgttact cacatagtct ttgctcattt 780
cattgtaatg cagataccaa gcgg 804

<210> SEQ ID NO 179
<211> LENGTH: 1396
<212> TYPE: DNA
<213> ORGANISM: Oryza sativa

<400> SEQUENCE: 179
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccagcc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata cccccccctc tcctcccatc cccccaaccc 840
taccaccacc accaccacca cctccacctc ctccccccctc gctgccggac gacgagctcc 900 tccccccctcc ccctccgccg ccgccgcgcc ggtaaccacc ccgcccctct cctctttctt 960
tctccgtttt tttttccgtc tcggtctcga tctttggcct tggtagtttg ggtgggcgag 1020
aggcggcttc gtgccgccca gatcggtgcg cgggaggggc gggatctcgc ggctggctct 1080
cgcccccgtg gatccggccc ggatctcgcg gggaatgggg ctctcggatg tagatctgcg 1140
atccgccgtt gttggggccg atgatggggc ccttaaaatt tccgccgtgc taaacaagat 1200
caggaagagg ggaaaagggc actatggttt atatttttat atatttctgc tgcttcgtca 1260
ggcttagatg tgctagatct ttctttcttc tttttgtggg tagaatttaa tccctcagca 1320
ttgttcatcg gtagttttc ttttcatgat tcgtgacaaa tgcagcctcg tgcggacgtt 1380
tttttgtagg tagaag 1396

<210> SEQ ID NO 180
<211> LENGTH: 2625
<212> TYPE: DNA
<213> ORGANISM: Setaria italica

<400> SEQUENCE: 180
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220
gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac aggtg 2625

<210> SEQ ID NO 181
<211> LENGTH: 2008
<212> TYPE: DNA
<213> ORGANISM: Zea mays subsp. Mexicana

<400> SEQUENCE: 181
gtcgtgcccc tctctagaga taaagagcat tgcatgtcta aagtataaaa aattaccaca 60
tatttttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccctttta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccccct ccacaccctc tttccccaac ctcgtgttcg ttcggagcgc 900
acacacacgc aaccagatct cccccaaatc cagccgtcgg cacctccgct tcaaggtacg 960
ccgctcatcc tccccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcagcgg 2008

<210> SEQ ID NO 182
<211> LENGTH: 1053
<212> TYPE: DNA
<213> ORGANISM: Zea mays subsp. Mexicana

<400> SEQUENCE: 182
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag cgg 1053

<210> SEQ ID NO 183
<211> LENGTH: 2625
<212> TYPE: DNA
<213> ORGANISM: Setaria italica

<400> SEQUENCE: 183
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040

-continued

```
agatgtgaaa gtcacgtatt gggacaaatt gatggtttag tgctatagtt ctatagttct   2100

gtgatacatc tatctgattt tttttggtct attggtgcct aacttatctg aaaatcatgg   2160

aacatgaggc tagtttgatc atggtttagt tcattgtgat taataatgta tgatttagta   2220

gctattttgg tgatcgtgtc attttatttg tgaatggaat cattgtatgt aaatgaagct   2280

agttcagggg ttacgatgta gctggctttg tattctaaag gctgctatta ttcatccatc   2340

gatttcacct atatgtaatc cagagctttt gatgtgaaat ttgtctgatc cttcactagg   2400

aaggacagaa cattgttaat attttggcac atctgtctta ttctcatcct ttgtttgaac   2460

atgttagcct gttcaaacag atactgttgt aatgtcctag ttatataggt acatatgtgt   2520

tctctattga gtttatggac ttttgtgtgt gaagttatat ttcattttgc tcaaaactca   2580

tgtttgcaag ctttctgaca ttattctatt gttctgaaac aggtg                   2625
```

PLANT REGULATORY ELEMENTS AND USES THEREOF

REFERENCE TO RELATED APPLICATIONS

This application is a divisional of U.S. patent application Ser. No. 15/798,319, filed Oct. 30, 2017, which is a divisional of U.S. patent application Ser. No. 14/686,602, filed Apr. 14, 2015, now issued as U.S. Pat. No. 9,834,777 which is a divisional of U.S. patent application Ser. No. 13/428,994, filed Mar. 23, 2012, now issued as U.S. Pat. No. 9,062,316, which claims the benefit of U.S. Provisional Application No. 61/467,875, filed Mar. 25, 2011, each of which is herein incorporated by reference in its entirety.

INCORPORATION OF SEQUENCE LISTING

The sequence listing that is contained in the file named "MONS282US_seq.txt", which is 347 KB (as measured in Microsoft Windows®) and was created on Mar. 21, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements for use in plants. The present invention also provides DNA constructs comprising the regulatory elements. The present invention also provides transgenic plant cells, plants, and seeds comprising the regulatory elements. The sequences may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule comprising a DNA sequence selected from the group consisting of: a) a sequence with at least about 85 percent sequence identity to any of SEQ ID NOs: 1-158 and 180-183; b) a sequence comprising any of SEQ ID NOs; 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the DNA molecule comprises at least about 90 percent, at least about 95 percent, at least about 98 percent, or at least about 99 percent sequence identity to the DNA sequence of any of SEQ ID NOs: 1-158 and 180-183. In certain embodiments of the DNA molecule, the DNA sequence comprises a regulatory element. In some embodiments the regulatory element comprises a promoter. In particular embodiments, the heterologous transcribable polynucleotide molecule comprises a gene of agronomic interest, such as a gene capable of providing herbicide resistance in plants, or a gene capable of providing plant pest resistance in plants.

The invention also provides a transgenic plant cell comprising a heterologous DNA construct provided by the invention, including a sequence of any of SEQ ID NOs: 1-158 and 180-183, or a fragment or variant thereof, wherein said sequence is operably linked to a heterologous transcribable polynucleotide molecule. In certain embodiments, the transgenic plant cell is a monocotyledonous plant cell. In other embodiments, the transgenic plant cell is a dicotyledonous plant cell.

Further provided by the invention is a transgenic plant, or part thereof, comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the transgenic plant may be a progeny plant of any generation that comprises the DNA molecule, relative to a starting transgenic plant comprising the DNA molecule. Still further provided is a transgenic seed comprising a DNA molecule according to the invention.

In yet another aspect, the invention provides a method of producing a commodity product comprising obtaining a transgenic plant or part thereof according to the invention and producing the commodity product therefrom. In one embodiment, a commodity product of the invention is protein concentrate, protein isolate, grain, starch, seeds, meal, flour, biomass, or seed oil. In another aspect, the invention provides a commodity produced using the above method. For instance, in one embodiment the invention provides a commodity product comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule.

In still yet another aspect, the invention provides a method of expressing a transcribable polynucleotide molecule that comprises obtaining a transgenic plant according to the invention, such as a plant comprising a DNA molecule as described herein, and cultivating plant, wherein a transcribable polynucleotide in the DNA molecule is expressed.

Throughout this specification and the claims, unless the context requires otherwise, the word "comprise" and its variations, such as "comprises" and "comprising," will be understood to imply the inclusion of a stated composition, step, and/or value, or group thereof, but not the exclusion of any other composition, step, and/or value, or group thereof.

BRIEF DESCRIPTION OF THE FIGURES

FIGS. 1*a*-1*h* depict alignment of promoter size variants corresponding to promoter elements isolated from the grass species *Andropogon gerardii*. In particular, FIGS. 1*a*-1*h* show alignment of the 2603 by promoter sequence P-ANDge.Ubq1-1:1:1 (SEQ ID NO: 2), found in the transcriptional regulatory expression element group EXP-ANDge.Ubq11:1:9 (SEQ ID NO: 1), with promoter sequences derived via deletion analysis of P-ANDge.Ubq1-1:1:11. Deletion, for instance of the 5' end of P-ANDge.Ubq1-1:1:11, produced the promoter P-ANDge.Ubq1-1:1:9 (SEQ ID NO: 6), a 2114 by sequence which is found within EXP-ANDge.Ubq1:1:7 (SEQ ID NO: 5). Other promoter sequences in FIG. 1 include P-ANDge.Ubq1-1:1:10 (SEQ ID NO: 9), a 1644 by sequence comprised within EXP-ANDge.Ubq1:1:8 (SEQ ID NO: 8); P-ANDge.Ubq1-1:1:12 (SEQ ID NO: 11), a 1472 by sequence comprised within EXP-ANDge.Ubq1:1:10 (SEQ ID NO: 10); P-ANDge.Ubq1-1:1:8 (SEQ ID NO: 13), a 11114 bp sequence comprised within EXP-ANDge.Ubq1:1.6 (SEQ ID NO: 12); P-ANDge.Ubq1-1:1:13 (SEQ ID NO: 15), a 771 by sequence comprised within EXP-ANDge.Ubq1:1:11 (SEQ ID NO: 14); and P-ANDge.Ubq1-1:1:14 (SEQ ID NO: 17), a 482 by sequence comprised within EXP-ANDge.Ubq1:1:12 (SEQ ID NO: 16).

FIGS. 2*a*-2*g* depict alignment of promoter variants isolated from the grass *Saccharum ravennae* (*Erianthus ravennae*). In particular, FIGS. 2*a*-2*g* show an alignment of the 2536 by promoter sequence P-ERIra.Ubq1-1:1:10 (SEQ ID NO: 19) (found, for instance, within the transcriptional regulatory expression element group EXP-ERIra.Ubq1 (SEQ ID NO: 18)) with promoter sequences derived from deletion analysis of P-ERIra.Ubq1-1:1:10: a 2014 bp promoter sequence P-ERIra.Ubq1-1:1:9 (SEQ ID NO: 23); a 1525 by promoter sequence P-ERIra.Ubq1-1:1:11 (SEQ ID NO: 26); a 1044 by promoter sequence P-ERIra.Ubq1-1:1:8 (SEQ ID NO: 28); a 796 bp sequence P-ERIra.Ubq1-1:1:112 (SEQ ID NO: 30); and a 511 bp sequence P-ERIra.Ubq1-1:1:13 (SEQ ID NO: 32).

FIGS. 3*a*-3*c* depict alignment of promoter size variants corresponding to promoter elements isolated from the grass species *Setaria viridis*. In particular, FIGS. 3*a*-3*c* show an alignment of a 1493 bp promoter sequence, P-Sv.Ubq1-1:1:1 (SEQ ID NO: 34) with promoters derived from deletion analysis of the 5' end of P-Sv.Ubq1-1:1:1: a 1035 by sized promoter P-Sv.Ubq1-1:1:2 (SEQ ID NO: 38); and a 681 by promoter sequence P-Sv.Ubq (SEQ ID NO: 40).

FIGS. 4*a*-4*e* depict alignment of transcriptional regulatory expression element group variants derived from the grass *Zea mays* subsp, mexicana. In particular, FIGS. 4*a*-4*e* compare a 2005 bp transcriptional regulatory expression element group termed EXP-Zm.UbqM1:1:2 (SEQ ID NO: 49) with allelic variant EXP-Zm.UbqM1:1:5 (SEQ ID NO: 53), as well as with size variants EXP-Zm.UbqM1:1:1 (SEQ ID NO: 41), which is 1922 bps in length, and EXP-Zm.UbqM1:1:4 (SEQ ID NO: 45), which is 1971 bps in length.

FIGS. 5*a*-5*b* depict alignment of promoter size variants isolated from the grass *Sorghum bicolor*. In particular, FIGS. 5*a*-5*b* shows alignment of the 791 by sized promoter element, P-Sb.Ubq6-1:1:2 (SEQ ID NO: 60) comprised within the transcriptional regulatory expression element group EXP-Sb.Ubq6 (SEQ ID NO: 59), with 855 by promoter element P-Sb.Ubq6-1:1:1 (SEQ ID NO: 64) comprised within EXP-Sb.Ubq6:1:1 (SEQ ID NO: 63).

FIGS. 6*a*-6*c* depict alignment of promoter size variants corresponding to promoter elements isolated from the grass *Setaria italica*. In particular, FIGS. 6*a*-6*c* show an alignment of the 1492 bp promoter variant P-SETit.Ubq1:1:1 (SEQ ID NO: 70) with 1492 bp promoter variant P-SETit.Ubq1-1:1:4 (SEQ ID NO: 74), 1034 bp promoter element P-SETit.Ubq1-1:11:2 (SEQ ID NO: 76), and 680 by promoter element P-SETit.Ubq1-1:1:3 (SEQ ID NO: 78).

FIGS. 7*a*-7*b* depict alignment of promoter size variants and an enhancer element corresponding to promoter elements isolated from the grass species *Coix lachryma-jobi*. In particular, FIGS. 7*a* and 7*b* show an alignment of the 837 by promoter variant, P-Cl.Ubq1-1:1:1 (SEQ ID NO: 80) found within transcriptional regulatory expression element group EXP-Cl.Ubq1:1:1 (SEQ ID NO: 79), with an enhancer fragment derived from P-Cl.Ubq1-1:1:1, termed E-Cl.Ubq1:1:1 (SEQ ID NO: 89) that is 798 bp in length, as well as with three 5' end deletion variants of P-Cl.Ubq1-1:1:1: a 742 bp element P-Cl.Ubq1-1:1:4 (SEQ ID NO: 84); a 401 by element P-Cl.Ubq1-1:1:3 (SEQ ID NO: 86); and a 54 bp minimal promoter element P-Cl.Ubq1-1:1:5 (SEQ ID NO: 88).

BRIEF DESCRIPTION OF THE SEQUENCES

Figure 8:
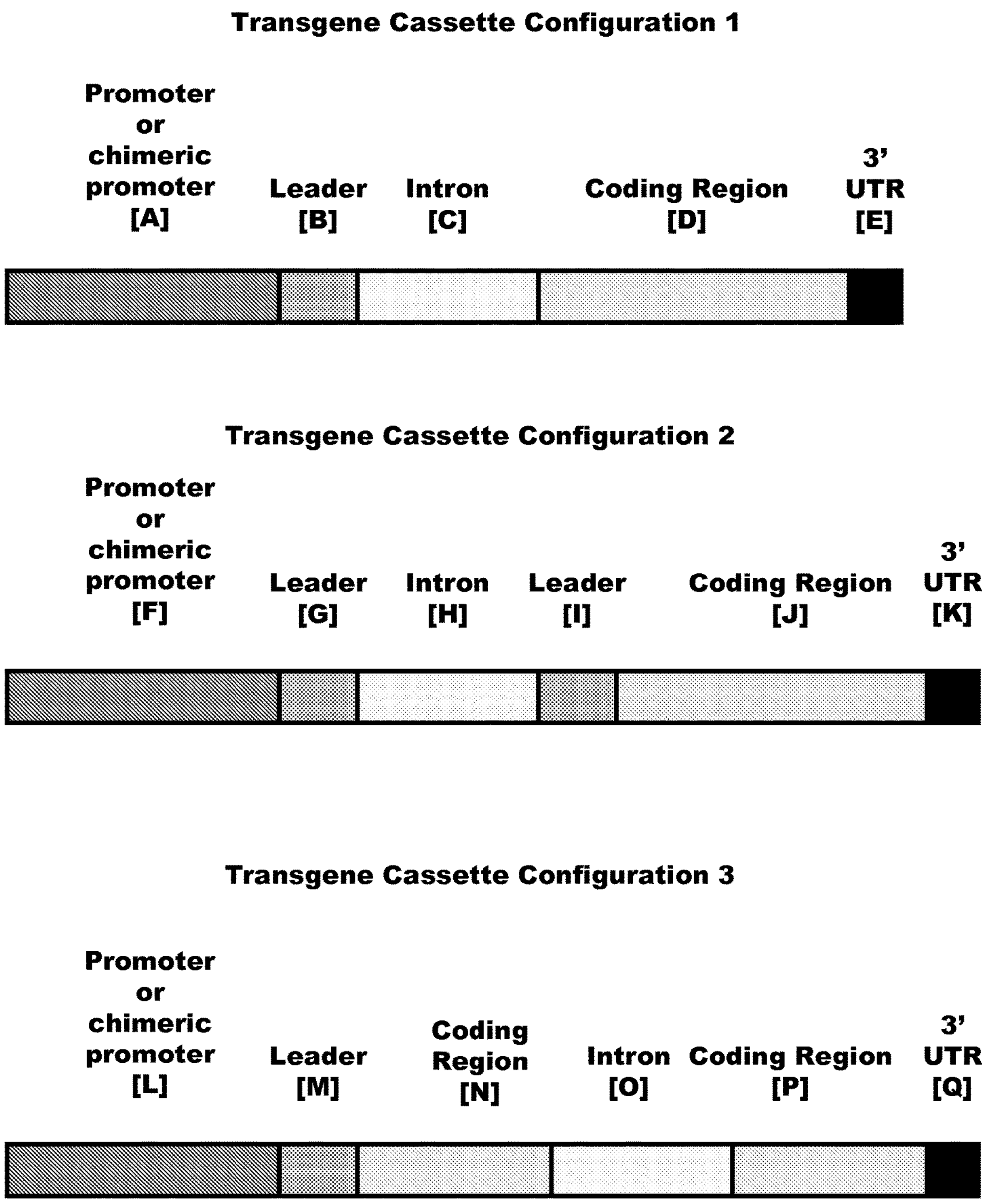
FIG. 8 depicts transgene cassette configurations of the present invention.

SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183 are sequences of transcriptional regulatory expression element groups or EXP sequences comprising a promoter sequence operably linked 5' to a leader sequence which is operably linked 5' to an intron sequence.

SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 are promoter sequences.

SEQ ID NOS: 3, 20, 35, 43, 47, 51, 57, 61, 67, 71 and 81 are leader sequences.

SEQ ID NOS: 4, 7, 21, 24, 36, 44, 48, 52, 54, 58, 62, 68, 72, 82, 92, 94, 101, 103, 105, 107, 109, III, 113, 118, 120, 122, 127, 129, 131, 138, 140, 142, 144, 146, 148, 150, 152, 154, 156, 158 and 182 are intron sequences.

SEQ ID NO: 89 is the sequence of an enhancer.

DETAILED DESCRIPTION OF THE INVENTION

The invention disclosed herein provides polynucleotide molecules having beneficial gene regulatory activity from plant species. The design, construction, and use of these polynucleotide molecules are provided by the invention. The nucleotide sequences of these polynucleotide molecules are provided among SEQ ID NOs: 1-158 and 180-183. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-158 and 180-183.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-158 and 180-183, has at least about 85 percent identity, at least about 90 percent identity, at least about 95 percent identity, at least about 96 percent identity, at least about 97 percent identity, at least about 98 percent identity, or at least about 99 percent identity to the reference sequence. In particular embodiments such sequences may be defined as having gene-regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group or "EXP" sequence may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions (or 3' UTRs) are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOS: 2, 6, 9, 11, 13, 15, 19, 23, 26, 28, 30, 32, 34, 38, 40, 42, 46, 50, 56, 60, 64, 66, 70, 74, 76, 78, 80, 84, 86, 88, 91, 96 and 135 and fragments or enhancers derived there from can be used to make chimeric transcriptional regulatory element compositions comprised of any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOS: 3, 20, 35, 43, 47, 51, 57, 61, 67, 71 and 81 or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOS: 3, 20, 35, 43, 47, 51, 57, 61, 67, 71 and 81 may be comprised of regulatory elements or may adopt secondary structures that can have an effect on transcription or translation of a transgene. The leader sequences presented as SEQ ID NOS: 3, 20, 35, 43, 47, 51, 57, 61, 67, 71 and 81 can be used in accordance with the invention to make chimeric regulatory elements that affect transcription or translation of a transgene. In addition, the leader sequences presented as SEQ ID NOS: 3, 20, 35, 43, 47, 51, 57, 61, 67, 71 and 81 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However multiple use of the same intron in one plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron.

This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al, (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Ghee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In WE Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause enhancement of expression at the DNA level or at the transcript level (IME).

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence provided as SEQ ID NOs: 1-158 and 180-183 may be used to create variants that are in composition similar, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the regulatory element as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked. In the present invention, a polynucleotide sequence provided as SEQ ID NOs: 1-158 and 180-183 provide a reference sequence wherein the constituent elements that comprise the reference sequence may be joined by methods known in the art and may comprise substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens ABI, C*58, or LB A4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual,* 3rd edition Volumes 1, 2, and 3 (2000) J. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153:253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' UTR.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 1150, 152, 154, 156, 158 and 182. Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbial Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001): Kuerstem and Goodwin, *Nature Reviews Genetics* 4:626-637 (2003)). Effective termination of RNA transcription is required to prevent unwanted transcription of trait—unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Big bluestem (*Andropogon gerardii*), Plume grass (*Saccharum ravennae* (*Erianthus ravennae*)), Green bristlegrass (*Setaria viridis*), Teosinte (*Zea mays* subsp. mexicana), Foxtail millet (*Setaria italica*), or *Coix* (*Coix lacryma-jobi*). Libraries of cDNA are made from tissues isolated from selected plant species using methods known to those skilled in the art from flower tissue, seed, leaf and root. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA, sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133, it has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-158 and 180-183, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,541,259; 5,985,605; and 6,171,640), biopolymers (U.S. Pat. Nos. USRE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via mRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphoric acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., Nucl. Acids Res. 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plain Physiol. Plant Mol. Biol.* 42: 205 (1991)).

Technology for introduction of a DNA, molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaciMan® Testing Matrix. Alternatively, the Invader® (Third Wave Technologies, Madison, Wis.) reagents and methods as described by the manufacturer can be used trans gene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Commodity Products

The present invention provides a commodity product comprising DNA molecules according to the invention. As used herein, a "commodity product" refers to any composition or product which is comprised of material derived from a plant, seed, plant cell or plant part comprising a DNA molecule of the invention. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Plants comprising a DNA molecule according to the invention can thus be used to manufacture any commodity product typically acquired from plants or parts thereof.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel ubiquitin transcriptional regulatory elements, or transcriptional regulatory expression element group (EXP) sequences were identified and isolated from genomic DNA of the monocot species Big bluestem (*Andropogon gerardii*), Plume Grass (*Saccharum ravennae* (*Erianthus ravennae*)), Green bristlegrass (*Setaria viridis*), Teosinte (*Zea mays* subsp. mexicana), Foxtail millet (*Setaria italica*), and Coix (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding transcriptional regulatory elements for the identified Ubiquitin gene, which comprises a promoter, leader (5' UTR) and first intron operably linked. The primers were used with GenorneWalker™ (Clontech Laboratories, Inc, Mountain View, Calif.) libraries constructed following the manufacturer's protocol to clone the 5' region of the corresponding genomic DNA sequence. Ubiquitin transcriptional regulatory elements were also isolated from the monocot *Sorghum bicolor* using public sequences that are homologs to the Ubiquitin 4, 6 and 7 genes of *Zea mays*.

Using the identified sequences, a bioinformatic analysis was conducted to identify regulatory elements within the amplified DNA. Using the results of this analysis, regulatory elements were defined within the DNA sequences and printers designed to amplify the regulatory elements. The corresponding DNA molecule for each regulatory element was amplified using standard polymerase chain reaction conditions with primers containing unique restriction enzyme sites and genomic DNA isolated from *A. gerardii, S. ravennae, S. viridis, Z. mays subsp. mexicana, S. italica, C. lacryma-jobi*, and *S. bicolor*. The resulting DNA fragments were ligated into base plant expression vectors and sequenced. An analysis of the regulatory element TSS and intron/exon splice junctions was then done using transformed plant protoplasts. Briefly, the protoplasts were transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, Calif. 92008) was used to confirm the regulatory element TSS and intron/exon splice junctions by analyzing the sequence of the mRNA transcripts produced thereby.

Sequences of the identified transcriptional regulatory expression element groups ("EXP's") are provided herein as SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183, as listed in Table 1 below. Promoter sequences are provided herein as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. Leader sequences are provided herein as SEQ ID NOS: 3, 20, 35, 43, 47, 51, 57, 61, 67, 71 and 81. Intron sequences are provided herein as SEQ ID NOS: 4, 7, 21, 24, 36, 44, 48, 52, 54, 58, 62, 68, 72, 82, 92, 94, 101, 103, 105, 107, 109, 111, 11.3, 118, 120, 122, 127, 129, 131, 138, 140, 142, 144, 146, 148, 150, 152, 154, 156, 158 and 182. An enhancer sequence is provided as SEQ ID NO: 89.

TABLE 1

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-ANDge.Ubq1:1:9 | 1 | 3741 | *A. gerardii* | EXP: P-ANDge.Ubq1-1:1:11 (SEQ ID NO: 2); L-ANDge.Ubq1-1:1:2 (SEQ ID NO: 3); I-ANDge.Ubq1-1:1:3 (SEQ ID NO: 4). | |
| P-ANDge.Ubq1-1:1:11 | 2 | 2603 | *A. gerardii* | promoter | |
| L-ANDge.Ubq1-1:1:2 | 3 | 99 | *A. gerardii* | leader | |
| I-ANDge.Ubq1-1:1:3 | 4 | 1039 | *A. gerardii* | intron | |
| EXP-ANDge.Ubq1:1:7 | 5 | 3255 | *A. gerardii* | EXP: P-ANDge.Ubq1-1:1:9 (SEQ ID NO: 6); L-ANDge.Ubq1-1:1:2 (SEQ ID NO: 3); I-ANDge.Ubq1-1:1:4 (SEQ ID NO: 7). | pMON136264, PCR0145892, pMON140896, PCR41 |
| P-ANDge.Ubq1-1:1:9 | 6 | 2114 | *A. gerardii* | promoter | |
| I-ANDge.Ubq1-1:1:4 | 7 | 1042 | *A. gerardii* | intron | |
| EXP-ANDge.Ubq1:1:8 | 8 | 2785 | *A. gerardii* | EXP: P-ANDge.Ubq1-1:1:10 (SEQ ID NO: 9); L-ANDge.Ubq1-1:1:2 (SEQ ID NO: 3); I-ANDge.Ubq1-1:1:4 (SEQ ID NO: 7). | pMON140917, PCR42 |
| P-ANDge.Ubq1-1:1:10 | 9 | 1644 | *A. gerardii* | promoter | |
| EXP-ANDge.Ubq1:1:10 | 10 | 2613 | *A. gerardii* | EXP: P-ANDge.Ubq1-1:1:12 (SEQ ID NO: 11); L-ANDge.Ubq1-1:1:2 (SEQ ID NO: 3); I-ANDge.Ubq1-1:1:4 (SEQ ID NO: 7). | PCR0145815, PCR43 |
| P-ANDge.Ubq1-1:1:12 | 11 | 1472 | *A. gerardii* | promoter | |
| EXP-ANDge.Ubq1:1:6 | 12 | 2255 | *A. gerardii* | EXP: P-ANDge.Ubq1-1:1:8 (SEQ ID NO: 13); L-ANDge.Ubq1-1:1:2 (SEQ ID NO: 3); I-ANDge.Ubq1-1:1:4 (SEQ ID NO: 7). | pMON136259, PCR0145893, pMON140898, PCR44 |
| P-ANDge.Ubq1-1:1:8 | 13 | 1114 | *A. gerardii* | promoter | |
| EXP-ANDge.Ubq1:1:11 | 14 | 1912 | *A. gerardii* | EXP: P-ANDge.Ubq1-1:1:13 (SEQ ID NO: 15); L-ANDge.Ubq1-1:1:2 (SEQ ID NO: 3); I-ANDge.Ubq1-1:1:4 (SEQ ID NO: 7). | PCR0145817, pMON140899, PCR45 |
| P-ANDge.Ubq1-1:1:13 | 15 | 771 | *A. gerardii* | promoter | |
| EXP-ANDge.Ubq1:1:12 | 16 | 1623 | *A. gerardii* | EXP: P-ANDge.Ubq1-1:1:14 (SEQ ID NO: 17); L-ANDge.Ubq1-1:1:2 (SEQ ID NO: 3); I-ANDge.Ubq1-1:1:4 (SEQ ID NO: 7). | PCR0145819, pMON140900, PCR46 |
| P-ANDge.Ubq1-1:1:14 | 17 | 482 | *A. gerardii* | promoter | |
| EXP-ERIra.Ubq1 | 18 | 3483 | *E. ravennae* | EXP: P-ERIra.Ubq1-1:1:10 (SEQ ID NO: 19); L-ERIra.Ubq1-1:1:2 (SEQ ID NO: 20); I-ERIra.Ubq1-1:1:1 (SEQ ID NO: 21). | |
| P-ERIra.Ubq1-1:1:10 | 19 | 2536 | *E. ravennae* | promoter | |
| L-ERIra.Ubq1-1:1:2 | 20 | 94 | *E. ravennae* | leader | |
| I-ERIra.Ubq1-1:1:1 | 21 | 1041 | *E. ravennae* | intron | |
| EXP-ERIra.Ubq1:1:9 | 22 | 3152 | *E. ravennae* | EXP: P-ERIra.Ubq1-1:1:9 (SEQ ID NO: 23); L-ERIra.Ubq1-1:1:2 (SEQ ID NO: 20); I-ERIra.Ubq1-1:1:2 (SEQ ID NO: 24). | pMON136263, PCR0145896, pMON140904, PCR50 |
| P-ERIra.Ubq1-1:1:9 | 23 | 2014 | *E. ravennae* | promoter | |
| I-ERIra.Ubq1-1:1:2 | 24 | 1044 | *E. ravennae* | intron | |
| EXP-ERIra.Ubq1:1:10 | 25 | 2663 | *E. ravennae* | EXP: P-ERIra.Ubq1-1:1:11 (SEQ ID NO: 26); L-ERIra.Ubq1-1:1:2 (SEQ ID NO: 20); I-ERIra.Ubq1-1:1:2 (SEQ ID NO: 24). | PCR0145820, pMON140905, PCR51 |
| P-ERIra.Ubq1-1:1:11 | 26 | 1525 | *E. ravennae* | promoter | |
| EXP-ERIra.Ubq1:1:8 | 27 | 2182 | *E. ravennae* | EXP: P-ERIra.Ubq1-1:1:8 (SEQ ID NO: 28); L-ERIra.Ubq1-1:1:2 (SEQ ID NO: 20); I-ERIra.Ubq1-1:1:2 (SEQ ID NO: 24). | pMON136258, PCR0145897, pMON140906, PCR52, pMON142864, pMON142862 |
| P-ERIra.Ubq1-1:1:8 | 28 | 1044 | *E. ravennae* | promoter | |
| EXP-ERIra.Ubq1:1:11 | 29 | 1934 | *E. ravennae* | EXP: P-ERIra.Ubq1-1:1:12 (SEQ ID NO: 30); L-ERIra.Ubq1-1:1:2 (SEQ ID NO: 20); I-ERIra.Ubq1-1:1:2 (SEQ ID NO: 24). | PCR0145821, pMON140907, PCR53 |
| P-ERIra.Ubq1-1:1:12 | 30 | 796 | *E. ravennae* | promoter | |
| EXP-ERIra.Ubq1:1:12 | 31 | 1649 | *E. ravennae* | EXP: P-ERIra.Ubq1-1:1:13 (SEQ ID NO: 32); L-ERIra.Ubq1-1:1:2 (SEQ ID NO: 20); I-ERIra.Ubq1-1:1:2 (SEQ ID NO: 24). | PCR0145822, pMON140908, PCR54 |
| P-ERIra.Ubq1-1:1:13 | 32 | 511 | *E. ravennae* | promoter | |
| EXP-Sv.Ubq1:1:2 | 33 | 2631 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:1 (SEQ ID NO: 36). | pMON140878, PCR0145909, pMON129203, pMON131958 |
| P-Sv.Ubq1-1:1:1 | 34 | 1493 | *S. viridis* | promoter | |
| L-Sv.Ubq1-1:1:2 | 35 | 127 | *S. viridis* | leader | |
| I-Sv.Ubq1-1:1:1 | 36 | 1011 | *S. viridis* | intron | |
| EXP-Sv.Ubq1:1:3 | 37 | 2173 | *S. viridis* | EXP: P-Sv.Ubq1-1:1:2 (SQ ID NO: 38); L-Sv.Ubq1-1:1:2 (SEQ ID NO: 35); I-Sv.Ubq1-1:1:1 (SEQ ID NO: 36). | PCR0145929, pMON129204 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-Sv.Ubq1-1:1:2 | 38 | 1035 | *S. viridis* | promoter | |
| EXP-Sv.Ubq1:1:5 | 39 | 1819 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:1 (SEQ ID NO: 36). | pMON129205, pMON131959 |
| P-Sv.Ubq1-1:1:3 | 40 | 681 | *S. viridis* | promoter | |
| EXP-Zm.UbqM1:1:1 (Allele-1) | 41 | 1922 | *Z. mays* subsp. *mexicana* | EXP: P-Zm.UbqM1-1:1:1 (SEQ ID NO: 42); L-Zm.UbqM1-1:1:1 (SEQ ID NO: 43); I-Zm.UbqM1-1:1:5 (SEQ ID NO: 44). | pMON140881, PCR0145914, pMON129210, pMON131961 |
| P-Zm.UbqM1-1:1:1 (Allele-1) | 42 | 850 | *Z. mays* subsp. *mexicana* | promoter | |
| L-Zm.UbqM1-1:1:1 (Allele-1) | 43 | 78 | *Z. mays* subsp. *mexicana* | leader | |
| I-Zm.UbqM1-1:1:5 (Allele-1) | 44 | 994 | *Z. mays* subsp. *mexicana* | intron | |
| EXP-Zm.UbqM1:1:4 (Allele-2) | 45 | 1971 | *Z. mays* subsp. *mexicana* | EXP: P-Zm.UbqM1-1:1:4 (SEQ ID NO: 46); L-Zm.UbqM1-1:1:5 (SEQ ID NO: 47); I-Zm.UbqM1-1:1:4 (SEQ ID NO: 48). | pMON140882, PCR0145915, pMON129212, pMON131963 |
| P-Zm.UbqM1-1:1:4 (Allele-2) | 46 | 887 | *Z. mays* subsp. *mexicana* | promoter | |
| L-Zm.UbqM1-1:1:5 (Allele-2) | 47 | 77 | *Z. mays* subsp. *mexicana* | leader | |
| I-Zm.UbqM1-1:1:4 (Allele-2) | 48 | 1007 | *Z. mays* subsp. *mexicana* | intron | |
| EXP-Zm.UbqM1:1:2 (Allele-3) | 49 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:11 (SEQ ID NO: 52). | PCR0145916, pMON129211, pMON131962, pMON132047 |
| P-Zm.UbqM1-1:1:5 (Allele-3) | 50 | 877 | *Z. mays* subsp. *mexicana* | promoter | |
| L-Zm.UbqM1-1:1:4 (Allele-3) | 51 | 78 | *Z. mays* subsp. *mexicana* | leader | |
| I-Zm.UbqM1-1:1:11 (Allele-3) | 52 | 1050 | *Z. mays* subsp. *mexicana* | intron | |
| EXP-Zm.UbqM1:1:5 (Allele-3) | 53 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:12 (SEQ ID NO: 54). | |
| I-Zm.UbqM1-1:1:12 (Allele-3) | 54 | 1050 | *Z. mays* subsp. *mexicana* | intron | |
| EXP-Sb.Ubq4:1:1 | 55 | 1632 | *S. bicolor* | EXP: P-Sb.Ubq4-1:1:1 (SEQ ID NO: 56); L-Sb.Ubq4-1:1:1 (SEQ ID NO: 57); I-Sb.Ubq4-1:1:1 (SEQ ID NO: 58). | pMON140886, PCR0145921, pMON129219, pMON132932 |
| P-Sb.Ubq4-1:1:1 | 56 | 401 | *S. bicolor* | promoter | |
| L-Sb.Ubq4-1:1:1 | 57 | 154 | *S. bicolor* | leader | |
| I-Sb.Ubq4-1:1:1 | 58 | 1077 | *S. bicolor* | intron | |
| EXP-Sb.Ubq6 | 59 | 2000 | *S. bicolor* | EXP: P-Sb.Ubq6-1:1:2 (SEQ ID NO: 60); L-Sb.Ubq6-1:1:1 (SEQ ID NO: 61); I-Sb.Ubq6-1:1:1 (SEQ ID NO: 62). | |
| P-Sb.Ubq6-1:1:2 | 60 | 791 | *S. bicolor* | promoter | |
| L-Sb.Ubq6-1:1:1 | 61 | 136 | *S. bicolor* | leader | |
| I-Sb.Ubq6-1:1:1 | 62 | 1073 | *S. bicolor* | intron | |
| EXP-Sb.Ubq6:1:1 | 63 | 2064 | *S. bicolor* | EXP: P-Sb.Ubq6-1:1:1 (SEQ ID NO: 64); L-Sb.Ubq6-1:1:1 (SEQ ID NO: 61); I-Sb.Ubq6-1:1:1 (SEQ ID NO: 62). | pMON140887, PCR0145920, pMON129218 |
| P-Sb.Ubq6-1:1:1 | 64 | 855 | *S. bicolor* | promoter | |
| EXP-Sb.Ubq7:1:1 | 65 | 2000 | *S. bicolor* | EXP: P-Sb.Ubq7-1:1:1 (SEQ ID NO: 66); L-Sb.Ubq7-1:1:1 (SEQ ID NO: 67); I-Sb.Ubq7-1:1:1 (SEQ ID NO: 68). | pMON132974 |
| P-Sb.Ubq7-1:1:1 | 66 | 565 | *S. bicolor* | promoter | |
| L-Sb.Ubq7-1:1:1 | 67 | 77 | *S. bicolor* | leader | |
| I-Sb.Ubq7-1:1:1 | 68 | 1358 | *S. bicolor* | intron | |
| EXP-SETit.Ubq1:1:1 | 69 | 2622 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:1 (SEQ ID NO: 72). | pMON140877, PCR0145900, pMON129200 |
| P-SETit.Ubq1-1:1:1 | 70 | 1492 | *S. italica* | promoter | |
| L-SETit.Ubq1-1:1:1 | 71 | 127 | *S. italica* | leader | |
| I-SETit.Ubq1-1:1:1 | 72 | 1003 | *S. italica* | intron | |
| EXP-SETit.Ubq1:1:4 | 73 | 2622 | *S. italica* | EXP: P-SETit.Ubq1-1:1:4 (SEQ ID NO: 74); L-SETit.Ubq1-1:1:1 (SEQ ID NO: 71); I-SETit.Ubq1-1:1:1 (SEQ ID NO: 72). | pMON132037 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-SETit.Ubq1-1:1:4 | 74 | 1492 | *S. italica* | promoter | |
| EXP-SETit.Ubq1:1:2 | 75 | 2164 | *S. italica* | EXP: P-SETit.Ubq1-1:1:2 (SEQ ID NO: 76); L-SETit.Ubq1-1:1:1 (SEQ ID NO: 71); I-SETit.Ubq1-1:1:1 (SEQ ID NO: 72). | |
| P-SETit.Ubq1-1:1:2 | 76 | 1034 | *S. italica* | promoter | |
| EXP-SETit.Ubq1:1:3 | 77 | 1810 | *S. italica* | EXP: P-SETit.Ubq1-1:1:3 (SEQ ID NO: 78); L-SETit.Ubq1-1:1:1 (SEQ ID NO: 71); I-SETit.Ubq1-1:1:1 (SEQ ID NO: 72). | PCR0145905, pMON129202, pMON131957 |
| P-SETit.Ubq1-1:1:3 | 78 | 680 | *S. italica* | promoter | |
| EXP-Cl.Ubq1:1:1 | 79 | 1940 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:1 (SEQ ID NO: 82). | pMON140889, PCR0145922, pMON140913, PCR19, pMON129221, pMON146795, pMON146796, pMON146797, pMON146798, pMON146799, pMON132047, pMON146800, pMON146801, pMON146802 |
| P-Cl.Ubq1-1:1:1 | 80 | 837 | *C. lacryma-jobi* | promoter | |
| L-Cl.Ubq1-1:1:1 | 81 | 86 | *C. lacryma-jobi* | leader | |
| I-Cl.Ubq1-1:1:1 | 82 | 1017 | *C. lacryma-jobi* | intron | |
| EXP-Cl.Ubq1:1:3 | 83 | 1845 | *C. lacryma-jobi* | EXP: P-Cl.Ubq1-1:1:4 (SEQ ID NO: 84); L-Cl.Ubq1-1:1:1 (SEQ ID NO: 81); I-Cl.Ubq1-1:1:1 (SEQ ID NO: 82). | PCR0145945, pMON140914, PCR20 |
| P-Cl.Ubq1-1:1:4 | 84 | 742 | *C. lacryma-jobi* | promoter | |
| EXP-Cl.Ubq1:1:4 | 85 | 1504 | *C. lacryma-jobi* | EXP: P-Cl.Ubq1-1:1:3 (SEQ ID NO: 86); L-Cl.Ubq1-1:1:1 (SEQ ID NO: 81); I-Cl.Ubq1-1:1:1 (SEQ ID NO: 82). | PCR0145946, pMON140915, PCR21 |
| P-Cl.Ubq1-1:1:3 | 86 | 401 | *C. lacryma-jobi* | promoter | |
| EXP-Cl.Ubq1:1:5 | 87 | 1157 | *C. lacryma-jobi* | EXP: P-Cl.Ubq1-1:1:5 (SEQ ID NO: 88); L-Cl.Ubq1-1:1:1 (SEQ ID NO: 81); I-Cl.Ubq1-1:1:1 (SEQ ID NO: 82). | PCR0145947, pMON140916, PCR22 |
| P-Cl.Ubq1-1:1:5 | 88 | 54 | *C. lacryma-jobi* | promoter | |
| E-Cl.Ubq1-1:1:1 | 89 | 798 | *C. lacryma-jobi* | enhancer | |
| EXP-Cl.Ubq1:1:12 | 90 | 3393 | *C. lacryma-jobi* | EXP: P-Cl.Ubq1-1:1:9 (SEQ ID NO: 91); L-Cl.Ubq1-1:1:1 (SEQ ID NO: 81); I-Cl.Ubq1-1:1:7 (SEQ ID NO: 92) | pMON142729 |
| P-Cl.Ubq1-1:1:9 | 91 | 2287 | *C. lacryma-jobi* | Promoter | |
| I-Cl.Ubq1-1:1:7 | 92 | 1020 | *C. lacryma-jobi* | Intron | |
| EXP-Cl.Ubq1:1:16 | 93 | 3393 | *C. lacryma-jobi* | EXP: P-Cl.Ubq1-1:1:9 (SEQ ID NO: 91); L-Cl.Ubq1-1:1:1 (SEQ ID NO: 81); I-Cl.Ubq1-1:1:6 (SEQ ID NO: 94) | pMON146750, pMON142748 |
| I-Cl.Ubq1-1:1:6 | 94 | 1020 | *C. lacryma-jobi* | Intron | |
| EXP-Cl.Ubq1:1:11 | 95 | 2166 | *C. lacryma-jobi* | EXP: P-Cl.Ubq1-1:1:10 (SEQ ID NO: 96); L-Cl.Ubq1-1:1:1 (SEQ ID NO: 81); I-Cl.Ubq1-1:1:7 (SEQ ID NO: 92) | pMON142730 |
| P-Cl.Ubq1-1:1:10 | 96 | 1060 | *C. lacryma-jobi* | Promoter | |
| EXP-Cl.Ubq1:1:17 | 97 | 2166 | *C. lacryma-jobi* | EXP: P-Cl.Ubq1-1:1:10 (SEQ ID NO: 96); L-Cl.Ubq1-1:1:1 (SEQ ID NO: 81); I-Cl.Ubq1-1:1:6 (SEQ ID NO: 94) | pMON146751, pMON142749 |
| EXP-Cl.Ubq1:1:10 | 98 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:6 (SEQ ID NO: 94) | pMON140889, PCR0145922, pMON140913, PCR19, pMON129221 |
| EXP-Cl.Ubq1:1:18 | 99 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:7 (SEQ ID NO: 92) | pMON146795 |
| EXP-Cl.Ubq1:1:19 | 100 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:8 (SEQ ID NO: 101) | pMON146796 |
| I-Cl.Ubq1-1:1:8 | 101 | 1020 | *C. lacryma-jobi* | Intron | |
| EXP-Cl.Ubq1:1:20 | 102 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:9 (SEQ ID NO: 103) | pMON146797 |
| I-Cl.Ubq1-1:1:9 | 103 | 1020 | *C. lacryma-jobi* | Intron | |
| EXP-Cl.Ubq1:1:21 | 104 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:10 (SEQ ID NO: 105) | pMON146798 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| I-Cl.Ubq1-1:1:10 | 105 | 1020 | *C. lacryma-jobi* | Intron | |
| EXP-Cl.Ubq1:1:22 | 106 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:11 (SEQ ID NO: 107) | pMON146799 |
| I-Cl.Ubq1-1:1:11 | 107 | 1020 | *C. lacryma-jobi* | Intron | |
| EXP-Cl.Ubq1:1:23 | 108 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:12 (SEQ ID NO: 109) | pMON132047, pMON146800 |
| I-Cl.Ubq1-1:1:12 | 109 | 1020 | *C. lacryma-jobi* | Intron | |
| EXP-Cl.Ubq1:1:24 | 110 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:13 (SEQ ID NO: 111) | pMON146801 |
| I-Cl.Ubq1-1:1:13 | 111 | 1020 | *C. lacryma-jobi* | Intron | |
| EXP-Cl.Ubq1:1:25 | 112 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:14 (SEQ ID NO: 113) | pMON146802 |
| I-Cl.Ubq1-1:1:14 | 113 | 1020 | *C. lacryma-jobi* | Intron | |
| EXP-Cl.Ubq1:1:13 | 114 | 1848 | *C. lacryma-jobi* | EXP: P-Cl.Ubq1-1:1:4 (SEQ ID NO: 84); L-Cl.Ubq1-1:1:1 (SEQ ID NO: 81); I-Cl.Ubq1-1:1:6 (SEQ ID NO: 94) | PCR0145945, pMON140914, PCR20 |
| EXP-Cl.Ubq1:1:14 | 115 | 1507 | *C. lacryma-jobi* | EXP: P-Cl.Ubq1-1:1:3 (SEQ ID NO: 86); L-C1.Ubq1-1:1:1 (SEQ ID NO: 81); I-Cl.Ubq1-1:1:6 (SEQ ID NO: 94) | PCR0145946, pMON140915, PCR21 |
| EXP-Cl.Ubq1:1:15 | 116 | 1160 | *C. lacryma-jobi* | EXP: P-Cl.Ubq1-1:1:5 (SEQ ID NO: 88); L-Cl.Ubq1-1:1:1 (SEQ ID NO: 81); I-Cl.Ubq1-1:1:6 (SEQ ID NO: 94) | PCR0145947, pMON140916, PCR22 |
| EXP-SETit.Ubq1:1:5 | 117 | 2625 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:2 (SEQ ID NO: 118) | pMON140877, PCR0145900, pMON129200 |
| I-SETit.Ubq1-1:1:2 | 118 | 1006 | *S. italica* | Intron | |
| EXP-SETit.Ubq1:1:10 | 119 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:3 (SEQ ID NO: 120) | pMON132037 |
| I-SETit.Ubq1-1:1:3 | 120 | 1006 | *S. italica* | Intron | |
| EXP-SETit.Ubq1:1:12 | 121 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:4 (SEQ ID NO: 122) | |
| I-SETit.Ubq1-1:1:4 | 122 | 1006 | *S. italica* | Intron | |
| EXP-SETit.Ubq1:1:7 | 123 | 2167 | *S. italica* | EXP: P-SETit.Ubq1-1:1:2 (SEQ ID NO: 71); L-SETit.Ubq1-1:1:1 (SEQ ID NO: 71); I-SETit.Ubq1-1:1:2 (SEQ ID NO: 118) | PCR0145928, pMON129201 |
| EXP-SETit.Ubq1:1:6 | 124 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:2 (SEQ ID NO: 118) | PCR0145905, pMON129202 |
| EXP-SETit.Ubq1:1:11 | 125 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:3 (SEQ ID NO: 120) | pMON131957 |
| EXP-SETit.Ubq1:1:13 | 126 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:5 (SEQ ID NO: 127) | |
| I-SETit.Ubq1-1:1:5 | 127 | 1006 | *S. italica* | Intron | |
| EXP-Sv.Ubq1:1:7 | 128 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:2 (SEQ ID NO: 129) | pMON140878, PCR0145909, pMON129203 |
| I-Sv.Ubq1-1:1:2 | 129 | 1014 | *S. viridis* | Intron | |
| EXP-Sv.Ubq1:1:11 | 130 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:3 (SEQ ID NO: 131) | pMON131958 |
| I-Sv.Ubq1-1:1:3 | 131 | 1014 | *S. viridis* | Intron | |
| EXP-Sv.Ubq1:1:8 | 132 | 2176 | *S. viridis* | EXP: P-Sv.Ubq1-1:1:2 (SEQ ID NO: 38); L-Sv.Ubq1-1:1:2 (SEQ ID NO: 35); I-Sv.Ubq1-1:1:2 (SEQ ID NO: 129) | PCR0145929, pMON129204 |
| EXP-Sv.Ubq1:1:9 | 133 | 1822 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:2 (SEQ ID NO: 129) | pMON129205 |
| EXP-Sv.Ubq1:1:10 | 134 | 1822 | *S. viridis* | EXP: P-Sv.Ubq1-1:1:4 (SEQ ID NO: 135); L-Sv.Ubq1-1:1:2 (SEQ ID NO: 35); I-Sv.Ubq1-1:1:2 (SEQ ID NO: 129) | PCR0145911 |
| P-Sv.Ubq1-1:1:4 | 135 | 681 | *S. viridis* | Promoter | |
| EXP-Sv.Ubq1:1:12 | 136 | 1822 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:3 (SEQ ID NO: 131) | pMON131959 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-Zm.UbqM1:1:6 (Allele-1) | 137 | 1925 | *Z. mays* subsp. *Mexicana* | EXP: P-Zm.UbqM1-1:1:1 (SEQ ID NO: 42); L-Zm.UbqM1-1:1:1 (SEQ ID NO: 43); I-Zm.UbqM1-1:1:13 (SEQ ID NO: 138) | pMON140881, PCR0145914, pMON129210 |
| I-Zm.UbqM1-1:1:13 (Allele-1) | 138 | 997 | *Z. mays* subsp. *Mexicana* | Intron | |
| EXP-Zm.UbqM1:1:10 (Allele-1) | 139 | 1925 | *Z. mays* subsp. *Mexicana* | EXP: P-Zm.UbqM1-1:1:1 (SEQ ID NO: 42); L-Zm.UbqM1-1:1:1 (SEQ ID NO: 43); I-Zm.UbqM1-1:1:17 (SEQ ID NO: 140) | pMON131961 |
| I-Zm.UbqM1-1:1:17 (Allele-1) | 140 | 997 | *Z. mays* subsp. *Mexicana* | Intron | |
| EXP-Zm.UbqM1:1:7 (Allele-2) | 141 | 1974 | *Z. mays* subsp. *Mexicana* | EXP: P-Zm.UbqM1-1:1:4 (SEQ ID NO: 46); L-Zm.UbqM1-1:1:5 (SEQ ID NO: 47); I-Zm.UbqM1-1:1:14 (SEQ ID NO: 142) | pMON140882, PCR0145915, pMON129212 |
| I-Zm.UbqM1-1:1:14 (Allele-2) | 142 | 1010 | *Z. mays* subsp. *Mexicana* | Intron | |
| EXP-Zm.UbqM1:1:12 (Allele-2) | 143 | 1974 | *Z. mays* subsp. *Mexicana* | EXP: P-Zm.UbqM1-1:1:4 (SEQ ID NO: 46); L-Zm.UbqM1-1:1:5 (SEQ ID NO: 47); I-Zm.UbqM1-1:1:19 (SEQ ID NO: 144) | pMON131963 |
| I-Zm.UbqM1-1:1:19 (Allele-2) | 144 | 1010 | *Z. mays* subsp. *Mexicana* | Intron | |
| EXP-Zm.UbqM1:1:8 (Allele-3) | 145 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:15 (SEQ ID NO: 146) | PCR0145916, pMON129211 |
| I-Zm.UbqM1-1:1:15 (Allele-3) | 146 | 1053 | *Z. mays* subsp. *Mexicana* | Intron | |
| EXP-Zm.UbqM1:1:9 (Allele-3) | 147 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:16 (SEQ ID NO: 148) | |
| I-Zm.UbqM1-1:1:16 (Allele-3) | 148 | 1053 | *Z. mays* subsp. *Mexicana* | Intron | |
| EXP-Zm.UbqM1:1:11 (Allele-3) | 149 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:18 (SEQ ID NO: 150) | pMON131962, pMON132047 |
| I-Zm.UbqM1-1:1:18 (Allele-3) | 150 | 1053 | *Z. mays* subsp. *Mexicana* | Intron | |
| EXP-Sb.Ubq4:1:2 | 151 | 1635 | *S. bicolor* | EXP: P-Sb.Ubq4-1:1:1 (SEQ ID NO: 56); L-Sb.Ubq4-1:1:1 (SEQ ID NO: 57); I-Sb.Ubq4-1:1:2 (SEQ ID NO: 152) | pMON140886, PCR0145921, pMON129219, pMON132932 |
| I-Sb.Ubq4-1:1:2 | 152 | 1080 | *S. bicolor* | Intron | |
| EXP-Sb.Ubq6:1:2 | 153 | 2067 | *S. bicolor* | EXP: P-Sb.Ubq6-1:1:1 (SEQ ID NO: 64); L-Sb.Ubq6-1:1:1 (SEQ ID NO: 57); I-Sb.Ubq6-1:1:2 (SEQ ID NO: 154) | pMON140887, PCR0145920, pMON129218, pMON132931 |
| I-Sb.Ubq6-1:1:2 | 154 | 1076 | *S. bicolor* | Intron | |
| EXP-Sb.Ubq6:1:3 | 155 | 2067 | *S. bicolor* | EXP: P-Sb.Ubq6-1:1:1 (SEQ ID NO: 64); L-Sb.Ubq6-1:1:1 (SEQ ID NO: 57); I-Sb.Ubq6-1:1:3 (SEQ ID NO: 1569) | pMON132931 |
| I-Sb.Ubq6-1:1:3 | 156 | 1076 | *S. bicolor* | Intron | |
| EXP-Sb.Ubq7:1:2 | 157 | 2003 | *S. bicolor* | EXP: P-Sb.Ubq7-1:1:1 (SEQ ID NO: 66); L-Sb.Ubq7-1:1:1 (SEQ ID NO: 67); I-Sb.Ubq7-1:1:A (SEQ ID NO: 158) | pMON132974 |
| I-Sb.Ubq7-1:1:2 | 158 | 1361 | *S. bicolor* | Intron | |
| EXP-SETit.Ubq1:1:E | 180 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:5 (SEQ ID NO: 127) | |
| EXP-Zm.UbqM1:1:13 (Allele-3) | 181 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:20 (SEQ ID NO: 182) | |
| I-Zm.UbqM1-1:1:20 (Allele-3) | 182 | 1053 | *Z. mays* subsp. *Mexicana* | Intron | |
| EXP-SETit.Ubq1:1:9 | 183 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:2 (SEQ ID NO: 118) | |

As shown in Table 1, for example, the transcriptional regulatory EXP sequence designated EXP-ANDge.Ubq1: 1:9 (SEQ ID NO: 1), with components isolated from *A. gerardii*, comprises a promoter element, P-ANDge.Ubq1-1: 1:11. (SEQ ID NO: 2), operably linked 5' to a leader element, L-ANDge.Ubq1-1:1:2 (SEQ ID NO: 3), operably linked 5' to an intron element, 1-ANDge.Ubq1-1:1:3 (SEQ ID NO: 4). Other EXP's are linked similarly, as outlined in Table 1.

As shown in Table 1, the sequence listing and FIGS. 1-7, variants of promoter sequences from the species *A. gerardii, E. ravennae, Z. mays subsp. mexicana, S. bicolor, C. lacryma-jobi, S. italica*, and *S. viridis* were engineered which comprise shorter promoter fragments of, for instance, P-ANDge.Ubq1-1:1:11 (SEQ ID NO:2), P-ERIra.Ubq1-1:1: 10 (SEQ ID NO:19) or other respective promoters from other species, and for instance resulting in P-ANDge.Ubq1-1:1:9 (SEQ ID NO: 6), P-ERIra.Ubq1-1:1:9 (SEQ ID NO: 23), P-Cl.Ubq1-1:1:10 (SEQ ID NO: 96), P-SETit.Ubq1-1: 1:2 (SEQ ID NO: 76) and P-Sv.Ubq1-1:1:2 (SEQ ID NO: 38), as well as other promoter fragments. P-SETit.Ubq1-1: 1:4 (SEQ ID NO: 74) comprises a single nucleotide change relative to P-SETit.Ubq1-1:1:1 (SEQ ID NO: 70). Likewise, P-Sv.Ubq1-1:1:3 (SEQ ID NO: 40) comprises a single nucleotide change relative to P-Sv.Ubq1-1:1:4 (SEQ ID NO: 1.35).

In some instances, variants of specific introns were created by altering the last 3' nucleotides of each respective intron following the sequence 5'-AG-3' of the 3' intron splice junction. These intron variants are shown in Table 2 below.

TABLE 2

3' end sequence of intron variants.

| Annotation | SEQ ID NO: | Intron 3' end nucleotides immediately following 3' splice site AG |
|---|---|---|
| I-Cl.Ubq1-1:1:7 | 92 | GTG |
| I-Cl.Ubq1-1:1:6 | 94 | GTC |
| I-Cl.Ubq1-1:1:8 | 101 | GCG |
| I-Cl.Ubq1-1:1:9 | 103 | GAC |
| I-Cl.Ubq1-1:1:10 | 105 | ACC |
| I-Cl.Ubq1-1:1:11 | 107 | GGG |
| I-Cl.Ubq1-1:1:12 | 109 | GGT |
| I-Cl.Ubq1-1:1:13 | 111 | CGT |
| I-Cl.Ubq1-1:1:14 | 113 | TGT |
| I-SETit.Ubq1-1:1:2 | 118 | GTG |
| I-SETit.Ubq1-1:1:3 | 120 | GGT |
| I-SETit.Ubq1-1:1:4 | 122 | ACC |
| I-SETit.Ubq1-1:1:5 | 127 | GGC |
| I-Sv.Ubq1-1:1:2 | 129 | GTG |
| I-Sv.Ubq1-1:1:3 | 131 | GGT |
| I-Zm.UbqM1-1:1:13 (Allele-1) | 138 | GTC |
| I-Zm.UbqM1-1:1:17 (Allele-1) | 140 | GGT |
| I-Zm.UbqM1-1:1:14 (Allele-2) | 142 | GTC |
| I-Zm.UbqM1-1:1:19 (Allele-2) | 144 | GGT |
| I-Zm.UbqM1-1:1:15 (Allele-3) | 146 | GTC |
| I-Zm.UbqM1-1:1:18 (Allele-3) | 148 | GGT |
| I-Sb.Ubq6-1:1:2 | 154 | GTG |
| I-Sb.Ubq6-1:1:3 | 156 | GGT |
| I-Zm.UbqM1-1:1:20 (Allele-3) | 182 | CGG |

Also listed in Table 1 are three allelic variants isolated using the same primer sets designed for amplification of genomic DNA from *Z. mays subsp. mexicana*. Allelic variants of the EXP sequences are comprised of sequence that shares some identity within various regions of other sequences, but insertions, deletions and nucleotide mismatches may also be apparent within each promoter, leader and/or intron of each of the EXP sequences. The EXP sequence designated EXP-Zm.UbqM1:1:1 (SEQ ID NO: 41) represents a first allele (Allele-1) of the *Z. mays subsp. mexicana* Ubq1 gene transcriptional regulatory expression element group. The EXP sequences designated EXP-ZmUbqM1:1:6 (SEQ ID NO: 137) and EXP-Zm.UbqM1:1: 10 (SEQ ID NO: 139) represent a first allele (Allele-1), with the only difference between the two EXPs occurring in the last 3' nucleotides of each respective intron following the sequence 5'-AG-3' of the 3' intron splice junction. The EXP sequence designated EXP-Zm.UbqM1:1:4 (SEQ ID NO: 45) represents a second allele (Allele-2) of the *Z. mays subsp. mexicana* Ubq1 gene transcriptional regulatory expression element group. The EXP sequences designated EXP-Zm.UbqM1:1:7 (SEQ ID NO: 141) and EXP-ZmUbqM1:1: 12 (SEQ ID NO: 143) represent a second allele (Allele-2), with the only difference between the two EXPs occurring in the last 3' nucleotides of each respective intron following the sequence 5'-AG-3' of the 3' intron splice junction. The EXP sequences EXP-Zm.UbqM1:1:2 (SEQ ID NO: 49) and EXP-Zm.UbqM1:1:5 (SEQ ID NO: 53) represents a third allele (Allele-3) of the *Z. mays subsp. mexicana* Ubq1 gene transcriptional regulatory expression element group and comprise a single nucleotide difference at position 1034 within their respective introns (G for I-Zm.UbqM1-1:1:11, SEQ ID NO: 52 and T for I-Zm.UbqM1-1:1:12, SEQ ID NO: 54). The EXP sequences designated EXP-Zm.UbqM1: 1:8 (SEQ ID NO: 145), EXP-Zm.UbqM1:1:9 (SEQ ID NO: 147), EXP-Zm.UbqM1:1:11 (SEQ ID NO: 149) and EXP-Zm.UbqM1:1:13 (SEQ ID NO: 181) also represent a third allele (Allele-3). The intron of EXP-Zm.UbqM1:1:9, (I-Zm.UbqM1-1:1:16 (SEQ ID NO: 148) comprises a thymine residue at position 1034, while the introns of EXP-Zm.UbqM1:1:8, EXP-Zm.UbqM1:1:11 and EXP-Zm.UbqM1:1:13 (I-Zm.UbqM1-1:1:15, SEQ ID NO: 146; I-Zm.UbqM1-1:11:18, SEQ ID NO: 11 and; I-Zm.UbqM1-1:1:20, SEQ ID NO: 182) each comprise a guanine residue at position 1034. In addition, the last 3, 3' end nucleotides of EXP-Zm.UbqM1:1:8 (SEQ ID NO: 145) and EXP-Zm.UbqM1:1:9 (SEQ ID NO: 147) differ from those of EXP-Zm.UbqM1:1:11 (SEQ ID NO: 149) and EXP-Zm.UbqM1:1:13 (SEQ ID NO: 181).

Example 2: Analysis of Regulatory Elements Driving GUS in Corn Protoplasts

Corn leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-ANDge.Ubq1: 1:7 (SEQ ID NO: 5), EXP-ANDge.Ubq1:1:6 (SEQ ID NO: 12), EXP-ERIa.Ubq1:1:9 (SEQ ID NO: 22) or EXP-ERIra.Ubq1:1:8 (SEQ ID NO: 27) was compared with expression from known constitutive promoters. The foregoing EXP sequences were cloned into plant expression vectors as shown in Table 3 below to yield vectors in which an EXP sequence is operably linked 5' to a β-glucuronidase (GUS) reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NOS: 159), which was operably linked 5' to a 3' UTR derived from the *A. tumefaciens* Nopaline synthase gene (T-AgRtu.nos-1:1:13, SEQ ID NO: 161) or the wheat Hsp17 gene (T-Ta.Hsp17-1:1:1, SEQ ID NO: 162).

TABLE 3

GUS plant expression plasmid construct and corresponding EXP sequence, GUS coding sequence and 3' UTR used for transformation of corn leaf protoplasts. "SEQ ID NO:" refers to given EXP sequence.

| Plasmid | EXP sequence | SEQ ID NO: | GUS | 3' UTR |
|---|---|---|---|---|
| pMON19469 | EXP-CaMV.35S-enh + Zm.DnaK:1:1 | 170 | GUS-1 | T-AGRtu.nos-1:1:13 |
| pMON65328 | EXP-CaMV.35S-enh + Ta.Lhcb1 + Os.Act1:1:1 | 163 | GUS-2 | T-Ta.Hsp17-1:1:1 |
| pMON25455 | EXP-Os.Act1:1:9 | 179 | GUS-1 | T-AGRtu.nos-1:1:13 |
| pMON122605 | EXP-Os.TubA-3:1:1 | 165 | GUS-1 | T-AGRtu.nos-1:1:13 |
| pMON136264 | EXP-ANDge.Ubq1:1:7 | 5 | GUS-1 | T-AGRtu.nos-1:1:13 |
| pMON136259 | EXP-ANDge.Ubq1:1:6 | 12 | GUS-1 | T-AGRtu.nos-1:1:13 |
| pMON136263 | EXP-ERIra.Ubq1:1:9 | 22 | GUS-1 | T-AGRtu.nos-1:1:13 |
| pMON136258 | EXP-ERIra.Ubq1:1:8 | 27 | GUS-1 | T-AGRtu.nos-1:1:13 |

Control plasmids (pMON19469, pMON65328, pMON25455 and pMON122605) used for comparison were constructed as described above and contain a known EXP sequence: EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), EXP-Os.Act1:1:9 (SEQ ID NO: 179), or EXP-Os.TubA-3:1:1 (SEQ ID NO: 165), respectively, operably linked 5' to a GUS coding sequence and 3' UTR. Three additional controls were provided to assess background GUS and luciferase expression: a no DNA control, an empty vector which is not designed for transgene expression, and an expression vector used to express green fluorescent protein (CTFP).

Two plasmids, for use in co-transformation and normalization of data, were also constructed using methods known in the art. Each plasmid contained a specific luciferase coding sequence that was driven by a constitutive EXP sequence. The plant vector pMON19437 comprises a transgene cassette with a constitutive promoter operably linked 5' to an intron, (EXP-CaMV.35S-enh+Zm.DnaK:1:1, SEQ ID NO: 170), operably linked 5' to a firefly (*Photinus pyralis*) luciferase coding sequence (LUCIFERASE:1:3, SEQ ID NO: 166), operably linked 5' to a 3' UTR from the *Agrobacterium tumefaciens* nopaline synthase gene (T-AGRtu.nos-1:11:13, SEQ ID NO: 161). The plant vector pMON63934 comprises a transgene cassette with a constitutive EXP sequence (EXP-CaMV.35S-enh-Lhcb1, SEQ ID NO: 168), operably linked 5' to a sea pansy (*Renilla reniformis*) luciferase coding sequence (CR-Ren.hRenilla Lucife-0:0:1, SEQ ID NO: 167), operably linked 5' to a 3' UTR from the *Agrobacterium tumefaciens* nopaline synthase gene (T-AGRtu.nos-1:1:13, SEQ ID NO: 161).

Corn leaf protoplasts were transformed using a PEG-based transformation method, as is well known in the art. Protoplast cells were transformed with pMON19437 plasmid DNA, pMON63934 plasmid DNA, and an equimolar quantity of one of the plasmids presented in Table 3 and incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 4. In this table, the firefly luciferase values (e.g. from expression of pMON19437) are provided in the column labeled "FLuc" and the *Renilla* luciferase values are provided as in the column labeled "RLuc."

TABLE 4

Mean GUS and Luciferase activity in transformed corn leaf protoplast cells.

| Plasmid | EXP sequence | SEQ ID NO: | Gus | RLuc | FLuc |
|---|---|---|---|---|---|
| pMON19469 | EXP-CaMV.35S-enh + Zm.DnaK:1:1 | 170 | 789147 | 298899 | 36568 |
| pMON65328 | EXP-CaMV.35S-enh + Ta.Lhcb1 + Os.Act1:1:1 | 163 | 508327 | 158227 | 17193 |
| pMON25455 | EXP-Os.Act1:1:9 | 179 | 460579 | 183955 | 53813 |
| pMON122605 | EXP-Os.TubA-3:1:1 | 165 | 25082 | 25821 | 21004 |
| pMON136264 | EXP-ANDge.Ubq1:1:7 | 5 | 926083 | 101213 | 23704 |
| pMON136259 | EXP-ANDge.Ubq1:1:6 | 12 | 845274 | 193153 | 51479 |
| pMON136263 | EXP-ERIra.Ubq1:1:9 | 22 | 901985 | 132765 | 41313 |
| pMON136258 | EXP-ERIra.Ubq1:1:8 | 27 | 1011447 | 210635 | 66803 |

To compare the relative activity of each EXP sequence, GUS values were expressed as a ratio of GUS to luciferase activity and normalized with respect to the expression levels observed for the EXP sequence EXP-Os.TubA-3:1:1 (SEQ ID NO: 165). Table 5 below shows the GUS/RLuc ratios of expression normalized with respect to EXP-Os.TubA-3:1:1 expression in corn protoplasts.

As can be seen in Table 5, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was 4.51 to 9.42 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher than that of EXP-CaMV.35S-enh+Zm.DnaK:1:11 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

TABLE 5

GUS/RLuc fold expression as relative to EXP-Os.TubA-3:1:1 expression in corn leaf protoplast cells.

| Plasmid | EXP sequence | SEQ ID NO: | Gus/RLuc | Gus/RLuc Normalized with respect to EXP-Os.TubA-3:1:1 |
|---|---|---|---|---|
| pMON19469 | EXP-CaMV.35S-enh + Zm.DnaK:1:1 | 170 | 2.640000 | 2.72 |
| pMON65328 | EXP-CaMV.35S-enh + Ta.Lhcb1 + Os.Act1:1:1 | 163 | 3.210000 | 3.31 |
| pMON25455 | EXP-Os.Act1:1:9 | 179 | 2.500000 | 2.57 |
| pMON122605 | EXP-Os.TubA-3:1:1 | 165 | 0.971000 | 1.00 |
| pMON136264 | EXP-ANDge.Ubq1:1:7 | 5 | 9.150000 | 9.42 |
| pMON136259 | EXP-ANDge.Ubq1:1:6 | 12 | 4.380000 | 4.51 |
| pMON136263 | EXP-ERIra.Ubq1:1:9 | 22 | 6.790000 | 6.99 |
| pMON136258 | EXP-ERIra.Ubq1:1:8 | 27 | 4.800000 | 4.94 |

Table 6 below show GUS/FLuc ratios of expression normalized with respect to EXP-Os.TubA-3:1:1 expression in corn protoplasts.

TABLE 6

GUS/FLuc fold expression as relative to EXP-Os.TubA-3:1:1 expression in corn leaf protoplast cells.

| Plasmid | EXP sequence | SEQ ID NO: | Gus/FLuc | Normalized with respect to EXP-Os.TubA-3:1:1 |
|---|---|---|---|---|
| pMON19469 | EXP-CaMV.35S-enh + Zm.DnaK:1:1 | 170 | 21.600000 | 18.15 |
| pMON65328 | EXP-CaMV.35S-enh + Ta.Lhcb1 + Os.Act1:1:1 | 163 | 29.600000 | 24.87 |
| pMON25455 | EXP-Os.Act1:1:9 | 179 | 8.560000 | 7.19 |
| pMON122605 | EXP-Os.TubA-3:1:1 | 165 | 1.190000 | 1.00 |
| pMON136264 | EXP-ANDge.Ubq1:1:7 | 5 | 39.100000 | 32.86 |
| pMON136259 | EXP-ANDge.Ubq1:1:6 | 12 | 16.400000 | 13.78 |
| pMON136263 | EXP-ERIra.Ubq1:1:9 | 22 | 21.800000 | 18.32 |
| pMON136258 | EXP-ERIra.Ubq1:1:8 | 27 | 15.100000 | 12.69 |

As can be seen in Table 6, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) demonstrated the same general trend when expressed as ratio of GUS/FLuc values and is normalized with respect to EXP-Os.TubA-3:1:1 (SEQ ID NO: 165). Expression was 12.69 to 32.86 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher in certain comparisons than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

Example 3: Analysis of Regulatory Elements Driving GUS in Corn Protoplasts Using GUS Transgene Cassette Amplicons Corn leaf protoplasts were transformed with DNA amplicons derived from plant expression vectors containing an EXP sequence, driving expression of the β-glucuronidase (GUS) transgene, and compared to leaf protoplast in which expression of GUS is driven by known constitutive promoters in a series of experiments presented below.

In a first set of experiments, corn protoplast cells, derived from leaf tissue were transformed as above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq.1:1:10 (SEQ ID NO: 98) with that of known constitutive promoters. Each EXP sequence comprising the amplification template from which the transgene cassette amplicon is produced was cloned using methods known in the art into a plant expression vector shown in Table 7 below under the heading of "Amplicon Template." The resulting plant expression vectors comprise a transgene cassette comprised of a EXP sequence, operably linked 5' to a coding sequence for β-glucuronidase (GUS) that either contains a processable intron ("GUS-2" as discussed in Example 2 above), or a contiguous GUS coding sequence ("GUS-1", as discussed above), operably linked 5' to a 3' UTR T-AGRtu.nos-1:1:13 or T-Ta.Hsp17-1:1:1, as also noted above. Amplicons were produced using methods known to those skilled in the art using the plasmid construct templates presented in Table 7 below. Briefly, a 5' oligonucleotide primer was designed to anneal to the promoter sequence and a 3' oligonucleotide primer, which anneals at the 3' end of the 3' UTR was used for amplification of each transgene cassette. Successive 5' deletions were introduced into the promoter sequences comprising the transgene cassettes, giving rise to different EXP sequences, by the use of different oligonucleotide primers which were designed to anneal at different positions within the promoter sequence comprising each amplicon template.

TABLE 7

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 179 | GUS-1 | T-AGRtu.nos-1:1:13 |
| PCR0145941 | pMON33449 | P-CAMV.35S-ENH-1:1:102/ L-CAMV.35S-1:1:2 | 169 | GUS-1 | T-AGRtu.nos-1:1:13 |
| PCR0145943 | pMON65328 | EXP-CaMV.35S-enh + Ta.Lhcb1 + Os.Act1:1:1 | 163 | GUS-2 | T-Ta.Hsp17-1:1:1 |
| PCR0145944 | pMON81552 | EXP-CaMV.35S-enh + Zm.DnaK:1:1 | 170 | GUS-1 | T-AGRtu.nos-1:1:13 |
| PCR0145892 | pMON136264 | EXP-ANDge.Ubq1:1:7 | 5 | GUS-1 | T-AGRtu.nos-1:1:13 |
| PCR0145815 | pMON136264 | EXP-ANDge.Ubq1:1:10 | 10 | GUS-1 | T-AGRtu.nos-1:1:13 |
| PCR0145893 | pMON136259 | EXP-ANDge.Ubq1:1:6 | 12 | GUS-1 | T-AGRtu.nos-1:1:13 |
| PCR0145817 | pMON136264 | EXP-ANDge.Ubq1:1:11 | 14 | GUS-1 | T-AGRtu.nos-1:1:13 |
| PCR0145819 | pMON136264 | EXP-ANDge.Ubq1:1:12 | 16 | GUS-1 | T-AGRtu.nos-1:1:13 |
| PCR0145896 | pMON136263 | EXP-ERIra.Ubq1:1:9 | 22 | GUS-1 | T-AGRtu.nos-1:1:13 |
| PCR0145820 | pMON136263 | EXP-ERIra.Ubq1:1:10 | 25 | GUS-1 | T-AGRtu.nos-1:1:13 |
| PCR0145897 | pMON136258 | EXP-ERIra.Ubq1:1:8 | 27 | GUS-1 | T-AGRtu.nos-1:1:13 |
| PCR0145821 | pMON136263 | EXP-ERIra.Ubq1:1:11 | 29 | GUS-1 | T-AGRtu.nos-1:1:13 |
| PCR0145822 | pMON136263 | EXP-ERIra.Ubq1:1:12 | 31 | GUS-1 | T-AGRtu.nos-1:1:13 |
| PCR0145900 | pMON140877 | EXP-SETit.Ubq1:1:5 | 117 | GUS-1 | T-AGRtu.nos-1:1:13 |
| PCR0145928 | pMON140877 | EXP-SETit.Ubq1:1:7 | 123 | GUS-1 | T-AGRtu.nos-1:1:13 |
| PCR0145905 | pMON140877 | EXP-SETit.Ubq1:1:6 | 124 | GUS-1 | T-AGRtu.nos-1:1:13 |
| PCR0145909 | pMON140878 | EXP-Sv.Ubq1:1:7 | 128 | GUS-1 | T-AGRtu.nos-1:1:13 |
| PCR0145929 | pMON140878 | EXP-Sv.Ubq1:1:8 | 132 | GUS-1 | T-AGRtu.nos-1:1:13 |
| PCR0145911 | pMON140878 | EXP-Sv.Ubq1:1:10 | 134 | GUS-1 | T-AGRtu.nos-1:1:13 |
| PCR0145914 | pMON140881 | EXP-Zm.UbqM1:1:6 | 137 | GUS-1 | T-AGRtu.nos-1:1:13 |
| PCR0145915 | pMON140882 | EXP-Zm.UbqM1:1:7 | 141 | GUS-1 | T-AGRtu.nos-1:1:13 |
| PCR0145921 | pMON140886 | EXP-Sb.Ubq4:1:2 | 151 | GUS-1 | T-AGRtu.nos-1:1:13 |
| PCR0145920 | pMON140887 | EXP-Sb.Ubq6:1:2 | 153 | GUS-1 | T-AGRtu.nos-1:1:13 |
| PCR0145922 | pMON140889 | EXP-Cl.Ubq1:1:10 | 98 | GUS-1 | T-AGRtu.nos-1:1:13 |

Plasmid constructs listed as amplicon templates in Table 7 served as templates for amplification of transgene expression cassettes comprising the listed EXP sequences of Table 7. Control plasmids used to generate GUS transgene amplicons for comparison were constructed as previously described with known constitutive EXP sequences described in Example 2. Negative controls for determination of GUS and luciferase background, a no DNA control, and a control sample in which the two luciferase plasmids are used in transformation along with a plasmid DNA that does not express a coding sequence were also used. Plasmids pMON19437 and pMON63934, as discussed in Example 2, were also employed for co-transformation and normalization of data.

Corn leaf protoplasts were transformed using a PEG-based transformation method as described in Example 2, above. Table 8 below shows the average GUS and luciferase expression values determined for each transgene cassette.

TABLE 8

Mean GUS and Luciferase activity in transformed corn leaf protoplast cells.

| EXP sequence | SEQ ID NO: | GUS | RLuc | FLuc |
|---|---|---|---|---|
| EXP-Os.Act1:1:9 | 179 | 1540.3 | 105416.8 | 2671.8 |
| P-CAMV.35S-ENH-1:1:102/ L-CAMV.35S-1:1:2 | 169 | 10426.3 | 344088.6 | 8604.1 |

TABLE 8-continued

Mean GUS and Luciferase activity in transformed corn leaf protoplast cells.

| EXP sequence | SEQ ID NO: | GUS | RLuc | FLuc |
|---|---|---|---|---|
| EXP-CaMV.35S-enh + Ta.Lhcb 1 + Os.Act1:1:1 | 163 | 12530.8 | 137722.6 | 3067.1 |
| EXP-CaMV.35S-enh + Zm.DnaK:1:1 | 170 | 61036.1 | 208125.3 | 5787.6 |
| EXP-ANDge.Ubq1:1:7 | 5 | 59447.4 | 84667.6 | 2578.4 |
| EXP-ANDge.Ubq1:1:10 | 10 | 40123.3 | 76753.8 | 2419.8 |
| EXP-ANDge.Ubq1:1:6 | 12 | 42621.0 | 121751.3 | 3974.8 |
| EXP-ANDge.Ubq1:1:11 | 14 | 44358.5 | 87105.8 | 2687.1 |
| EXP-ANDge.Ubq1:1:12 | 16 | 48219.0 | 107762.1 | 3279.6 |
| EXP-ERIra.Ubq1:1:9 | 22 | 31253.0 | 171684.1 | 6476.1 |
| EXP-ERIra.Ubq1:1:10 | 25 | 7905.8 | 21235.6 | 462.4 |
| EXP-ERIra.Ubq1:1:8 | 27 | 39935.8 | 173766.6 | 5320.3 |
| EXP-ERIra.Ubq1:1:11 | 29 | 34141.3 | 111626.8 | 3377.6 |
| EXP-ERIra.Ubq1:1:12 | 31 | 11540.3 | 42362.1 | 1045.3 |
| EXP-SETit.Ubq1:1:5 | 117 | 20496.5 | 88695.8 | 2358.8 |
| EXP-SETit.Ubq1:1:7 | 123 | 75728.5 | 185223.8 | 4723.1 |
| EXP-SETit.Ubq1:1:6 | 124 | 44148.3 | 161216.3 | 4962.1 |
| EXP-Sv.Ubq1:1:7 | 128 | 15043.8 | 74670.6 | 1888.3 |
| EXP-Sv.Ubq1:1:8 | 132 | 31997.8 | 113787.1 | 3219.8 |
| EXP-Sv.Ubq1:1:10 | 134 | 38952.8 | 220208.6 | 7011.3 |
| EXP-Zm.UbqM1:1:6 | 137 | 30528.3 | 90113.1 | 2453.6 |
| EXP-Zm.UbqM1:1:7 | 141 | 34986.3 | 105724.7 | 2553.8 |
| EXP-Sb.Ubq4:1:2 | 151 | 9982.3 | 72593.8 | 2171.6 |
| EXP-Sb.Ubq6:1:2 | 153 | 33689.0 | 114709.6 | 3879.6 |
| EXP-Cl.Ubq1:1:10 | 98 | 50622.3 | 107084.3 | 2621.3 |

To compare the relative activity of each EXP sequence GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 9 below shows the GUS/RLuc ratios of expression normalized with respect to EXP-Os.Act1:1:1 and EXP-CaMV.35S-enh+Ta.Lhcb1+Os.Act1:1:1 driven expression in corn protoplasts. Table 10 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 9

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-Os.Act1:1:9 | 179 | 0.16 | 0.14 |
| P-CAMV.35S-ENH-1:1:102/ L-CAMV.35S-1:1:2 | 169 | 0.33 | 0.30 |
| EXP-CaMV.35S-enh + Ta.Lhcb1 + Os.Act1:1:1 | 163 | 1.00 | 1.00 |
| EXP-CaMV.35S-enh + Zm.DnaK:1:1 | 170 | 3.22 | 2.58 |
| EXP-ANDge.Ubq1:1:7 | 5 | 7.72 | 5.64 |
| EXP-ANDge.Ubq1:1:10 | 10 | 5.75 | 4.06 |
| EXP-ANDge.Ubq1:1:6 | 12 | 3.85 | 2.62 |
| EXP-ANDge.Ubq1:1:11 | 14 | 5.60 | 4.04 |
| EXP-ANDge.Ubq1:1:12 | 16 | 4.92 | 3.60 |
| EXP-ERIra.Ubq1:1:9 | 22 | 2.00 | 1.18 |
| EXP-ERIra.Ubq1:1:10 | 25 | 4.09 | 4.18 |
| EXP-ERIra.Ubq1:1:8 | 27 | 2.53 | 1.84 |

TABLE 9-continued

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-ERIra.Ubq1:1:11 | 29 | 3.36 | 2.47 |
| EXP-ERIra.Ubq1:1:12 | 31 | 2.99 | 2.70 |
| EXP-SETit.Ubq1:1:5 | 117 | 2.54 | 2.13 |
| EXP-SETit.Ubq1:1:7 | 123 | 4.49 | 3.92 |
| EXP-SETit.Ubq1:1:6 | 124 | 3.01 | 2.18 |
| EXP-Sv.Ubq1:1:7 | 128 | 2.21 | 1.95 |
| EXP-Sv.Ubq1:1:8 | 132 | 3.09 | 2.43 |
| EXP-Sv.Ubq1:1:10 | 134 | 1.94 | 1.36 |
| EXP-Zm.UbqM1:1:6 | 137 | 3.72 | 3.05 |
| EXP-Zm.UbqM1:1:7 | 141 | 3.64 | 3.35 |
| EXP-Sb.Ubq4:1:2 | 151 | 1.51 | 1.13 |
| EXP-Sb.Ubq6:1:2 | 153 | 3.23 | 2.13 |
| EXP-Cl.Ubq1:1:10 | 98 | 5.20 | 4.73 |

TABLE 10

GUS/RLuc and GUS/FLuc ratios of expression normalized with respect to EXP-Os.Act1:1:9 (SEQ ID NO: 179) in corn leaf protoplasts.

| EXP sequence | SEQ ID NO: | GUS/RLuc Relative to EXP-Os.Act1:1:9 | GUS/FLuc Relative to EXP-Os.Act1:1:9 |
|---|---|---|---|
| EXP-Os.Act1:1:9 | 179 | 1.00 | 1.00 |
| P-CAMV.35S-ENH-1:1:102/ L-CAMV.35S-1:1:2 | 169 | 2.07 | 2.10 |
| EXP-CaMV.35S-enh + Ta.Lhcb1 + Os.Act1:1:1 | 163 | 6.23 | 7.09 |
| EXP-CaMV.35S-enh + Zm.DnaK:1:1 | 170 | 20.07 | 18.29 |
| EXP-ANDge.Ubq1:1:7 | 5 | 48.05 | 39.99 |
| EXP-ANDge.Ubq1:1:10 | 10 | 35.78 | 28.76 |
| EXP-ANDge.Ubq1:1:6 | 12 | 23.96 | 18.60 |
| EXP-ANDge.Ubq1:1:11 | 14 | 34.85 | 28.64 |
| EXP-ANDge.Ubq1:1:12 | 16 | 30.62 | 25.50 |
| EXP-ERIra.Ubq1:1:9 | 22 | 12.46 | 8.37 |
| EXP-ERIra.Ubq1:1:10 | 25 | 25.48 | 29.66 |
| EXP-ERIra.Ubq1:1:8 | 27 | 15.73 | 13.02 |
| EXP-ERIra.Ubq1:1:11 | 29 | 20.93 | 17.53 |
| EXP-ERIra.Ubq1:1:12 | 31 | 18.64 | 19.15 |
| EXP-SETit.Ubq1:1:5 | 117 | 15.82 | 15.07 |
| EXP-SETit.Ubq1:1:7 | 123 | 27.98 | 27.81 |
| EXP-SETit.Ubq1:1:6 | 124 | 18.74 | 15.43 |
| EXP-Sv.Ubq1:1:7 | 128 | 13.79 | 13.82 |
| EXP-Sv.Ubq1:1:8 | 132 | 19.25 | 17.24 |
| EXP-Sv.Ubq1:1:10 | 134 | 12.11 | 9.64 |
| EXP-Zm.UbqM1:1:6 | 137 | 23.19 | 21.58 |
| EXP-Zm.UbqM1:1:7 | 141 | 22.65 | 23.76 |
| EXP-Sb.Ubq4:1:2 | 151 | 9.41 | 7.97 |
| EXP-Sb.Ubq6:1:2 | 153 | 20.10 | 15.06 |
| EXP-Cl.Ubq1:1:10 | 98 | 32.35 | 33.50 |

As can be seen in Tables 9 and 10, nearly all of the EXP sequences were capable of driving GUS transgene expression in corn cells. Average GUS expression was higher for EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) when compared to GUS expression driven by EXP-Os.Act1:1:1 or EXP-CaMV.35S-enh+Ta.Lhcb1+Os.Act1:1:1.

In a second set of experiments, a GUS cassette amplicon comprising the EXP sequence EXP-Zm.UbqM1:1:8 (SEQ ID NO: 145) was compared to the control amplicons, PCR0145942 (EXP-Os.Act1:1:9, SEQ ID NO: 179) and PCR0145944 (EXP-CaMV.35S-enh+Zm.DnaK:1:1, SEQ ID NO: 170) with respect to GUS expression. GUS expression driven by the EXP sequence EXP-ZmUbqM1:1:8 was higher than that of the two controls. Table 11 below shows the mean GUS and luciferase values determined for each amplicon. Table 12 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 11

Mean GUS and Luciferase activity in transformed corn leaf protoplast cells.

| Amplicon | EXP sequence | SEQ ID NO: | GUS | RLuc | FLuc |
|---|---|---|---|---|---|
| PCR0145942 | EXP-Os.Act1:1:9 | 179 | 1512.25 | 190461 | 11333.8 |
| PCR0145944 | EXP-CaMV.35S-enh + Zm.DnaK:1:1 | 170 | 41176.5 | 330837 | 13885.8 |
| PCR0145916 | EXP-Zm.UbqM1:1:8 | 145 | 79581.5 | 330756 | 15262.5 |

TABLE 12

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.06 | 0.04 |
| EXP-CaMV.35S-enh + Zm.DnaK:1:1 | 170 | 15.68 | 22.22 | 1.00 | 1.00 |
| EXP-Zm.UbqM1:1:8 | 145 | 30.30 | 39.08 | 1.93 | 1.76 |

In a third set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 13 below shows the mean GUS and luciferase values determined for each amplicon. Table 14 below shows the GUS/RLuc ratios of expression normalized with respect to EXP-Os.Act1:1:9 and EXP-CaMV.35S-enh+Zm.DnaK:1:1 driven expression in corn protoplasts.

TABLE 13

Mean GUS and Luciferase activity in transformed corn leaf protoplast cells.

| Amplicon ID | EXP sequence | SEQ ID NO: | GUS | RLuc |
|---|---|---|---|---|
| PCR0145942 | EXP-Os.Act1:1:9 | 179 | 9445.25 | 929755 |
| PCR0145944 | EXP-CaMV.35S-enh + Zm.DnaK:1:1 | 170 | 78591.25 | 445127 |
| PCR0146628 | EXP-ANDge.Ubq1:1:8 | 8 | 192056.75 | 972642 |
| PCR0145922 | EXP-Cl.Ubq1:1:10 | 98 | 175295.25 | 395563 |
| PCR0145945 | EXP-Cl.Ubq1:1:13 | 114 | 173674.5 | 402966 |
| PCR0145946 | EXP-Cl.Ubq1:1:14 | 115 | 185987.5 | 390052 |
| PCR0145947 | EXP-Cl.Ubq1:1:15 | 116 | 9435 | 320749 |

TABLE 14

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 17.38 | 1.00 |
| EXP-ANDge.Ubq1:1:8 | 8 | 19.44 | 1.12 |
| EXP-Cl.Ubq1:1:10 | 98 | 43.62 | 2.51 |
| EXP-Cl.Ubq1:1:13 | 114 | 42.43 | 2.44 |
| EXP-Cl.Ubq1:1:14 | 115 | 46.94 | 2.70 |
| EXP-Cl.Ubq1:1:15 | 116 | 2.90 | 0.17 |

As can be seen in Table 114 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 1116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a fourth set of experiments, amplicon GUS transgene cassettes were made as described above and assayed for expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK:1:1 (SEQ ID NO: 170). Table 15 below shows the mean GUS and luciferase values determined for each amplicon. Table 16 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 15

Mean GUS and Luciferase activity in transformed corn leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 5333.5 | 171941.75 | 77817.88 |
| PCR0145944 | EXP-CaMV.35S-enh + Zm.DnaK:1:1 | 170 | 88517 | 177260.25 | 54207.38 |
| PCR0145922 | EXP-Cl.Ubq1:1:10 | 98 | 130125.75 | 194216 | 32055 |
| pMON146750 | EXP-Cl.Ubq1:1:16 | 93 | 134101.75 | 182317.5 | 32434.5 |
| pMON146751 | EXP-Cl.Ubq1:1:17 | 97 | 107122.5 | 151783.25 | 51354.38 |

TABLE 16

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zsm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.06 | 0.04 |
| PCR0145944 | EXP-CaMV.35S-enh + Zm.DnaK:1:1 | 170 | 16.10 | 23.83 | 1.00 | 1.00 |
| PCR0145922 | EXP-Cl.Ubq1:1:10 | 98 | 21.60 | 59.23 | 1.34 | 2.49 |
| pMON146750 | EXP-Cl.Ubq1:1:16 | 93 | 23.71 | 60.32 | 1.47 | 2.53 |
| pMON146751 | EXP-Cl.Ubq1:1:17 | 97 | 22.75 | 30.43 | 1.41 | 1.28 |

As can be seen in Table 16, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fifth set of experiments, amplicon GUS transgene cassettes were made as described above assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:1:1 (SEQ ID NO: 163). Table 17 below shows the mean GUS and luciferase values determined for each amplicon. Table 18 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 17

Mean GUS and Luciferase activity in transformed corn leaf protoplast cells.

| Template | Amplicon | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 70352.00 | 79028.75 |
| pMON25455 | PCR0145942 | EXP-Os.Act1:1:9 | 179 | 33155.25 | 92337.00 |
| pMON131962 | pMON131962 | EXP-Zm.UbqM1:1:11 | 149 | 18814.75 | 33663.00 |
| pMON132047 | pMON132047 | EXP-Cl.Ubq1:1:23 | 108 | 15387.50 | 40995.50 |

TABLE 18

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in corn leaf protoplasts.

| Amplicon | EXP sequence | SEQ ID NO: | GUS/RLuc relative to EXP-Os.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 2.48 | 1.00 |
| PCR0145942 | EXP-Os.Act1:1:9 | 179 | 1.00 | 0.40 |
| pMON131962 | EXP-Zm.UbqM1:1:11 | 149 | 1.56 | 0.63 |
| pMON132047 | EXP-Cl.Ubq1:1:23 | 108 | 1.05 | 0.42 |

As can be seen in Table 18 above, the EXP sequences, EXP-Zm.UbqM1:1:11 (SEQ ID NO: 149) and EXP-Cl.Ubq1:1:23 (SEQ ID NO: 108) were able to drive GUS expression in corn leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the β-glucuronidase (GUS) transgene, and compared to leaf protoplast in which expression of GUS is driven by known constitutive promoters. Likewise, regulatory elements driving CP4 expression from amplicons in corn or wheat protoplasts may be similarly studied.

Example 4: Analysis of Regulatory Elements Driving GUS in Wheat Protoplasts Using GUS Transgene Cassette Amplicons Wheat leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Wheat protoplast cells derived from leaf tissue were transformed using methods known in the art with amplicons produced from amplification of GUS transgene cassettes comprising plant expression vectors to compare expression of a transgene (GUS) driven by the EXP sequences listed in Tables 10-11 with that of known constitutive promoters with methodology as described in a previous example (Example 3), using the same GUS cassette amplicons as that used for assay in Corn in Example 3 above. Control GUS cassette amplicons and Luciferase plasmids used for wheat protoplast transformation were also the same as those presented in the previous example and provided in Table 7 above in Example 3. Likewise, negative controls were used for the determination of GUS and luciferase background, as described above. Wheat leaf protoplasts were transformed using a PEG-based transformation method, as described in Example 3 above. Table 19 lists mean GUS and LUC activity seen in transformed wheat leaf protoplast cells, and Table 20 shows normalized GUS/RLuc ratios of expression in wheat protoplasts.

TABLE 19

Mean GUS and Luciferase activity in transformed wheat leaf protoplast cells.

| EXP sequence | SEQ ID NO: | GUS | RLuc | GUS/RLuc |
|---|---|---|---|---|
| EXP-Os.Act1:1:9 | 179 | 2976.33 | 53334.8 | 0.0558047 |
| P-CAMV.35S-ENH-1:1:102/L-CAMV.35S-1:1:2 | 169 | 1431.33 | 55996.1 | 0.0255612 |
| EXP-CaMV.35S-enh + Ta.Lhcb1 + Os.Act1:1:1 | 163 | 29299.3 | 50717.4 | 0.5776973 |
| EXP-CaMV.35S-enh + Zm.DnaK:1:1 | 170 | 34294.3 | 63307.9 | 0.5417066 |
| EXP-ANDge.Ubq1:1:7 | 5 | 68444.3 | 60329.1 | 1.1345158 |
| EXP-ANDge.Ubq1:1:10 | 10 | 60606.3 | 60659.4 | 0.9991245 |
| EXP-ANDge.Ubq1:1:6 | 12 | 33386.3 | 56712.1 | 0.5886984 |
| EXP-ANDge.Ubq1:1:11 | 14 | 43237.3 | 48263.4 | 0.8958609 |
| EXP-ANDge.Ubq1:1:12 | 16 | 51712.7 | 64702.8 | 0.7992341 |
| EXP-ERIra.Ubq1:1:9 | 22 | 20998.3 | 60273.4 | 0.3483845 |
| EXP-ERIra.Ubq1:1:10 | 25 | 17268.3 | 25465.4 | 0.6781084 |

TABLE 19-continued

Mean GUS and Luciferase activity in transformed wheat leaf protoplast cells.

| EXP sequence | SEQ ID NO: | GUS | RLuc | GUS/RLuc |
|---|---|---|---|---|
| EXP-ERIra.Ubq1:1:8 | 27 | 34635.7 | 59467.1 | 0.5824341 |
| EXP-ERIra.Ubq1:1:11 | 29 | 28979 | 56153.8 | 0.516065 |
| EXP-ERIra.Ubq1:1:12 | 31 | 41409.7 | 55152.4 | 0.7508221 |
| EXP-SETit.Ubq1:1:5 | 117 | 39427.7 | 57463.1 | 0.6861388 |
| EXP-SETit.Ubq1:1:7 | 123 | 108091 | 49330.4 | 2.191169 |
| EXP-SETit.Ubq1:1:6 | 124 | 58703 | 46110.1 | 1.2731047 |
| EXP-Sv.Ubq1:1:7 | 128 | 29330 | 43367.1 | 0.676319 |
| EXP-Sv.Ubq1:1:8 | 132 | 53359 | 40076.4 | 1.3314306 |
| EXP-Sv.Ubq1:1:10 | 134 | 49122.7 | 53180.8 | 0.9236922 |
| EXP-Zm.UbqM1:1:6 | 137 | 37268 | 54088.1 | 0.6890239 |
| EXP-Zm.UbqM1:1:7 | 141 | 51408 | 47297.4 | 1.0869087 |
| EXP-Sb.Ubq4:1:2 | 151 | 35660.3 | 62591.1 | 0.5697347 |
| EXP-Sb.Ubq6:1:2 | 153 | 27543 | 57826.4 | 0.4763046 |
| EXP-Cl.Ubq1:1:10 | 98 | 54493.3 | 41964.1 | 1.2985699 |

TABLE 20

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| EXP sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 179 | 1.00 | 0.10 |
| P-CAMV.35S-ENH-1:1:102/ L-CAMV.35S-1:1:2 | 169 | 0.46 | 0.04 |
| EXP-CaMV.35S-enh + Ta.Lhcb1 + Os.Act1:1:1 | 163 | 10.35 | 1.00 |
| EXP-CaMV.35S-enh + Zm.DnaK:1:1 | 170 | 9.71 | 0.94 |
| EXP-ANDge.Ubq1:1:7 | 5 | 20.33 | 1.96 |
| EXP-ANDge.Ubq1:1:10 | 10 | 17.90 | 1.73 |
| EXP-ANDge.Ubq1:1:6 | 12 | 10.55 | 1.02 |
| EXP-ANDge.Ubq1:1:11 | 14 | 16.05 | 1.55 |
| EXP-ANDge.Ubq1:1:12 | 16 | 14.32 | 1.38 |
| EXP-ERIra.Ubq1:1:9 | 22 | 6.24 | 0.60 |
| EXP-ERIra.Ubq1:1:10 | 25 | 12.15 | 1.17 |
| EXP-ERIra.Ubq1:1:8 | 27 | 10.44 | 1.01 |
| EXP-ERIra.Ubq1:1:11 | 29 | 9.25 | 0.89 |
| EXP-ERIra.Ubq1:1:12 | 31 | 13.45 | 1.30 |
| EXP-SETit.Ubq1:1:5 | 117 | 12.30 | 1.19 |
| EXP-SETit.Ubq1:1:7 | 123 | 39.26 | 3.79 |
| EXP-SETit.Ubq1:1:6 | 124 | 22.81 | 2.20 |
| EXP-Sv.Ubq1:1:7 | 128 | 12.12 | 1.17 |
| EXP-Sv.Ubq1:1:8 | 132 | 23.86 | 2.30 |
| EXP-Sv.Ubq1:1:10 | 134 | 16.55 | 1.60 |
| EXP-Zm.UbqM1:1:6 | 137 | 12.35 | 1.19 |
| EXP-Zm.UbqM1:1:7 | 141 | 19.48 | 1.88 |
| EXP-Sb.Ubq4:1:2 | 151 | 10.21 | 0.99 |
| EXP-Sb.Ubq6:1:2 | 153 | 8.54 | 0.82 |
| EXP-Cl.Ubq1:1:10 | 98 | 23.27 | 2.25 |

As can be seen in Table 20 above, nearly all of the EXP sequences were capable of driving GUS transgene expression in wheat cells. GUS transgene expression driven by EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) was much higher than GUS expression driven by EXP-Os.Act1:11:9. GUS expression of the amplicons in wheat leaf protoplast cells relative to EXP-CaMV.35S-enh+Ta.Lhcb1+Os.Act1:1:1 was slightly different from the expression observed in corn protoplast cells. Each of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ IIS NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141) and EXP-Cl.Ubq1:1:10 (SEQ ID NO: 98) demonstrated higher levels of GUS expression relative to EXP-CaMV.35S-enh+Ta.Lhcb1+Os.Act1:1:1. The EXP sequences EXP-ERIra.Ubq1:1:9 (SEQ ID NO: 22), EXP-ERIra.Ubq1:1:11 (SEQ ID NO: 29), EXP-Sb.Ubq4:1:2 (SEQ ID NO: 151) and EXP-Sb.Ubq6:1:2 (SEQ ID NO: 153) demonstrated lower levels of GUS expression relative to EXP-CaMV.35S-enh+Ta.Lhcb1+Os.Act1:1:1.

In a second set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 21 below shows the mean. GUS and luciferase values determined for each amplicon. Table 22 below shows the GUS/RLuc ratios of expression normalized with respect to EXP-Os.Act1:1:9 and EXP-CaMV.35S-enh+Zm.DnaK:1:1 driven expression in corn protoplasts.

TABLE 21

Mean GUS and Luciferase activity in transformed wheat leaf protoplast cells.

| Amplicon ID | EXP sequence | SEQ ID NO: | GUS | RLuc |
|---|---|---|---|---|
| PCR0145942 | EXP-Os.Act1:1:9 | 179 | 1234 | 176970.5 |
| PCR0145944 | EXP-CaMV.35S-enh + Zm.DnaK:1:1 | 170 | 12883.5 | 119439 |
| PCR0146628 | EXP-ANDge.Ubq1:1:8 | 8 | 38353.3 | 171535.3 |
| PCR0145922 | EXP-Cl.Ubq1:1:10 | 98 | 34938 | 154245.8 |
| PCR0145945 | EXP-Cl.Ubq1:1:13 | 114 | 32121 | 122220.8 |
| PCR0145946 | EXP-Cl.Ubq1:1:14 | 115 | 56814 | 143318.3 |
| PCR0145947 | EXP-Cl.Ubq1:1:15 | 116 | 1890.5 | 167178.5 |

TABLE 22

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 15.47 | 1.00 |
| EXP-ANDge.Ubq1:1:8 | 8 | 32.07 | 2.07 |
| EXP-Cl.Ubq1:1:10 | 98 | 32.48 | 2.10 |
| EXP-Cl.Ubq1:1:13 | 114 | 37.69 | 2.44 |
| EXP-Cl.Ubq1:1:14 | 115 | 56.85 | 3.68 |
| EXP-Cl.Ubq1:1:15 | 116 | 1.62 | 0.10 |

As can be seen in Table 22 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a third set of experiments, amplicon GUS transgene cassettes were made as described above to assay expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK:1:1 (SEQ ID NO: 170). Table 23 below shows the mean GUS and luciferase values determined for each amplicon. Table 24 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 23

Mean GUS and Luciferase activity in transformed wheat leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 478 | 46584.5 | 2709.75 |
| PCR0145944 | EXP-CaMV.35S-enh + Zm.DnaK:1:1 | 170 | 8178.5 | 43490.8 | 2927.25 |
| PCR0145922 | EXP-Cl.Ubq1:1:10 | 98 | 22068.3 | 47662.3 | 1289 |
| pMON146750 | EXP-Cl.Ubq1:1:16 | 93 | 34205 | 45064.5 | 1379.63 |
| pMON146751 | EXP-Cl.Ubq1:1:17 | 97 | 31758 | 45739.3 | 2820.75 |

TABLE 24

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| Amplicon ID | EXP sequence | SEQ ID NO: | GUS/RLuc relative to EXP-OsAct:1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.05 | 0.06 |
| PCR0145944 | EXP-CaMV.35S-enh + Zm.DnaK:1:1 | 170 | 18.33 | 15.84 | 1.00 | 1.00 |
| PCR0145922 | EXP-Cl.Ubq1:1:10 | 98 | 45.12 | 97.05 | 2.46 | 6.13 |
| pMON146750 | EXP-Cl.Ubq1:1:16 | 93 | 73.97 | 140.55 | 4.04 | 8.87 |
| pMON146751 | EXP-Cl.Ubq1:1:17 | 97 | 67.67 | 63.82 | 3.69 | 4.03 |

As can be seen in Table 24 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fourth set of experiments, amplicon GUS transgene cassettes were made as described above to assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:11:1 (SEQ ID NO: 163). Table 25 below shows the mean GUS and luciferase values determined for each amplicon. Table 26 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 25

Mean GUS and Luciferase activity in transformed wheat leaf protoplast cells.

| Template | Amplicon ID | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 67459.13 | 11682.00 |
| pMON25455 | PCR0145942 | EXP-Os.Act1:1:9 | 179 | 56618.33 | 16654.83 |
| pMON131962 | pMON131962 | EXP-Zm.UbqM1:1:11 | 149 | 53862.13 | 10313.75 |
| pMON132047 | pMON132047 | EXP-Cl.Ubq1:1:23 | 108 | 38869.38 | 12279.00 |

TABLE 26

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| Amplicon ID | EXP sequence | SEQ ID NO: | GUS/RLuc relative to EXP-Os.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 1.70 | 1.00 |
| PCR0145942 | EXP-Os.Act1:1:9 | 179 | 1.00 | 0.59 |
| pMON131962 | EXP-Zm.UbqM1:1:11 | 149 | 1.54 | 0.90 |
| pMON132047 | EXP-Cl.Ubq1:1:23 | 108 | 0.93 | 0.55 |

As can be seen in Table 26 above, the EXP sequences, EXP-Zm.UbqM1:1:11 (SEQ ID NO: 149) and EXP-Cl.Ubq1:1:23 (SEQ ID NO: 108) were able to drive GUS expression in wheat leaf protoplasts. Expression was similar to that of the control, EXP-Os.Act1:11:9 (SEQ ID NO: 179) and lower than that of EXP-CaMV.35S-enh+Ta.Lhcb1+Os.Act1:1:1 (SEQ ID NO: 163).

Example 5: Analysis of Regulatory Elements Driving GUS in Sugarcane Protoplasts Using GUS Transgene Cassette Amplicons Sugarcane leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Sugarcane protoplast cells derived from leaf tissue were transformed using a PEG-based transformation method, as described in Example 3 above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) and presented in Table 27 below, with that of known constitutive promoters.

TABLE 27

GUS plant expression amplicons and corresponding plasmid construct amplicon template and EXP sequence.

| Amplicon ID | Amplicon Template | EXP sequence | SEQ ID NO: |
|---|---|---|---|
| PCR0145942 | pMON25455 | EXP-Os.Act1:1:9 | 179 |
| PCR0145944 | pMON81552 | EXP-CaMV.35S-enh + Zm.DnaK:1:1 | 170 |
| PCR0145892 | pMON136264 | EXP-ANDge.Ubq1:1:7 | 5 |
| PCR0145815 | pMON136264 | EXP-ANDge.Ubq1:1:10 | 10 |
| PCR0145893 | pMON136259 | EXP-ANDge.Ubq1:1:6 | 12 |
| PCR0145817 | pMON136264 | EXP-ANDge.Ubq1:1:11 | 14 |
| PCR0145819 | pMON136264 | EXP-ANDge.Ubq1:1:12 | 16 |
| PCR0145896 | pMON136263 | EXP-ERIra.Ubq1:1:9 | 22 |
| PCR0145820 | pMON136263 | EXP-ERIra.Ubq1:1:10 | 25 |
| PCR0145897 | pMON136258 | EXP-ERIra.Ubq1:1:8 | 27 |
| PCR0145821 | pMON136263 | EXP-ERIra.Ubq1:1:11 | 29 |
| PCR0145822 | pMON136263 | EXP-ERIra.Ubq1:1:12 | 31 |
| PCR0145922 | pMON140889 | EXP-Cl.Ubq1:1:10 | 98 |
| PCR0145945 | pMON140889 | EXP-Cl.Ubq1:1:13 | 114 |
| PCR0145946 | pMON140889 | EXP-Cl.Ubq1:1:14 | 115 |
| PCR0145947 | pMON140889 | EXP-Cl.Ubq1:1:15 | 116 |

Control GUS cassette amplicons and Luciferase plasmids used for sugarcane protoplast transformation were also the same as those presented in Examples 2 through 4 and provided in Table 7 above in Example 3. Likewise, negative controls were used for the determination of GUS and luciferase background, as described above. Table 28 lists mean GUS and Luc activity seen in transformed sugarcane leaf protoplast cells, and Table 29 shows normalized GUS/RLuc ratios of expression in sugarcane leaf protoplasts.

TABLE 28

Mean GUS and Luciferase activity in transformed wheat leaf protoplast cells.

| EXP sequence | SEQ ID NO: | GUS | RLuc | FLuc |
|---|---|---|---|---|
| EXP-Os.Act1:1:9 | 179 | 6667.5 | 3024.5 | 1129.25 |
| EXP-CaMV.35S-enh + Zm.DnaK:1:1 | 170 | 14872.8 | 5171 | 2019.5 |
| EXP-ANDge.Ubq1:1:7 | 5 | 15225 | 4618.25 | 1775.75 |
| EXP-ANDge.Ubq1:1:10 | 10 | 17275.3 | 4333 | 1678 |
| EXP-ANDge.Ubq1:1:6 | 12 | 17236 | 5633.25 | 2240 |
| EXP-ANDge.Ubq1:1:11 | 14 | 22487.8 | 6898.25 | 2878 |
| EXP-ANDge.Ubq1:1:12 | 16 | 22145.3 | 6240.25 | 2676.5 |
| EXP-ERIra.Ubq1:1:9 | 22 | 16796.5 | 7759.75 | 3179 |
| EXP-ERIra.Ubq1:1:10 | 25 | 16267.5 | 5632.75 | 2436.75 |
| EXP-ERIra.Ubq1:1:8 | 27 | 25351 | 9019.5 | 4313.5 |
| EXP-ERIra.Ubq1:1:11 | 29 | 16652.3 | 3672.25 | 1534 |
| EXP-ERIra.Ubq1:1:12 | 31 | 12654.5 | 3256.75 | 1261.5 |
| EXP-Cl.Ubq1:1:10 | 98 | 22383.8 | 7097.5 | 3109.25 |
| EXP-Cl.Ubq1:1:13 | 114 | 14532.3 | 2786.5 | 1198.25 |
| EXP-Cl.Ubq1:1:14 | 115 | 19244.5 | 3455.25 | 1475 |
| EXP-Cl.Ubq1:1:15 | 116 | 6676.5 | 3870.25 | 1497.75 |

TABLE 29

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in sugarcane leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.77 | 0.80 |
| EXP-CaMV.35S-enh + Zm.DnaK:1:1 | 170 | 1.30 | 1.25 | 1.00 | 1.00 |
| EXP-ANDge.Ubq1:1:7 | 5 | 1.50 | 1.45 | 1.15 | 1.16 |
| EXP-ANDge.Ubq1:1:10 | 10 | 1.81 | 1.74 | 1.39 | 1.40 |
| EXP-ANDge.Ubq1:1:6 | 12 | 1.39 | 1.30 | 1.06 | 1.04 |
| EXP-ANDge.Ubq1:1:11 | 14 | 1.48 | 1.32 | 1.13 | 1.06 |
| EXP-ANDge.Ubq1:1:12 | 16 | 1.61 | 1.40 | 1.23 | 1.12 |
| EXP-ERIra.Ubq1:1:9 | 22 | 0.98 | 0.89 | 0.75 | 0.72 |
| EXP-ERIra.Ubq1:1:10 | 25 | 1.31 | 1.13 | 1.00 | 0.91 |
| EXP-ERIra.Ubq1:1:8 | 27 | 1.27 | 1.00 | 0.98 | 0.80 |
| EXP-ERIra.Ubq1:1:11 | 29 | 2.06 | 1.84 | 1.58 | 1.47 |
| EXP-ERIra.Ubq1:1:12 | 31 | 1.76 | 1.70 | 1.35 | 1.36 |
| EXP-Cl.Ubq1:1:10 | 98 | 1.43 | 1.22 | 1.10 | 0.98 |
| EXP-Cl.Ubq1:1:13 | 114 | 2.37 | 2.05 | 1.81 | 1.65 |
| EXP-Cl.Ubq1:1:14 | 115 | 2.53 | 2.21 | 1.94 | 1.77 |
| EXP-Cl.Ubq1:1:15 | 116 | 0.78 | 0.75 | 0.60 | 0.61 |

As can be seen in Table 29 above, the EXP sequences EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), (SEQ ID NO: 29), EXP-ERIra.Ubq1:1:12 ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were all capable of driving transgene expression in sugarcane protoplasts. The EXP sequences, EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) expressed GUS higher than EXP-CaMV.35S-enh+Zm.DnaK:1:1 (SEQ ID NO: 170) in this experiment.

Example 6: Analysis of Regulatory Elements Driving CP4 in Corn Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151) and EXP-Sb.Ubq6:1:2 (SEQ ID NO: 153) in driving expression of glyphosate tolerance gene CP4 in corn protoplasts. These EXP sequences were cloned into plant binary transformation plasmid constructs using methods known in the art. The resulting plant expression vectors contained a right border region from *A. tumefaciens*, an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 3' UTR and a left border region from *A. tumefaciens* (B-AGRtu.left border). The resulting plasmid constructs were used to transform corn leaf protoplasts cells using methods known in the art.

Plasmid constructs listed in Table 30, with EXP sequences as defined in Table 1, were utilized. Three control plasmids (pMON30098, pMON42410, and pMON30167), with known constitutive regulatory elements driving either CP4 or GFP, were constructed and used to compare the relative CP4 expression levels driven by these EXP sequences with CP4 expression driven by known constitutive expression elements. Two other plasmids (pMON19437 and pMON63934) were also used as described above to evaluate transformation efficiency and viability. Each plasmid contains a specific luciferase coding sequence driven by a constitutive EXP sequence.

Corn leaf protoplasts were transformed using a PEG-based transformation method, as described in Example 2 above. Measurements of both CP4 and luciferase were conducted similarly to Example 2 above. The average levels of CP4 protein expression expressed as part per million (ppm) is shown in Table 30 below.

TABLE 30

Average CP4 protein expression in corn leaf protoplasts.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON42410 | EXP-CaMV.35S-enh + Ta.Lhcb1 + Os.Act1:1:1 | 163 | 34.1 | 15.6 |
| pMON30167 | EXP-Os.Act1:1:1 | 164 | 40.4 | 11.6 |
| pMON129203 | EXP-Sv.Ubq1:1:7 | 128 | 45.2 | 6.2 |
| pMON129204 | EXP-Sv.Ubq1:1:8 | 132 | 101.9 | 13.8 |
| pMON129205 | EXP-Sv.Ubq1:1:9 | 133 | 71.1 | 8.7 |
| pMON129210 | EXP-Zm.UbqM1:1:6 | 137 | 137.1 | 14.8 |
| pMON129211 | EXP-Zm.UbqM1:1:8 | 145 | 136.5 | 12.3 |
| pMON129212 | EXP-Zm.UbqM1:1:7 | 141 | 170.2 | 18.1 |
| pMON129200 | EXP-SETit.Ubq1:1:5 | 117 | 44.3 | 9.5 |
| pMON129201 | EXP-SETit.Ubq1:1:7 | 123 | 105.1 | 8.4 |
| pMON129202 | EXP-SETit.Ubq1:1:6 | 124 | 124.9 | 33.7 |
| pMON129219 | EXP-Sb.Ubq4:1:2 | 151 | 14.3 | 1 |
| pMON129218 | EXP-Sb.Ubq6:1:2 | 153 | 75.7 | 8.9 |

As can be seen in Table 30, EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124) and EXP-Sb.Ubq6:1:2 (SEQ ID NO: 153) drove expression of the CP4 transgene at levels close to or higher than CP4 expression levels driven by EXP-CaMV.35S-enh+Ta.Lhcb1+Os.Act1:1:1 and EXP-Os.Act1:1:1. The EXP sequence, EXP-Sb.Ubq4:1:2 (SEQ ID NO: 151) demonstrated the ability to drive expression of CP4, but the level of expression was lower than that of the constitutive controls.

Similar data to that above may also be obtained from plants stably transformed with plasmid constructs described above, for instance, plants of progeny generation(s) $R_0$, $R_1$ or $F_1$ or later. Likewise, expression from other plasmid constructs may be studied. For instance, pMON141619, comprises the EXP sequence EXP-ANDge.Ubq1:1:8, while pMON142862 is comprised of the EXP sequence EXP-ERIra.Ubq1:1:8. These and other constructs may be analyzed in this manner.

Example 7: Analysis of Regulatory Elements Driving CP4 in Corn Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in corn protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 3' TIM and a left border region from *A. tumefaciens*. The resulting amplicons were used to transform corn leaf protoplasts cells.

Corn leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 31 and 32 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed corn leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 31 below.

TABLE 31

Average CP4 protein expression in corn leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.0 | 0.0 |
| pMON30098 | | GFP (negative control) | | 0.0 | 0.0 |
| pMON19469 | PCR24 | EXP-CaMV.35S-enh + Zm.DnaK:1:1 | 170 | 605.5 | 27.6 |
| pMON30167 | PCR25 | EXP-Os.Act1:1:1 | 164 | 50.6 | 14.2 |
| pMON140896 | PCR41 | EXP-ANDge.Ubq1:1:7 | 5 | 459.0 | 60.9 |
| pMON140917 | PCR42 | EXP-ANDge.Ubq1:1:8 | 8 | 258.2 | 38.4 |
| pMON140897 | PCR43 | EXP-ANDge.Ubq1:1:10 | 10 | 324.8 | 21.6 |

TABLE 31-continued

| Average CP4 protein expression in corn leaf protoplasts. | | | | | |
|---|---|---|---|---|---|
| Amplicon Template | Amplicon ID | EXP sequence | SEQ ID NO: | CP4 ng/mg total protein Average | CP4 ng/mg total protein STDEV |
| pMON140898 | PCR44 | EXP-ANDge.Ubq1:1:6 | 12 | 394.9 | 66.4 |
| pMON140899 | PCR45 | EXP-ANDge.Ubq1:1:11 | 14 | 508.7 | 89.6 |
| pMON140900 | PCR46 | EXP-ANDge.Ubq1:1:12 | 16 | 329.3 | 14.5 |
| pMON140904 | PCR50 | EXP-ERIra.Ubq1:1:9 | 22 | 148.6 | 24.4 |
| pMON140905 | PCR51 | EXP-ERIra.Ubq1:1:10 | 25 | 215.8 | 22.6 |
| pMON140906 | PCR52 | EXP-ERIra.Ubq1:1:8 | 27 | 376.6 | 44.1 |
| pMON140907 | PCR53 | EXP-ERIra.Ubq1:1:11 | 29 | 459.9 | 104.7 |
| pMON140908 | PCR54 | EXP-ERIra.Ubq1:1:12 | 31 | 221.6 | 15.9 |
| pMON140913 | PCR19 | EXP-Cl.Ubq1:1:10 | 98 | 287.8 | 50.9 |
| pMON140914 | PCR20 | EXP-Cl.Ubq1:1:13 | 114 | 585.8 | 47.9 |
| pMON140915 | PCR21 | EXP-Cl.Ubq1:1:14 | 115 | 557.5 | 76.6 |
| pMON140916 | PCR22 | EXP-Cl.Ubq1:1:15 | 116 | 33.2 | 9.5 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIa.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were lower than that of EXP-CaMV.35S-enh+Zm.DnaK:1:1 (SEQ ID NO: 170).

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed corn leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 32

| Average CP4 protein expression in corn leaf protoplasts. | | | | | |
|---|---|---|---|---|---|
| Amplicon Template | Amplicon ID | EXP sequence | SEQ ID NO: | Maize Leaf CP4 mg/total protein Avg | Maize Leaf CP4 mg/total protein StdDev |
| pMON30167 | PCR25 | EXP-Os.Act1:1:1 | 164 | 12.2 | 1.69 |
| pMON140913 | PCR19 | EXP-Cl.Ubq1:1:10 | 98 | 307.5 | 24.21 |
| pMON142748 | pMON142748 | EXP-Cl.Ubq1:1:16 | 93 | 245.95 | 30.14 |
| pMON142749 | pMON142749 | EXP-Cl.Ubq1:1:17 | 97 | 302.85 | 25.32 |

As can be seen in Table 32 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 8: Analysis of Regulatory Elements Driving CP4 in Wheat Protoplasts

This example illustrates the ability of EXP-Sv.Ubq1:1:7 (SEQ ID NO: 128), EXP-Sv.Ubq1:1:18 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151) and EXP-Sb.Ubq6:1:2 (SEQ ID NO: 153) to drive CP4 expression in wheat leaf protoplasts. These EXP sequences were cloned into plant binary transformation plasmid constructs using methods known in the art, and as described in Examples 2 and 5 above.

Three control plasmids (pMON30098, pMON42410, as previously described, and pMON43647 comprising a right border region from *Agrobacterium tumefaciens* with EXP-Os.Act1+CaMV.35S.2xA1-B3+Os.Ac1:1:1 (SEQ ID NO: 138) operably linked 5' to a plastid targeted glyphosate tolerance coding sequence (CP4, U.S. Pat. No. RE39247), operably linked 5' to T-AGRtu.nos-1:1:1.3, and a left border region (B-AGRtu.left border) with known constitutive regulatory elements driving either CP4 or GFP were constructed as outlined in Example 5.

Wheat leaf protoplasts were transformed using a PEG-based transformation method as described in the previous examples with the exception that $1.5\times10^5$ protoplast cells per assay were used. Assays of luciferase and CP4 transgene expression were performed as described in Example 6 above. The mean CP4 expression levels determined by CP4 ELISA are presented in Table 34 below.

TABLE 34

| Mean CP4 Protein Expression in Wheat Leaf Protoplast Cells. | | | | |
|---|---|---|---|---|
| Plasmid | EXP sequence | SEQ ID NO: | CP4 Average ppm | CP4 STDEV ppm |
| No DNA | No DNA | | 0 | 0 |
| pMON30098 | GFP | | 0 | 0 |
| pMON43647 | EXP-Os.Act1 + CaMV.35S.2xA1-B3 + Os.Act1:1:1 | 172 | 656.2 | 124.5 |
| pMON42410 | EXP-CaMV.35S-enh + Ta.Lhcb1 + Os.Act1:1:1 | 163 | 438.3 | 78.9 |
| pMON30167 | EXP-Os.Act1:1:1 | 164 | 583 | 107.4 |
| pMON129203 | EXP-Sv.Ubq1:1:7 | 128 | 156.9 | 25.1 |
| pMON129204 | EXP-Sv.Ubq1:1:8 | 132 | 39.5 | 7 |
| pMON129205 | EXP-Sv.Ubq1:1:9 | 133 | 154.5 | 56.5 |
| pMON129210 | EXP-Zm.UbqM1:1:6 | 137 | 1500 | 0 |
| pMON129211 | EXP-Zm.UbqM1:1:8 | 145 | 199.7 | 64.9 |
| pMON129212 | EXP-Zm.UbqM1:1:7 | 141 | 234.6 | 66.9 |
| pMON129200 | EXP-SETit.Ubq1:1:5 | 117 | 725.7 | 149.7 |
| pMON129201 | EXP-SETit.Ubq1:1:7 | 123 | 64.9 | 14.5 |
| pMON129202 | EXP-SETit.Ubq1:1:6 | 124 | 122.9 | 48.7 |
| pMON129219 | EXP-Sb.Ubq4:1:2 | 151 | 113.1 | 32.8 |

The total amount of CP4 expression in wheat protoplasts driven by the EXP sequences and the known constitutive EXP sequence EXP-CaMV.35S-enh+Ta.Lhcb1+Os.Act1:1:1 demonstrated different levels of CP4 expression in wheat protoplasts when compared to corn protoplasts.

Several EXP sequences drove CP4 expression at lower levels in wheat protoplasts than the known constitutive EXP sequences EXP-Os.Act1+CaMV.35S.2xA1-B3+Os.Act1:1:1 and EXP-CaMV.35S-enh+Ta.Lhcb1+Os.Act1:1:1. Two EXP sequences, EXP-Zm.UbqM1:1:6 (SEQ ID NO: 137), and EXP-SETit.Ubq1:1:5 (SEQ ID NO: 117), provide higher levels of CP4 expression in wheat protoplasts than the known constitutive, EXP sequences in this assay. EXP-Zm.UbqM1:1:2 drove expression of CP4 at the highest level, with expression levels being 2.2 to 3.4 fold higher than EXP-Os.Act1+CaMV.35S.2xA1-B3+Os.Act1:1:1 and EXP-CaMV.35S-enh+Ta.Lhcb1+Os.Act1:1:1, respectively. All EXP sequences assayed demonstrated the capacity to drive expression of CP4 in wheat cells.

Example 9: Analysis of Regulatory Elements Driving CP4 in Wheat Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in wheat protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 3' UTR and a left border region from *A. tumefaciens*. The resulting amplicons were used to transform corn leaf protoplasts cells.

Wheat leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 35 and 36 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 35 below.

TABLE 35

| Average CP4 protein expression in wheat leaf protoplasts. | | | | | |
|---|---|---|---|---|---|
| Amplicon Template | Amplicon ID | EXP sequence | SEQ ID NO: | CP4 ng/mg total protein Average | CP4 ng/mg total protein STDEV |
| | | no DNA | | 0.00 | 0.00 |
| pMON30098 | | GFP (negative control) | | 0.00 | 0.00 |
| pMON19469 | PCR24 | EXP-CaMV.35S-enh + Zm.DnaK:1:1 | 170 | 76.11 | 18.65 |
| pMON30167 | PCR25 | EXP-Os.Act1:1:1 | 164 | 3.83 | 0.73 |
| pMON140896 | PCR41 | EXP-ANDge.Ubq1:1:7 | 5 | 103.46 | 16.31 |
| pMON140917 | PCR42 | EXP-ANDge.Ubq1:1:8 | 8 | 61.48 | 1.99 |
| pMON140897 | PCR43 | EXP-ANDge.Ubq1:1:10 | 10 | 62.65 | 4.58 |
| pMON140898 | PCR44 | EXP-ANDge.Ubq1:1:6 | 12 | 48.74 | 3.09 |
| pMON140899 | PCR45 | EXP-ANDge.Ubq1:1:11 | 14 | 54.91 | 3.50 |
| pMON140900 | PCR46 | EXP-ANDge.Ubq1:1:12 | 16 | 42.81 | 5.97 |
| pMON140904 | PCR50 | EXP-ERIra.Ubq1:1:9 | 22 | 31.26 | 1.69 |

TABLE 35-continued

| Average CP4 protein expression in wheat leaf protoplasts. | | | | | |
|---|---|---|---|---|---|
| Amplicon Template | Amplicon ID | EXP sequence | SEQ ID NO: | CP4 ng/mg total protein Average | CP4 ng/mg total protein STDEV |
| pMON140905 | PCR51 | EXP-ERIra.Ubq1:1:10 | 25 | 49.82 | 5.96 |
| pMON140906 | PCR52 | EXP-ERIra.Ubq1:1:8 | 27 | 37.43 | 4.52 |
| pMON140907 | PCR53 | EXP-ERIra.Ubq1:1:11 | 29 | 27.17 | 0.96 |
| pMON140908 | PCR54 | EXP-ERIra.Ubq1:1:12 | 31 | 17.41 | 4.13 |
| pMON140913 | PCR19 | EXP-Cl.Ubq1:1:10 | 98 | 66.66 | 13.45 |
| pMON140914 | PCR20 | EXP-Cl.Ubq1:1:13 | 114 | 79.42 | 10.74 |
| pMON140915 | PCR21 | EXP-Cl.Ubq1:1:14 | 115 | 75.53 | 9.32 |
| pMON140916 | PCR22 | EXP-Cl.Ubq1:1:15 | 116 | 0.00 | 0.00 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were around the same level or lower than that of EXP-CaMV.35S-enh+Zm.DnaK:1:1 (SEQ ID NO: 170) for most of the EXP sequences.

In a second series of experiments, expression of CP4 driven by amplicons comprised of the EXP sequences EXP-Cl.Ubq1:11:10 (SEQ ID NO: 98), EXP-Cl.Ubq1:1:16 (SEQ ID NO: 93) and EXP-Cl.Ubq1:1:17 (SEQ ID NO: 97) were assayed in transformed wheat leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 36

| Average CP4 protein expression in wheat leaf protoplasts. | | | | | |
|---|---|---|---|---|---|
| Amplicon Template | Amplicon ID | EXP sequence | SEQ ID NO: | Maize Leaf CP4 mg/total protein Avg | Maize Leaf CP4 mg/total protein StdDev |
| pMON30167 | PCR25 | EXP-Os.Act1:1:1 | 164 | 15.84 | 2.12 |
| pMON140913 | PCR19 | EXP-Cl.Ubq1:1:10 | 98 | 736.32 | 79.56 |
| pMON142748 | pMON142748 | EXP-Cl.Ubq1:1:16 | 93 | 593.72 | 80.22 |
| pMON142749 | pMON142749 | EXP-Cl.Ubq1:1:17 | 97 | 763.95 | 86.94 |

As can be seen in Table 36 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 10: Analysis of Regulatory Elements Driving CP4 in Sugarcane Protoplasts This example illustrates the ability of EXP-Sv.Ubq1:1:7 (SEQ ID NO: 128), EXP-Sv.Ubq0:1:8 (SEQ ID NO: 132), EXP-Sv.Ubq1:1:9 (SEQ ID NO: 133), EXP-ZmUbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) in driving expression of CP4 in sugar cane leaf protoplasts. The EXP sequences were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 (SEQ ID NO: 127) or T-CaMV.35S-1:1:1 (SEQ ID NO: 140) 3' UTR and a left border region from *A. tumefaciens* (B-AGRtu.left border). The resulting plasmid constructs were used to transform sugarcane leaf protoplasts cells using PEG transformation method.

Plasmid constructs pMON129203, pMON12904, pMON112905, pMON129210, pMON129211, pMON129212, pMON129200, pMON1.29201, pMON129202, pMON129219, and pMON1129218 are as described in Table 12 above.

Three control plasmids (pMON301.67 described above; pMON130803 also comprising EXP-Os.Act1:1:1 (SEQ ID NO: 1.64); and pMON132804 comprising EXP-P-CaMV.35S-enh-1:1:13/L-CaMV.35S-1:1:2/I-Os.Act1-1:1:19 (SEQ ID NO: 139), with known constitutive regulatory elements driving CP4 were constructed and used to compare the relative CP4 expression levels driven by the ubiquitin EXP sequences listed in Table 37 below.

Sugarcane leaf protoplasts were transformed using a PEG-based transformation method. The mean CP4 expression levels determined by CP4 ELISA are presented in Table 37 below.

TABLE 37

Mean CP4 Protein Expression in Sugarcane Leaf Protoplast Cells.

| Plasmid Construct | EXP sequence | SEQ ID NO: | Experiment 1 CP4 Average ppm | Experiment 1 CP4 STDEV ppm | Experiment 2 CP4 Average ppm | Experiment 2 CP4 STDEV ppm |
|---|---|---|---|---|---|---|
| pMON132804 | EXP-P-CaMV.35S-enh-1:1:13/L-CaMV.35S-1:1:2/I-Os.Act1-1:1:19 | 173 | 557.97 | 194.05 | 283.63 | 95.8 |
| pMON30167 | EXP-Os.Act1:1:1 | 164 | 57.15 | 20.99 | 18.36 | 5.41 |
| pMON130803 | EXP-Os.Act1:1:1 | 164 | 34.26 | 1.61 | 16.57 | 3.71 |
| pMON129203 | EXP-Sv.Ubq1:1:7 | 128 | 89.2 | 32.46 | 56.86 | 9.55 |
| pMON129204 | EXP-Sv.Ubq1:1:8 | 132 | 87.2 | 45.87 | 98.46 | 12.93 |
| pMON129205 | EXP-Sv.Ubq1:1:9 | 133 | 263.57 | 70.14 | 72.53 | 9.25 |
| pMON129210 | EXP-Zm.UbqM1:1:6 | 137 | 353.08 | 29.16 | 199.31 | 41.7 |
| pMON129211 | EXP-Zm.UbqM1:1:8 | 145 | 748.18 | 15.1 | 411.24 | 17.12 |
| pMON129212 | EXP-Zm.UbqM1:1:7 | 141 | 454.88 | 75.77 | 215.06 | 23.22 |
| pMON129200 | EXP-SETit.Ubq1:1:5 | 117 | 150.74 | 63.21 | 91.71 | 41.35 |
| pMON129201 | EXP-SETit.Ubq1:1:7 | 123 | 119.57 | 58.1 | 102.72 | 31.12 |
| pMON129202 | EXP-SETit.Ubq1:1:6 | 124 | 43.79 | 25.77 | 97.63 | 46.07 |
| pMON129219 | EXP-Sb.Ubq4:1:2 | 151 | 95.63 | 38.69 | | |
| pMON129218 | EXP-Sb.Ubq6:1:2 | 153 | 343.34 | 119.2 | 179.75 | 51.16 |
| pMON129221 | EXP-Cl.Ubq1:1:10 | 98 | 374.8 | 205.28 | 258.93 | 38.03 |

As can be seen in Table 37 above, the EXP sequences demonstrated the ability to drive expression CP4 expression in sugarcane protoplasts. The levels of expression were similar to or greater than that of CP4 expression driven by EXP-Os.Act1:1:1 (SEQ ID NO: 164). One EXP sequence, EXP-Zm.UbqM1:1:8 (SEQ ID NO: 145), demonstrated higher levels of expression when compared to EXP-P-CaMV.35S-enh-1:1:13/L-CaMV.35S-1:1:2/I-Os.Act1-1:1:19 (SEQ ID NO: 139) in sugarcane protoplasts.

Example 11: Analysis of Regulatory Elements Driving CP4 in Sugarcane Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) in driving expression of the glyphosate tolerance gene CP4 in sugarcane protoplasts.

These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 3' TIM and a left border region from *A. tumefaciens*. The resulting amplicons were used to transform sugarcane leaf protoplasts cells.

Sugarcane leaf protoplasts were transformed using a PEG-based transformation method, as described in Example 2 above. Measurements of both CP4 were conducted using an ELBA-based assay.

Expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Table 38 below.

TABLE 38

Average CP4 protein expression in sugarcane leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON19469 | PCR24 | EXP-CaMV.35S-enh + Zm.DnaK:1:1 | 170 | 99.6 | 7.2 |
| pMON30167 | PCR25 | EXP-Os.Act1:1:1 | 164 | 0.0 | 0.0 |
| pMON140896 | PCR41 | EXP-ANDge.Ubq1:1:7 | 5 | 21.9 | 3.3 |
| pMON140917 | PCR42 | EXP-ANDge.Ubq1:1:8 | 8 | 15.4 | 1.9 |

TABLE 38-continued

| Average CP4 protein expression in sugarcane leaf protoplasts. | | | | | |
|---|---|---|---|---|---|
| Amplicon Template | Amplicon ID | EXP sequence | SEQ ID NO: | CP4 ng/mg total protein Average | CP4 ng/mg total protein STDEV |
| pMON140897 | PCR43 | EXP-ANDge.Ubq1:1:10 | 10 | 20.7 | 2.2 |
| pMON140898 | PCR44 | EXP-ANDge.Ubq1:1:6 | 12 | 21.8 | 2.8 |
| pMON140899 | PCR45 | EXP-ANDge.Ubq1:1:11 | 14 | 36.9 | 7.2 |
| pMON140900 | PCR46 | EXP-ANDge.Ubq1:1:12 | 16 | 51.7 | 5.6 |
| pMON140904 | PCR50 | EXP-ERIra.Ubq1:1:9 | 22 | 10.3 | 1.1 |
| pMON140905 | PCR51 | EXP-ERIra.Ubq1:1:10 | 25 | 25.3 | 4.7 |
| pMON140906 | PCR52 | EXP-ERIra.Ubq1:1:8 | 27 | 29.9 | 4.6 |
| pMON140907 | PCR53 | EXP-ERIra.Ubq1:1:11 | 29 | 44.0 | 7.1 |
| pMON140908 | PCR54 | EXP-ERIra.Ubq1:1:12 | 31 | 37.0 | 5.4 |
| pMON140913 | PCR19 | EXP-Cl.Ubq1:1:10 | 98 | 19.2 | 1.3 |
| pMON140914 | PCR20 | EXP-Cl.Ubq1:1:13 | 114 | 20.5 | 2.1 |
| pMON140915 | PCR21 | EXP-Cl.Ubq1:1:14 | 115 | 23.2 | 1.6 |
| pMON140916 | PCR22 | EXP-Cl.Ubq1:1:15 | 116 | 0.0 | 0.0 |

As can be seen in Table 38 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) were able to drive CP4 expression. EXP-Cl.Ubq1:1:15 (SEQ ID NO: 116) did not appear to express CP4 expression in this assay.

Example 12: Analysis of Regulatory Elements Driving GUS in Transgenic Corn

Corn plants were transformed with plant expression vectors containing a EXP sequences driving expression of the β-glucuronidase (GUS) transgene, and the resulting plants were analyzed for GUS protein expression. The ubiquitin EXP sequences were cloned into plant binary transformation plasmid constructs using methods known in the art.

The resulting plant expression vectors contain a right border region from *A. tumefaciens*, a first transgene cassette to assay the EXP sequence operably linked to a coding sequence for β-glucuronidase (GUS) that possesses the processable intron GUS-2, described above, operably linked 5' to the 3' UTR from the rice lipid transfer protein gene (T-Os.LTP-1:1:1, SEQ ID NO: 141); a second transgene selection cassette used for selection of transformed plant cells that confers resistance to the herbicide glyphosate (driven by the rice Actin 1 promoter), and a left border region from *A. tumefaciens*. The resulting plasmids were used to transform corn plants. Table 39 lists the plasmid designations, the EXP sequences and the SEQ ID NOs, which are also described in Table 1.

TABLE 39

| Binary plant transformation plasmids and the associated EXP sequences. | | | |
|---|---|---|---|
| Plasmid Construct | EXP sequence | SEQ ID NO: | Data |
| pMON142865 | EXP-ANDge.Ubq1:1:8 | 8 | $R_0$ and $R_1$ |
| pMON142864 | EXP-ERIra.Ubq1:1:8 | 27 | $R_0$ and $R_1$ |
| pMON142729 | EXP-Cl.Ubq1:1:12 | 90 | $R_0$ |
| pMON142730 | EXP-Cl.Ubq1:1:11 | 95 | $R_0$ |
| pMON132047 | EXP-Cl.Ubq1:1:23 | 108 | $R_0$ |
| pMON132037 | EXP-SETit.Ubq1:1:10 | 119 | $R_0$ and $F_1$ |
| pMON131957 | EXP-SETit.Ubq1:1:11 | 125 | F1 |
| pMON131958 | EXP-Sv.Ubq1:1:11 | 130 | $R_0$ and $F_1$ |
| pMON131959 | EXP-Sv.Ubq1:1:12 | 136 | $R_0$ |
| pMON131961 | EXP-Zm.UbqM1:1:10 | 139 | $R_0$ |
| pMON131963 | EXP-Zm.UbqM1:1:12 | 143 | $R_0$ |
| pMON131962 | EXP-Zm.UbqM1:1:11 | 149 | $R_0$ |
| pMON132932 | EXP-Sb.Ubq4:1:2 | 151 | $R_0$ |
| pMON132931 | EXP-Sb.Ubq6:1:3 | 155 | $R_0$ |
| pMON132974 | EXP-Sb.Ubq7:1:2 | 157 | $R_0$ and $F_1$ |

Plants were transformed using *Agrobacterium*-mediated transformations, for instance as described in U.S. Patent Application Publication 20090138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves as well as the anther, silk and developing seed and embryo 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 40 and 41 below. The $R_0$ GUS assay performed on transformants transformed with pMON1:31957 (EXP-SETit.Ubq1:1:11, SEQ ID NO:125) did not pass quality standards. These transformants were assayed at F1 generation and are presented further below in this example.

TABLE 40

Average $R_0$ GUS expression in root and leaf tissue.

| EXP sequence | SEQ ID NO: | V3 Root | V4 Root | V7 Root | VT Moot | V3 Leaf | V4 Leaf | V7 Leaf | VT Leaf |
|---|---|---|---|---|---|---|---|---|---|
| EXP-ANDge.Ubq1:1:8 | 8 | nd | 255 | 199 | 70 | nd | 638 | 168 | 130 |
| EXP-ERIra.Ubq1:1:8 | 27 | nd | 477 | 246 | 62 | nd | 888 | 305 | 242 |
| EXP-Cl.Ubq1:1:12 | 90 | nd | 27 | 147 | 52 | nd | 75 | 189 | 199 |
| EXP-Cl.Ubq1:1:11 | 95 | nd | 28 | 77 | 50 | nd | 101 | 177 | 223 |
| EXP-Cl.Ubq1:1:23 | 108 | 0 | nd | 75 | 34 | 201 | nd | 194 | 200 |
| EXP-SETit.Ubq1:1:10 | 119 | 0 | nd | 29 | 57 | 58 | nd | 37 | 46 |
| EXP-Sv.Ubq1:1:11 | 130 | nd | nd | nd | 9 | 20 | nd | 55 | 29 |
| EXP-Sv.Ubq1:1:12 | 136 | 63 | nd | 0 | 28 | 184 | nd | 27 | 16 |
| EXP-Zm.UbqM1:1:10 | 139 | 0 | nd | 237 | 18 | 221 | nd | 272 | 272 |
| EXP-Zm.UbqM1:1:12 | 143 | 0 | nd | 21 | 43 | 234 | nd | 231 | 196 |
| EXP-Zm.UbqM1:1:11 | 149 | 124 | nd | 103 | 112 | 311 | nd | 369 | 297 |
| EXP-Sb.Ubq4:1:2 | 151 | 125 | nd | 0 | 95 | 233 | nd | 150 | 88 |
| EXP-Sb.Ubq6:1:3 | 155 | 154 | nd | 13 | 128 | 53 | nd | 39 | 55 |
| EXP-Sb.Ubq7:1:2 | 157 | 37 | nd | 22 | 18 | 165 | nd | 89 | 177 |

TABLE 41

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-ANDge.Ubq1:1:8 | 8 | 247 | 256 | 24 | 54 |
| EXP-ERIra.Ubq1:1:8 | 27 | 246 | 237 | 36 | 61 |
| EXP-Cl.Ubq1:1:12 | 90 | 420 | 121 | 26 | 220 |
| EXP-Cl.Ubq1:1:11 | 95 | 326 | 227 | 41 | 221 |
| EXP-Cl.Ubq1:1:23 | 108 | 598 | 416 | 212 | 234 |
| EXP-SETit.Ubq1:1:10 | 119 | 132 | 85 | 50 | 63 |
| EXP-Sv.Ubq1:1:11 | 130 | 217 | 3 | 45 | 92 |
| EXP-Sv.Ubq1:1:12 | 136 | 120 | 21 | 49 | 112 |
| EXP-Zm.UbqM1:1:10 | 139 | 261 | 506 | 403 | 376 |
| EXP-Zm.UbqM1:1:12 | 143 | 775 | 362 | 253 | 247 |
| EXP-Zm.UbqM1:1:11 | 149 | 551 | 452 | 234 | 302 |
| EXP-Sb.Ubq4:1:2 | 151 | 213 | 0 | 25 | 79 |
| EXP-Sb.Ubq6:1:3 | 155 | 295 | 87 | 51 | 61 |
| EXP-Sb.Ubq7:1:2 | 157 | 423 | 229 | 274 | 90 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, high levels of GUS expression were observed in early stages of root development (V4 and V7) for EXP-ANDge.Ubq1:1:8 (SEQ ID NO: 8) and EXP-ERIra.Ubq1:1:8 (SEQ ID NO: 27) and declined by VT stage. Root expression driven by EXP-Zm.UbqM1:1:10 (SEQ ID NO: 139) demonstrated no expression at V3 but was high at V7 and then dropped by VT stage. Root expression driven by EXP-Zm.UbqM1:1:11 (SEQ ID NO: 149) was maintained to a similar level throughout development from stages V3, V7 through VT. Root expression was observed to increase from early development (V3/V4) to V7 stage and then drop from V7 to V8 stage in plants transformed with EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108). GUS expression levels showed dramatic differences in leaf tissue as well. The highest levels of leaf expression were conferred in early development (V3/V4) with EXP-ANDge.Ubq1:1:8 (SEQ ID NO: 8) and EXP-ERIra.Ubq1:1:8 (SEQ ID NO: 27) which decline at V7 through VT stage. GUS expression is retained from V3 through VT stage using EXP-ZmUbqM1:1:10 (SEQ ID NO: 139), EXP-Zm.UbqM1:1:11 (SEQ ID NO: 149), EXP-Zm.UbqM1:1:12 (SEQ ID NO: 143) and EXP-Cl.Ubq1:1:23 (SEQ ID NO: 108); and to a lower extent using. EXP-SETit.Ubq1:1:10 (SEQ ID NO: 119) and EXP-Sb.Ubq6:1:3 (SEQ ID NO: 155). Expression in the leaf increased from V3 to V7 to VT stage using EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108) while expression declined from V3 to VT stage using EXP-Sv.Ubq1:1:12 (SEQ ID NO: 136) and EXP-Sb.Ubq4:1:2 (SEQ ID NO: 151).

Likewise, with respect to reproductive tissue (anther and silk) and developing seed (21DAP embryo and endosperm) different patterns of expression were observed unique to each EXP sequence. For example, High levels of expression were observed in anther and silk as well as the developing seed using EXP-Zm.UbqM1:1:10 (SEQ ID NO: 139), EXP-Zm.UbqM1:1:11 (SEQ ID NO: 149), EXP-Zm.UbqM1:1:12 (SEQ ID NO: 143) and EXP-Cl.Ubq1:1:23 (SEQ ID NO: 108). Expression was high in the anther and silk but low in the developing seed using EXP-ANDge.Ubq1:1:8 (SEQ ID NO: 8) and EXP-ERIra.Ubq1:1:8 (SEQ ID NO: 27). Expression driven by EXP-Sb.Ubq7:1:2 (SEQ ID NO: 157) was high in reproductive tissue and high in the developing embryo but was lower in the developing endosperm. The EXP sequence, EXP-Sb.Ubq4:1:2 (SEQ ID NO: 151) only demonstrated expression in the anther but not in the silk and expressed much lower in the developing seed. EXP-Sv.Ubq1:1:11 (SEQ ID NO: 130) demonstrated a similar pattern as EXP-Sb.Ubq4:1:2 (SEQ ID NO: 151) with respect to reproductive tissue and developing seed, but whereas EXP-Sb.Ubq4:1:2 (SEQ ID NO: 151) showed expression in root and leaf tissues, EXP-Sv.Ubq1:1:11 (SEQ ID NO: 130) expressed much lower in these same tissues.

$R_0$ generation transformants, selected for single copy insertions were crossed with a non-transgenic LH244 line (resulting in $F_1$) or were self-pollinated (resulting in $R_1$) in order to produce an $F_1$ or $R_1$ population of seeds. In either case, heterozygous $F_1$ or $R_1$ plants were selected for study. GUS expression levels were measured in selected tissues over the course of development as previously described. The $F_1$ or $R_1$ tissues used for this study included: imbibed seed embryo, imbibed seed endosperm, root and coleoptide at 4 days after germination (DAG); leaf and root at V3 stage; root and mature leaf at V8 stage; root, mature leaves, VT stage (at tasseling, prior to reproduction) anther, pollen, leaf and senescing leaf; R1 cob, silk, root and internode; kernel 12 days after pollination (DAP) and; embryo and endosperm 21 and 38 DAP. Selected tissue samples were also analyzed for $F_1$ plants exposed to conditions of drought and cold stress for transformants comprising pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11 SEQ ID NO: 130) and pMON132974 (EXP-Sb.Ubq7:1:2, SEQ ID NO: 157). V3 root and leaf tissue was sampled after cold and drought exposure.

Drought stress was induced in $F_1$, V3 plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubq7:1:2, SEQ ID NO: 157) by withholding watering for 4 days allowing the water content to be reduced by at least 50% of the original water content of the fully watered plant. The drought protocol was comprised essentially of the following steps. V3 stage plants were deprived of water. As a corn plant experiences drought, the shape of the leaf will change from the usual healthy and unfolded appearance to a leaf demonstrating folding at the mid-rib vascular bundle and appearing V-shaped when viewed from the leaf tip to the stem. This change in morphology usually began to occur by about 2 days after the cessation of watering and was shown in earlier experiments to be associated with water loss of around 50% as measured by weight of pots prior to cessation of watering and weight of pots when the leaf curl morphology was observed in un-watered plants. Plants were considered to be under drought conditions, when the leaves showed wilting as evidenced by an inward curling (V-shape) of the leaf. This level of stress is considered to be a form of sub-lethal stress. Once each plant demonstrated drought induction as defined above, the plant was destroyed to acquire both root and leaf samples.

In addition to drought, $F_1$ V3 stage plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubq7:1:2, SEQ ID NO: 157) were also exposed to conditions of cold to determine if the regulatory elements demonstrated cold-induced expression of GUS. Whole plants were assayed for induction of GUS expression under cold stress at V3 stage. V3 stage corn plants were exposed to a temperature of 12° C. in a growth chamber for 24 hours. Plants in the growth chamber were grown under a white light fluence of 800 micro moles per meter squared per second with a light cycle of ten hours of white light and fourteen hours of darkness. After cold exposure, leaf and root tissues were sampled for quantitative GUS expression.

GUS expression was measured as described above. The average $F_1$ GUS expression determined for each tissue sample is presented in Tables 42 and 43 below.

TABLE 42

Average $F_1$ GUS expression in plants transformed with pMON142864 and pMON142865.

| Organ | pMON142864 | pMON142865 |
|---|---|---|
| V3 Leaf | 86 | 74 |
| V3 Root | 41 | 52 |
| V8 Leaf | 109 | 123 |
| V8 Root | 241 | 252 |
| VT Flower, anthers | 168 | 208 |
| VT Leaf | 158 | 104 |
| R1 Cob | 171 | 224 |
| R1 silk | 314 | 274 |
| R1 Root | 721 | 308 |
| R1 internode | 428 | 364 |
| R2 Seed-12 DAP | 109 | 72 |
| R3 Seed-21 DAP-Embryo | 45 | 32 |
| R3 Seed-21 DAP-Endosperm | 175 | 196 |
| R5 Seed-38 DAP-Embryo | 163 | 58 |
| R5 Seed-38 DAP-Endosperm | 90 | 69 |

TABLE 43

Average $F_1$ GUS expression in plants transformed with pMON132037, pMON131957, pMON131958 and pMON132974.

| Organ | pMON132037 | pMON131957 | pMON131958 | pMON132974 |
|---|---|---|---|---|
| Imbibed Seed Embryo | 536 | 285 | 288 | 1190 |
| Imbibed Seed Endosperm | 95 | 71 | 73 | 316 |
| Coleoptile-4 DAG | 218 | 60 | 143 | 136 |
| Root-4 DAG | 74 | 33 | 101 | 48 |
| V3 Leaf | 104 | 120 | 66 | 52 |
| V3 Root | 74 | 71 | 81 | 194 |
| V3 Leaf-cold | 73 | 15 | 72 | N/A |
| V3 Root-cold | 113 | 44 | 89 | 49 |
| V3 Leaf-drought | 97 | 344 | 103 | 157 |
| V3 Root-drought | 205 | 153 | 129 | 236 |
| V8 Leaf | 185 | 142 | 77 | 282 |
| V8 Root | 33 | 16 | 61 | 28 |
| VT Flower-anthers | 968 | 625 | 619 | 888 |

TABLE 43-continued

| Average $F_1$ GUS expression in plants transformed with pMON132037, pMON131957, pMON131958 and pMON132974. | | | | |
|---|---|---|---|---|
| Organ | pMON132037 | pMON131957 | pMON131958 | pMON132974 |
| VT Leaf | 138 | 89 | 132 | 268 |
| VT Leaf-senescing | 121 | 100 | 156 | 345 |
| VT Pollen | 610 | 1119 | 332 | 4249 |
| R1 Cob | 291 | 70 | 168 | 127 |
| R1 silk | 164 | 124 | 167 | 101 |
| R1 Root | 36 | 39 | 39 | 21 |
| R1 internode | 255 | 89 | 232 | 141 |
| R2 Seed-12 DAP | 138 | 170 | 165 | 169 |
| R3 Seed-21 DAP-Embryo | 94 | 97 | 489 | 389 |
| R3 Seed-21 DAP-Endosperm | 57 | 118 | 52 | 217 |
| R5 Seed-38 DAP-Embryo | 600 | 147 | 377 | 527 |
| R5 Seed-38 DAP-Endosperm | 58 | 36 | 57 | 106 |

In $F_1$ corn plants, GUS expression levels in the various tissues sampled differed amongst the ubiquitin EXP sequences. While all of the EXP sequences demonstrated the ability to drive GUS transgene expression in stably transformed $F_1$ corn plants, each EXP sequence demonstrated a unique pattern of expression relative to the others. For example, R1 root expression is about twice that for EXP-ERIra.Ubq1:1:8 (SEQ ID NO: 27) than EXP-ANDge.Ubq1:1:8 (SEQ ID NO: 8). GUS expression in the developing seed embryo at 38 DAP is almost three fold higher for EXP-ERIra.Ubq1:1:8 (SEQ ID NO: 27) than EXP-ANDge.Ubq1:1:8 (SEQ ID NO: 8). In contrast leaf and root expression at V3 and V8 stage is about the same for EXP-ERIra.Ubq1:1:8 (SEQ ID NO: 27) than EXP-ANDge.Ubq1:1:8 (SEQ ID NO: 8).

The $F_1$ GUS expression in imbided seeds (embryo and endosperm tissues) was much higher in plants transformed with EXP-Sb.Ubq7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Drought caused an increase in V3 root expression in plants transformed with EXP-SETit.Ubq1:1:10 (SEQ ID NO: 119), EXP-SETit.Ubq1:1:11 (SEQ ID NO: 125), EXP-Sv.Ubq1:1:11 (SEQ ID NO: 130) and EXP-Sb.Ubq7:1:2 (SEQ ID NO: 157), but only increased leaf expression in plants transformed with EXP-SETit.Ubq1:1:11. (SEQ ID NO: 125), EXP-Sv.Ubq1:1:11. (SEQ ID NO: 130) and EXP-Sb.Ubq7:11:2 (SEQ ID NO: 157). The drought enhanced V3 expression was greatest using EXP-SETit.Ubq1:1:11 (SEQ ID NO: 125). Pollen expression was also much higher in plants transformed with EXP-Sb.Ubq7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Expression in the R1 internode was greatest with EXP-SETit.Ubq1:1:10 (SEQ ID NO: 119) and EXP-Sv.Ubq1:1:11 (SEQ ID NO: 130) and least in plants transformed with EXP-SETit.Ubq1:1:11 (SEQ ID NO: 125).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 13: Analysis of Regulatory Elements Driving CP4 in Transgenic Corn

Corn plants were transformed with plant expression vectors containing EXP sequences driving expression of the CP4 transgene, and the resulting plants were analyzed for CP4 protein expression.

The EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:17 (SEQ ID NO: 141) were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. Pat. No. RE39247), operably linked 5' to the T-AGRtu.nos-1:1:13 (SEQ ID NO: 127) 3' UTR and a left border region from *A. tumefaciens*. Table 44 below shows the plasmid constructs used to transform corn and the corresponding EXP sequences.

TABLE 44

| CP4 plasmid constructs and corresponding EXP sequences used to transform corn. | | | |
|---|---|---|---|
| Plasmid Construct | EXP sequence | SEQ ID NO: | Data |
| pMON141619 | EXP-ANDge.Ubq1:1:8 | 8 | $R_0$ and $F_1$ |
| pMON142862 | EXP-ERIra.Ubq1:1:8 | 27 | $R_0$ and $F_1$ |
| pMON129221 | EXP-Cl.Ubq1:1:10 | 98 | $R_0$ and $F_1$ |

TABLE 44-continued

CP4 plasmid constructs and corresponding EXP sequences used to transform corn.

| Plasmid Construct | EXP sequence | SEQ ID NO: | Data |
|---|---|---|---|
| pMON129205 | EXP-Sv.Ubq1:1:9 | 133 | $R_0$ and $F_1$ |
| pMON129212 | EXP-Zm.UbqM1:1:7 | 141 | $R_0$ |

The resulting plasmids were used to transform corn plants. Transformed plants were selected for one or two copies of the inserted T-DNA and grown in the greenhouse. Selected tissues were sampled from the $R_0$ transformed plants at specific stages of development and CP4 protein levels were measured in those tissues using an CP4 ELISA assay. The average CP4 expression observed for each transformation is presented in Tables 45 and 46 below and graphically in FIG. 7.

TABLE 45

Average leaf and root CP4 expression in $R_0$ transformed corn plants.

| EXP sequence | SEQ ID NO: | V4 Leaf | V7 Leaf | VT Leaf | V4 Root | V7 Root | VT Root |
|---|---|---|---|---|---|---|---|
| EXP-ANDge.Ubq1:1:8 | 8 | 20.90 | 18.53 | 25.49 | 11.50 | 26.54 | 17.20 |
| EXP-ERIra.Ubq1:1:8 | 27 | 19.92 | 16.60 | 25.58 | 9.92 | 26.31 | 13.33 |
| EXP-Cl.Ubq1:1:10 | 98 | 10.70 | 12.49 | 17.42 | 7.56 | 13.95 | 6.68 |
| EXP-Sv.Ubq1:1:9 | 133 | 3.72 | 4.34 | 4.48 | 2.90 | 6.99 | 2.78 |
| EXP-Zm.UbqM1:1:7 | 141 | 13.42 | 21.89 | 38.78 | 9.56 | 16.69 | 11.15 |

TABLE 46

Average CP4 expression in reproductive tissue and developing seed in $R_0$ transformed corn plants.

| EXP sequence | SEQ ID NO: | VT Tassel | R1 Silk | R3 Embryo | R3 Endosperm |
|---|---|---|---|---|---|
| EXP-ANDge.Ubq1:1:8 | 8 | 24.14 | 5.55 | 7.29 | 4.91 |
| EXP-ERIra.Ubq1:1:8 | 27 | 19.20 | 10.27 | 12.60 | 4.70 |
| EXP-Cl.Ubq1:1:10 | 98 | 18.70 | 16.21 | 8.26 | 8.82 |
| EXP-Sv.Ubq1:1:9 | 133 | 7.10 | 4.72 | 3.13 | 1.74 |
| EXP-Zm.UbqM1:1:7 | 141 | 67.25 | 11.21 | 7.85 | 10.69 |

As can be seen in Tables 45 and 46, each of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 140 was able to drive CP4 expression in all tissues sampled from the $R_0$ transformed plants. Higher expression of CP4 in the root and leaf of transformants comprising EXP-ANDge.Ubq1:1:8 (SEQ ID NO: 8) and EXP-ERIra.Ubq1:1:8 (SEQ ID NO: 27) driving CP4 than EXP-Cl.Ubq1:1:10 (SEQ ID NO: 98) driving CP4 may be related to the level of vegetative tolerance to glyphosate application as observed for these populations of transformants (see Example 14 below).

Each EXP sequence exhibited a unique expression pattern with respect to the level of expression for each tissue sampled. For example, while CP4 expression in leaf, root and tassel were similar for the EXP sequences, EXP-ANDge.Ubq1:1:8 (SEQ ID NO: 8) and EXP-ERIra.Ubq1:1:8 (SEQ ID NO: 27), expression in silk using EXP-ANDge.Ubq1:1:8 (SEQ ID NO: 8) was half that of expression driven by ERIra.Ubq1:1:8 (SEQ ID NO: 21). This might be advantageous for expression of transgenes in which constitutive expression is desired but less expression in silk tissue would be preferred. The EXP sequences demonstrate unique patterns of CP4 constitutive expression in $R_0$ transformed corn plants.

The $R_0$ transformed corn plants were crossed with a non-transgenic LH244 variety to produce $F_1$ seed. The resulting $F_1$ generation seed was analyzed for segregation of the transgene cassette and plants heterozygous for the CP4 cassette were selected for analysis of CP4 expression. Seed was grown in the greenhouse and two groups of plants were produced, one group was sprayed with glyphosate while the other was left unsprayed. Expression of CP4 was analyzed in selected tissues using a standard ELISA based assay. The average CP4 expression is shown in Tables 47 and 48 below.

TABLE 47

Average CP4 expression in $F_1$ transformed corn plants.

| Organ | pMON141619 | pMON142862 | pMON129221 |
|---|---|---|---|
| V4 Leaf | 11.50 | 13.51 | 7.68 |
| V4 Root | 12.48 | 12.60 | 10.29 |
| V7 Leaf | 16.59 | 20.21 | 12.01 |
| V7 Root | 11.00 | 13.62 | 8.15 |
| VT Leaf | 39.88 | 44.85 | 29.42 |
| VT Root | 17.43 | 21.83 | 13.43 |
| VT Flower, anthers | 52.74 | 55.72 | 53.62 |
| R1 Silk | 16.01 | 23.81 | 14.42 |
| R3 Seed-21 DAP-Embryo | 33.29 | 57.96 | 51.64 |
| R3 Seed-21 DAP-Endosperm | 2.99 | 3.20 | 6.44 |

As can be seen in Table 47 above, CP4 expression in leaf and root was higher in $F_1$ transformants transformed with pMON141619 (EXP-ANDge.Ubq1:1:8, SEQ ID NO: 5) and pMON142862 (EXP-ERIra.Ubq1:1:8, SEQ ID NO: 27) than in those transformed with pMON129221 (EXP-Cl.Ubq1:1:10, SEQ ID NO: 98). Expression in the anther tissue was similar for all three EXP sequences while expression in the silk was highest using EXP-ERIra.Ubq1:1:8 (SEQ ID NO: 27). Expression in the developing embryo (21 DAP) was highest in transformants comprising EXP-ERIra.Ubq1:1:8 (SEQ ID NO: 27) and EXP-Cl.Ubq1:1:10 (SEQ ID NO: 98) driving CP4. Expression in the developing endosperm was higher in transformants comprising EXP-Cl.Ubq1:1:10 (SEQ ID NO: 98) driving CP4.

TABLE 48

Average CP4 expression in $F_1$ transformed corn plants.

| Organ | pMON129205 |
|---|---|
| V4 Leaf | 1.73 |
| V4 Root | 2.44 |
| V7 Leaf | 2.84 |
| V7 Root | 1.51 |
| VT Leaf | 3.29 |
| VT Root | 2.63 |
| VT Flower, anthers | 7.52 |
| R1 Silk | 1.99 |
| R3 Seed-21 DAP-Embryo | 3.40 |
| R3 Seed-21 DAP-Endosperm | 1.79 |

As can be seen in Tables 47-48 above, CP4 expression was lower in all tissues of $F_1$ transformants transformed with pMON129205 (EXP-Sv.Ubq1:1:9, SEQ ID NO: 133) than those transformed with pMON141619 (EXP-ANDge.Ubq1:1:8, SEQ ID NO: 8), pMON142862 (EXP-ERIra.Ubq1:1:8, SEQ ID NO: 27) and pMON129221 (EXP-Cl.Ubq1:1:10, SEQ ID NO: 98).

The unique patterns of expression conferred by each of the EXP sequences assayed provide an opportunity to produce a transgenic plant in which expression can be fine-tuned to make small adjustments in transgene expression for optimal performance or effectiveness. In addition, empirical testing of these EXP sequences driving different transgene expression may produce results in which one particular EXP sequence is most suitable for expression of a specific transgene or class of transgenes while another EXP sequence is found to be best for a different transgene or class of transgenes.

Example 14: Analysis of Vegetative Glyphosate Tolerance in $R_0$ Transgenic Corn Plants Corn plants were transformed with plant expression vectors containing EXP sequences driving expression of the CP4 transgene, and the resulting plants were assessed for vegetative and reproductive tolerance to glyphosate application.

$F_1$ transformed corn plants described in Example 13 above transformed with pMON141619, pMON142862, pMON129221, pMON129205 and pMON129212 and comprised of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 141), respectively driving CP4 were assessed for both vegetative and reproductive tolerance when sprayed with glyphosate. Ten $F_1$ plants for each event were divided into two groups, the first group consisting of five plants that received glyphosate spray and V4 and V8 stage of development; and a second group of five plants that were left unsprayed (i.e. control). Glyphosate was applied by broadcast foliar spray application using Roundup WeatherMax® at an application rate of 1.5 a.e./acre (a.e. acid equivalent). After seven to ten days, the leaves of each plant were assessed for damage. Vegetative tolerance (Veg Tol in Table 49) was assessed comparing the unsprayed and sprayed plants for each event and a damage rating scale was used to provide a final rating for vegetative tolerance (T=tolerant, NT=not tolerant). In addition seed set was assayed for all of the plants in each event. Seed set measures between control plants and sprayed plants was compared and an assignment of reproductive tolerance (Repro Tol in Table 49) was given for each event based upon the percent seed set of sprayed plants relative to the controls (T=tolerant, NT=not tolerant). Table 49 below shows the vegetative and reproductive tolerance ratings for each event sprayed at V4 and V8 stage. The letter "T" denotes tolerant and "NT" denotes not tolerant.

TABLE 49

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| pMON141619 | EXP-ANDge.Ubq1:1:8 | 8 | Event 1 | T | T | NT |
| | | | Event 2 | T | T | T |
| | | | Event 3 | T | T | NT |
| | | | Event 4 | T | T | NT |
| | | | Event 5 | T | T | T |
| | | | Event 6 | T | T | NT |
| | | | Event 7 | T | T | T |
| | | | Event 8 | T | T | T |
| | | | Event 9 | T | T | NT |
| pMON142862 | EXP-ERIra.Ubq1:1:8 | 27 | Event 1 | T | T | T |
| | | | Event 2 | T | T | NT |
| | | | Event 3 | T | T | T |
| | | | Event 4 | T | T | T |
| | | | Event 5 | T | T | NT |
| | | | Event 6 | T | T | T |
| | | | Event 7 | T | T | NT |
| | | | Event 8 | T | T | T |
| | | | Event 9 | T | T | T |
| pMON129221 | EXP-Cl.Ubq1:1:10 | 98 | Event 1 | T | T | NT |
| | | | Event 2 | T | T | NT |
| | | | Event 3 | NT | NT | T |
| | | | Event 4 | NT | NT | T |
| | | | Event 5 | T | T | NT |
| | | | Event 6 | NT | NT | T |
| | | | Event 7 | T | T | T |
| pMON129205 | EXP-Sv.Ubq1:1:9 | 133 | Event 1 | NT | NT | |
| | | | Event 2 | NT | NT | NT |
| | | | Event 3 | T | T | NT |
| | | | Event 4 | NT | NT | |
| | | | Event 5 | NT | NT | NT |
| | | | Event 6 | NT | NT | NT |
| | | | Event 7 | NT | NT | NT |

TABLE 49-continued

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| pMON129212 | EXP-Zm.UbqM1:1:7 | 141 | Event 1 | T | T | |
| | | | Event 2 | T | T | |
| | | | Event 3 | T | T | |
| | | | Event 4 | T | T | |
| | | | Event 5 | T | T | |
| | | | Event 6 | T | T | |
| | | | Event 7 | T | T | |
| | | | Event 8 | T | T | |
| | | | Event 9 | T | T | |
| | | | Event 10 | T | T | |

From Table 49 above, all transformed events assayed comprising CP4 transgene cassettes comprising the EXP sequences EXP-ANDge.Ubq1:1:8 (SEQ ID NO: 8), EXP-ERIra.Ubq1:1:8 (SEQ ID NO: 27) and EXP-Zm.UbqM1:1:7 (SEQ ID NO: 140 demonstrated full vegetative tolerance based upon damage ratings that did not exceed a score of ten. Four events of nine comprising EXP-ANDge.Ubq1:1:8 (SEQ ID NO: 8) and six events of nine comprising EXP-ERIra.Ubq1:1:8 (SEQ ID NO: 27) were both vegetatively and reproductively tolerant to glyphosate application. In contrast, events comprising EXP-Cl.Ubq1:1:10 (SEQ ID NO: 98) were either vegetatively tolerant or reproductively tolerant but not both. Only one event comprising EXP-Sv.Ubq1:1:9 (SEQ ID NO: 133) demonstrated vegetative tolerance and none of the events tested were reproductive tolerant. All events comprising EXP-Zm.UbqM1:1:7 (SEQ ID NO: 141) demonstrated vegetative tolerance but and assessment of reproductive tolerance is still in progress.

Example 15: Analysis of Expression Using Different 3' End Intron/Exon Splice Junction Sequences Corn and Wheat leaf protoplast cells were transformed with plant expression constructs comprising EXP sequences driving GUS expression that comprise the same promoter and leader but have different 3' end nucleotides following the intron/exon splice junction sequence, 5'-AG-3' to see if expression is affected by the slight change in sequence. Expression was also compared to that of two constitutive control plasmids.

Plant expression constructs are built comprising a GUS expression cassette. The resulting vectors are comprised of the *Coix lacryma-jobi* ubiquitin promoter, P-Cl.Ubq1-1:1:1 (SEQ ID NO: 80) operably linked 5' to the leader sequence, L-Cl.Ubq1-1:1:1. (SEQ ID NO: 81), operably linked 5' to an intron element shown in Table 50 below which each comprise different nucleotides at the very 3' end just after the intron/exon splice junction 5'-AG-3' sequence, operably linked 5' to a GUS coding sequence which is operably linked 5' to T-AGRtu.nos-1:1:13 (SEQ ID NO: 127) 3' UTR. Table 50 below shows the plant expression constructs and the corresponding 3' end sequence.

TABLE 50

Plant expression constructs, introns and 3' end sequence following the intron/exon splice junction sequence 5'-AG-3'.

| Plasmid construct | EXP sequence | SEQ ID NO: | Intron Variant | Intron 3' end nucleotides immediately following 3' splice site AG |
|---|---|---|---|---|
| pMON140889 | EXP-Cl.Ubq1:1:10 | 98 | I-Cl.Ubq1-1:1:6 (SEQ ID NO: 94) | GTC |
| pMON146795 | EXP-Cl.Ubq1:1:18 | 99 | I-Cl.Ubq1-1:1:7 (SEQ ID NO: 92) | GTG |
| pMON146796 | EXP-Cl.Ubq1:1:19 | 100 | I-Cl.Ubq1-1:1:8 (SEQ ID NO: 101) | GCG |
| pMON146797 | EXP-Cl.Ubq1:1:20 | 102 | I-Cl.Ubq1-1:1:9 (SEQ ID NO: 103) | GAC |
| pMON146798 | EXP-Cl.Ubq1:1:21 | 104 | I-Cl.Ubq1-1:1:10 (SEQ ID NO: 105) | ACC |
| pMON146799 | EXP-Cl.Ubq1:1:22 | 106 | I-Cl.Ubq1-1:1:11 (SEQ ID NO: 107) | GGG |
| pMON146800 | EXP-Cl.Ubq1:1:23 | 108 | I-Cl.Ubq1-1:1:12 (SEQ ID NO: 109) | GGT |
| pMON146801 | EXP-Cl.Ubq1:1:24 | 110 | I-Cl.Ubq1-1:1:13 (SEQ ID NO: 111) | CGT |
| pMON146802 | EXP-Cl.Ubq1:1:25 | 112 | I-Cl.Ubq1-1:1:14 (SEQ ID NO: 113) | TGT |
| pMON25455 | EXP-Os.Act1:1:9 | 179 | | Constitutive Control |

TABLE 50-continued

Plant expression constructs, introns and 3' end sequence following the intron/exon splice junction sequence 5'-AG-3'.

| Plasmid construct | EXP sequence | SEQ ID NO: | Intron Variant | Intron 3' end nucleotides immediately following 3' splice site AG |
|---|---|---|---|---|
| pMON65328 | EXP-CaMV.35S-enh + Ta.Lhcb1 + Os.Act1:1:1 | 163 | | Constitutive Control |

Corn and Wheat protoplasts were transformed as previously described and assayed for GUS and luciferase expression. Table 51 below shows the average GUS and RLuc values for both corn and wheat protoplast expression.

TABLE 51

Average GUS and RLuc values for corn and wheat protoplast cells.

| | Intron 3' end nucleotides immed. | Corn | | | Wheat | | |
|---|---|---|---|---|---|---|---|
| EXP sequence | following 3' splice site AG | Average GUS | Average RLuc | GUS/ RLuc | Ave. GUS | Ave. RLuc | GUS/ RLuc |
| EXP-Cl.Ubq1:1:10 | GTC | 140343.0 | 93870.75 | 1.50 | 40906.25 | 17381.75 | 2.35 |
| EXP-Cl.Ubq1:1:18 | GTG | 143106.25 | 60565.25 | 2.36 | 56709.00 | 17898.75 | 3.17 |
| EXP-Cl.Ubq1:1:19 | GCG | 136326.83 | 88589.75 | 1.54 | 43211.00 | 17352.50 | 2.49 |
| EXP-Cl.Ubq1:1:20 | GAC | 138110.83 | 104751.42 | 1.32 | 31711.50 | 17953.75 | 1.77 |
| EXP-Cl.Ubq1:1:21 | ACC | 137906.75 | 72519.50 | 1.90 | 54164.17 | 17772.83 | 3.05 |
| EXP-Cl.Ubq1:1:22 | GGG | 137306.83 | 92643.42 | 1.48 | 55198.25 | 14476.75 | 3.81 |
| EXP-Cl.Ubq1:1:23 | GGT | 144085.50 | 64351.25 | 2.24 | 43008.83 | 13911.50 | 3.09 |
| EXP-Cl.Ubq1:1:24 | CGT | 142061.50 | 65884.00 | 2.16 | 51210.50 | 15041.00 | 3.40 |
| EXP-Cl.Ubq1:1:25 | TGT | 140353.00 | 61249.50 | 2.29 | 49577.75 | 15348.25 | 3.23 |
| EXP-Os.Act1:1:9 | Constitutive Control | 37665.25 | 65835.50 | 0.57 | 10830.25 | 17716.50 | 0.61 |
| EXP-CaMV.35S-enh + Ta.Lhcb1 + Os.Act1:1:1 | Constitutive Control | 49833.75 | 41268.75 | 1.21 | 15598.83 | 14877.50 | 1.05 |

The GUS/RLuc values for each *Coix lacryma-jobi* ubiquitin EXP sequence from Table 46 above were used to normalize the expression relative to the two constitutive controls EXP-Os.Act1:1:9 (SEQ ID NO: 179) and EXP-CaMV.35S-enh+Ta.Lhcb1+Os.Act1:1:1 (SEQ ID NO: 163) and are presented in Table 52 below.

TABLE 52

Normalized expression values of the *Coix lacryma-jobi* ubiquitin EXP sequences relative to EXP-Os.Act1:1:9 (SEQ ID NO: 179) and EXP-CaMV.35S-enh + Ta.Lhcb1 + Os.Act1:1:1 (SEQ ID NO: 163).

| | | Corn | | Wheat | |
|---|---|---|---|---|---|
| EXP sequence | Intron 3' end nucleotides immediately following 3' splice site AG | GUS/RLuc Normalized with respect to EXP-Os.Act1:1:9 | GUS/RLuc Normalized with respect to EXP-CaMV.35S-enh + Ta.Lhcb1 + Os.Act1:1:1 | GUS/Rluc Normalized with respect to EXP-Os.Act1:1:9 | GUS/Rluc Normalized with respect to EXP-CaMV.35S-enh + Ta.Lhcb1 + Os.Act1:1:1 |
| EXP-Cl.Ubq1:1:10 | GTC | 2.61 | 1.24 | 3.85 | 2.24 |
| EXP-Cl.Ubq1:1:18 | GTG | 4.13 | 1.96 | 5.18 | 3.02 |
| EXP-Cl.Ubq1:1:19 | GCG | 2.69 | 1.27 | 4.07 | 2.38 |
| EXP-Cl.Ubq1:1:20 | GAC | 2.30 | 1.09 | 2.89 | 1.68 |
| EXP-Cl.Ubq1:1:21 | ACC | 3.32 | 1.57 | 4.99 | 2.91 |
| EXP-Cl.Ubq1:1:22 | GGG | 2.59 | 1.23 | 6.24 | 3.64 |
| EXP-Cl.Ubq1:1:23 | GGT | 3.91 | 1.85 | 5.06 | 2.95 |
| EXP-Cl.Ubq1:1:24 | CGT | 3.77 | 1.79 | 5.57 | 3.25 |
| EXP-Cl.Ubq1:1:25 | TGT | 4.01 | 1.90 | 5.28 | 3.08 |

TABLE 52-continued

Normalized expression values of the *Coix lacryma-jobi* ubiquitin EXP sequences relative to EXP-Os.Act1:1:9 (SEQ ID NO: 179) and EXP-CaMV.35S-enh + Ta.Lhcb1 + Os.Act1:1:1 (SEQ ID NO: 163).

| | | Corn | | Wheat | |
|---|---|---|---|---|---|
| EXP sequence | Intron 3' end nucleotides immediately following 3' splice site AG | GUS/RLuc Normalized with respect to EXP-Os.Act1:1:9 | GUS/RLuc Normalized with respect to EXP-CaMV.35S-enh + Ta.Lhcb1 + Os.Act1:1:1 | GUS/Rluc Normalized with respect to EXP-Os.Act1:1:9 | GUS/Rluc Normalized with respect to EXP-CaMV.35S-enh + Ta.Lhcb1 + Os.Act1:1:1 |
| EXP-Os.Act1:1:9 | Constitutive Control | 1.00 | 0.47 | 1.00 | 0.58 |
| EXP-CaMV.35S-enh + Ta.Lhcb1 + Os.Act1:1:1 | Constitutive Control | 2.11 | 1.00 | 1.72 | 1.00 |

As is shown in Table 52 above, each of the *Coix lacryma-jobi* ubiquitin EXP sequences provided expression that was greater than either constitutive control in both corn and wheat. Expression in corn protoplasts was relatively similar for all of the *Coix* ubiquitin EXP sequences. Expression in wheat was a little more variable. The use of different 3' end nucleotides following the intron/exon splice junction sequence, 5'-AG-3' did not appear to dramatically affect expression of GUS with the exception of GUS driven by EXP-Cl.Ubq1:1:20 (SEQ ID NO: 102). EXP-Cl.Ubq1:1:20 comprises the 3' end nucleotide sequences, 5'-GAC-3' following the intron/exon splice junction 5'-AG-3' sequence and caused expression to drop slightly relative to the other *Coix* ubiquitin EXP sequences. Assessment of the resulting spliced messenger RNA showed that approximately 10% of the mRNA expressed using EXP-Cl.Ubq1:1:20 (SEQ ID NO: 102) to drive GUS expression was improperly spliced. The mRNA resulting from GUS expression using the other *Coix* ubiquitin EXP sequences appeared to process properly. This experiment provides evidence that any of the 3' end nucleotides for any of the intron variants presented in Table 2 of Example 1 with the exception of the 3' end sequence 5'-GAC-3' which is found associated only with the intron element, I-Cl.Ubq1-1:1:9 (SEQ ID NO: 103) should be suitable for use in transgene expression cassettes without significant loss of activity and processing.

Example 16: Enhancers Derived from the Regulatory Elements

Enhancers are derived from the promoter elements provided herein, such as those presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream sequence from the promoters that allow transcription to be initiated from the promoters provided herein as described above, including fragments thereof, in which the TATA box or functionally similar elements and sequence downstream of the TATA box are removed. The enhancer element, E-Cl.Ubq1-1:1:1 (SEQ ID NO: 89) which is derived from the promoter element, P-Cl.Ubq1-1:1:1 is provided herein to demonstrate enhancers derived from a promoter element.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first transgene cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1. SEQ ID NO: 144) or any of the introns presented herein or any other intron, operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161) or the 3' UTR from the rice lipid transfer protein gene (T-Os.LTP-1:1:1, SEQ ID NO: 175); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays.

GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 17: Analysis of Intron Enhancement of GUS Activity Using Plant Derived Protoplasts An intron is selected based upon experimentation and comparison with an intronless expression vector control to empirically select an intron and configuration within the vector T-DNA element arrangement for optimal expression of a transgene. For example, in the expression of an herbicide resistance gene, such as CP4 which confers tolerance to glyphosate, it is desirable to have transgene expression within the reproductive tissues as well as the vegetative tissues, to prevent the loss of yield when applying the herbicide. An intron in this instance would be selected upon its ability when operably linked to a constitutive promoter, to enhance expression of the herbicide resistance conferring transgene, particularly within the reproductive cells and tissues of the transgenic plant and thus providing both vegetative and reproductive tolerance to the transgenic plant, when sprayed with the herbicide. In most ubiquitin genes, the 5' UTR is comprised of a leader, which has an intron sequence embedded within it. The expression elements derived from such genes are therefore assayed using the entire 5' UTR comprising the promoter, leader, and intron. To achieve different expression profiles or to modulate the level of transgene expression, the intron from such an expression element may be removed or substituted with a heterologous intron.

Introns presented herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a transcriptional regulatory element and leader fragment and operably linked 5' to either a second leader fragment or to coding sequences, for instance as depicted in the two transgene cassettes presented in FIG. 1.

Thus, for instance, a first possible transgene cassette (Transgene Cassette Configuration 1 in FIG. 8) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible transgene cassette (Transgene Cassette Configuration 2 in FIG. 8) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible transgene cassette (Transgene Cassette Configuration 3 in FIG. 8) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Transgene Cassette Configuration 3 is designed to allow splicing of the intron in such a manner as to produce a complete open reading frame without a frame shift between the first and second fragment of the coding sequence.

The first 6 nucleotides on the 5' end and the last 6 nucleotides on the 3' end of the introns presented as SEQ ID NOS: 4, 7, 21, 24, 36, 4.4, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 represent nucleotides before and after the intron/exon splice junction, respectively. These short 6 nucleotide sequences, for example, can be modified by having additional sequence appended (i.e. native or artificial) to facilitate cloning of the intron into a plant transformation vector, so long as the first and second nucleotides from the 5' end (GT) and the fourth and fifth nucleotide from the 3' end (AG) of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are preserved, thus preserving the intron/exon splice junction of the intron. As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177), operably linked 5' to a test intron element (e.g. one of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182), operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161). Protoplast cells derived from corn or other genus plant tissue are transformed with the base plant vector and luciferase control vectors as described previously in Example 2 above and assayed for activity. To compare the relative ability of the intron to enhance expression, GUS values are expressed as a ratio of GUS to luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 178) as well as a construct comprising the constitutive promoter but without an intron operably linked to the promoter.

For stable plant assay of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182, a GUS expression plant transformation vector is constructed similar to the constructs described in the previous examples in which the resulting plant expression vectors contains a right border region from *A. tumefaciens*, a first transgene cassette to test the intron comprised of a constitutive promoter such as the Cauliflower mosaic virus promoter, P-CaMV.35S-enh-1:1:9 (SEQ ID NO: 176), operably linked 5' to a leader element, L-CaMV.35S (SEQ ID NO: 177), operably linked 5' to a test intron element provided herein, operably linked to a coding sequence for β-glucuronidase (GUS) that either possesses a processable intron (GUS-2, SEQ ID NO: 160) or no intron (GUS-1, SEQ ID NO: 158), operably linked to the Nopaline synthase 3' UTR from *A. tumefaciens* (T-AGRtu.nos-1:1:13, SEQ ID NO: 161); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be modified in a number of ways, such as deleting fragments within the intron sequence, which may reduce expression or duplication of fragments with the intron that may enhance expression. In addition, sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi or animal cells, so long as the intron provides enhancement or attenuation or specificity of expression of the transgene to which it is operably linked.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A DNA molecule comprising a DNA sequence selected from the group consisting of:

a) a sequence with at least 99 percent sequence identity to SEQ ID NO: 50;

b) a sequence with at least 95 percent sequence identity to SEQ ID NO: 147; and c) a sequence comprising SEQ ID NO: 50 or 147;

wherein said sequence is operably linked to a heterologous transcribable polynucleotide molecule.

2. The DNA molecule of claim 1, wherein said sequence comprises at least 99% identity to the DNA sequence of SEQ ID NO: 147.

3. The DNA molecule of claim 1, wherein the heterologous transcribable polynucleotide molecule comprises a gene of agronomic interest.

4. The DNA molecule of claim 3, wherein the gene of agronomic interest confers herbicide tolerance in plants.

5. The DNA molecule of claim 3, wherein the gene of agronomic interest confers pest resistance in plants.

6. A transgenic plant cell comprising a heterologous DNA molecule comprising a sequence selected from the group consisting of:

a) a sequence with at least 99 percent sequence identity to SEQ ID NO: 50;

b) a sequence with at least 95 percent sequence identity to SEQ ID NO: 147; and c) a sequence comprising SEQ ID NO: 50 or 147;

wherein said sequence is operably linked to a heterologous transcribable polynucleotide molecule.

7. The transgenic plant cell of claim 6, wherein said transgenic plant cell is a monocotyledonous plant cell.

8. The transgenic plant cell of claim 6, wherein said transgenic plant cell is a dicotyledonous plant cell.

9. A transgenic plant, or part thereof, comprising the DNA molecule of claim 1.

10. A progeny plant of the transgenic plant of claim 9, or a part thereof, wherein the progeny plant or part thereof comprises said DNA molecule.

11. A transgenic seed, wherein the seed comprises the DNA molecule of claim 1.

12. A method of producing a commodity product comprising obtaining a transgenic plant or part thereof according to claim 9 and producing the commodity product therefrom.

13. The method of claim 12, wherein the commodity product is protein concentrate, protein isolate, grain, starch, seeds, meal, flour, biomass, or seed oil.

14. A commodity product comprising the DNA molecule of claim 1.

15. The commodity product of claim 14, wherein the commodity product is protein concentrate, protein isolate, grain, starch, seeds, meal, flour, biomass, or seed oil.

16. A method of expressing a transcribable polynucleotide molecule comprising obtaining a transgenic plant according to claim 9 and cultivating plant, wherein the transcribable polynucleotide is expressed.

17. The DNA molecule of claim 1, wherein said sequence comprises at least 99 percent sequence identity to SEQ ID NO: 50.

18. The DNA molecule of claim 1, wherein said sequence comprises at least 95 percent sequence identity to SEQ ID NO: 147.

19. The transgenic plant cell of claim 6, wherein said sequence comprises at least 99 percent sequence identity to SEQ ID NO: 50.

20. The transgenic plant cell of claim 6, wherein said sequence comprises at least 95 percent sequence identity to SEQ ID NO: 147.

* * * * *